US010415097B2

(12) United States Patent
Neilan et al.

(10) Patent No.: US 10,415,097 B2
(45) Date of Patent: Sep. 17, 2019

(54) CYANOBACTERIA SAXITOXIN GENE CLUSTER AND DETECTION OF CYANOTOXIC ORGANISMS

(71) Applicant: Newsouth Innovations PTY Limited, Sydney, NSW (AU)

(72) Inventors: Brett A. Neilan, Maroubra (AU); Troco Kaan Mihali, Tamarama (AU); Ralf Kellmann, Nesttun (NO); Young Jae Jeon, Kensington (AU)

(73) Assignee: Newsouth Innovations PTY Limited, Sydney (AU)

( * ) Notice: Subject to any disclaimer, the term of this patent is extended or adjusted under 35 U.S.C. 154(b) by 449 days.

(21) Appl. No.: 14/942,830

(22) Filed: Nov. 16, 2015

(65) Prior Publication Data

US 2016/0153030 A1 Jun. 2, 2016

Related U.S. Application Data

(63) Continuation of application No. 12/989,394, filed as application No. PCT/AU2008/001805 on Dec. 5, 2008, now abandoned.

(30) Foreign Application Priority Data

Apr. 24, 2008 (AU) ................................ 2008902056

(51) Int. Cl.

| | |
|---|---|
| ***C12P 19/34*** | (2006.01) |
| ***C12Q 1/689*** | (2018.01) |
| ***C07K 14/195*** | (2006.01) |
| ***C12N 9/02*** | (2006.01) |
| ***C12N 9/10*** | (2006.01) |
| ***C12N 9/20*** | (2006.01) |
| ***C12N 9/78*** | (2006.01) |
| ***C12N 9/90*** | (2006.01) |
| ***C07K 16/00*** | (2006.01) |
| ***C07K 16/12*** | (2006.01) |
| ***C12Q 1/6888*** | (2018.01) |
| ***G01N 33/569*** | (2006.01) |

(52) U.S. Cl.

CPC ............ *C12Q 1/689* (2013.01); *C07K 14/195* (2013.01); *C07K 16/00* (2013.01); *C07K 16/12* (2013.01); *C12N 9/001* (2013.01); *C12N 9/0069* (2013.01); *C12N 9/0071* (2013.01); *C12N 9/10* (2013.01); *C12N 9/1018* (2013.01); *C12N 9/13* (2013.01); *C12N 9/20* (2013.01); *C12N 9/78* (2013.01); *C12N 9/90* (2013.01); *C12Q 1/6888* (2013.01); *G01N 33/569* (2013.01); *G01N 33/56911* (2013.01); *C12Q 2600/136* (2013.01); *C12Q 2600/158* (2013.01); *G01N 2500/04* (2013.01)

(58) Field of Classification Search

CPC ...... C07K 14/195; C07K 16/00; C07K 16/12; C12N 9/001; C12N 9/0069; C12N 9/0071; C12N 9/10; C12N 9/1018; C12N 9/13; C12N 9/20; C12N 9/78; C12N 9/90; C12Q 1/6888; C12Q 1/689; C12Q 2600/136; C12Q 2600/158; G01N 2500/04; G01N 33/569; G01N 33/56911

USPC .................................................. 435/91.2, 6.1

See application file for complete search history.

(56) References Cited

U.S. PATENT DOCUMENTS

| | | | |
|---|---|---|---|
| 7,314,974 | B2 | 1/2008 | Cao et al. |
| 2007/0020625 | A1 | 1/2007 | Duschand et al. |

FOREIGN PATENT DOCUMENTS

| | | | |
|---|---|---|---|
| WO | WO 2006/092449 | A2 | 9/2006 |
| WO | WO 2007/056723 | A2 | 5/2007 |
| WO | WO 2007/087815 | A2 | 8/2007 |
| WO | WO 2009/129558 | A1 | 10/2009 |

OTHER PUBLICATIONS

Nabout et al., Biodivers. Conserv., 22: 2907-2918, (Year: 2013).*
Akoh, et. al., GDSL family of serine esterases/lipases, Progress in Lipid Research 2004, 43:534-552, Elsevier.
Alexander, et. al., Evolutionary relationships among pyridoxal-5'-phosphate-dependent enzymes Regio-specific a, b and y families, Eur. J. Biochem. 1994, 219:953-960. FEBS.
Altschul, et al., Basic Local Alignment Search Tool, J. Mol. Biol. 1990, 215:403-410. Academic Press Limited.
Altschul, et al., Gapped BLAST and PSI-BLAST: a new generation of protein database search programs, Nucleic Acids Research 1997, 25(17):3389-3402. Oxford University Press.
Anderson et al., (1990) Marine Biology 104:511-524.
Anderson, et al., Dynamics and physiology of saxitoxin production by the dinoflagellates *Alexandrium* spp. Marine Biology 1990, 104:511-524. Springer-Verlag.
Arakawa, et al., A New Saxitoxin Analogue from a Xanthid Crab Atergatis Floridus, Toxicon 1995, 33(12):1577-1584. Elsevier Science Ltd., Great Britain.
Arakawa, et al., Occurrence of Carbamoyl-N-Hydroxy Derivatives of Saxitoxin and Neosaxitoxin in a Xanthid Crab Zosimus Aeneus, Toxicon 1994, 32(2):175-183. Elsevier Science Ltd, Great Britain.

(Continued)

*Primary Examiner* — Cynthia B Wilder

(74) *Attorney, Agent, or Firm* — Duane Morris LLP

(57) ABSTRACT

The present invention provides methods for the detection of cyanobacteria, and in particular, methods for the detection of cyanotoxic organisms. The invention further relates to methods of screening for compounds that modulate the activity of polynucleotides and/or polypeptides of the saxitoxin biosynthetic pathways.

19 Claims, 17 Drawing Sheets

Specification includes a Sequence Listing.

(56) References Cited

OTHER PUBLICATIONS

Baker, et al. Monitoring Changing Toxigenicity of a Cyanobacterial Bloom by Molecular Methods, Applied and Environmental Microbiology Dec. 2002, 68(12):6070-6076. American Society for Microbiology.
Baldwin, et al. Rules for Ring Closure: Ring Formation by Conjugate Addition of Oxygen Nucleophiles. J. Org. Chem. 1977, 42(24):3846-3852. ACS Publications.
Banker, et al., Identification of Cylindrospermopsin in Aphanizomenon Ovalisporum (Cyanophyceae) Isolated From Lake Kinneret, Israel. J. Phycol. 1997, 33:613-616. Wiley-Blackwell.
Banker, et al., Uracil Moiety is Required for Toxicity of the Cyanobacterial Hepatotoxin Cylindrospermopsin. Journal of Toxicology and Environmental Health, Part A 2001, 62(4):281-288/ Taylor & Francis Informa Ltd., England.
Beaucage, et al., Deoxynucleoside Phosphoramidites—A New Class of Key Intermediates for Deoxypolynucleotide Synthesis. Tetrahedron Letters 1981, 22(20):1859-1862. Pergamon Press Ltd., Great Britain.
Bourke, et al., An Outbreak of Hepato-Enteritis (The Palm Island Mystery Disease) Possibly Caused by Algal Intoxication. Toxicon 1983, Suppl. 3: 45-48. Pergamon Press Ltd., Great Britain.
Brown, et al., Chemical Synthesis and Cloning of a Tyrosine tRNA Gene. Methods in Enzymology 1979, 68:109-151. Academic Press, Inc.
Brutlag, et al., Improved sensitivity of biological sequence database searches. Comput Appl Biosci. Jul. 1990;6(3):237-45 Abstract Pub Med ID 2207748 available at http://www. ncbi.nlm.nih.gov/pubmed/ 2207748 (downloaded on Nov. 28, 2011, 2:00PM) Bethesda, MD.
Burgoyne, et. al., Biosynthesis of Cylindrospermopsin. J. Org. Chem. 2000, 65:152-156. American Chemical Society. Published on Web Dec. 16, 1999.
Carmichael, et. al. Isolation and identification of the cyanotoxin cylindrospermopsin and deoxy-cylindrospermopsin from a Thailand strain of Cylindrospermopsis raciborskii (Cyanobacteria). Toxicon, 2001, 39:973-980. Elsevier Science Ltd.
Carmichael, et. al., Evidence for paralytic shellfish poisons in the freshwater cyanobacterium *Lyngbya wollei* (Farlow ex Gomont) comb. nov. Appl. Environ. Microbiol. Aug. 1997, 63(8):3104-3110. American Society for Microbiology.
Carmichael, et. al., Human Fatalities form Cyanobacteria: Chemical and Biological Evidence for Cyanotoxins. Enviromental Health Perspectives Jul. 2001, 109(7):663-668. Environmental Institute of Environmental Health Sciences.
Cassier-Chauvat, et. al., Three insertion sequences from the cyanobacterium Synechocystis PCC6803 support the occurrence of horizontal DNA transfer among bacteria. Gene 1997, 195:257-266. Elsevier Science B.V.
Castro, et al. The effect of temperature on growth and production of paralytic shellfish poisoning toxins by the cyanobacterium Cylindrospermopsis raciborskii C10. Toxicon, 2004, 44:483-489. Elsevier Ltd.
Chonudomkul, et. al., Morphology, genetic diversity, temperature tolerance and toxicity of Cylindrospermopsis raciborskii (Nostocales, Cyanobacteria) strains from Thailand and Japan. FEMS Microbiology Ecology 2004, 48:345-355. Elsevier.
Cole, et al, The EBV-Hybridoma Technique and its Application to Human Lung Cancer. Monoclonal Antibodies and Cancer Therapy, 1985, 77-96. UCLA Symposia on Molecular and Cellular Biology New Series, vol. 27. Alan R. Liss, Inc., New York, USA.
Communication pursuant to Rules 70(2) and 70a(2)EPC from the European Patent Office for Application No. 08874034.5-2402. dated Jun. 14, 2011.
Dias, et. al., Production of Paralytic Shellfish Toxins by *Aphanizomenon* Sp. Lmecya 31 (Cyanobacteria). J. Phycol. 2002, 38:705-712. Wiley-Blackwell.
Edwards, et. al., Structure and Biosynthesis of the Jamaicamides, New Mixed Polyketide-Peptide Neurotoxins from the Marine Cyanobacterium Lyngbya majuscula. Chemistry & Biology Jun. 2004, 11:817-833. Elsevier Ltd.
Ehira, et. al., NrrA, a nitrogen-responsive response regulator facilitates heterocyst development in the cyanobacterium *Anabaena* sp. strain PCC 7120. Molecular Microbiology 2006, 59(6):1692-1703. Wiley-Blackwell, First published online Jan. 25, 2006. JJan. 2006uary 2006.
Fastner, et al., Cylindrospermopsin occurrence in two German lakes and preliminary assessment of toxicity and toxin production of Cylindrospermopsis raciborskii (Cyanobacteria) isolates, Toxicon, 2003, 42(3):313-321, Elsevier.
Fergusson, et. al. Molecular Phylogeny of Anabaena circinalis and its Identification in Environmental Samples by PCR. Applied and Enviromental Microbiology Sep. 2000, 66(9):4145-4148, American Society for Microbiology.
Fields, et. al., A novel genetic system to detect protein-protein interactions. Letters to Nature Jul. 20, 1989, 340:245-246, Nature Publishing Group.
Flanagan, et. al., The kit Ligand: A Cell Surface Molecule Altered in Steel Mutant Fibroblasts. Cell, Oct. 5, 1990, 63:185-194. Cell Press.
Forst, et. al. Phosphorylation of OmpR by the osmosensor EnvZ modulates expression of the ompF and ompC genes in *Escherichia coli*. Proc. Natl. Acad. Sci. USA Aug. 1989 86:6052-6056. Biochemistry.
Froscio, et. al. Cylindrospermospsin-Induced Protein Synthesis Inhibition and Its Dissociation from Acute Toxicity in Mouse Hepatocytes. Environ Toxicol, 2003, 18:243-251. Wiley Periodicals, Inc.
Fuhrman, et. al. Tetrodoxotin, Tarichatoxin, and Chiriquitoxin: historical perspectives. Annals New York Academy of Sciences Dec. 16, 1986, 479:1-14. Wiley. Article first published online.
Fulston, et. al. Clavulanic acid biosynthesis; the final steps. J Chem Soc Perk Trans, 2001, 1(9):1122-1130. The Royal Society of Chemistry, First published on the web Apr. 11, 2001.
Gen Bank No. AF030525.1, Nostoc PCC73102 hupS homolog and hupL homolog genes, complete cds, available at http://www.ncbi.nlm.nih.gov/nuccore/AF030525.1 (downloaded on Jan. 5, 2012 6:57PM) Bethesda, MD.
Gen Bank No. BA000020.2, *Nostoc* sp. PCC 7120 plasmid pCC7120alpha DNA, complete genome, available at http://www.ncbi.nlm.nih.gov/nuccore/BA000020.2 (downloaded on Jan. 5, 2012 7:07PM) Bethesda, MD.
GenBank AAF86624.1, clavaldehyde dehydrogenase (*Streptomyces clavuligerus* ATCC 27064) available at http://www.ncbi.nlm.nih.gov/protein/AAF86624.1 (downloaded on Jan. 5, 2012, 6:47PM) Bethesda, MD.
GenBank AAM33468.1, peptide synthetase (Aphanizomenon ovalisporum), available at http://www.ncbi.nlm.nih.gov/protein/AAM33468.1 (downloaded on Jan. 6, 2012 12:04 PM) Bethesda, MD.
GenBank AAM33470.1, polyketide synthase (Aphanizomenon ovalisporum), available at http://www.ncbi.nlm.nih.gov/protein/AAM33470.1 (downloaded on Jan. 6, 2012 12:04 PM) Bethesda, MD.
GenBank AAT70096.1 CurA (Lyngbya majuscula), available at http://www.ncbi.nlm.nih.gov/protein/AAT70096.1 (downloaded on Jan. 5, 2012 7:15 PM) Bethesda, MD.
GenBank AAX81898.1, AoaA (Cylindrospermopsis raciborskii), available at http://www.ncbi.nlm.nih.gov/protein/AAX81898.1 (downloaded on Jan. 6, 2012 12:01 PM) Bethesda, MD.
GenBank ABA05575.1, amidinotransferase (Nitrobacter winogradskyi Nb-255), available at http://www.ncbi.nlm.nih.gov/protein/ABA05575.1, (downloaded on Jan. 5, 2012 7:22 PM) Bethesda, MD.
GenBank ABA20206.1, Integrins alpha chain (Anabaena variabilis ATCC 29413), available at http://www.ncbi.nlm.nih.gov/protein/ABA20206.1 (downloaded on Jan. 5, 2012 11:45 AM) Bethesda, MD.

(56) References Cited

OTHER PUBLICATIONS

GenBank ABA22975.1, histidine kinase (Anabaena variabilis ATCC 29413), available at http://www.ncbi.nlm.nih.gov/protein/ABA22975.1 (downloaded on Jan. 5, 2012 11:48AM) Bethesda, MD.
GenBank ABA22979.1,1-(5-phosphoribosyl)-5-[(5-phosphoribosylamino)methylideneamino] imidazole-4-carboxamide isomerase (Anabaena variabilis ATCC 29413)avl.at http://www.ncbi.nlm.nih.gov/protein/aba22979.1 (downloaded on Jan. 6, 2012,11:54 AM) Bethesda, MD. BethesdaD.
GenBank ABA23591.1, Short-chain dehydrogenase/reductase SDR (Anabaena variabilis ATCC 29413) available at http://www.ncbi.nlm.nih.gov/protein/ABA23591.1 (downloaded on Jan. 6, 2012, 12:03 PM) Bethesda, MD.
GenBank ABA24604.1, Fumerate reductase/succinate dehydrogenase flavoprotein-like proten (Anabaena variabilis ATCC 29413) available at http://www.ncbi.nlm.nih.gov/protein/ ABA24604.1 (downloaded on Jan. 5, 2012, 7:45 PM) Bethesda, MD.
GenBank ABB06365.1, Prolyl 4-hydroxylase, alpha subunit (*Burkholderia* sp. 383) available at http://www.ncbi.nlm.nih.gov/protein/ABB06365.1 (downloaded on Jan. 6, 2012, 11:57AM) Bethesda, MD.
GenBank ABC44739.1, putative multidrug resistance protein NorM (Salinibacter ruber DSM 13855) available at http://www.ncbi.nlm.nih.gov/protein/ABC44739.1 (downloaded on Jan. 5, 2012, 7:20PM) Bethesda, MD.
GenBank ABD13093.1, aminotransferase, class I and II (*Frankia* sp. CcI3) available at http://www.ncbi.nlm.nih.gov/protein/ABD13093.1 (downloaded on Jan. 5, 2012, 7:17PM) Bethesda, MD.
GenBank ABE53436.1, hypothetical protein Sden_0139 (Shewanella denitrificans OS217) available at http://www.ncbi.nlm.nih.gov/protein/ABE53436.1 (downloaded on Jan. 5, 2012, 7:19PM) Bethesda, MD.
GenBank ABF89568.1, polyketide synthase (Myxococcus xanthus DK 1622) available at http://www.ncbi.nlm.nih.gov/protein/ABF89568.1 (downloaded on Jan. 5, 2012, 7:13PM) Bethesda, MD.
GenBank ABG30370.1, phytanoyl-CoA dioxygenase family protein (Roseobacter denitrificans OCh 114) available at http://www.ncbi.nlm.nih.gov/protein/ABG30370.1 (downloaded on Jan. 6, 2012, 11:35AM) Bethesda, MD.
GenBank ABG50679.1, Cephalosporin hydroxylase (Trichodesmium erythraeum IMS101) available at http://www.ncbi.nlm.nih.gov/protein/ABG50679.1 (downloaded on Jan. 5, 2012, 7:42PM) Bethesda, MD.
GenBank ABG50952.1, conserved hypothetical protein (Trichodesmium erythraeum IMS101) available at http://www.ncbi.nlm.nih.gov/protein/abg50952.1 (downloaded on Jan. 5, 2012, 7:39PM) Bethesda, MD.
GenBank ABG50954.1, conserved hypothetical protein (Trichodesmium erythraeum IMS101) available at http://www.ncbi.nlm.nih.gov/protein/ABG50954.1 (downloaded on Jan. 5, 2012, 7:28PM) Bethesda, MD.
GenBank ABG50968.1, Carbamoyltransferase (Trichodesmium erythraeum IMS101) available at http://www.ncbi.nlm.nih.gov/protein/ABG50968.1 (downloaded on Jan. 5, 2012, 7:26PM) Bethesda, MD.
GenBank ABG50981.1, hypothetical protein Tery_1717 (Trichodesmium erythraeum IMS101) available at http://www.ncbi.nlm.nih.gov/protein/ABG50981.1 (downloaded on Jan. 6, 2012, 12:05PM) Bethesda, MD.
GenBank ABG52264.1, Sterol desaturase-like (Trichodesmium erythraeum IMS101) available at http://www.ncbi.nlm.nih.gov/protein/ABG52264.1 (downloaded on Jan. 5, 2012, 7:09PM) Bethesda, MD.
GenBank ABG53102.1, putative branched-chain amino acid aminotransferase (Trichodesmium erythraeum IMS101) available at http://www.ncbi.nlm.nih.gov/protein/abg 53102.1 (downloaded on Jan. 5, 2012, 7:41PM) Bethesda, MD.
GenBank ABM21570.1, CrpB (*Nostoc* sp. ATCC 53789) available at http://www.ncbi.nlm.nih.gov/protein/abm21570.1 (downloaded on Jan. 6, 2012, 11:55AM) Bethesda, MD.
GenBank ABX60164.1, adenylylsulfate kinase (Cylindrospermopsis raciborskii AWT205) available at http://www.ncbi.nlm.nih.gov/protein/ABX60164.1 (downloaded on Jan. 10, 2012, 11:33AM) Bethesda, MD.
GenBank BAB76200.1, phosphate regulon transcriptional regulator (*Nostoc* sp. PCC 7120) available at http://www.ncbi.nlm.nih.gov/protein/BAB76200.1 (downloaded on Jan. 6, 2012, 11:47AM) Bethesda, MD.
GenBank BAB76205.1, phosphorybosilformimino-5-amino-phosphorybosil- 4-imidazolecarboxamideisomerase [*Nostoc* sp. PCC 7120] available at http://www.ncbi. nlm.nih.gov/protein/BAB76205.1 (downloaded on Jan. 10, 2012, 11:32AM) Bethesda, MD.
GenBank BAB76734.1, alr5035 [*Nostoc* sp. PCC 7120] available at http://www.ncbi.nlm.nih.gov/protein/BAB76734.1 (downloaded on Jan. 10, 2012, 11:31AM) Bethesda, MD.
GenBank BAF59909.1, cytosine deaminase and related metal-dependent hydrolases [Pelotomaculum thermopropionicum SI] available at http://www.ncbi.nlm.nih. gov/protein/BAF59909.1 (downloaded on Jan. 6, 2012, 11:56AM) Bethesda, MD.
GenBank CAE11914.1, InsA protein [Microcystic aeruginosa PCC 7806] available at http://www.ncbi.nlm.nih.gov/protein/CAE11914.1 (downloaded Jan. 5, 2012, 7:10PM) Bethesda, MD.
GenBank CAE11915.2, putative InsAB protein [Microcystic aeruginosa PCC 7806], available at http://www.ncbi.nlm.nih.gov/protein/CAE11915.2 (downloaded on Jan. 5, 2012, 7:10PM) Bethesda, MD.
GenBank CAM76460.1, Adenylylsulfate kinase:Small GTP-binding protein domain: Sulfate adenylyltransferase, large subunit [Magnetospirillum gryphiswaldense MSR-1] available at http://www.ncbi.nlm.nih.gov/protein/CAM76460.1 (downloaded on Jan. 6, 2012) Bethesda, MD.
GenBank DQ787200.1, Cylindrospermopsis raciborskii T3 toxin biosynthesis gene cluster, complete sequence available at http://www.ncbi.nlm.nih.gov/nuccore/DQ787200.1 (downloaded on Jan. 5, 2012, 6:54PM) Bethesda, MD.
GenBank EAM51043.1, hypothetical protein CwatDRAFT_4083 [Crocosphaera watsonii WH 8501] available at http://www.ncbi.nlm.nih.gov/protein/EAM51043.1 (downloaded on Jan. 5, 2012, 7:27PM) Bethesda, MD.
GenBank EAO22567.1, Transposase, IS4 [Syntrophobacter fumaroxidans MPOB] available at http://www.ncbi.nlm.nih.gov/protein/EAO22567.1?report=genpept (downloaded on Jan. 6, 2012, 11:46AM) Bethesda, MD.
GenBank EAR64935.1, hypothetical protein B14911_19640 [*Bacillus* sp. NRRL B-14911] available at http://www.ncbi.nlm.nih.gov/protein/EAR64935.1 (downloaded on Jan. 6, 2012, 11:44AM) Bethesda, MD.
GenBank EAS64681.1, cytidine deaminase [Photobacterium angustum S14] available at http://www.ncbi.nlm.nih.gov/protein/EAS64681.1 (downloaded on Jan. 5, 2012, 7:12PM) Bethesda, MD.
GenBank EAW39051.1, DNA-damage-inducible protein [*Lyngbya* sp. PCC 8106] available at http://www.ncbi.nlm.nih.gov/protein/EAW39051.1 (downloaded on Jan. 6, 2012, 11:58AM) Bethesda, MD.
GenBank EAW46978.1, hypothetical protein N9414_14900 [Nodularia spumigena CCY9414] available at http://www.ncbi.nlm.nih.gov/protein/EAW46978.1 (downloaded on Jan. 6, 2012, 12:07PM) Bethesda, MD.
GenBank ED287359.1, AUAC-aag62g01.b1 Ascaris suum whole genome shotgun library (PMAJ_4 GSS) Ascaris suum genomic, genomic survey sequence, available at http://www. ncbi.nlm.nih.gov/nucgss/ED287359.1 (downloaded on Jan. 10, 2012, 11:35AM) Bethesda, MD.
GenBank EU140798.1, Cylindrospermopsis raciborskii AWT205 cylindrospermopsin biosynthesis gene cluster, complete sequence, available at http://www.ncbi.nlm. nih.gov/nuccore/EU140798.1 (downloaded on Jan. 5, 2012, 6:43PM) Bethesda, MD.
GenBank HQ682085.1, Cylindrospermopsis raciborskii AWT205 cylindrospermopsin (cyrA) gene, partial cds, available at http://

(56) References Cited

OTHER PUBLICATIONS www.ncbi.nlm.nih.gov/protein/HQ682085.1 (downloaded on Jan. 5, 2012, 6:52PM) Bethesda, MD.
GenBank ZP_00053494.2. COG2895: GTPases—Sulfate adenylate transferase subunit 1 [Magnetospirillum magnetotacticum MS-1], available at http://www.ncbi.nlm.nih.gov/ protein/ZP_00053494.2 (downloaded on Jan. 6, 2012, 12:18PM). Bethesda, MD.
GenBank ZP_00106179.2. COG1146: Ferredoxin [Nostoc punctiforme PCC 73102], available at http://www.ncbi.nlm.nih.gov/protein/ZP_ 00106179.2?report=genpept (downloaded on Jan. 6, 2012, 12:23PM) Bethesda, MD.
GenBank ZP_00108178.2.Npun_F4214 two component transcriptional regulator [ Nostoc punctiforme PCC 73102 ], available at http://www.ncbi.nlm.nih.gov/gene?term=ZP_ 00108178.2 (downloaded on Jan. 6, 2012, 12:14PM) Bethesda, MD.
GenBank ZP_00111652.1. COG4221: Short-chain alcohol dehydrogenase of unknown specificity [Nostoc punctiforme PCC 73102], available at http://www.ncbi.nlm.nih.gov/pro tein/ZP_ 00111652.1?report=genpept, (downloaded on Jan. 6, 2012, 12:22PM). Bethesda MD.
GenBank ZP_00243439.1.COG4638:Phenylpropionate dioxygenase and related ring-hydr oxylating dioxygenases, large terminal subunit [Rubrivivax gelatinosus PM1], avai. http:// www.ncbi.nlm.nih.gov/protein/ZP_00243439.1?report=genpept (dwn on Jan. 6, 2012 12:21PM).
GenBank ZP_00345366.1. hypothetical protein Npun02005122 [Nostoc punctiforme PCC73102], available at http://www.ncbi.nlm.nih.gov/ protein/ZP_00345366.1?report=genpept (downloaded on Jan. 6, 2012, 12:15PM) Bethesda, MD.
GenBank ZP_01619109.1. nodulation protein [*Lyngbya* sp. PCC 8106], available at http://www.ncbi.nlm.nih.gov/protein/ZP_ 01619109.1 (downloaded on Jan. 10, 2012, 11:33AM). Bethesda, MD.
GenBank ZP_01727402.1. transposase, IS4 [*Cyanothece* sp. CCY0110], available at http://www.ncbi.nlm.nih.gov/protein/126656018 (downloaded on Jan. 10, 2012, 11:34AM). Bethesda, MD.
Gogarten, et. al. Horizontal Gene Transfer, Genome Innovation and Evolution, Nat Rev Microbio1,2005, 3:679-687. Reviews.
Hackett, et. al. Insights into a dinoflagellate genome through expressed sequence tag analysis. BMC Genomics 2005, 6:80. BioMed Central.
Hallegraeff, et. al., (Eds) IOC Manual and Guides No. 33, UNESCO 1995. United Nations Educational, Scientific and Cultural Organization. Paris, France.
Hansel, et. al. Cloning and characterisation of a hyp gene cluster in the filamentous cyanobacterium *Nostoc* sp. strain PCC 73102. FEMS Microbiology letters, 2001, 201:59-64. Elsevier Science B.V.
Harda, et. al. Isolation of Cylindrospermopsin from a Cyanobacterium Umezakia Natans and its Screening Method. Toxicon, 1994, 32(1):73-84. Pergamon Press Ltd. Great Britain.
Hawkins, et. al. Isolation and Toxicity of Cylindrospermopsis Raciborskii from an Ornamental Lake. Toxicon 1997, 35(3):341-346. Elsevier Science Ltd.
Hederstedt, et. al. Succinate dehydrogenase—a comparative review. Microbiol. Rev. 1981, 45(4):542-555. ASM.
Henikoff, et.al. Amino acid substitution matrices from protein blocks. Proc. Natl. Acad. Sci. Nov. 1992, 89:10915-10919. National Academy of Sciences.
Humpage, et. al. Micronucleus induction and chromosome loss in transformed human white cells indicate clastogenic and aneugenic action of the cyanobacterial toxin, cylindrospermopsin. Mutation Research 2000, 472:155-161. Elsevier Science B.V.
Huse, et. al. Generaltion of a large combinatorial library of the immunoglobulin repoertoire in phage lambda. Science, New Series. Dec. 8, 1989, 246(4935):1275-1281. American Association for the Advanced of Science.
International Preliminary Report on Patentability for International App. No. PCT/AU2008/001805. Date of Completion of the Report: Aug. 10, 2010.
Itakura, et. al. Synthesis and use of synthetic oligonucleotides. Ann. Rev. Biochem. 1984, 53:323-56. Annual Reviews Inc.
Kaas, et. al. Saxitoxins (PSP Toxins) in Danish lakes. Wat. Res. 2000, 34(7):2089-2097. Elsevier Science Ltd. Great Britain.
Kagan, et. al. Widespread occurrence of three sequence motifs in diverse S-Adenosy lmethionine-Dependent Methyltransferases suggests a common structure for these enzymes. Arch of Biochemistry and Biophysics May 1, 1994, 310(2):417-427.Academic Press. Inc.
Kakuta, et. al. Crystal structure of estrogen sulphotransferase. Nature Structural Bio., Nov. 1997, 4(11):904-908. Nature Publishing Group.
Kao and Levinson. Tetrodotoxin, Saxitoxin and the molecular biology of the sodium channel, Annals of the New York Academy of Sciences, 1986, vol. 479:1-445.
Karlin, et. al. Applications and statistics for multiple high-score segments in molecular sequences. Proc. Natl. Acad. Sci., Jun. 1993, 90:5873-5877.
Kellmann et al. (published online May 16, 2006) Applied and Environmental Microbiol. vol. 74 No. 13, pp. 4044 and 4053.
Kellmann, et. al. Biochemical characterization of paralytic shellfish toxin biosynthesis in vitro. J. Phycol., 2007, 43:497-503. Phycological Society of America.
Kellmann, et. al. Biosynthetic intermediate analysis and functional homology reveal a saxitoxin gene cluster in cyanobacteria. Appl. Environ. Microbiol. 2008, 74(13):4044-4056. American Society for Microbiology.
Kellmann, et. al. Functional modeling and phylogenetic distribution of putative cylindrospermopsin biosynthesis enzymes. J Mol. Evol., 2006, 62:267-280. Springer Science+Business Media, Inc.
Kellmann, et. al. Identification of a saxitoxin biosynthesis gene with a history of frequent horizontal gene transfers. J. Mol. Evol., 2008, 67:526-538.
Kellmann, Ralph. PhD Thesis, 2005, "The Molecular Genetics of Cylindrospermopsin and Saxitoxin Biosynthesis.".
Kiss, et. al. Membrane effects of toxins isolated from a cyanobacterium, Cylindrospermopsis raciborskii, on identified molluscan neurones. Comparative Biochemistry and Physiology Part C 2002, 131:167-176. Elsevier Science Inc.
Kohler, et. al. Continuous cultures of fused cells secreting antibody of predefined specificity. Nature Aug. 7, 1975, 256:495-497. Nature Publishing Group.
Kozbor, et. al. The production of monoclonal antibodies from human lymphocytes. Immonology Today 1983, 4(3):72-79. Elsevier Biomedical Press.
Lagos, et. al. The first evidence of paralytic shellfish toxins in the freshwater cyanobacterium Cylindrospermopsis raciborskii, isolated from Brazil. Toxicon 1999, 37:1359-1373. Elsevier Science Ltd.
Lambolat, et. al. A new enzyme superfamily—the phosphopantetheinyl transferases. Chemistry & Biology 1996, 3:923-936. Current Biology.
Li, et al. First report of the cyanotoxins cylindrospermopsin and deoxycylindrospermopsin from Raphidiopsis Curvata (cyanobacteria). J. Phycol. 2001, 37:1121-1126.
Li, et al. Isolation and identification of the cyanotoxin cylindrospermopsin and deoxy-cylindrospermopsin from a Thailand strain of Cylindrospermopsis raciborskii (Cyanobacteria). Toxicon 2001, 39:973-980. Elsevier Science, Ltd.
Lieber, et. al. Selection of efficient cleavage sites in target RNAs by using a ribozyme expression library. Mol. Cell. Biol. 1995, 15(1):540-551. American Society for Microbiology.
Llewellyn, L.E., et al. Radioreceptor Assays for Sensitive Detection and Quantitation of Saxitoxin and Its Analogues from Strains of the Freshwater Cyanobacterium, Anabaena circinalis, Env Sci and Tech, 2001, 35(7):1445-1451, ACS Publications.
Mahmood, et. al. Paralytic shellfish poisons produced by the freshwater cyanobacterium aphanizomenon FLOS-AQUAE NH-5. Toxicon 1986, 24(2):175-186. Pergamon Press Ltd. Great Britain.
Mihal et al. (online print date Dec. 7, 2007), Appl. Environ. Microbiol. (2008) vol. 74(3):716-722.
Moffitt, et. al. Characterization of the nodularin synthetase gene cluster and proposed theory of the evolution of cyanobacterial hepatotoxins. Appl. Environ. Microbiol. 2004, 70(11):6353-6362. American Society for Microbiology.

(56) References Cited

OTHER PUBLICATIONS

Narang, S.A., et al. Improved Phosphotriester Method for the Synthesis of Gene Frangments, Methods in Enzymology, 1979, 68:90-98, Academic Press, Inc.
Needleman, et. al. A general method applicable to the search for similarities in the amino acid sequence of two proteins. J. Mol. Biol. 1970, 48:443-453. Elsevier.
Negri, et. al. Three novel hydroxybenzoate saxitoxin analogues isolated from the dinoflagellate gymnodinium catenatum. Chem. Res. Toxicol. 2003, 16:1029-1033. American Chemical Society. Published on the web Jul. 29, 2003.
Neilan, et. al. Phylogeography of the invasive cyanobacterium Cylindrospermopsis raciborskii. Molecular Ecology 2003, 12:133-140. Blackwell Publishing Ltd.
Neilan, et. al. Genetic diversity and phylogeny of toxic cyanobacteria determined by DNA polymorphisms within the phycocyanin locus. Applied and Environmental Microbioloby. 1995, 61(11):3875-3883. American Society for Microbiology.
Neilan, et. al. Molecular identification of cyanobacteria associated with stromalities from distinct geographical locations. Astrobiology 2(3):271-280. Mary Ann Liebert, Inc. New York, USA.
Neilan, et. al. rRNA sequences and evolutionary relationships among toxic and nontoxic cyanobacteria of the genus microcystis. International Journal of Systematic Bacteriology, Jul. 1997, 47(3):693-697. The Society for General Microbiology, United Kingdom.
Neilan, et. al. The genetics and genomics of caynobacterial toxicity. Advances in Experimental Medicine and Biology, Ch. 17. pp. 417-452, Jan. 1, 2008, Springer, US.
Neuwald, et. al. GCNS related histone N-acetyltransferases belong to a diverse superfamily that includes the yeast SPT10 protein. TIBS May 1999, 22:154-155. Elsevier Science Ltd.
Norris, et. al. Deoxycylindrospermopsin, an Analog of cylindrospermopsin from cylindrospermopsis raciborskii. Environ Toxicol, Feb. 1999, 14(1):163-165. John Wiley & Sons, Inc.
Norris, et. al. Extraction and purification of the zwitterions cylindrospermopsin and deoxycylindrospermopsin from cylindrospermopsis raciborskii. Environ Toxicol. 2001, 16:391-396. John Wiley & Sons, Inc.
Ohtani, et al, Cylindrospermopsin: A potent hepatotoxin from the blue-green alga cylindrospermopsis raciborskii. J Am Chem Soc, 1992, 114:7941-7942. American Chemical Society.
Onodera, et. al. New saxitoxin analogues from the freshwater filamentous cyanobacterium lyngbya wollei. Natural Toxins 1997, 5:146-151. Wiley-Liss, Inc.
Oshima, Yasukatsu, Postcolumn Derivatization Liquid Chromatographic Method for Paralytic Shellfish Toxins, Journal of AOAC International 1995, 78(2):528-532, AOAC International.
Otsuka, et. al. Identification of Essential Amino Acid Residues of the NorM Na+/Multidrug antiporter in vibrio parahaemolyticus. J. Bacteriol. 2005, 187(5):1552-1558. American Society for Microbiology.
Palenik, et. al. The genome of a motile marine synechococcus. Letters to Nature Aug. 28, 2003, 424:1037-1042. Nature Publishing Group.
Pallen, Mark, Microcorrespondence RpoN-dependent transcription of rpoH? Molecular Biology 1999, 31(1):393-395. Blackwell Science Ltd.
Pearson, et. al. Inactivation of an ABC Transporter Gene, mcyH, results in loss of microcystin production in the canobacterium microcystis aeruginosa PCC 7806. Appl. Environ. Microbiol. 2004, 70(11):6370-6378. American Society for Microbiology.
Pereira, et. al. Paralytic shellfish toxins in the freshwater cyanobacterium Aphanizomenon flos-aquae, isolated from Montargil reservoir, Portugal. Toxicon 2000, 38:1689-1702. Elsevier Science Ltd.
Piel, et. al. Unprecedented diversity of catalytic domains in the first four modules of the putative pederin polyketide synthase. Chem Bio Chem 2004, 5:9398. Wiley-VCH Verlag GmbH & Co. KGaA, Weinheim.
Plumley, et. al. Purification of an enzyme involved in saxitoxin synthesis. J. Phycol. 2001, 31:926-931.
Pollingher, et. al. Aphanizomenon ovalisporum (Forti) in Lake Kinneret, Israel. Journal of Plankton Research 1998, 20(7):1321-1339. Oxford University Press.
Pomati, et. al. Identification of an Na+-Dependent transporter associated with saxitoxin-producing strains of the cyanobacterium anabaena circinalis. Appl. Environ. Microbiol. 2004, 70(8):4711-4719. ASM.
Pomati, et. al. Interactions between intracellular Na+ levels and saxitoxin production in Cylindrospermopsis raciborskii T3. Microbiology, 2004, 150:455:461. SGM. Great Britain.
Pomati, et. al. PCR-based positive hybridization to detect genomic diversity associated with bacterial secondary metabolism. Nucleic Acids Research, 2004, 32(1)e7:1-9. Published online Jan. 12, 2004.
Prescott, et. al. The iron(II) and 2-oxoacid-dependent dioxygenases and their role in metabolism. Nat. Prod. Rep. 2000, 17:367-383. The Royal Society of Chemistry. First published on the web Jun. 19, 2000.
Preubel, et al. First report on cylindrospermopsin producing Aphanizomenon flos-aquae (Cyanoacteria) siolated from two German lakes. Toxicon 2006, 47:156-162. Elsevier.
Runnegar, et. al. Inhibition of reduced glutathione synthesis by cyanobacterial alkaloid cylindrospermopsin in cultured rat hepatocytes. Biochemical Pharmacology. Elsevier Science Ltd. Great Britain.
Runnegar, et. al. The role of glutathione in the toxicity of a novel cyanobacterial alkaloid cylindrospermopsin in cultured rat hepacytes. Biochemical & Biophysical Research Communications, May 30, 1994, 201(1):235-241. Academic Press, Inc.
Saker, et. al. Cattle mortality attributed to the toxic cyanobacterium cylindrospermopsis raciborskii in an outback region of north Queensland. Environ Toxicol, 1999, 14:179-182. John Wiley & Sons, Inc.
Saker, et. al. First report and toxicological assessment of the cyanobacterium Cylindrospermopsis raciborskii from Portuguese freshwaters. Ecotoxicology and Environmental Safety 2003, 55:243-250, Elsevier Science USA.
Saker, et. al. The effect of temperature on growth and cylindrospermopsin content of seven isolates of Cylindrospermopsis raciborskii (Nostocales, Cyanophyceae) from water bodies in northern Australia. Phycologia, 200038(4):349-354. Allen Press.
Saker, et. al. Two morphological forms of cylindrospermopsis raciborskii (cyanobacteria) isolated from Solomon Dam, Palm Island, Queensland. J. Phycol. 1999, 35:599-606.
Sako, et. al. Purification and characterization of a sulfotransferase specific to N-21 of Saxitoxin and Gonjautoxin 2+3 from the toxic dinoflagellate gymnodinium catenatum (dinophyceae). J. Phycol. 2001 37:1044-1051.
Schembri, et. al. Identification of genes implicated in toxin production in the cyanobacterium cylindrospermopsis raciborskii. Envrion Toxicol, 2001, 16:413-421. John Wiley & Sons, Inc.
Schwedock, et. al. Rhizobium meliloti genes involved in sulfate activation: the two copies of nodPQ and a new locus, saa. Genetics, Dec. 1992, 132:899-909. Genetics Society of America.
Shalev-Alon, et. al. A novel gene encoding amidinotransferase in the cylindrospermopsin producting cyanobacterium Aphanizomenon ovalisporum. FEMS Microbiology Letters 2002, 209:87-91. Elsevier Science B.V.
Shaw, et. al. Blooms of the cylindrospermopsin containing cyanobacterium, Aphanizomenon ovalisporum (Forti), in newly constructed lakes, Queensland, Australia. Envrion Toxicol, 1999, 14:167-177. John Wiley & Sons, Inc.
Shimizu, et. al. Distinct responses of 3T3-L1 cells to dihydroteleocidin B and the phorbol ester tumor promoters: relation to adipocyte differentiation, DNA synthesis and cell division. Princess Takamatsu Symp, 984,14:115-122 Japan Sci. Soc. Press, Tokyo/VNU.
Shimizu, et. al. Microalgal Metabolites. Chem. Rev. 1993, 93:1685-1698. American Chemical Society.
Siebert, et. al. An improved PCR method for walking in uncloned genomic DNA. Nucleic Acids Research 1995, 23(6):1087-1088.
Sleno, et. al. Assigning product ions from complex MS/MS spectra: the importance of mass uncertainty and resolving power. J. Am. Soc. Mass. Spectrom. 2005, 16:183-198. Elsevier, Inc.
Sleno, et. al. Gas-Phase dissociation reactions of protonated saxitoxin and neosaxitoxin. American Society for Mass Spectrometry 2004, 15:462-477. Elsevier Inc.

(56) References Cited

OTHER PUBLICATIONS

Smith, et. al. Comparison of biosequences. Adv. App. Math. 1981, 2:482-489. Academic Press, Inc.

Spoof, et. al. First observation of cylindrospermopsin in Anabaena lapponica isolated from the Boreal environment (Finland) Env. Tox.2006, 21:552-560 Wiley Periodicals, Inc.

Steed, et. al. Use of the rep technique for allele replacement to construct mutants with deletions of the pstSCAB-phoU operon: evidence of a new rolefor the PhoU protein in the phosphate regulon. J of Bact. Nov 1993, 175(21):6797-6809. ASM.

Stirling, et. al. First report of the cyanobacterial toxin cylindrospermopsin in New Zealand. Toxicon 2001, 39:1219:1222. Elsevier Science Ltd.

Su, et. al. Saxitoxin blocks L-type Ica. J Pharm Exp Ther, 2004, 308:324-329. The American Society for Pharmacology and Experimental Therapeutics. USA.

Tamagnini, et. al. Hydrogenases and hydrogen metabolism of cyanobacteria. Microbiol. Mol. Biol. Rev. 2002, 66:1-20. ASM.

Thomas, et. al. Deciphering Tuberactinomycin Biosynthesis: Isolation, Sequencing, and Annotation of the Viomycin Biosynthetic Gene Cluster. Antimicrob. Agents Chemother. 2003, 47(9):2823. ASM.

Tillett, et. al. Structural organization of microcystin biosynthesis in Microcystis aeruginosa PCC7806: an integrated peptide-polyketide synthetase system. Chem. & Bio., 2000, 7(10):753-764. Elsevier Science Ltd.

Velzeboer, et. al. Geographical patterns of occurrence and composition of saxitoxins in the cyanobacterial genus Anabaena (Nostocales, Cyanophyta) in Australia. Phycologia 2000, 39(5):395-407.

Vermeij, et. al. Genetic organization of sulphur-controlled aryl desulphonation in Pseudomonas putida S-313. Mol. Micro. 1999, 32(5):913-926. Blackwell Science Ltd.

Vishwanathan, et. al. Determination of arginine and methylated arginines in human plasma by liquid chromatography-tandem mass spectrometry. J. of Chroma. B, 2000, 748:157-166. Elsevier Science B.V.

Wang, et. al. Saxitoxin is a gating modifier of hERG K+ Channels. J. Gen. Physiol. Jun. 2003, 121:583-598. The Rockefeller University Press.

Ward, et. al. Binding activities of a repertoire of single immunoglobulin variable domains secreted from *Escherichia coli*. Letters to Nature Oct. 12, 1989, 342:544-546. Nature Publishing Group.

Wilson, et. al. Molecular Characterization of the toxic cyanobacterium cylindrospermopsis raciborskii and design of a species-specific PCR. Appl. Environ. Microbiol. 2000, 66(1):332-338. ASM.

Written Opinion of the International Searching Authority for International App. No. PCT/AU2008/001805, dated Mar. 20, 2009.

Yin, et. al. Identification and cloning of genes encoding viomycin biosynthesis from *Streptomyces vinaceus* and evidence for involvement of a rare oxygenase. Gene 2003, 215-224. Elsevier Science B.V.

Yoshida, et. al. Purification and characterization of sulfotransferase specific to O-22 of 11-hydroxy saxitoxin from the toxic dinoflagellate Gymnodinium catenatum (dinophyceae). Fisheries Science 2002, 68:634-642.

Zaman, et. al. Occurrence of a methyl derivative of saxitoxin in Bangladeshi freshwater puffers. Toxicon 1998, 36(4):627-630. Elsevier Science Ltd. Great Britain.

GenBank AAU26161.1 transferase enzyme (*Legionella pneumophila* subsp. pneumophila str. Philadelphia 1 ), available at http://www.ncbi.nlm.nih.gov/protein/AAU26161.1 (downloaded on Jan. 5, 2012 11 :36 AM) Bethesda MD.

Gen Bank AAV97870, OnnB (symbiont bacterium of Theonella swinhoei), available at http://www.ncbi.nlm.nih.gov/protein/AAV97870 (downloaded on Jan. 5, 2012 7:16 PM) Bethesda MD.

Genbank Accession# BAB76200 (phosphate regulon transcriptional regulator) Dec. 21, 2007, [*Nostoc* sp. PCC 7120], available at https://www.ncbi.nlm.nih.gov/protein/BAB76200.

* cited by examiner

FIGURE 1A

| Cyanobacteria Strains | Toxicity (Ref) | *sxtA* | *sxtG* | *sxtH* | *sxtI* | *sxtX* |
|---|---|---|---|---|---|---|
| *A. circinalis* AWQC118C | PSP (54) | + | + | + | + | - |
| *A. circinalis* AWQC131C | PSP (25) | + | + | + | + | - |
| *A. circinalis* AWQC134C | PSP (54) | + | + | + | + | - |
| *A. circinalis* AWQC150E | PSP (54) | + | + | + | + | - |
| *A. circinalis* AWQC173A | PSP (54) | + | + | + | + | - |
| *A. circinalis* AWQC271C | - (54) | - | - | - | - | - |
| *A. circinalis* AWQC306A | - (54) | - | - | - | - | - |
| *A. circinalis* AWQC310F | - (54) | - | - | - | - | - |
| *A. circinalis* AWQC342D | - (54) | - | - | - | - | - |
| *Aph. flos-aquaea* NH-5 | PSP (26) | + | + | + | + | + |
| *Aph. ovalisporum* APH028A | CYLN (46) | - | - | - | - | - |
| *C. raciborskii* T3 | PSP (23) | + | + | + | + | + |
| *C. raciborskii* 23B | CYLN (58) | - | - | - | - | - |
| *C. raciborskii* GOON | CYLN (43) | - | - | - | - | - |
| *C. raciborskii* GERM1 | - (30) | - | - | - | - | - |
| *C. raciborskii* MARAU1 | - (30) | - | - | - | - | - |
| *L. wollei* | PSP (7) | + | + | + | + | + |

FIGURE 1B

| Primer | From | To | Direction | Sequence | Gene | |
|---|---|---|---|---|---|---|
| SEQ ID NO:133 | 1917 | 1937 | --> | GCAAATTTTGCAGGAGTAATG | sterole desaturase | sxtD |
| SEQ ID NO:134 | 2744 | 2763 | --> | AGAGATGCTATGCTTTTCAA | InsB | orf3 |
| SEQ ID NO:135 | 2889 | 2911 | --> | TTTTGGGTAAACTTTATAGCCAT | InsB | orf3 |
| SEQ ID NO:136 | 3020 | 3041 | <-- | TGGGTCTGGACAGTTGTAGATA | InsA | orf4 |
| SEQ ID NO:137 | 3306 | 3328 | <-- | AAGGGGAAAACAAAATTATCAAT | InsA | orf4 |
| SEQ ID NO:138 | 3396 | 3415 | --> | GGCGATCGCCTGCTAAAAAT | InsA | orf4 |
| SEQ ID NO:139 | 3717 | 3739 | --> | CCTCATTTTCATTTCTAGACGTT | SPUR | sxtC |
| SEQ ID NO:140 | 4201 | 4220 | --> | CCACTTCAACTAAAACAGCA | cytidine deaminase | sxtB |
| SEQ ID NO:141 | 4362 | 4381 | <-- | AAAAATTTTGGAGGGGTAGC | cytidine deaminase | sxtB |
| SEQ ID NO:142 | 4932 | 4951 | --> | ATCCAAGATGCGACAACACT | cytidine deaminase | sxtB |
| SEQ ID NO: 70 | 5193 | 5212 | --> | TTAATTGCTTGGTCTATCTC | PKS | sxtA |
| SEQ ID NO: 71 | 5206 | 5225 | <-- | CAATACCGAAGAGGAGATAG | PKS | sxtA |
| SEQ ID NO: 72 | 5345 | 5364 | <-- | TAGGCGTGTTAGTGGGAGAT | PKS | sxtA |
| SEQ ID NO: 73 | 5415 | 5434 | --> | TGTGTAACCAATTTGTGAGT | PKS | sxtA |
| SEQ ID NO: 74 | 5478 | 5497 | <-- | TTAGCCGGATTACAGGTGAA | PKS | sxtA |
| SEQ ID NO: 75 | 6136 | 6155 | <-- | CTGGACTCGGCTTGTTGCTT | PKS | sxtA |
| SEQ ID NO: 76 | 6933 | 6952 | --> | CAGCGAGTTACACCCACCAC | PKS | sxtA |
| SEQ ID NO: 76 | 7033 | 7054 | <-- | CTCGCACTAAATATTCTACC | PKS | sxtA |
| SEQ ID NO: 78 | 7434 | 7452 | --> | AAAACCTCAGCTTCCACAA | PKS | sxtA |
| SEQ ID NO: 79 | 7537 | 7558 | <-- | ATGATTTTGGAGGTCCATTGTT | PKS | sxtA |
| SEQ ID NO: 113 | 7820 | 7841 | --> | CCCAATATCTCCCTGTAAAACT | PKS | sxtA |
| SEQ ID NO: 114 | 8170 | 8189 | <-- | TGGCAATTGTCTCTCCGTAT | PKS | sxtA |
| SEQ ID NO: 115 | 8742 | 8761 | <-- | CTCGCCGATGAAAGTCCTCT | PKS | sxtA |
| SEQ ID NO: 116 | 8772 | 8791 | <-- | GCGTGTCGAGAAAAAGGTGT | PKS | sxtA |
| SEQ ID NO: 117 | 8782 | 8801 | --> | CTCGACACGCAAGAATAACG | PKS | sxtA |
| SEQ ID NO: 143 | 9390 | 9410 | --> | GGTCCTTGCGCAGATAGAGTG | chaperon-like | sxtE |
| SEQ ID NO: 144 | 9390 | 9410 | <-- | CACTCTATCTGCGCAAGGACC | chaperon-like | sxtE |
| SEQ ID NO: 145 | 9856 | 9876 | <-- | TGACTGCATTCGCTGTATAAA | MATE 1 | sxtF |
| SEQ ID NO: 118 | 10080 | 10100 | --> | ATGCTTCTGCTTTGGCATGGC | amidinotransferase | sxtG |
| SEQ ID NO: 119 | 11468 | 11488 | <-- | TAACTCGACGAACTTTGACCC | amidinotransferase | sxtG |

FIGURE 1B (cont)

| Primer | From | To | Direction | Sequence | Gene | |
|---|---|---|---|---|---|---|
| SEQ ID NO: 120 | 11551 | 11569 | --> | GCCGCCAATCCTCGCGATG | amidinotransferase | sxtG |
| SEQ ID NO: 121 | 12256 | 12277 | <-- | GAACGTCTAATGTTGCACAGTG | amidinotransferase | sxtG |
| SEQ ID NO: 122 | 12410 | 12432 | --> | CTGGTACGTAGTCGCAAAGGTGG | dioxygenase I | sxtH |
| SEQ ID NO: 123 | 13292 | 13317 | --> | CTGACGGTACATGTATTTCCTGTGAC | dioxygenase I | sxtH |
| SEQ ID NO: 124 | 13540 | 13561 | --> | cgtctcatATGCAGATCTTAGGAATTTCAG | carbamoyltransferase | sxtI |
| SEQ ID NO: 125 | 13561 | 13585 | --> | GCTTACTACCACGATAGTGCTGCCG | carbamoyltransferase | sxtI |
| SEQ ID NO: 126 | 14451 | 14472 | --> | TCTATGTTTAGCAGGTGGTGTC | carbamoyltransferase | sxtI |
| SEQ ID NO: 127 | 14735 | 14754 | <-- | TTCTGCAAGACGAGCCATAA | carbamoyltransferase | sxtI |
| SEQ ID NO: 128 | 15211 | 15230 | <-- | GGTTCGCCGCGGACATTAAA | carbamoyltransferase | sxtI |
| SEQ ID NO: 146 | 15709 | 15730 | --> | TTCATAAGACGGCTGTTGAATC | hypothetical protein | sxtJ |
| SEQ ID NO: 147 | 15966 | 15989 | <-- | ctcgagTTAAAAAAGAGTGTAAATGAAAGG | hypothetical protein | sxtK |
| SEQ ID NO: 148 | 16326 | 16348 | <-- | TTCTATAACTGCTGCCAAATTTT | GDSL-lipase | sxtL |
| SEQ ID NO: 149 | 16400 | 16422 | --> | AATTTTGGAGTGACTGGTTATGG | GDSL-lipase | sxtL |
| SEQ ID NO: 150 | 16400 | 16422 | <-- | CCATAACCAGTCACTCCAAAATT | GDSL-lipase | sxtL |
| SEQ ID NO: 151 | 16929 | 16949 | --> | TTTTAGTTGTTACTTTTGGCG | GDSL-lipase | sxtL |
| SEQ ID NO: 152 | 17215 | 17234 | --> | ACAGCAGATGAGAGAAAGTA | GDSL-lipase | sxtL |
| SEQ ID NO: 153 | 18054 | 18073 | --> | GGGTTGTCTTGCTGATTTTC | MATE II | sxtM |
| SEQ ID NO: 154 | 18721 | 18742 | <-- | CATTAAAATAAGTCCGGACAGG | MATE II | sxtM |
| SEQ ID NO: 155 | 19133 | 19152 | <-- | TTAAACAGAATGAGGAGCAA | MATE II | sxtM |
| SEQ ID NO: 156 | 19260 | 19279 | <-- | AAACAACACACCCATCTAAG | sulfotransferase | sxtN |
| SEQ ID NO: 157 | 19531 | 19550 | --> | TTAATAAGGCATCCCCAAGA | sulfotransferase | sxtN |
| SEQ ID NO: 158 | 19728 | 19747 | <-- | GAAATGGCTGTGTAAAAACT | sulfotransferase | sxtN |
| SEQ ID NO: 129 | 20584 | 20603 | <-- | ATGCTAATGCGGTGGGAGTA | cephalosporin hydroxylase | sxtX |
| SEQ ID NO: 130 | 20643 | 20662 | --> | AAAGCAGTTCCGACGACATT | cephalosporin hydroxylase | sxtX |
| SEQ ID NO: 131 | 20831 | 20853 | --> | CCTATTTCGATTATTGTTTTCGG | cephalosporin hydroxylase | sxtX |
| SEQ ID NO: 132 | 21252 | 21271 | <-- | GATACCGATCATAAACTACG | cephalosporin hydroxylase | sxtX |
| SEQ ID NO: 159 | 21290 | 21309 | --> | TCTGCCATATCCCCAACCTA | ferredoxin | sxtW |
| SEQ ID NO: 160 | 21445 | 21464 | <-- | GATCGCCCGACAGGAAGACT | ferredoxin | sxtW |
| SEQ ID NO: 161 | 22020 | 22039 | --> | TCCGGCTTGACCTGCTGGAC | succinate dehydrogenase | sxtV |

FIGURE 1B (cont)

| Primer | From | To | Direction | Sequence | Gene | |
|---|---|---|---|---|---|---|
| SEQ ID NO: 162 | 22715 | 22734 | --> | TGCGATGATTTTGCCTCTGT | succinate dehydrogenase | sxtV |
| SEQ ID NO: 163 | 22801 | 22820 | --> | AAAATTTGCACACCCACACG | succinate dehydrogenase | sxtV |
| SEQ ID NO: 164 | 22942 | 22968 | --> | TTGGATTGAACGTGTAATTGAAAAAGC | succinate dehydrogenase | sxtV |
| SEQ ID NO: 186 | 22942 | 22968 | <-- | GCTTTTTCAATTACACGTTCAATCCAA | succinate dehydrogenase | sxtV |
| SEQ ID NO: 165 | 23434 | 23453 | <-- | GTTTAGTCGATACGCCATTT | succinate dehydrogenase | sxtV |
| SEQ ID NO: 166 | 23434 | 23453 | --> | AAATGGCGTATCGACTAAC | succinate dehydrogenase | sxtV |
| SEQ ID NO: 167 | 24095 | 24115 | --> | ATATAGGAGCGCATAAAGTGC | succinate dehydrogenase | sxtV |
| SEQ ID NO: 168 | 24728 | 24747 | --> | CTTGGTATAAGTCTTGTGAT | dioxygenase II | sxtT |
| SEQ ID NO: 169 | 25426 | 25445 | <-- | AACACTCATTAGATTCATCT | phytanoyl-CoA dioxygenase | sxtS |
| SEQ ID NO: 170 | 25979 | 25999 | <-- | TCCACTAAATCCTTTGAATTG | phytanoyl-CoA dioxygenase | sxtS |
| SEQ ID NO: 171 | 26279 | 26299 | --> | TGTTTGTCTGGATGCGATCCT | unknown protein | orf24 |
| SEQ ID NO: 172 | 26451 | 26470 | --> | GCAGTTCAGGTCCATGAAAC | unknown protein | orf25 |
| SEQ ID NO: 173 | 27155 | 27174 | --> | AGCCCAGTCACAACCTTCGT | GNAT transferase | sxtR |
| SEQ ID NO: 174 | 27508 | 27528 | --> | TCTGGAAGTACTTGCACTGTC | unknown protein | sxtQ |
| SEQ ID NO: 175 | 28197 | 28218 | --> | TGTAACTCCGTCAGGACATAAA | unknown protein | sxtQ |
| SEQ ID NO: 176 | 28395 | 28417 | <-- | TGCAAATTTTAGTAGCAATAACG | RTX-toxin like | sxtP |
| SEQ ID NO: 177 | 29532 | 29558 | <-- | CTTTACTAATTATAGCGGGGATATTAT | RTX-toxin like | sxtP |
| SEQ ID NO: 178 | 29868 | 29887 | <-- | CAGTGGGGAAATAGATGGAT | adenylylsulphate kinase | sxtO |
| SEQ ID NO: 179 | 30249 | 30268 | <-- | TGGTCATAAAAGCGGGATTC | adenylylsulphate kinase | sxtO |
| SEQ ID NO: 180 | 31745 | 31762 | --> | GGATCTTGGCGCAATTTA | IS4 | orf29 |
| SEQ ID NO: 181 | 33031 | 33053 | <-- | GTTAGAGACTTGGAACGTATTGG | PhoU | sxtY |
| SEQ ID NO: 182 | 34711 | 34729 | --> | CCAAACCCAGAAGAAATCC | histidine kinase | sxtZ |
| SEQ ID NO: 183 | 35100 | 35121 | --> | AATCTATAGCCAAAACCCCTAA | ribotide isomerase | |
| SEQ ID NO: 184 | 36447 | 36465 | --> | ACTGTGTGAACAATTCCCC | ribotide isomerase | |
| SEQ ID NO: 185 | 36652 | 36680 | --> | GCAACAAGACTACATTTAGTAGATTTAGA | ribotide isomerase | |

FIGURE 2

| Name | Enzyme Family | Size (bp) | Blast Similarity Match | (%) | Putative Function |
|---|---|---|---|---|---|
| *orf1* | unknown protein | 1320 | BAB76734.1 *Nostoc* PCC7120 | 82 | unknown |
| *sxtD* | sterole desaturase-like | 759 | ABG52264.1 *Trichodesmium erythraeum* | 63 | desaturation |
| *orf3* | transposase InsB | 392 | CAE11915.2 *Microcystis aeruginosa* | 86 | transposition |
| *orf4* | transposase InsA | 360 | CAE11914.1 *Microcystis aeruginosa* | 71 | transposition |
| *sxtC* | unknown protein | 354 | no similarity found | | regulatory |
| *sxtB* | cytidine deaminase | 957 | EAS64681.1 *Vibrio angustum* | 62 | cyclisation |
| *sxtA* | methyltransferase | 1506 | ABF89568.1 *Myxococcus xanthus* | 64 | methylation |
| | GNAT | 633 | AAT70096.1 CurA *Lyngbya majuscula* | 64 | loading of ACP |
| | acyl carrier protein | 324 | AAV97870 OnnB *Theonella swinhoei* | 59 | ACP |
| | AONS | 1275 | ABD13093.1 *Frankia* sp. CcI3 | 61 | Claisen condensation |
| *sxtE* | unknown protein | 387 | ABE53436.1 *Shewanella denitrificans* | 52 | unknown |
| *sxtF* | MATE | 1416 | NorM ABC44739.1 *Salinibacter ruber* | 52 | export of PSTs |
| *sxtG* | amidinotransferase | 1134 | ABA05575.1 *Nitrobacter winogradskyi* | 71 | amidinotransfer |
| *sxtH* | phenylpropionate dioxygenase | 1005 | ZP_00243439.1 *Rubrivivax gelatinosus* | 50 | C-12 hydroxylation |
| *sxtI* | carbamoyltransferase | 1839 | ABG50968.1 *Trichodesmium erythraeum* | 82 | carbamoylation |

FIGURE 2 (cont)

| | | | | | |
|---|---|---|---|---|---|
| *sxtJ* | unknown protein | 444 | EAM51043.1 *Crocosphaera watsonii* | 72 | regulatory |
| *sxtK* | unknown protein | 165 | ABG50954.1 *Trichodesmium erythraeum* | 81 | regulatory |
| *sxtL* | GDSL-lipase | 1299 | ABG50952.1 *Trichodesmium erythraeum* | 60 | cyclisation |
| *sxtM* | MATE | 1449 | NorM ABC44739.1 *Salinibacter ruber* | 53 | export of PSTs |
| *sxtN* | sulfotransferase | 831 | ABG53102.1 *Trichodesmium erythraeum* | 57 | sulfotransfer |
| *sxtX* | cephalosporin hydroxylase | 774 | ABG50679.1 *Trichodesmium erythraeum* | 77 | N-1 hydroxylation |
| *sxtW* | ferredoxin | 327 | ZP_00106179.2 *Nostoc punctiforme* | 99 | electron carrier |
| *sxtV* | succinate dehydrogenase | 1653 | ABA24604.1 *Anabaena variabilis* | 92 | dioxygenase reductase |
| *sxtU* | alcohol dehydrogenase | 750 | ZP_00111652.1 *Nostoc punctiforme* | 83 | reduction of C-1 |
| *sxtT* | phenylpropionate dioxygenase | 1005 | ZP_00243439.1 *Rubrivivax gelatinosus* | 48 | C-12 hydroxylation |
| *sxtS* | phytanoyl-CoA dioxygenase | 726 | ABG30370.1 *Roseobacter denitrificans* | 41 | ring formation |
| *orf24* | unknown protein | 576 | no similarity found | | unknown |
| *sxtR* | acyl transferase | 777 | AAU26161.1 *Legionella pneumophila* | 54 | unknown |
| *sxtQ* | unknown protein | 777 | EAR64935.1 *Bacillus* sp. NRRL B-14911 | 46 | unknown |
| *sxtP* | RTX-toxin | 1227 | ABA20206.1 *Anabaena variabilis* | 68 | binding of PSTs |
| *sxtO* | adenylylsulfate kinase | 603 | ZP_00053494.2 *Magnetospirillum magnetotacticum* | 76 | PAPS biosynthesis |
| *orf29* | transposase, IS4 | 1350 | EAO22567.1 *Syntrophobacter fumaroxidans* | 61 | transposition |
| *sxtY* | PhoU | 666 | BAB76200.1 *Nostoc* PCC7120 | 87 | signal transduction |
| *sxtZ* | histidine kinase | 1353 | ABA22975.1 *Anabaena variabilis* | 78 | signal transduction |
| *ompR* | OmpR | 819 | ZP_00108178.2 *Nostoc punctiforme* | 91 | signal transduction |
| *hisA* | PROFAR isomerase | 774 | ABA22979.1 *Anabaena variabilis* | 90 | histidine biosynthesis |
| *orf34* | unknown protein | 396 | ZP_00345366.1 *Nostoc punctiforme* | 84 | unknown |

FIGURE 6

| Name | Enzyme Family | Size (bp) | Psi-Blast similarity match | % ID | Putative function |
|---|---|---|---|---|---|
| *cyrD* | PKS CrpB | 5631 | ABM21570.1 *Nostoc sp.* ATCC 53789 | 58 | PKS KS-AT-DH-KR-ACP |
| *cyrF* | PKS CrpB | 4074 | ABM21570.1 *Nostoc sp.* ATCC 53789 | 68 | PKS KS-AT-ACP |
| *cyrG* | cytosine deaminase /Aminohydrolase/ Dihydroorotase | 1437 | BAF59909.1 *Pelotomaculum thermopropionicum* SI | 50 | Uracil ring formation |
| *cyrI* | Prolyl 4-Hydroxylase | 831 | ABB06365.1 *Burkholderia* sp. 383 | 43 | Hydroxylation of C7 |
| *cyrK* | MatE Na+-driven multidrug efflux pump | 1398 | EAW39051.1 *Lyngbya* sp. PCC 8106 | 65 | Exporter |
| *cyrL* | Transposase | 750 | ABG50981.1 *Trichodesmium erythraeum* IMS101 | 70 | Transposase |
| *cyrH* | cytosine deaminase /Aminohydrolase/ Dihydroorotase | 1431 | BAF59909.1 *Pelotomaculum thermopropionicum* SI | 50 | Uracil ring formation |
| *cyrJ* | branched-chain amino acid aminotransferase | 780 | *Trichodesmium erythraeum* IMS101 | 53 | sulfotransferase |
| *cyrA* | Amidinotransferase AoaA | 1176 | AAX81898.1 *Cylindrospermopsis raciborskii* | 100 | amidinotransferase |
| *cyrB* | NRPS/PKS AoaB | 8754 | AAM33468.1 *Aphanizomenon ovalisporum* | 97 | NRPS/PKS A-domain, pp, KS, AT, DH, Met, KR, ACP |
| *cyrE* | PKS | 5667 | ABA23591.1 *Anabaena variabilis* ATCC 29413 | 62 | PKS KS-AT-DH-KR-ACP |
| *cyrC* | PKS AoaC | 5005 | AAM33470.1 *Aphanizomenon ovalisporum* | 97 | PKS KS-AT-KR-ACP |
| *cyrM* | Partial Transposase | 318 | ABG50981.1 *Trichodesmium erythraeum* IMS101 | 70 | Transposase |
| *cyrN* | Adenylylsulfate kinase (PAPS) | 600 | CAM76460.1 *Magnetospirillum gryphiswaldense* MSR-1 | 75 | Adenylylsulfate kinase (PAPS) |
| *cyrO* | hypothetical protein | 1548 | EAW46978.1 *Nodularia spumigena* CCY9414 | 74 | Regulator |

FIGURE 7

| Cyanobacterial Strain | 16s rRNA | *cyrJ* | Toxicity | Reference |
|---|---|---|---|---|
| *Cylindrospermopsis raciborskii* T3 | + | - | SXT | Lagos et al. (1999) |
| *Anabaena circinalis* 344B | + | - | N.D. | AWQC |
| *Cylindrospermopsis raciborskii* Germ1 | + | - | N.D. | Neilan et al. (2003) |
| *Anabaena circinalis* 310F | + | - | N.D. | AWQC |
| *Cylindrospermopsis raciborskii* 44D | + | - | N.D. | NA |
| *Anabaena circinalis* 118C | + | - | SXT | Fergusson et al. (2000) |
| *Anabaena circinalis* 323A | + | - | N.D. | AWQC |
| *Anabaena circinalis* 323H | + | - | N.D. | AWQC |
| *Cylindrospermopsis raciborskii* VOLL2 | + | - | N.D. | Neilan et al. (2003) |
| *Cylindrospermopsis raciborskii* VOLL1 | + | - | N.D. | Neilan et al. (2003) |
| *Cylindrospermopsis raciborskii* HUNG1 | + | - | N.D. | NA |
| *Cylindrospermopsis raciborskii* 023B | + | + | CYLN | Wilson et al. (2000) |
| *Cylindrospermopsis raciborskii* 05E | + | + | CYLN | Schembri et al. (2001) |
| *Cylindrospermopsis raciborskii* 4799 | + | + | CYLN | Neilan et al. (2003) |
| *Cylindrospermopsis raciborskii* 24C | + | + | CYLN | Schembri et al. (2001) |
| *Cylindrospermopsis raciborskii* AWT 205 | + | + | CYLN | Hawkins et al. (1997) |
| *Aphanizomenon ovalisporum* AO/QH | + | + | CYLN | NA |

CYANOBACTERIA SAXITOXIN GENE CLUSTER AND DETECTION OF CYANOTOXIC ORGANISMS

RELATED APPLICATIONS

This application is a continuation of U.S. National Stage application Ser. No. 12/989,394, filed on Feb. 7, 2011, which is a National Stage Application under 35 U.S.C. § 371 of International Application No. PCT/AU2008/001805 filed on Dec. 5, 2008, which claims the benefit of priority to Australian Patent Application No. 2008902056 filed on Apr. 24, 2008, the disclosures of each of which are incorporated herein by reference in their entirety.

TECHNICAL FIELD

The present invention relates to methods for the detection of cyanobacteria, dinofiagellates, and in particular, methods for the detection of cyanotoxic organisms. Kits for the detection of cyanobacteria, dinofiagellates, and cyanotoxic organisms are provided. The invention further relates to methods of screening for compounds that modulate the activity of polynucleotides and/or polypeptides of the saxitoxin and cylindrospermopsin biosynthetic pathways.

BACKGROUND

Cyanobacteria, also known as blue-green algae, are photosynthetic bacteria widespread in marine and freshwater environments. Of particular significance for water quality and human and animal health are those cyanobacteria which produce toxic compounds. Under eutrophic conditions cyanobacteria tend to form large blooms which drastically promote elevated toxin concentrations. Cyanobacterial blooms may flourish and expand in coastal waters, streams, lakes, and in drinking water and recreational reservoirs. The toxins they produce can pose a serious health risk for humans and animals and this problem is internationally relevant since most toxic cyanobacteria have a global distribution.

A diverse range of cyanobacterial genera are well known for the formation of toxic blue-green algal blooms on water surfaces. Saxitoxin (SXT) and its analogues cause the paralytic shellfish poisoning (PSP) syndrome, which afflicts human health and impacts on coastal shellfish economies worldwide. PSP toxins are unique alkaloids, being produced by both prokaryotes and eukaryotes. PSP toxins are among the most potent and pervasive algal toxins and are considered a serious toxicological health-risk that may affect humans, animals and ecosystems worldwide. These toxins block voltage-gated sodium and calcium channels, and prolong the gating of potassium channels preventing the transduction of neuronal signals. It has been estimated that more than 2000 human cases of PSP occur globally every year. Moreover, coastal blooms of producing microorganisms result in millions of dollars of economic damage due to PSP toxin contamination of seafood and the continuous requirement for costly biotoxin monitoring programs. Early warning systems to anticipate paralytic shellfish toxin (PST)-producing algal blooms, such as PCR and ELISA-based screening, are as yet unavailable due to the lack of data on the genetic basis of PST production.

SXT is a tricyclic perhydropurine alkaloid which can be substituted at various positions leading to more than 30 naturally occurring SXT analogues. Although SXT biosynthesis seems complex and unique, organisms from two kingdoms, including certain species of marine dinoflagellates and freshwater cyanobacteria, are capable of producing these toxins, apparently by the same biosynthetic route. In spite of considerable efforts none of the enzymes or genes involved in the biosynthesis and modification of SXT have been previously identified.

The occurrence of the cyanobacterial genus *Cylindrospermopsis* has been documented on all continents and therefore poses a significant public health threat on a global scale. The major toxin produced by *Cylindrospermopsis* is cylindrospermopsin (CYR). Besides posing a threat to human health, cylindrospermopsin also causes significant economic losses for farmers due to the poisoning of livestock with cylindrospermopsin-contaminated drinking water. Cylindrospermopsin has hepatotoxic, general cytotoxic and neurotoxic effects and is a potential carcinogen. Its toxicity is due to the inhibition of glutathione and protein synthesis as well as inhibiting cytochrome P450. Six cyanobacterial species have so far been identified to produce cylindrospermopsin; *Cylindrospermopsis raciborskii, Aphanizomenon ovalisporum, Aphanizomenon flos-aquae, Umezakia natans, Rhaphdiopsis curvata* and *Anabaena bergii*. Incidents of human poisoning with cylindrospermopsin have only been reported in sub-tropical Australia to date, however *C. raciborskii* and *A. flos-aquae* have recently been detected in areas with more temperate climates. The tendency of *C. raciborskii* to form dense blooms and the invasiveness of the producer organisms gives rise to global concerns for drinking water quality and necessitates the monitoring of drinking water reserves for the presence of cylindrospermopsin producers.

There is a need for rapid and accurate methods detecting cyanobacteria, and in particular those strains which are capable of producing cyanotoxins such as saxitoxin and cylindrospermopsin. Rapid and accurate methods for detecting cyanotoxic organisms are needed for assessing the potential health hazard of cyanobacterial blooms and for the implementation of effective water management strategies to minimize the effects of toxic bloom outbreaks.

SUMMARY

In a first aspect, there is provided an isolated polynucleotide comprising a sequence according to SEQ ID NO: 1 or a variant or fragment thereof.

In one embodiment of the first aspect, the fragment comprises a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof.

In a second aspect, there is provided an isolated ribonucleic acid or an isolated complementary DNA encoded by a sequence according to the first aspect.

In a third aspect, there is provided an isolated polypeptide comprising an amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and variants and fragments thereof.

In one embodiment, there is provided a probe or primer that hybridises specifically with one or more of: a polynucleotide according to the first aspect, a ribonucleic acid or complementary DNA according to the second aspect, or a polypeptide according the third aspect.

In another embodiment, there is provided a vector comprising a polynucleotide according to the first aspect, or a ribonucleic acid or complementary DNA according the second aspect. The vector may be an expression vector.

In another embodiment, a host cell is provided comprising the vector.

In another embodiment, there is provided an isolated antibody capable of binding specifically to a polypeptide according to the third aspect.

In a fourth aspect, there is provided a method for the detection of cyanobacteria, the method comprising the steps of obtaining a sample for use in the method and analyzing the sample for the presence of one or more of:

(i) a polynucleotide comprising a sequence according to the first aspect (ii) a ribonucleic acid or complementary DNA according to the second aspect (iii) a polypeptide comprising a sequence according to third aspect wherein said presence is indicative of cyanobacteria in the sample.

In a fifth aspect, there is provided a method for detecting a cyanotoxic organism, the method comprising the steps of obtaining a sample for use in the method and analyzing the sample for the presence of one or more of:

(i) a polynucleotide comprising a sequence selected from the group consisting of: SEQ ID NO: 14, SEQ ID NO: 20, SEQ ID NO: 22, SEQ ID NO: 24, SEQ ID NO: 36, and variants and fragments thereof (ii) a ribonucleic acid or complementary DNA encoded by a sequence according to (i)

(iii) a polypeptide comprising a sequence selected from the group consisting of: SEQ ID NO: 15, SEQ ID NO: 21, SEQ ID NO: 23, SEQ ID NO: 25, SEQ ID NO: 37, and variants and fragments thereof, wherein said presence is indicative of cyanotoxic organisms in the sample.

In one embodiment of the fifth aspect, the cyanotoxic organism is a cyanobacteria or a dinoflagellate.

In one embodiment of the fourth and fifth aspects, analyzing the sample comprises amplification of DNA from the sample by polymerase chain reaction and detecting the amplified sequences. The polymerase chain reaction may utilise one or more primers comprising a sequence selected from the group consisting of SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, and variants and fragments thereof.

In another embodiment of the fourth and fifth aspects, the method comprises further analyzing the sample for the presence of one or more of:

(i) a polynucleotide comprising a sequence selected from the group consisting of: SEQ ID NO: 80, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and variants and fragments thereof, (ii) a ribonucleic acid or complementary DNA encoded by a sequence according to (i), (iii) a polypeptide comprising a sequence selected from the group consisting of: SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and SEQ ID NO: 110, and variants and fragments thereof.

The further analysis of the sample may comprise amplification of DNA from the sample by polymerase chain reaction. The polymerase chain reaction may utilise one or more primers comprising a sequence selected from the group consisting of SEQ ID NO: 111, SEQ ID NO: 112, or variants or fragments thereof.

In a sixth aspect, there is provided a method for the detection of dinoflagellates, the method comprising the steps of obtaining a sample for use in the method and analyzing the sample for the presence of one or more of:

(i) a polynucleotide comprising a sequence according to the first aspect, (ii) a ribonucleic acid or complementary DNA according to the second aspect, (iii) a polypeptide comprising a sequence according to the third aspect, wherein said presence is indicative of dinoflagellates in the sample.

In one embodiment of the sixth aspect, analysing the sample comprises amplification of DNA from the sample by polymerase chain reaction and detecting the amplified sequences.

In one embodiment of the fourth, fifth, and sixth aspects, the detection comprises one or both of gel electrophoresis and nucleic acid sequencing. The sample may comprise one or more isolated or cultured organisms. The sample may be an environmental sample. The environmental sample may be derived from salt water, fresh water or a blue-green algal bloom.

In a seventh aspect, there is provided a kit for the detection of cyanobacteria, the kit comprising at least one agent for detecting the presence of one or more of:

(i) a polynucleotide comprising a sequence according to the first aspect, (ii) a ribonucleic acid or complementary DNA according to the second aspect, (iii) a polypeptide comprising a sequence according to the third aspect, wherein said presence is indicative of cyanobacteria in the sample.

In an eighth aspect, there is provided a kit for the detection of cyanotoxic organisms, the kit comprising at least one agent for detecting the presence of one or more of:

(i) a polynucleotide comprising a sequence selected from the group consisting of: SEQ ID NO: 14, SEQ ID NO: 20, SEQ ID NO: 22, SEQ ID NO: 24, SEQ ID NO: 36, and variants and fragments thereof, (ii) a ribonucleic acid or complementary DNA encoded by a sequence according to (i), (iii) a polypeptide comprising a sequence selected from the group consisting of: SEQ ID NO: 15, SEQ ID NO: 21, SEQ ID NO: 23, SEQ ID NO: 25, SEQ ID NO: 37, and variants and fragments thereof, wherein said presence is indicative of cyanotoxic organisms in the sample.

In one embodiment of the seventh and eighth aspects, the at least one agent is a primer, antibody or probe. The primer or probe may comprise a sequence selected from the group consisting of SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, and variants and fragments thereof.

In another embodiment of the seventh and eighth aspects, the kit further comprises at least one additional agent for detecting the presence of one or more of:

(i) a polynucleotide comprising a sequence selected from the group consisting of: SEQ ID NO: 80, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and variants and fragments thereof, (ii) a ribonucleic acid or complementary DNA encoded by a sequence according to (i), (iii) a polypeptide comprising a sequence selected from the group consisting of: SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and SEQ ID NO: 110, and variants and fragments thereof.

The at least one additional agent may be a primer, antibody or probe. The primer or probe may comprise a sequence selected from the group consisting of SEQ ID NO: 109, SEQ ID NO: 110, and variants and fragments thereof.

In a ninth aspect, there is provided a kit for the detection of dinoflagellates, the kit comprising at least one agent for detecting the presence of one or more of:

(i) a polynucleotide comprising a sequence according to the first aspect, (ii) a ribonucleic acid or complementary DNA according to the second aspect, (iii) a polypeptide comprising a sequence according to the third aspect, wherein said presence is indicative of dinoflagellates in the sample.

In a tenth aspect, there is provided a method of screening for a compound that modulates the expression or activity of one or more polypeptides according to the third aspect, the method comprising contacting the polypeptide with a candidate compound under conditions suitable to enable interaction of the candidate compound and the polypeptide, and assaying for activity of the polypeptide.

In one embodiment of the tenth aspect, modulating the expression or activity of one or more polypeptides comprises inhibiting the expression or activity of said polypeptide.

In another embodiment of the tenth aspect, modulating the expression or activity of one or more polypeptides comprises enhancing the expression or activity of said polypeptide.

In an eleventh aspect, there is provided an isolated polynucleotide comprising a sequence according to SEQ ID NO: 80 or a variant or fragment thereof.

In one embodiment of the eleventh aspect, the fragment comprises a sequence selected from the group consisting of SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and variants and fragments thereof.

In a twelfth aspect, there is provided a ribonucleic acid or complementary DNA encoded by a sequence according to the eleventh aspect.

In a thirteenth aspect, there is provided an isolated polypeptide comprising an amino acid sequence selected from the group consisting of SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, and variants and fragments thereof.

In one embodiment, there is provided a probe or primer that hybridises specifically with one or more of: a polynucleotide according to the eleventh aspect, a ribonucleic acid or complementary DNA according to the twelfth aspect, or a polypeptide according to the thirteenth aspect.

In another embodiment, there is provided a vector comprising a polynucleotide according to the eleventh aspect, or a ribonucleic acid or complementary DNA according to the twelfth aspect. The vector may be an expression vector. In one embodiment, a host cell is provided comprising the vector.

In another embodiment, there is provided an isolated antibody capable of binding specifically to a polypeptide according to the thirteenth aspect.

In a fourteenth aspect, there is provided a method for the detection of cyanobacteria, the method comprising the steps of obtaining a sample for use in the method and analyzing the sample for the presence of one or more of:

(i) a polynucleotide comprising a sequence according to the eleventh aspect, (ii) a ribonucleic acid or complementary DNA according to the twelfth aspect, (iii) a polypeptide comprising a sequence according to thirteenth aspect, wherein said presence is indicative of cyanobacteria in the sample.

In a fifteenth aspect, there is provided a method for detecting a cyanotoxic organism, the method comprising the steps of obtaining a sample for use in the method and analyzing the sample for the presence of one or both of:

(i) a polynucleotide comprising a sequence according to SEQ ID NO: 95 or a variant or fragment thereof, (ii) a ribonucleic acid or complementary DNA encoded by a sequence according to (i), (iii) a polypeptide comprising a sequence according to SEQ ID NO: 96, or a variant or fragment thereof, wherein said presence is indicative of a cyanotoxic organism in the sample.

In one embodiment of the fifteenth aspect, the cyanotoxic organism is a cyanobacteria.

In one embodiment of the fourteenth and fifteenth aspects, analyzing the sample comprises amplification of DNA from the sample by polymerase chain reaction and detecting the amplified sequences. The polymerase chain reaction may utilise one or more primers comprising a sequence selected from the group consisting of SEQ ID NO: 111, SEQ ID NO: 112 and variants and fragments thereof.

In another embodiment of the fourteenth and fifteenth aspects, the method comprises analyzing the sample for the presence of one or more of:

(i) a polynucleotide comprising a sequence selected from the group consisting of: SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof, (ii) a ribonucleic acid or complementary DNA encoded by a sequence according to (i), (iii) a polypeptide comprising a sequence selected from the group consisting of: SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19 SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and variants and fragments thereof.

The further analysis of the sample may comprise amplification of DNA from the sample by polymerase chain reaction. The polymerase chain reaction may utilise one or more primers comprising a sequence selected from the group consisting of SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, and variants and fragments thereof.

In a sixteenth aspect, there is provided a method for detecting a cylindrospermopsin-producing organism, the method comprising the steps of obtaining a sample for use in the method and analyzing the sample for the presence of one or both of:

(i) a polynucleotide comprising a sequence according to SEQ ID NO: 95 or a variant or fragments thereof, (ii) a ribonucleic acid or complementary DNA encoded by a sequence according to (i), (iii) a polypeptide comprising a sequence according to SEQ ID NO: 96, or a variant or fragments thereof, wherein said presence is indicative of a cylindrospermopsin-producing organism in the sample.

In one embodiment of the sixteenth aspect, the cyanotoxic organism is a cyanobacteria. In another embodiment of the sixteenth aspect, analyzing the sample comprises amplification of DNA from the sample by polymerase chain reaction and detecting the amplified sequences. The polymerase chain reaction may utilise one or more primers comprising a sequence selected from the group consisting of SEQ ID NO: 111, SEQ ID NO: 112 and variants and fragments thereof.

In one embodiment of the fourteenth, fifteenth, and sixteenth aspects, the detection comprises one or both of gel electrophoresis and nucleic acid sequencing. The sample may comprise one or more isolated or cultured organisms. The sample may be an environmental sample. The environmental sample may be derived from salt water, fresh water or a blue-green algal bloom.

In a seventeenth aspect, there is provided a kit for the detection of cyanobacteria, the kit comprising at least one agent for detecting the presence of one or more of:

(i) a polynucleotide comprising a sequence according to the eleventh aspect, (ii) a ribonucleic acid or complementary DNA according to the twelfth aspect, (iii) a polypeptide comprising a sequence according to the thirteenth aspect, wherein said presence is indicative of cyanobacteria in the sample.

In an eighteenth aspect, there is provided a kit for the detection of cyanotoxic organisms, the kit comprising at least one agent for detecting the presence of one or more of:

(i) a polynucleotide comprising a sequence according to SEQ ID NO: 95 or a variant or fragment thereof, (ii) a ribonucleic acid or complementary DNA encoded by a sequence according to (i), (iii) a polypeptide comprising a sequence according to SEQ ID NO: 96, or a variant or fragment thereof, wherein said presence is indicative of cyanotoxic organisms in the sample.

In one embodiment of the seventeenth and eighteenth aspects, the at least one agent is a primer, antibody or probe. The primer or probe may comprise a sequence selected from the group consisting of SEQ ID NO: 111, SEQ ID NO: 112 and variants and fragments thereof.

In another embodiment of the seventeenth and eighteenth aspects, the kit may further comprise at least one additional agent for detecting the presence of one or more nucleotide sequences selected from the group consisting of:

(i) a polynucleotide comprising a sequence selected from the group consisting of: SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof, (ii) a ribonucleic acid or complementary DNA encoded by a sequence according to (i), (iii) a polypeptide comprising a sequence selected from the group consisting of: SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19 SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and variants and fragments thereof.

The at least one additional agent may be a primer, antibody or probe. The primer or probe may comprise a sequence selected from the group consisting of SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, and variants and fragments thereof.

In a nineteenth aspect, there is provided a kit for the detection of cylindrospermopsin-producing organisms, the kit comprising at least one agent for detecting the presence of one or more of:

(i) a polynucleotide comprising a sequence according to SEQ ID NO: 95 or a variant or fragment thereof, (ii) a ribonucleic acid or complementary DNA encoded by a sequence according to (i), (iii) a polypeptide comprising a sequence according to SEQ ID NO: 96, or a variant or fragment thereof, wherein said presence is indicative of a cylindrospermopsin-producing organism in the sample.

In a twentieth aspect, there is provided a method of screening for a compound that modulates the expression or activity of one or more polypeptides according to the thirteenth aspect, the method comprising contacting the polypeptide with a candidate compound under conditions suitable to enable interaction of the candidate compound and the polypeptide, and assaying for activity of the polypeptide.

In one embodiment of the twentieth aspect, modulating the expression or activity of one or more polypeptides comprises inhibiting the expression or activity of said polypeptide.

In another embodiment of the twentieth aspect, modulating the expression or activity of one or more polypeptides comprises enhancing the expression or activity of said polypeptide.

Definitions

As used in this application, the singular form "a", "an" and "the" include plural references unless the context clearly dictates otherwise. For example, the term "a stem cell" also includes a plurality of stem cells.

As used herein, the term "comprising" means "including." Variations of the word "comprising", such as "comprise" and "comprises," have correspondingly varied meanings. Thus, for example, a polynucleotide "comprising" a sequence encoding a protein may consist exclusively of that sequence or may include one or more additional sequences.

As used herein, the terms "antibody" and "antibodies" include IgG (including IgG1, IgG2, IgG3, and IgG4), IgA (including IgA1 and IgA2), IgD, IgE, or IgM, and IgY, whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin. Antigen-binding antibody fragments, including single-chain antibodies, may comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies may be monoclonal, polyclonal, chimeric, multispecific, humanized, and human monoclonal and polyclonal antibodies which specifically bind the biological molecule.

As used herein, the terms "polypeptide" and "protein" are used interchangeably and are taken to have the same meaning.

As used herein, the terms "nucleotide sequence" and "polynucleotide sequence" are used interchangeably and are taken to have the same meaning.

As used herein, the term "kit" refers to any delivery system for delivering materials. In the context of the detection assays described herein, such delivery systems include systems that allow for the storage, transport, or delivery of reaction reagents (for example labels, reference samples, supporting material, etc. in the appropriate containers) and/or supporting materials (for example, buffers, written instructions for performing the assay etc.) from one location to another. For example, kits include one or more enclosures, such as boxes, containing the relevant reaction reagents and/or supporting materials.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention before the priority date of this application.

For the purposes of description all documents referred to herein are incorporated by reference unless otherwise stated.

BRIEF DESCRIPTION OF THE DRAWINGS

A preferred embodiment of the present invention will now be described, by way of an example only, with reference to the accompanying drawings wherein:

FIG. 1A is a table showing the distribution of the sxt genes in toxic and non-toxic cyanobacteria. PSP, saxitoxin; CYLN, cylindrospermopsin; +, gene fragment amplified; –no gene detected.

FIG. 1B is a table showing primer sequences used to amplify various SXT genes.

FIG. 2 is a table showing sxt genes from the saxitoxin gene cluster of *C. raciborskii* T3, their putative length, their BLAST similarity match with similar protein sequences from other organisms, and their predicted function.

FIG. 5A, arginine (m/z 175); FIG. 5B, saxitoxin (m/z 300); FIG. 5C, intermediate A' (m/z 187); FIG. 5D, intermediate C' (m/z 211); FIG. 5E, intermediate E' (m/z 225).

FIG. 6 is a table showing the cyr genes from the cylindrospermopsin gene cluster of *C. raciborskii* AWT205, their putative length, their BLAST similarity match with similar protein sequences from other organisms, and their predicted function.

FIG. 7 is a table showing the distribution of the sulfotransferase gene (cyrJ) in toxic and non-toxic cyanobacteria. 16S rRNA gene amplification is shown as a positive control. CYLN, cylindrospermopsin; SXT, saxitoxin; N.D., not detected; +, gene fragment amplified; –, no gene detected; NA, not available; AWQC, Australian Water Quality Center.

DESCRIPTION

Figure 3:
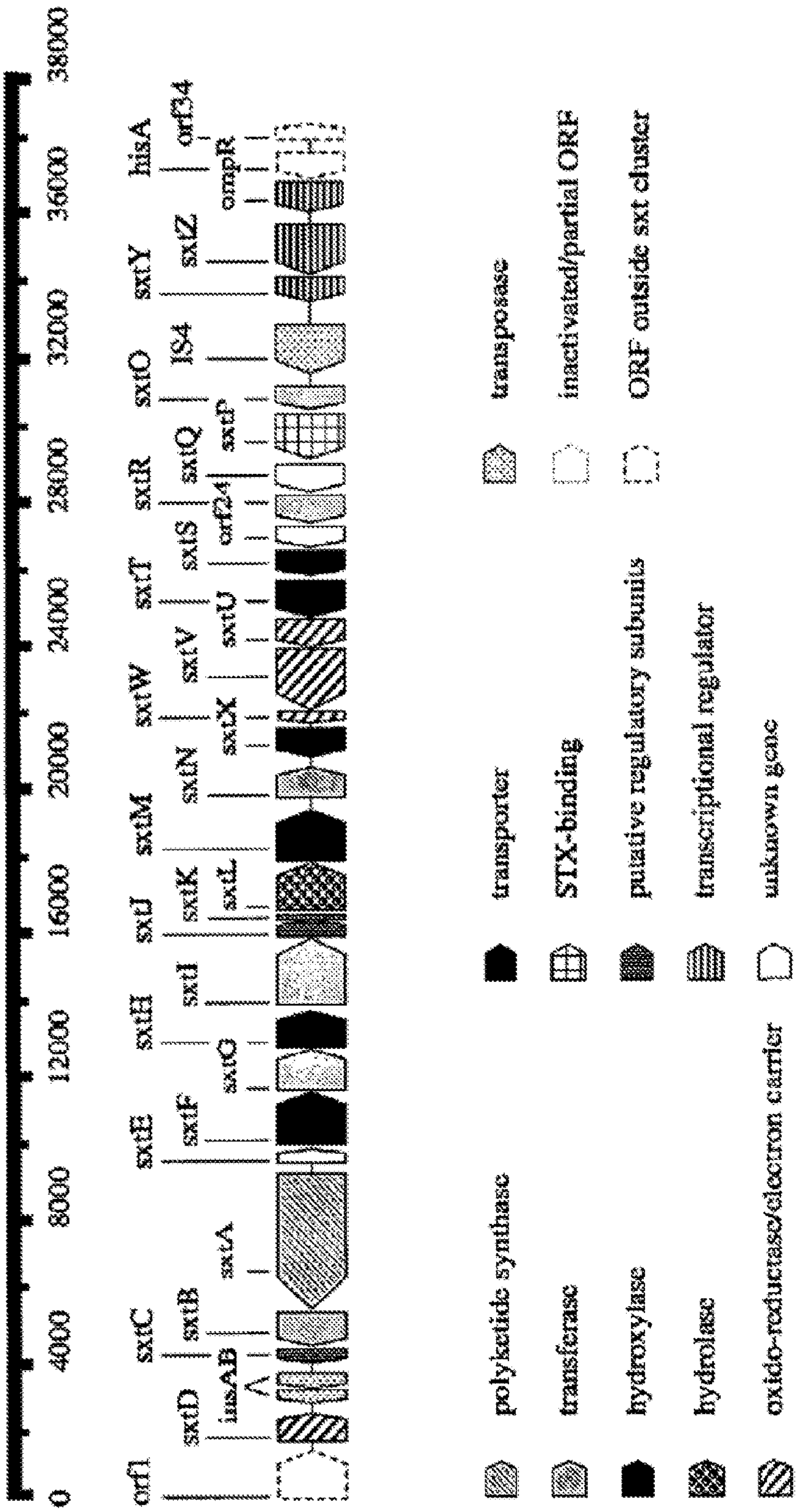
FIG. 3 is a diagram showing the structural organisation of the sxt gene cluster from *C. raciborskii* T3. Abbreviations used are: IS4, insertion sequence 4; at, aminotransferase; dmt, drug metabolite transporter; ompR, transcriptional regulator of ompR family; penP, penicillin binding; smf, gene predicted to be involved in DNA uptake. The scale indicates the gene cluster length in base pairs.

The inventors have identified a gene cluster responsible for saxitoxin biosynthesis (the SXT gene cluster) and a gene cluster responsible for cylindrospermopsin biosynthesis (the CYR gene cluster). The full sequence of each gene cluster has been determined and functional activities assigned to each of the genes identified therein. Based on this information, the inventors have elucidated the full saxitoxin and cylindrospermopsin biosynthetic pathways.

Accordingly, the invention provides polynucleotide and polypeptide sequences derived from each of the SXT and CYR gene clusters and in particular, sequences relating to the specific genes within each pathway. Methods and kits for the detection of cyanobacterial strains in a sample are provided based on the presence (or absence) in the sample of one or more of the sequences of the invention. The inventors have determined that certain open-reading frames present in the SXT gene cluster of saxitoxin-producing microorganisms are absent in the SXT gene cluster of microorganisms that do not produce saxitoxin. Similarly, it has been discovered that one open-reading frame present in the CYR gene cluster of cylindrospermopsin-producing microorganisms is absent in non-cylindrospermopsin-producing microorganisms. Accordingly, the invention provides methods and kits for the detection of toxin-producing microorganisms.

Also provided by the invention are screening methods for the identification of compounds capable of modulating the expression or activity of proteins in the saxitoxin and/or cylindrospermopsin biosynthetic pathways.

Polynucleotides and Polypeptides

The inventors have determined the full polynucleotide sequence of the saxitoxin (SXT) gene cluster and the cylindrospermopsin (CYR) gene cluster.

In accordance with aspects and embodiments of the invention, the SXT gene cluster may have, but is not limited to, the polynucleotide sequence as set forth SEQ ID NO: 1 (GenBank accession number DQ787200), or display sufficient sequence identity thereto to hybridise to the sequence of SEQ ID NO: 1.

The SXT gene cluster comprises 31 genes and 30 intergenic regions.

Gene 1 of the SXT gene cluster is a 759 base pair (bp) nucleotide sequence set forth in SEQ ID NO: 4. The nucleotide sequence of SXT Gene 1 ranges from the nucleotide in position 1625 up to the nucleotide in position 2383 of SEQ ID NO: 1. The polypeptide sequence encoded by Gene 1 (SXTD) is set forth in SEQ ID NO: 5.

Gene 2 of the SXT gene cluster is a 396 bp nucleotide sequence set forth in SEQ ID NO: 6. The nucleotide sequence of SXT Gene 2 ranges from the nucleotide in position 2621 up to the nucleotide in position 3016 of SEQ ID NO: 1. The polypeptide sequence encoded by Gene 2 (ORF3) is set forth in SEQ ID NO: 7.

Gene 3 of the SXT gene cluster is a 360 bp nucleotide sequence set forth in SEQ ID NO: 8. The nucleotide sequence of SXT Gene 3 ranges from the nucleotide in position 2955 up to the nucleotide in position 3314 of SEQ ID NO: 1. The polypeptide sequence encoded by Gene 3 (ORF4) is set forth in SEQ ID NO: 9.

Gene 4 of the SXT gene cluster is a 354 bp nucleotide sequence set forth in SEQ ID NO: 10. The nucleotide sequence of SXT Gene 4 ranges from the nucleotide in position 3647 up to the nucleotide in position 4000 of SEQ ID NO: 1. The polypeptide sequence encoded by Gene 4 (SXTC) is set forth in SEQ ID NO: 11.

Gene 5 of the SXT gene cluster is a 957 bp nucleotide sequence set forth in SEQ ID NO: 12. The nucleotide sequence of SXT Gene 5 ranges from the nucleotide in position 4030 up to the nucleotide in position 4986 of SEQ ID NO: 1. The polypeptide sequence encoded by Gene 5 (SXTB) is set forth in SEQ ID NO: 13.

Gene 6 of the SXT gene cluster is a 3738 bp nucleotide sequence set forth in SEQ ID NO: 14. The nucleotide sequence of SXT Gene 6 ranges from the nucleotide in position 5047 up to the nucleotide in position 8784 of SEQ ID NO: 1. The polypeptide sequence encoded by Gene 6 (SXTA) is set forth in SEQ ID NO: 15.

Gene 7 of the SXT gene cluster is a 387 bp nucleotide sequence set forth in SEQ ID NO: 16. The nucleotide sequence of SXT Gene 7 ranges from the nucleotide in position 9140 up to the nucleotide in position 9526 of SEQ ID NO: 1. The polypeptide sequence encoded by Gene 7 (SXTE) is set forth in SEQ ID NO: 17.

Gene 8 of the SXT gene cluster is a 1416 bp nucleotide sequence set forth in SEQ ID NO: 18. The nucleotide sequence of SXT Gene 8 ranges from the nucleotide in position 9686 up to the nucleotide in position 11101 of SEQ ID NO: 1. The polypeptide sequence encoded by Gene 8 (SXTF) is set forth in SEQ ID NO: 19.

Gene 9 of the SXT gene cluster is an 1134 bp nucleotide sequence set forth in SEQ ID NO: 20. The nucleotide sequence of SXT Gene 9 ranges from the nucleotide in position 11112 up to the nucleotide in position 12245 of SEQ ID NO: 1. The polypeptide sequence encoded by SXT Gene 9 (SXTG) is set forth in SEQ ID NO: 21.

Gene 10 of the SXT gene cluster is a 1005 bp nucleotide sequence set forth in SEQ ID NO: 22. The nucleotide sequence of SXT Gene 10 ranges from the nucleotide in position 12314 up to the nucleotide in position 13318 of SEQ ID NO: 1. The polypeptide sequence encoded by Gene 10 (SXTH) is set forth in SEQ ID NO: 23.

Gene 11 of the SXT gene cluster is an 1839 bp nucleotide sequence set forth in SEQ ID NO: 24. The nucleotide sequence of SXT Gene 11 ranges from the nucleotide in position 13476 up to the nucleotide in position 15314 of SEQ ID NO: 1. The polypeptide sequence encoded by Gene 11 (SXTI) is set forth in SEQ ID NO: 25.

Gene 12 of the SXT gene cluster is a 444 bp nucleotide sequence set forth in SEQ ID NO: 26. The nucleotide sequence of SXT Gene 12 ranges from the nucleotide in position 15318 up to the nucleotide in position 15761 of SEQ ID NO: 1. The polypeptide sequence encoded by Gene 12 (SXTJ) is set forth in SEQ ID NO: 27.

Gene 13 of the SXT gene cluster is a 165 bp nucleotide sequence set forth in SEQ ID NO: 28. The nucleotide sequence of SXT Gene 13 ranges from the nucleotide in position 15761 up to the nucleotide in position 15925 of SEQ ID NO: 1. The polypeptide sequence encoded by Gene 13 (SXTK) is set forth in SEQ ID NO: 29.

Gene 14 of the SXT gene cluster is a 1299 bp nucleotide sequence set forth in SEQ ID NO: 30. The nucleotide sequence of SXT Gene 14 ranges from the nucleotide in position 15937 up to the nucleotide in position 17235 of SEQ ID NO: 1. The polypeptide sequence encoded by Gene 14 (SXTL) is set forth in SEQ ID NO: 31.

Gene 15 of the SXT gene cluster is a 1449 bp nucleotide sequence set forth in SEQ ID NO: 32. The nucleotide sequence of SXT Gene 15 ranges from the nucleotide in position 17323 up to the nucleotide in position 18771 of SEQ ID NO: 1. The polypeptide sequence encoded by Gene 16 (SXTM) is set forth in SEQ ID NO: 33.

Gene 16 of the SXT gene cluster is an 831 bp nucleotide sequence set forth in SEQ ID NO: 34. The nucleotide sequence of SXT Gene 16 ranges from the nucleotide in position 19119 up to the nucleotide in position 19949 of SEQ ID NO: 1. The polypeptide sequence encoded by Gene 16 (SXT1V) is set forth in SEQ ID NO: 35.

Gene 17 of the SXT gene cluster is a 774 bp nucleotide sequence set forth in SEQ ID NO: 36. The nucleotide sequence of SXT Gene 17 ranges from the nucleotide in position 20238 up to the nucleotide in position 21011 of SEQ ID NO: 1. The polypeptide sequence encoded by Gene 17 (SXTX) is set forth in SEQ ID NO: 37.

Gene 18 of the SXT gene cluster is a 327 bp nucleotide sequence set forth in SEQ ID NO: 38. The nucleotide sequence of SXT Gene 18 ranges from the nucleotide in position 21175 up to the nucleotide in position 21501 of SEQ ID NO: 1. The polypeptide sequence encoded by Gene 18 (SXTW) is set forth in SEQ ID NO: 39.

Gene 19 of the SXT gene cluster is a 1653 bp nucleotide sequence set forth in SEQ ID NO: 40. The nucleotide sequence of SXT Gene 219 ranges from the nucleotide in position 21542 up to the nucleotide in position 23194 of SEQ ID NO: 1. The polypeptide sequence encoded by Gene 19 (SXTV) is set forth in SEQ ID NO: 41.

Gene 20 of the SXT gene cluster is a 750 bp nucleotide sequence set forth in SEQ ID NO: 42. The nucleotide sequence of SXT Gene 20 ranges from the nucleotide in position 23199 up to the nucleotide in position 23948 of SEQ ID NO: 1. The polypeptide sequence encoded by Gene 20 (SXTU) is set forth in SEQ ID NO: 43.

Gene 21 of the SXT gene cluster is a 1005 bp nucleotide sequence set forth in SEQ ID NO: 44. The nucleotide sequence of SXT Gene 21 ranges from the nucleotide in position 24091 up to the nucleotide in position 25095 of SEQ ID NO: 1. The polypeptide sequence encoded by Gene 21 (SXTT) is set forth in SEQ ID NO: 45.

Gene 22 of the SXT gene cluster is a 726 bp nucleotide sequence set forth in SEQ ID NO: 46. The nucleotide sequence of SXT Gene 22 ranges from the nucleotide in position 25173 up to the nucleotide in position 25898 of SEQ ID NO: 1. The polypeptide sequence encoded by Gene 22 (SXTS) is set forth in SEQ ID NO: 47.

Gene 23 of the SXT gene cluster is a 576 bp nucleotide sequence set forth in SEQ ID NO: 48. The nucleotide sequence of SXT Gene 23 ranges from the nucleotide in position 25974 up to the nucleotide in position 26549 of SEQ ID NO: 1. The polypeptide sequence encoded by Gene 23 (ORF24) is set forth in SEQ ID NO: 49.

Gene 24 of the SXT gene cluster is a 777 bp nucleotide sequence set forth in SEQ ID NO: 50. The nucleotide sequence of SXT Gene 24 ranges from the nucleotide in position 26605 up to the nucleotide in position 27381 of SEQ ID NO: 1. The polypeptide sequence encoded by Gene 24 (SXTR) is set forth in SEQ ID NO: 51.

Gene 25 of the SXT gene cluster is a 777 bp nucleotide sequence set forth in SEQ ID NO: 52. The nucleotide sequence of SXT Gene 25 ranges from the nucleotide in position 27392 up to the nucleotide in position 28168 of SEQ ID NO: 1. The polypeptide sequence encoded by Gene 25 (SXTQ) is set forth in SEQ ID NO: 53.

Gene 26 of the SXT gene cluster is a 1227 bp nucleotide sequence set forth in SEQ ID NO: 54. The nucleotide sequence of SXT Gene 26 ranges from the nucleotide in position 28281 up to the nucleotide in position 29507 of SEQ ID NO: 1. The polypeptide sequence encoded by Gene 26 (SXTP) is set forth in SEQ ID NO: 55.

Gene 27 of the SXT gene cluster is a 603 bp nucleotide sequence set forth in SEQ ID NO: 56. The nucleotide sequence of SXT Gene 27 ranges from the nucleotide in position 29667 up to the nucleotide in position 30269 of SEQ ID NO: 1. The polypeptide sequence encoded by Gene 27 (SXTO) is set forth in SEQ ID NO: 57.

Gene 28 of the SXT gene cluster is a 1350 bp nucleotide sequence set forth in SEQ ID NO: 58. The nucleotide sequence of SXT Gene 28 ranges from the nucleotide in position 30612 up to the nucleotide in position 31961 of SEQ ID NO: 1. The polypeptide sequence encoded by Gene 28 (ORF29) is set forth in SEQ ID NO: 59.

Gene 29 of the SXT gene cluster is a 666 bp nucleotide sequence set forth in SEQ ID NO: 60. The nucleotide sequence of SXT Gene 29 ranges from the nucleotide in position 32612 up to the nucleotide in position 33277 of SEQ ID NO: 1. The polypeptide sequence encoded by Gene 29 (SXTY) is set forth in SEQ ID NO: 61.

Gene 30 of the SXT gene cluster is a 1353 bp nucleotide sequence set forth in SEQ ID NO: 62. The nucleotide sequence of SXT Gene 30 ranges from the nucleotide in position 33325 up to the nucleotide in position 34677 of SEQ ID NO: 1. The polypeptide sequence encoded by Gene 30 (SXTZ) is set forth in SEQ ID NO: 63.

Gene 31 of the SXT gene cluster is an 819 bp nucleotide sequence set forth in SEQ ID NO: 64. The nucleotide sequence of SXT Gene 31 ranges from the nucleotide in position 35029 up to the nucleotide in position 35847 of SEQ ID NO: 1. The polypeptide sequence encoded by Gene 31 (OMPR) is set forth in SEQ ID NO: 65.

The 5' border region of SXT gene cluster comprises a 1320 bp gene (orfl), the sequence of which is set forth in SEQ ID NO: 2. The nucleotide sequence of orfl ranges from the nucleotide in position 1 up to the nucleotide in position 1320 of SEQ ID NO: 1. The polypeptide sequence encoded by orfl is set forth in SEQ ID NO: 3.

The 3' border region of SXT gene cluster comprises a 774 bp gene (hisA), the sequence of which is set forth in SEQ ID NO: 66. The nucleotide sequence of hisA ranges from the nucleotide in position 35972 up to the nucleotide in position 36745 of SEQ ID NO: 1. The polypeptide sequence encoded by hisA is set forth in SEQ ID NO: 67.

The 3' border region of SXT gene cluster also comprises a 396 bp gene (orfA), the sequence of which is set forth in SEQ ID NO: 68. The nucleotide sequence of orfA ranges from the nucleotide in position 37060 up to the nucleotide in position 37455 of SEQ ID NO: 1. The polypeptide sequence encoded by orfA is set forth in SEQ ID NO: 69.

In accordance with other aspects and embodiments of the invention, the CYR gene cluster may have, but is not limited to, the nucleotide sequence as set forth SEQ ID NO: 80 (GenBank accession number EU140798), or display sufficient sequence identity thereto to hybridise to the sequence of SEQ ID NO: 80.

The CYR gene cluster comprises 15 genes and 14 intergenic regions.

Gene 1 of the CYR gene cluster is a 5631 bp nucleotide sequence set forth in SEQ ID NO: 81. The nucleotide sequence of CYR Gene 1 ranges from the nucleotide in position 444 up to the nucleotide in position 6074 of SEQ ID NO: 80. The polypeptide sequence encoded by Gene 1 (CYRD) is set forth in SEQ ID NO: 82.

Gene 2 of the CYR gene cluster is a 4074 bp nucleotide sequence set forth in SEQ ID NO: 83. The nucleotide sequence of CYR Gene 2 ranges from the nucleotide in position 6130 up to the nucleotide in position 10203 of SEQ ID NO: 80. The polypeptide sequence encoded by Gene 2 (CYRF) is set forth in SEQ ID NO: 84.

Gene 3 of the CYR gene cluster is a 1437 bp nucleotide sequence set forth in SEQ ID NO: 85. The nucleotide sequence of CYR Gene 3 ranges from the nucleotide in position 10251 up to the nucleotide in position 11687 of SEQ ID NO: 80. The polypeptide sequence encoded by Gene 3 (CYRG) is set forth in SEQ ID NO: 86.

Gene 4 of the CYR gene cluster is an 831 bp nucleotide sequence set forth in SEQ ID NO: 87. The nucleotide sequence of CYR Gene 4 ranges from the nucleotide in position 11741 up to the nucleotide in position 12571 of SEQ ID NO: 80. The polypeptide sequence encoded by Gene 4 (CYRI) is set forth in SEQ ID NO: 88.

Gene 5 of the CYR gene cluster is a 1398 bp nucleotide sequence set forth in SEQ ID NO: 89. The nucleotide sequence of CYR Gene 5 ranges from the nucleotide in position 12568 up to the nucleotide in position 13965 of SEQ ID NO: 80. The polypeptide sequence encoded by Gene 5 (CYRK) is set forth in SEQ ID NO: 90.

Gene 6 of the CYR gene cluster is a 750 bp nucleotide sequence set forth in SEQ ID NO: 91. The nucleotide sequence of CYR Gene 6 ranges from the nucleotide in position 14037 up to the nucleotide in position 14786 of SEQ ID NO: 80. The polypeptide sequence encoded by Gene 6 (CYRL) is set forth in SEQ ID NO: 92.

Gene 7 of the CYR gene cluster is a 1431 bp nucleotide sequence set forth in SEQ ID NO: 93. The nucleotide sequence of CYR Gene 7 ranges from the nucleotide in position 14886 up to the nucleotide in position 16316 of SEQ ID NO: 80. The polypeptide sequence encoded by Gene 7 (CYRH) is set forth in SEQ ID NO: 94.

Gene 8 of the CYR gene cluster is a 780 bp nucleotide sequence set forth in SEQ ID NO: 95. The nucleotide sequence of CYR Gene 8 ranges from the nucleotide in position 16893 up to the nucleotide in position 17672 of SEQ ID NO: 80. The polypeptide sequence encoded by Gene 8 (CYRJ) is set forth in SEQ ID NO: 96.

Gene 9 of the CYR gene cluster is an 1176 bp nucleotide sequence set forth in SEQ ID NO: 97. The nucleotide sequence of CYR Gene 9 ranges from the nucleotide in position 18113 up to the nucleotide in position 19288 of SEQ ID NO: 80. The polypeptide sequence encoded by Gene 9 (CYRA) is set forth in SEQ ID NO: 98.

Gene 10 of the CYR gene cluster is an 8754 bp nucleotide sequence set forth in SEQ ID NO: 99. The nucleotide sequence of CYR Gene 10 ranges from the nucleotide in position 19303 up to the nucleotide in position 28056 of SEQ ID NO: 80. The polypeptide sequence encoded by Gene 10 (CYRB) is set forth in SEQ ID NO: 100.

Gene 11 of the CYR gene cluster is a 5667 bp nucleotide sequence set forth in SEQ ID NO: 101. The nucleotide sequence of CYR Gene 11 ranges from the nucleotide in position 28061 up to the nucleotide in position 33727 of SEQ ID NO: 80. The polypeptide sequence encoded by Gene 11 (CYRE) is set forth in SEQ ID NO: 102.

Gene 12 of the CYR gene cluster is a 5004 bp nucleotide sequence set forth in SEQ ID NO: 103. The nucleotide sequence of CYR Gene 12 ranges from the nucleotide in position 34299 up to the nucleotide in position 39302 of SEQ ID NO: 80. The polypeptide sequence encoded by Gene 12 (CYRC) is set forth in SEQ ID NO: 104.

Gene 13 of the CYR gene cluster is a 318 bp nucleotide sequence set forth in SEQ ID NO: 105. The nucleotide sequence of CYR Gene 13 ranges from the nucleotide in position 39366 up to the nucleotide in position 39683 of SEQ ID NO: 80. The polypeptide sequence encoded by Gene 13 (CYRM) is set forth in SEQ ID NO: 106.

Gene 14 of the CYR gene cluster is a 600 bp nucleotide sequence set forth in SEQ ID NO: 107. The nucleotide sequence of CYR Gene 14 ranges from the nucleotide in position 39793 up to the nucleotide in position 40392 of SEQ ID NO: 80. The polypeptide sequence encoded by Gene 14 (CYRN) is set forth in SEQ ID NO: 108.

Gene 15 of the CYR gene cluster is a 1548 bp nucleotide sequence set forth in SEQ ID NO: 109. The nucleotide sequence of CYR Gene 15 ranges from the nucleotide in position 40501 up to the nucleotide in position 42048 of SEQ ID NO: 80. The polypeptide sequence encoded by Gene 15 (CYRO) is set forth in SEQ ID NO: 110.

In general, the nucleic acids and polypeptides of the invention are of an isolated or purified form.

In addition to the SXT and CYR polynucleotides and polypeptide sequences set forth herein, also included within the scope of the present invention are variants and fragments thereof.

SXT and CYR polynucleotides disclosed herein may be deoxyribonucleic acids (DNA), ribonucleic acids (RNA) or complementary deoxyribonucleic acids (cDNA).

RNA may be derived from RNA polymerase-catalyzed transcription of a DNA sequence. The RNA may be a primary transcript derived transcription of a corresponding DNA sequence. RNA may also undergo post-transcriptional processing. For example, a primary RNA transcript may undergo post-transcriptional processing to form a mature RNA. Messenger RNA (mRNA) refers to RNA derived from a corresponding open reading frame that may be translated into protein by the cell. cDNA refers to a double-stranded DNA that is complementary to and derived from mRNA. Sense RNA refers to RNA transcript that includes the mRNA and so can be translated into protein by the cell. Antisense RNA refers to an RNA transcript that is complementary to all or part of a target primary transcript or mRNA and may be used to block the expression of a target gene.

The skilled addresse will recognise that RNA and cDNA sequences encoded by the SXT and CYR DNA sequences disclosed herein may be derived using the genetic code. An RNA sequence may be derived from a given DNA sequence by generating a sequence that is complementary the particular DNA sequence. The complementary sequence may be generated by converting each cytosine ('C') base in the DNA sequence to a guanine ('G') base, each guanine ('G') base in the DNA sequence to a cytosine ('C') base, each thymidine ('T') base in the DNA sequence to an adenine ('A') base, and each adenine ('A') base in the DNA sequence to a uracil ('U') base.

A complementary DNA (cDNA) sequence may be derived from a DNA sequence by deriving an RNA sequence from the DNA sequence as above, then converting the RNA sequence into a cDNA sequence. An RNA sequence can be converted into a Cdna sequence by converting each cytosine ('C') base in the RNA sequence to a guanine ('G') base, each guanine ('G') base in the RNA sequence to a cytosine ('C') base, each uracil ('U') base in the RNA sequence to an adenine ('A') base, and each adeneine ('A') base in the RNA sequence to a thymidine (T') base.

The term "variant" as used herein refers to a substantially similar sequence. In general, two sequences are "substantially similar" if the two sequences have a specified percentage of amino acid residues or nucleotides that are the same (percentage of "sequence identity"), over a specified region, or, when not specified, over the entire sequence. Accordingly, a "variant" of a polynucleotide and polypeptide sequence disclosed herein may share at least 40%, 45%, 50%, 55%, 60%, 65%, 70%, 75%, 80%, 83% 85%, 88%, 90%, 93%, 95%, 96%, 97%, 98% or 99% sequence identity with the reference sequence.

In general, polypeptide sequence variants possess qualitative biological activity in common. Polynucleotide sequence variants generally encode polypeptides which generally possess qualitative biological activity in common. Also included within the meaning of the term "variant" are homologues of polynucleotides and polypeptides of the invention. A polynucleotide homologue is typically from a different bacterial species but sharing substantially the same biological function or activity as the corresponding polynucleotide disclosed herein. A polypeptide homologue is typically from a different bacterial species but sharing substantially the same biological function or activity as the corresponding polypeptide disclosed herein. For example, homologues of the polynucleotides and polypeptides disclosed herein include, but are not limited to those from different species of cyanobacteria.

Further, the term "variant" also includes analogues of the polypeptides of the invention. A polypeptide "analogue" is a polypeptide which is a derivative of a polypeptide of the invention, which derivative comprises addition, deletion, substitution of one or more amino acids, such that the polypeptide retains substantially the same function. The term "conservative amino acid substitution" refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

In general, the percentage of sequence identity between two sequences may be determined by comparing two optimally aligned sequences over a comparison window.

The portion of the sequence in the comparison window may, for example, comprise deletions or additions (i.e. gaps) in comparison to the reference sequence (for example, a polynucleotide or polypeptide sequence disclosed herein), which does not comprise deletions or additions, in order to align the two sequences optimally. A percentage of sequence identity may then be calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In the context of two or more nucleic acid or polypeptide sequences, the percentage of sequence identity refers to the specified percentage of amino acid residues or nucleotides that are the same over a specified region, (or, when not specified, over the entire sequence), when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be determined conventionally using known computer programs, including, but not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

The BESTFIT program (Wisconsin Sequence Analysis Package, for Unix, Genetics Computer Group, University Research Park, 575 Science Drive, Madison, Wis. 53711) uses the local homology algorithm of Smith and Waterman to find the best segment of homology between two sequences (Smith and Waterman, Advances in Applied Mathematics 2:482-489 (1981)). When using BESTFIT or any other sequence alignment program to determine the degree of homology between sequences, the parameters may be set such that the percentage of identity is calculated over the full length of the reference nucleotide sequence and that gaps in homology of up to 5% of the total number of nucleotides in the reference sequence are allowed.

GAP uses the algorithm described in Needleman and Wunsch (1970) J. Mol. Biol. 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP presents one member of the family of best alignments.

Another method for determining the best overall match between a query sequence and a subject sequence, also referred to as a global sequence alignment, can be determined using the FASTDB computer program based on the algorithm of Brutlag and colleagues (Comp. App. Biosci. 6:237-245 (1990)). In a sequence alignment the query and subject sequences are both DNA sequences. An RNA sequence can be compared by converting U's to T's. The result of said global sequence alignment is in percent identity.

The BLAST and BLAST 2.0 algorithms, may be used for determining percent sequence identity and sequence similarity. These are described in Altschul et al. (1977) Nuc. Acids Res. 25:3389-3402, and Altschul et al (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci USA 89:10915) alignments (B) of 50, expectation (E) of 10, M=5, N=−4, and a comparison of both strands. [0028] The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The invention also contemplates fragments of the polypeptides disclosed herein. A polypeptide “fragment” is a polypeptide molecule that encodes a constituent or is a constituent of a polypeptide of the invention or variant thereof. Typically the fragment possesses qualitative biological activity in common with the polypeptide of which it is a constituent. The peptide fragment may be between about 5 to about 3000 amino acids in length, between about 5 to about 2750 amino acids in length, between about 5 to about 2500 amino acids in length, between about 5 to about 2250 amino acids in length, between about 5 to about 2000 amino acids in length, between about 5 to about 1750 amino acids in length, between about 5 to about 1500 amino acids in length, between about 5 to about 1250 amino acids in length, between about 5 to about 1000 amino acids in length, between about 5 to about 900 amino acids in length, between about 5 to about 800 amino acids in length, between about 5 to about 700 amino acids in length, between about 5 to about 600 amino acids in length, between about 5 to about 500 amino acids in length, between about 5 to about 450 amino acids in length, between about 5 to about 400 amino acids in length, between about 5 to about 350 amino acids in length, between about 5 to about 300 amino acids in length, between about 5 to about 250 amino acids in length, between about 5 to about 200 amino acids in length, between about 5 to about 175 amino acids in length, between about 5 to about 150 amino acids in length, between about 5 to about 125 amino acids in length, between about 5 to about 100 amino acids in length, between about 5 to about 75 amino acids in length, between about 5 to about 50 amino acids in length, between about 5 to about 40 amino acids in length, between about 5 to about 30 amino acids in length, between about 5 to about 20 amino acids in length, and between about 5 to about 15 amino acids in length. Alternatively, the peptide fragment may be between about 5 to about 10 amino acids in length.

Also contemplated are fragments of the polynucleotides disclosed herein. A polynucleotide “fragment” is a polynucleotide molecule that encodes a constituent or is a constituent of a polynucleotide of the invention or variant thereof. Fragments of a polynucleotide do not necessarily need to encode polypeptides which retain biological activity. The fragment may, for example, be useful as a hybridization probe or PCR primer. The fragment may be derived from a polynucleotide of the invention or alternatively may be synthesized by some other means, for example by chemical synthesis.

Certain embodiments of the invention relate to fragments of SEQ ID NO: 1. A fragment of SEQ ID NO: 1 may comprise, for example, a constituent of SEQ ID NO: 1 in which the 5' gene border region gene orfl is absent. Alternatively, a fragment of SEQ ID NO: 1 may comprise, for example, a constituent of SEQ ID NO: 1 in which the 3' gene border region gene hisA is absent. Alternatively, a fragment of SEQ ID NO: 1 may comprise, for example, a constituent of SEQ ID NO: 1 in which the 3' gene border region gene orfA is absent. Alternatively, a fragment of SEQ ID NO: 1 may comprise, for example, a constituent of SEQ ID NO: 1 in which the 5' gene border region gene orfl is absent and the 3' border region gene orfA is absent. Alternatively, a fragment of SEQ ID NO: 1 may comprise, for example, a constituent of SEQ ID NO: 1 in which the 5' gene border region gene orfl is absent and the 3' border region genes hisA and orfA are absent.

In other embodiments, a fragment of SEQ ID NO: 1 may comprise one or more SXT open reading frames. The SXT open reading frame may be selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants thereof.

Additional embodiments of the invention relate to fragments of SEQ ID NO: 80. The fragment of SEQ ID NO: 80 may comprise one or more CYR open reading frames. The CYR open reading frame may be selected from the group consisting of SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and variants thereof.

In particular embodiments, the polynucleotides of the invention may be cloned into a vector. The vector may comprise, for example, a DNA, RNA or complementary DNA (cDNA) sequence. The vector may be a plasmid vector, a viral vector, or any other suitable vehicle adapted for the insertion of foreign sequences, their introduction into cells and the expression of the introduced sequences. Typically the vector is an expression vector and may include expression control and processing sequences such as a promoter, an enhancer, ribosome binding sites, polyadenylation signals and transcription termination sequences. The invention also contemplates host cells transformed by such vectors. For example, the polynucleotides of the invention may be cloned into a vector which is transformed into a bacterial host cell, for example *E. coli*. Methods for the construction of vectors and their transformation into host cells are generally known in the art, and described in, for example, *Molecular Cloning: A Laboratory Manual* (2nd ed., Cold Spring Harbor Laboratory Press, Plainview, N.Y., and, Ausubel F. M. et al. (Eds) *Current Protocols in Molecular* Biology (2007), John Wiley and Sons, Inc.

Nucleotide Probes, Primers and Antibodies

The invention contemplates nucleotides and fragments based on the sequences of the polynucleotides disclosed herein for use as primers and probes for the identification of homologous sequences.

The nucleotides and fragments may be in the form of oligonucleotides. Oligonucleotides are short stretches of nucleotide residues suitable for use in nucleic acid amplification reactions such as PCR, typically being at least about 5 nucleotides to about 80 nucleotides in length, more typically about 10 nucleotides in length to about 50 nucleotides in length, and even more typically about 15 nucleotides in length to about 30 nucleotides in length.

Probes are nucleotide sequences of variable length, for example between about 10 nucleotides and several thousand nucleotides, for use in detection of homologous sequences, typically by hybridization. Hybridization probes may be genomic DNA fragments, cDNA fragments, RNA fragments, or other oligonucleotides.

Methods for the design and/or production of nucleotide probes and/or primers are generally known in the art, and are described in Sambrook et al. (1989) *Molecular Cloning: A Laboratory Manual* (2nd ed., Cold Spring Harbor Laboratory Press, Plainview, N.Y.; Itakura K. et al. (1984) Annu. Rev. Biochem. 53:323; Innis et al., (Eds) (1990) *PCR Protocols: A Guide to Methods and Applications* (Academic Press, New York); Innis and Gelfand, (Eds) (1995) *PCR Strategies* (Academic Press, New York); and Innis and Gelfand, (Eds) (1999) *PCR Methods Manual* (Academic Press, New York). Nucleotide primers and probes may be prepared, for example, by chemical synthesis techniques for example, the phosphodiester and phosphotriester methods (see for example Narang S. A. et al. (1979) Meth. Enzymol. 68:90; Brown, E. L. (1979) et al. Meth. Enzymol. 68:109; and U.S. Pat. No. 4,356,270), the diethylphosphoramidite method (see Beaucage S. L. et al. (1981) Tetrahedron Letters, 22:1859-1862). A method for synthesizing oligonucleotides on a modified solid support is described in U.S. Pat. No. 4,458,066.

The nucleic acids of the invention, including the above-mentioned probes and primers, may be labelled by incorporation of a marker to facilitate their detection. Techniques for labelling and detecting nucleic acids are described, for example, in Ausubel F. M. et al. (Eds) *Current Protocols in Molecular* Biology (2007), John Wiley and Sons, Inc. Examples of suitable markers include fluorescent molecules (e.g. acetylaminofluorene, 5-bromodeoxyuridine, digoxigenin, fluorescein) and radioactive isotopes (e.g. 32P, 35S, 3H, 33P). Detection of the marker may be achieved, for example, by chemical, photochemical, immunochemical, biochemical, or spectroscopic techniques.

The probes and primers of the invention may be used, for example, to detect or isolate cyanobacteria and/or dinoflagellates in a sample of interest. Additionally or alternatively, the probes and primers of the invention may be used to detect or isolate a cyanotoxic organism and/or a cylindrospermopisn-producing organism in a sample of interest. Additionally or alternatively, the probes or primers of the invention may be used to isolate corresponding sequences in other organisms including, for example, other bacterial species. Methods such as the polymerase chain reaction (PCR), hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In hybridization techniques, all or part of a known nucleotide sequence is used to generate a probe that selectively hybridizes to other corresponding nucleic acid sequences present in a given sample. The hybridization probes may be genomic DNA fragments, cDNA fragments, RNA fragments, or other oligonucleotides, and may be labelled with a detectable marker. Thus, for example, probes for hybridization can be made by labelling synthetic oligonucleotides based on the sequences of the invention.

The level of homology (sequence identity) between probe and the target sequence will largely be determined by the stringency of hybridization conditions. In particular the nucleotide sequence used as a probe may hybridize to a homologue or other variant of a polynucleotide disclosed herein under conditions of low stringency, medium stringency or high stringency. There are numerous conditions and factors, well known to those skilled in the art, which may be employed to alter the stringency of hybridization. For instance, the length and nature (DNA, RNA, base composition) of the nucleic acid to be hybridized to a specified nucleic acid; concentration of salts and other components, such as the presence or absence of formamide, dextran sulfate, polyethylene glycol etc; and altering the temperature of the hybridization and/or washing steps.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C., and a wash in 0.5× to 1×SSC at 55° C. to 60° C. Exemplary high stringency conditions include hybridization in 50% formamide, 1 M NaCl, 1% SDS at 37° C., and a final wash in 0.1×SSC at 60° C. to 65° C. for at least about 20 minutes. Optionally, wash buffers may comprise about 0.1% to about 1% SDS. The duration of hybridization is generally less than about 24 hours, usually about 4 to about 12 hours.

Under a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2nd ed., Cold Spring Harbor Laboratory Press, Plainview, N.Y.); Ausubel F. M. et al. (Eds) *Current Protocols in Molecular* Biology (2007), John Wiley and Sons, Inc; Maniatis et al. *Molecular Cloning* (1982), 280-281; Innis et al. (Eds) (1990) *PCR Protocols: A Guide to Methods and Applications* (Academic Press, New York); Innis and Gelfand, (Eds) (1995) *PCR Strategies* (Academic Press, New York); and Innis and Gelfand, (Eds) (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

The skilled addressee will recognise that the primers described herein for use in PCR or RT-PCR may also be used as probes for the detection of SXT or CYR sequences.

Also contemplated by the invention are antibodies which are capable of binding specifically to the polypeptides of the invention. The antibodies may be used to qualitatively or quantitatively detect and analyse one or more SXT or CYR polypeptides in a given sample. By "binding specifically" it will be understood that the antibody is capable of binding to the target polypeptide or fragment thereof with a higher affinity than it binds to an unrelated protein. For example, the antibody may bind to the polypeptide or fragment thereof with a binding constant in the range of at least about $10^{-4}$M to about $10^{-10}$M. Preferably the binding constant is at least about $10^{-5}$M, or at least about $10^{-6}$M, more preferably the binding constant of the antibody to the SXT or CYR polypeptide or fragment thereof is at least about $10^{-7}$M, at least about $10^{-8}$M, or at least about $10^{-9}$M or more.

Antibodies of the invention may exist in a variety of forms, including for example as a whole antibody, or as an antibody fragment, or other immunologically active fragment thereof, such as complementarity determining regions. Similarly, the antibody may exist as an antibody fragment having functional antigen-binding domains, that is, heavy and light chain variable domains. Also, the antibody fragment may exist in a form selected from the group consisting of, but not limited to: Fv, $F_{ab}$, $F(ab)_2$, scFv (single chain Fv), dAb (single domain antibody), chimeric antibodies, bi-specific antibodies, diabodies and triabodies.

An antibody 'fragment' may be produced by modification of a whole antibody or by synthesis of the desired antibody fragment. Methods of generating antibodies, including antibody fragments, are known in the art and include, for example, synthesis by recombinant DNA technology. The skilled addressee will be aware of methods of synthesising antibodies, such as those described in, for example, U.S. Pat. No. 5,296,348 and Ausubel F. M. et al. (Eds) *Current Protocols in Molecular Biology* (2007), John Wiley and Sons, Inc.

Preferably antibodies are prepared from discrete regions or fragments of the SXT or CYR polypeptide of interest. An antigenic portion of a polypeptide of interest may be of any appropriate length, such as from about 5 to about 15 amino acids. Preferably, an antigenic portion contains at least about 5, 6, 7, 8, 9, 10, 11, 12, 13 or 14 amino acid residues.

In the context of this specification reference to an antibody specific to a SXT or CYR polypeptide of the invention includes an antibody that is specific to a fragment of the polypeptide of interest.

Antibodies that specifically bind to a polypeptide of the invention can be prepared, for example, using the purified SXT or CYR polypeptides or their nucleic acid sequences using any suitable methods known in the art. For example, a monoclonal antibody, typically containing Fab portions, may be prepared using hybridoma technology described in Harlow and Lane (Eds) *Antibodies-A Laboratory Manual*, (1988), Cold Spring Harbor Laboratory, N.Y; Coligan, *Current Protocols in Immunology* (1991); Goding, *Monoclonal Antibodies: Principles and Practice* (1986) 2nd ed; and Kohler & Milstein, (1975) Nature 256: 495-497. Such techniques include, but are not limited to, antibody preparation by selection of antibodies from libraries of recombinant antibodies in phage or similar vectors, as well as preparation of polyclonal and monoclonal antibodies by immunizing rabbits or mice (see, for example, Huse et al. (1989) Science 246: 1275-1281; Ward et al. (1989) Nature 341: 544-546).

It will also be understood that antibodies of the invention include humanised antibodies, chimeric antibodies and fully human antibodies. An antibody of the invention may be a bi-specific antibody, having binding specificity to more than one antigen or epitope. For example, the antibody may have specificity for one or more SXT or CYR polypeptide or fragments thereof, and additionally have binding specificity for another antigen. Methods for the preparation of humanised antibodies, chimeric antibodies, fully human antibodies, and bispecific antibodies are known in the art and include, for example as described in U.S. Pat. No. 6,995,243 issued Feb. 7, 2006 to Garabedian, et al. and entitled "Antibodies that recognize and bind phosphorylated human glucocorticoid receptor and methods of using same".

Generally, a sample potentially comprising SXT or CYR polypeptides can be contacted with an antibody that specifically binds the SXT or CYR polypeptide or fragment thereof. Optionally, the antibody can be fixed to a solid support to facilitate washing and subsequent isolation of the complex, prior to contacting the antibody with a sample. Examples of solid supports include, for example, microtitre plates, beads, ticks, or microbeads. Antibodies can also be attached to a ProteinChip array or a probe substrate as described above.

Detectable labels for the identification of antibodies bound to the SXT or CYR polypeptides of the invention include, but are not limited to fluorochromes, fluorescent dyes, radiolabels, enzymes such as horse radish peroxide, alkaline phosphatase and others commonly used in the art, and colorimetric labels including colloidal gold or coloured glass or plastic beads. Alternatively, the marker in the sample can be detected using an indirect assay, wherein, for example, a second, labelled antibody is used to detect bound marker-specific antibody.

Methods for detecting the presence of or measuring the amount of, an antibody-marker complex include, for example, detection of fluorescence, chemiluminescence, luminescence, absorbance, birefringence, transmittance, reflectance, or refractive index such as surface plasmon resonance, ellipsometry, a resonant mirror method, a grating coupler wave guide method or interferometry. Radio frequency methods include multipolar resonance spectroscopy. Electrochemical methods include amperometry and voltametry methods. Optical methods include imaging methods and non-imaging methods and microscopy.

Useful assays for detecting the presence of or measuring the amount of, an antibody-marker complex include, include, for example, enzyme-linked immunosorbent assay (ELISA), a radioimmune assay (RIA), or a Western blot assay. Such methods are described in, for example, Clinical Immunology (Stites & Terr, eds., 7th ed. 1991); Methods in Cell Biology: Antibodies in Cell Biology, volume 37 (Asai, ed. 1993); and Harlow & Lane, supra.

Methods and Kits for Detection

The invention provides methods and kits for the detection and/or isolation of SXT nucleic acids and polypeptides. Also provided are methods and kits for the detection and/or isolation CYR nucleic acids and polypeptides.

In one aspect, the invention provides a method for the detection of cyanobacteria. The skilled addressee will understand that the detection of "cyanobacteria" encompasses the detection of one or more cyanobacteria. The method comprises obtaining a sample for use in the method, and detecting the presence of one or more SXT polynucleotides or polypeptides as disclosed herein, or a variant or fragment thereof. The presence of SXT polynucleotides, polypeptides, or variants or fragments thereof, is indicative of cyanobacteria in the sample.

The SXT polynucleotide may comprise a sequence selected from the group consisting of SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof.

Alternatively, the SXT polynucleotide may be an RNA or cDNA encoded by a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof and/or polypeptides as disclosed herein, or a variant or fragment thereof.

The SXT polypeptide may comprising an amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and variants and fragments thereof.

The inventors have determined that several genes of the SXT gene cluster exist in saxitoxin-producing organisms, and are absent in organisms with the SXT gene cluster that do not produce saxitoxin. Specifically, the inventors have identified that gene 6 (sxtA) (SEQ ID NO: 14), gene 9 (sxtG) (SEQ ID NO: 20), gene 10 (sxtH) (SEQ ID NO: 22), gene 11 (sxtI) (SEQ ID NO: 24) and gene 17 (sxtX) (SEQ ID NO: 36) of the SXT gene cluster are present only in organisms that produce saxitoxin.

Accordingly, in another aspect the invention provides a method of detecting a cyanotoxic organism. The method comprises obtaining a sample for use in the method, and detecting a cyanotoxic organism based on the detection of one or more SXT polynucleotides comprising a sequence set forth in SEQ ID NO: 14 (sxtA, gene 6), SEQ ID NO: 20 (sxtG, gene 9), SEQ ID NO: 22 (sxtH, gene 10), SEQ ID NO: 24 (sxtI, gene 11), SEQ ID NO: 36 (sxtX, gene 17), or variants or fragments thereof. Additionally or alternatively, a cyanotoxic organism may be detected based on the detection of an RNA or cDNA comprising a sequence encoded by SEQ ID NO: 14 (sxtA, gene 6), SEQ ID NO: 20 (sxtG, gene 9), SEQ ID NO: 22 (sxtH, gene 10), SEQ ID NO: 24 (sxtI, gene 11), SEQ ID NO: 36 (sxtX, gene 17), or variants or fragments thereof. Additionally or alternatively, a cyanotoxic organism may be detected based on the detection of one or more polypeptides comprising a sequence set forth in SEQ ID NO: 15 (SXTA), SEQ ID NO: 21 (SXTG), SEQ ID NO: 23 (SXTH), SEQ ID NO: 25 (SXTI), SEQ ID NO: 37 (SXTX), or variants or fragments thereof, in a sample suspected of comprising one or more cyanotoxic organisms. The cyanotoxic organism may be any organism capable of producing saxitoxin. In a preferred embodiment of the invention, the cyanotoxic organism is a cyanobacteria or a dinoflagellate.

In certain embodiments of the invention, the methods for detecting cyanobacteria or the methods for detecting cyanotoxic organisms may further comprise the detection of one or more CYR polynucleotides or CYR polypeptides as disclosed herein, or a variant or fragment thereof. The CYR polynucleotide may comprise a sequence selected from the group consisting of SEQ ID NO: 80, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and variants or fragments thereof.

Alternatively, the CYR polynucleotide may be an RNA or cDNA encoded by a polynucleotide sequence selected from the group consisting of SEQ ID NO: 80, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and variants or fragments thereof.

The CYR polypeptide may comprise a sequence selected from the group consisting of SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and SEQ ID NO: 110, and variants or fragments thereof.

The inventors have determined gene 8 (cyrJ) (SEQ ID NO: 95) of the CYR gene cluster exists in cylindrospermopsin-producing organisms, and is absent in organisms with the CYR gene cluster that do not produce cylindrospermopsin. Accordingly, the methods for detecting cyanobacteria or the methods for detecting cyanotoxic organisms may further comprise the detection of a cylindrospermopsin-producing organism based on the detection of a CYR polynucleotide comprising a sequence set forth in SEQ ID NO: 95, or a variant or fragment thereof. Additionally or alternatively, the methods for detecting cyanobacteria or the methods for detecting cyanotoxic organisms may further comprise the detection of a cylindrospermopsin-producing organism based on the detection of an RNA or cDNA comprising a sequence encoded by SEQ ID NO: 95, or a variant or fragment thereof. Additionally or alternatively, the methods for detecting cyanobacteria or the methods for detecting cyanotoxic organisms may further comprise the detection of a cylindrospermopsin-producing organism based on the detection of a CYR polypeptide comprising a sequence set forth in SEQ ID NO: 96, or a variant or fragment thereof.

In another aspect, the invention provides a method for the detection of cyanobacteria. The skilled addressee will understand that the detection of "cyanobacteria" encompasses the detection of one or more cyanobacteria. The method comprises obtaining a sample for use in the method, and detecting the presence of one or more CYR polynucleotides or polypeptides as disclosed herein, or a variant or fragment thereof. The presence of CYR polynucleotides, polypeptides, or variants or fragments thereof, is indicative of cyanobacteria in the sample.

The CYR polynucleotide may comprise a sequence selected from the group consisting of SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109 and variants and fragments thereof.

Alternatively, the CYR polynucleotide may be an RNA or cDNA encoded by a sequence selected from the group consisting of SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109 and variants and fragments thereof.

The CYR polypeptide may comprise a sequence selected from the group consisting of SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and SEQ ID NO: 110, and variants or fragments thereof.

In another aspect of the invention there is provided a method of detecting a cylindrospermopsin-producing organism based on the detection of CYR gene 8 (cyrJ). The method comprises obtaining a sample for use in the method, and detecting the presence of a CYR polynucleotide comprising a sequence set forth in SEQ ID NO: 95, or a variant or fragment thereof. Additionally or alternatively, the method for detecting a cylindrospermopsin-producing organism based on the detection of CYR gene 8 (cyrJ) may comprise the detection of an RNA or cDNA comprising a sequence encoded by SEQ ID NO: 95, or a variant or fragment thereof. Additionally or alternatively, the method for detecting a cylindrospermopsin-producing organism based on the detection of CYR gene 8 (cyrJ) may comprise the detection of a CYR polypeptide comprising a sequence set forth in SEQ ID NO: 96, or a variant or fragment thereof.

In certain embodiments of the invention, the methods for detecting cyanobacteria comprising the detection of CYR sequences or variants or fragments thereof further comprise the detection of one or more SXT polynucleotides or SXT polypeptides as disclosed herein, or a variant or fragment thereof.

The SXT polynucleotide may comprise a sequence selected from the group consisting of SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof.

Alternatively, the SXT polynucleotide may be an RNA or cDNA encoded by a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof and/or polypeptides as disclosed herein, or a variant or fragment thereof.

The SXT polypeptide may comprising an amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and variants and fragments thereof.

In another aspect, the invention provides a method for the detection of dinoflagellates. The skilled addressee will understand that the detection of "dinoflagellates" encompasses the detection of one or more dinoflagellates. The method comprises obtaining a sample for use in the method, and detecting the presence of one or more SXT polynucleotides or polypeptides as disclosed herein, or a variant or fragment thereof. The presence of SXT polynucleotides, polypeptides, or variants or fragments thereof, is indicative of dinoflagellates in the sample.

The SXT polynucleotide may comprise a sequence selected from the group consisting of SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof.

Alternatively, the SXT polynucleotide may be an RNA or cDNA encoded by a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof and/or polypeptides as disclosed herein, or a variant or fragment thereof.

The SXT polypeptide may comprising an amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and variants and fragments thereof.

A sample for use in accordance with the methods described herein may be suspected of comprising one or more cyanotoxic organisms. The cyanotoxic organisms may be one or more cyanobacteria and/or one or more dinoflagellates. Additionally or alternatively, a sample for use in accordance with the methods described herein may be suspected of comprising one more cyanobacteria and/or one or more dinoflagellates. A sample for use in accordance with the methods described herein may be a comparative or control sample, for example, a sample comprising a known concentration or density of a cyanobacteria and/or dinoflagellates, or a sample comprising one or more known species or strains of cyanobacteria and/or dinoflagellates.

A sample for use in accordance with the methods described herein may be derived from any source. For example, a sample may be an environmental sample. The environmental sample may be derived, for example, from salt water, fresh water or a blue-green algal bloom. Alternatively, the sample may be derived from a laboratory source, such as a culture, or a commercial source.

It will be appreciated by those in the art that the methods and kits disclosed herein are generally suitable for detecting any organisms in which the SXT and/or CYR gene clusters are present. Suitable cyanobacteria to which the methods of the invention are applicable may be selected from the orders Oscillatoriales, Chroococcales, Nostocales and Stigonematales. For example, the cyanobacteria may be selected from the genera *Anabaena, Nostoc, Microcystis, Planktothrix, Oscillatoria, Phormidium*, and *Nodularia*. For example, the cyanobacteria may be selected from the species *Cylindrospermopsis raciborskii* T3, *Cylindrospermopsis raciborskii* AWT205, *Aphanizomenon ovalisporum, Aphanizomenon flos-aquae, Aphanizomenon* sp., *Umezakia natans, Raphidiopsis curvata, Anabaena bergii, Lyngbya wollei*, and *Anabaena circinalis*. Examples of suitable dinoflagellates to which the methods and kits of the invention are applicable may be selected from the genera *Alexandrium, Pyrodinium* and *Gymnodinium*. The methods and kits of the invention may also be employed for the discovery of novel hepatotoxic species or genera in culture collections or from environmental samples. The methods and kits of the invention may also be employed to detect cyanotoxins that accumulate in other animals, for example, fish and shellfish.

Detection of SXT and CYR polynucleotides and polypeptides disclosed herein may be performed using any suitable method. For example, methods for the detection of SXT and CYR polynucleotides and/or polypeptides disclosed herein may involve the use of a primer, probe or antibody specific for one or more SXT and CYR polynucleotides and polypeptides. Suitable techniques and assays in which the skilled addressee may utilise a primer, probe or antibody specific for one or more SXT and CYR polynucleotides and polypeptides include, for example, the polymerase chain reaction (and related variations of this technique), antibody based assays such as ELISA and flow cytometry, and fluorescent microscopy. Methods by which the SXT and CYR polypeptides disclosed herein may be identified are generally known in the art, and are described for example in Coligan J. E. et al. (Eds) *Current Protocols in Protein Science* (2007), John Wiley and Sons, Inc; Walker, J. M., (Ed) (1988) *New Protein Techniques: Methods in Molecular Biology*, Humana Press, Clifton, N.J. and Scopes, R. K. (1987) *Protein Purification: Principles and Practice,* 3rd. Ed., Springer-Verlag, New York, N.Y. For example, SXT and CYR polypeptides disclosed herein may be detected by western blot or spectrophotometric analysis. Other examples of suitable methods for the detection of SXT and CYR polypeptides are described, for example, in U.S. Pat. Nos. 4,683,195, 6,228,578, 7,282,355, 7,348,147 and PCT publication No. W0/2007/056723.

In a preferred embodiment of the invention, the detection of SXT and CYR polynucleotides and polypeptides is achieved by amplification of DNA from the sample of interest by polymerase chain reaction, using primers that hybridise specifically to the SXT and/or CYR sequence, or a variant or fragment thereof, and detecting the amplified sequence.

Nucleic acids and polypeptides for analysis using methods and kits disclosed herein may be extracted from organisms either in mixed culture or as individual species or genus isolates. Accordingly, the organisms may be cultured prior to nucleic acid and/or polypeptide isolation or alternatively nucleic acid and/or polypeptides may be extracted directly from environmental samples, such as water samples or blue-green algal blooms.

Suitable methods for the extraction and purification of nucleic acids for analysis using the methods and kits invention are generally known in the art and are described, for example, in Ausubel F. M. et al. (Eds) *Current Protocols in Molecular* Biology (2007), John Wiley and Sons, Inc; Neilan (1995) Appl. Environ. Microbiol. 61:2286-2291; and Neilan et al. (2002) Astrobiol. 2:271-280. The skilled addressee will readily appreciate that the invention is not limited to the specific methods for nucleic acid isolation described therein and other suitable methods are encompassed by the invention. The invention may be performed without nucleic acid isolation prior to analysis of the nucleic acid.

Suitable methods for the extraction and purification of polypeptides for the purposes of the invention are generally known in the art and are described, for example, in Coligan J. E. et al. (Eds) *Current Protocols in Protein Science* (2007), John Wiley and Sons, Inc; Walker, J. M., (Ed) (1988) *New Protein Techniques: Methods in Molecular Biology*, Humana Press, Clifton, N.J. and Scopes, R. K. (1987) *Protein Purification: Principles and Practice,* 3rd. Ed., Springer-Verlag, New York, N.Y. Examples of suitable techniques for protein extraction include, but are not limited to dialysis, ultrafiltration, and precipitation. Protein purification techniques suitable for use include, but are not limited to, reverse-phase chromatography, hydrophobic interaction chromatography, centrifugation, gel filtration, ammonium sulfate precipitation, and ion exchange.

In accordance with the methods and kits of the invention, SXT and CYR polynucleotides or variants or fragments thereof may be detected by any suitable means known in the art. In a preferred embodiment of the invention, SXT and CYR polynucleotides are detected by PCR amplification. Under the PCR approach, oligonucleotide primers can be designed for use in PCR reactions to amplify SXT and CYR polynucleotides of the invention. Also encompassed by the invention is the PCR amplification of complementary DNA (cDNA) amplified from messenger RNA (mRNA) derived from reverse-transcription of SXT and CYR sequences (RT-PCR). Known methods of PCR include, but are not limited to, methods using paired primers, nested primers, single specific primers, degenerate primers, gene-specific primers, vector-specific primers, partially-mismatched primers, and the like. Methods for designing PCR and RT-PCR primers are generally known in the art and are disclosed, for example, in Ausubel F. M. et al. (Eds) *Current Protocols in Molecular* Biology (2007), John Wiley and Sons, Inc; Maniatis et al. *Molecular Cloning* (1982), 280-281; Innis et al. (Eds) (1990) *PCR Protocols: A Guide to Methods and Applications* (Academic Press, New York); Innis and Gelfand, (Eds) (1995) *PCR Strategies* (Academic Press, New York); Innis and Gelfand, (Eds) (1999) *PCR Methods Manual* (Academic Press, New York); and Sambrook et al. (1989) *Molecular Cloning: A Laboratory Manual* (2nd ed., Cold Spring Harbor Laboratory Press, Plainview, N.Y.

The skilled addressee will readily appreciate that various parameters of PCR and RT-PCR procedures may be altered without affecting the ability to achieve the desired product. For example, the salt concentration may be varied or the time and/or temperature of one or more of the denaturation, annealing and extension steps may be varied. Similarly, the amount of DNA, cDNA, or RNA template may also be varied depending on the amount of nucleic acid available or the optimal amount of template required for efficient amplification. The primers for use in the methods and kits of the present invention are typically oligonucleotides typically being at least about 5 nucleotides to about 80 nucleotides in length, more typically about 10 nucleotides in length to about 50 nucleotides in length, and even more typically about 15 nucleotides in length to about 30 nucleotides in length. The skilled addressee will recognise that the primers described herein may be useful for a number of different applications, including but not limited to PCR, RT-PCR, and use of probes for the detection of SXT or CYR sequences.

Such primers can be prepared by any suitable method, including, for example, direct chemical synthesis or cloning and restriction of appropriate sequences. Not all bases in the primer need reflect the sequence of the template molecule to which the primer will hybridize, the primer need only contain sufficient complementary bases to enable the primer to hybridize to the template. A primer may also include mismatch bases at one or more positions, being bases that are not complementary to bases in the template, but rather are designed to incorporate changes into the DNA upon base extension or amplification. A primer may include additional bases, for example in the form of a restriction enzyme recognition sequence at the 5' end, to facilitate cloning of the amplified DNA.

The invention provides a method of detecting a cyanotoxic organism based on the detection of one or more of SXT gene 6 (sxtA), SXT gene 9 (sxtG), SXT gene 10 (sxtH), SXT gene 11 (sxtI) and SXT gene 17 (sxtX) (SEQ ID NOS: 14, 20, 22, 24, and 36 respectively), or fragments or variants thereof. Additionally or alternatively, a cyanotoxic organism may be detected based on the detection of one or more of the following SXT polypeptides: SXTA (SEQ ID NO: 15), SXTG (SEQ ID NO: 21), SXTH (SEQ ID NO: 23), SXTI (SEQ ID NO: 25), SXTX (SEQ ID NO: 37), or fragments or variants thereof.

The skilled addressee will recognise that any primers capable of the amplifying the stated SXT and/or CYR sequences, or variants or fragments thereof, are suitable for use in the methods of the invention. For example, suitable oligonucleotide primer pairs for the PCR amplification of SXT gene 6 (sxtA) may comprise a first primer comprising the sequence of SEQ ID NO: 70 and a second primer comprising the sequence of SEQ ID NO: 71, a first primer comprising the sequence of SEQ ID NO: 72 and a second primer comprising the sequence of SEQ ID NO: 73, a first primer comprising the sequence of SEQ ID NO: 74 and a second primer comprising the sequence of SEQ ID NO: 75, a first primer comprising the sequence of SEQ ID NO: 76 and a second primer comprising the sequence of SEQ ID NO: 77, a first primer comprising the sequence of SEQ ID NO: 78 and a second primer comprising the sequence of SEQ ID NO: 79, a first primer comprising the sequence of SEQ ID NO: 113 and a second primer comprising the sequence of SEQ ID NO: 114, or a first primer comprising the sequence of SEQ ID NO: 115 or SEQ ID NO: 116 and a second primer comprising the sequence of SEQ ID NO: 117.

Suitable oligonucleotide primer pairs for the amplification of SXT gene 9 (sxtG) may comprise a first primer comprising the sequence of SEQ ID NO: 118 and a second primer comprising the sequence of SEQ ID NO: 119, or a first primer comprising the sequence of SEQ ID NO: 120 and a second primer comprising the sequence of SEQ ID NO: 121.

Suitable oligonucleotide primer pairs for the amplification of SXT gene 10 (sxtH) may comprise a first primer comprising the sequence of SEQ ID NO: 122 and a second primer comprising the sequence of SEQ ID NO: 123.

Suitable oligonucleotide primer pairs for the amplification of SXT gene 11 (sxtI) may comprise a first primer comprising the sequence of SEQ ID NO: 124 or SEQ ID NO: 125 and a second primer comprising the sequence of SEQ ID NO: 126, or a first primer comprising the sequence of SEQ ID NO: 127 and a second primer comprising the sequence of SEQ ID NO: 128.

Suitable oligonucleotide primer pairs for the amplification of SXT gene 17 (sxtX) may comprise a first primer comprising the sequence of SEQ ID NO: 129 and a second primer comprising the sequence of SEQ ID NO: 130, or a first primer comprising the sequence of SEQ ID NO: 131 and a second primer comprising the sequence of SEQ ID NO: 132.

The skilled addressee will recognise that fragments and variants of the above-mentioned primer pairs may also efficiently amplify SXT gene 6 (sxtA), SXT gene 9 (sxtG), SXT gene 10 (sxtH), SXT gene 11 (sxtI) or SXT gene 17 (sxtX) sequences.

In certain embodiments of the invention, polynucleotide sequences derived from the CYR gene are detected based on the detection of CYR gene 8 (cyrJ) (SEQ ID NO: 95). Suitable oligonucleotide primer pairs for the PCR amplification of CYR gene 8 (cyrJ) may comprise a first primer having the sequence of SEQ ID NO: 111 or a fragment or variant thereof and a second primer having the sequence of SEQ ID NO: 112 or a fragment thereof.

Also included within the scope of the present invention are variants and fragments of the exemplified oligonucleotide primers. The skilled addressee will also recognise that the invention is not limited to the use of the specific primers exemplified, and alternative primer sequences may also be used, provided the primers are designed appropriately so as to enable the amplification of SXT and/or CYR sequences. Suitable primer sequences can be determined by those skilled in the art using routine procedures without undue experimentation. The location of suitable primers for the amplification of SXT and/or CYR sequences may be determined by such factors as G+C content and the ability for a sequence to form unwanted secondary structures.

Suitable methods of analysis of the amplified nucleic acids are well known to those skilled in the art and are described for example, in, Sambrook et al. (1989) *Molecular Cloning: A Laboratory Manual* (2nd ed., Cold Spring Harbor Laboratory Press, Plainview, N.Y.); Ausubel F. M. et al. (Eds) *Current Protocols in Molecular* Biology (2007), John Wiley and Sons, Inc; and Maniatis et al. *Molecular Cloning* (1982), 280-281. Suitable methods of analysis of the amplified nucleic acids include, for example, gel electrophoresis which may or may not be preceded by restriction enzyme digestion, and/or nucleic acid sequencing. Gel electrophoresis may comprise agarose gel electrophoresis or polyacrylamide gel electrophoresis, techniques commonly used by those skilled in the art for separation of DNA fragments on the basis of size. The concentration of agarose or polyacrylamide in the gel in large part determines the resolution ability of the gel and the appropriate concentration of agarose or polyacrylamide will therefore depend on the size of the DNA fragments to be distinguished.

In other embodiments of the invention, SXT and CYR polynucleotides and variants or fragments thereof may be detected by the use of suitable probes. The probes of the invention are based on the sequences of SXT and/or CYR polynucleotides disclosed herein. Probes are nucleotide sequences of variable length, for example between about 10 nucleotides and several thousand nucleotides, for use in detection of homologous sequences, typically by hybridization. Hybridization probes of the invention may be genomic DNA fragments, cDNA fragments, RNA fragments, or other oligonucleotides.

Methods for the design and/or production of nucleotide probes are generally known in the art, and are described, for example, in Robinson P. J., et al. (Eds) *Current Protocols in Cytometry* (2007), John Wiley and Sons, Inc; Ausubel F. M. et al. (Eds) *Current Protocols in Molecular* Biology (2007), John Wiley and Sons, Inc; Sambrook et al. (1989) *Molecular Cloning: A Laboratory Manual* (2nd ed., Cold Spring Harbor Laboratory Press, Plainview, N.Y.; and Maniatis et al. *Molecular Cloning* (1982), 280-281. Nucleotide probes may be prepared, for example, by chemical synthesis techniques, for example, the phosphodiester and phosphotriester methods (see for example Narang S. A. et al. (1979) Meth. Enzymol. 68:90; Brown, E. L. (1979) et al. Meth. Enzymol. 68:109; and U.S. Pat. No. 4,356,270), the diethylphosphoramidite method (see Beaucage S. L et al. (1981) Tetrahedron Letters, 22:1859-1862). A method for synthesizing oligonucleotides on a modified solid support is described in U.S. Pat. No. 4,458,066.

The probes of the invention may be labelled by incorporation of a marker to facilitate their detection. Techniques for labelling and detecting nucleic acids are described, for example, in Ausubel F. M. et al. (Eds) *Current Protocols in Molecular* Biology (2007), John Wiley and Sons, Inc. Examples of suitable markers include fluorescent molecules (e.g. acetylaminofiuorene, 5-bromodeoxyuridine, digoxigenin, fluorescein) and radioactive isotopes (e.g. 32P, 35S, 3H, 33P). Detection of the marker may be achieved, for example, by chemical, photochemical, immunochemical, biochemical, or spectroscopic techniques.

The methods and kits of the invention also encompass the use of antibodies which are capable of binding specifically to the polypeptides of the invention. The antibodies may be used to qualitatively or quantitatively detect and analyse one or more SXT or CYR polypeptides in a given sample. Methods for the generation and use of antibodies are generally known in the art and described in, for example, Harlow and Lane (Eds) *Antibodies-A Laboratory Manual*, (1988), Cold Spring Harbor Laboratory, N.Y., Coligan, *Current Protocols in Immunology* (1991); Goding, *Monoclonal Antibodies: Principles and Practice* (1986) 2nd ed; and Kohler & Milstein, (1975) Nature 256: 495-497. The antibodies may be conjugated to a fluorochrome allowing detection, for example, by flow cytometry, immunohistochemisty or other means known in the art. Alternatively, the antibody may be bound to a substrate allowing colorimetric or chemiluminescent detection. The invention also contemplates the use of secondary antibodies capable of binding to one or more antibodies capable of binding specifically to the polypeptides of the invention.

The invention also provides kits for the detection of cyanotoxic organisms and/or cyanobacteria, and/or dinoflagellates. In general, the kits of the invention comprise at least one agent for detecting the presence of one or more SXT and/or CYR polynucleotide or polypeptides disclosed herein, or a variant or fragment thereof. Any suitable agent capable of detecting SXT and/or CYR sequences of the invention may be included in the kit. Non-limiting examples include primers, probes and antibodies.

In one aspect, the invention provides a kit for the detection of cyanobacteria, the kit comprising at least one agent for detecting the presence the presence of one or more SXT polynucleotides or polypeptides as disclosed herein, or a variant or fragment thereof.

The SXT polynucleotide may comprise a sequence selected from the group consisting of SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof.

Alternatively, the SXT polynucleotide may be an RNA or cDNA encoded by a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof and/or polypeptides as disclosed herein, or a variant or fragment thereof.

The SXT polypeptide may comprise an amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and variants and fragments thereof.

Also provided is a kit for the detection of cyanotoxic organisms. The kit comprises at least one agent for detecting the presence of one or more SXT polynucleotides or polypeptides as disclosed herein, or a variant or fragment thereof.

The SXT polynucleotide may comprise a sequence selected from the group consisting of SEQ ID NO: 14, SEQ ID NO: 20, SEQ ID NO: 22, SEQ ID NO: 24, SEQ ID NO: 36, and variants and fragments thereof.

Alternatively, the SXT polynucleotide may be an RNA or cDNA encoded by a sequence selected from the group consisting of SEQ ID NO: 14, SEQ ID NO: 20, SEQ ID NO: 22, SEQ ID NO: 24, SEQ ID NO: 36, and variants and fragments thereof.

The SXT polypeptide may comprising an amino acid sequence selected from the group consisting of consisting of SEQ ID NO: 15, SEQ ID NO: 21, SEQ ID NO: 23, SEQ ID NO: 25, SEQ ID NO: 37, and variants and fragments thereof.

The at least one agent may be any suitable reagent for the detection of SXT polynucleotides and/or polypeptides disclosed herein. For example, the agent may be a primer, an antibody or a probe. By way of exemplification only, the primers or probes may comprise a sequence selected from the group consisting of SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, and variants and fragments thereof.

In certain embodiments of the invention, the kits for the detection of cyanobacteria or cyanotoxic organisms may further comprise at least one additional agent capable of detecting one or more CYR polynucleotide and/or CYR polypeptide sequences as disclosed herein, or a variant or fragment thereof.

The CYR polynucleotide may comprise a polynucleotide comprising a sequence selected from the group consisting of: SEQ ID NO: 80, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and variants and fragments thereof.

Alternatively, the CYR polynucleotide may comprise a ribonucleic acid or complementary DNA encoded by a sequence selected from the group consisting of: SEQ ID NO: 80, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and variants and fragments thereof.

The CYR polypeptide may comprise a polypeptide comprising a sequence selected from the group consisting of: SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and SEQ ID NO: 110, and variants and fragments thereof.

The at least one additional agent may be selected, for example, from the group consisting of primers, antibodies and probes. A suitable primer or probe may comprise a sequence selected from the group consisting of SEQ ID NO: 111, SEQ ID NO: 112, and variants and fragments thereof.

In another aspect, the invention provides a kit for the detection of cyanobacteria, the kit comprising at least one agent for detecting the presence the presence of one or more CYR polynucleotides or polypeptides as disclosed herein, or a variant or fragment thereof.

The CYR polynucleotide may comprise a sequence selected from the group consisting of SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and variants and fragments thereof.

Alternatively, the CYR polynucleotide may be an RNA or cDNA encoded by a sequence selected from the group consisting of SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and variants and fragments thereof.

The CYR polypeptide may comprise a sequence selected from the group consisting of SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and SEQ ID NO: 110, and variants or fragments thereof.

In certain embodiments of the invention, the kits for detecting cyanobacteria comprising one or more agents for the detection of CYR sequences or variants or fragments thereof, may further comprise at least one additional agent capable of detecting one or more of the SXT polynucleotides and/or SXT polypeptides disclosed herein, or variants or fragments thereof.

The SXT polynucleotide may comprise a sequence selected from the group consisting of SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof.

Alternatively, the SXT polynucleotide may be an RNA or cDNA encoded by a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO:

34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof and/or polypeptides as disclosed herein, or a variant or fragment thereof.

The at least one agent may be any suitable reagent for the detection of CYR polynucleotides and/or polypeptides disclosed herein. For example, the agent may be a primer, an antibody or a probe. By way of exemplification only, the primers or probes may comprise a sequence selected from the group consisting of SEQ ID NO: 111, SEQ ID NO: 112, and variants and fragments thereof.

Also provided is a kit for the detection of dinoflagellates, the kit comprising at least one agent for detecting the presence one or more SXT polynucleotides or polypeptides as disclosed herein, or a variant or fragment thereof.

The SXT polynucleotide may comprise a sequence selected from the group consisting of SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof.

Alternatively, the SXT polynucleotide may be an RNA or cDNA encoded by a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, and variants and fragments thereof and/or polypeptides as disclosed herein, or a variant or fragment thereof.

The SXT polypeptide may comprise an amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and variants and fragments thereof.

In general, the kits of the invention may comprise any number of additional components. By way of non-limiting examples the additional components may include, reagents for cell culture, reference samples, buffers, labels, and written instructions for performing the detection assay.

Methods of Screening

The polypeptides and polynucleotides of the present invention, and fragments and analogues thereof are useful for the screening and identification of compounds and agents that interact with these molecules. In particular, desirable compounds are those that modulate the activity of these polypeptides and polynucleotides. Such compounds may exert a modulatory effect by activating, stimulating, increasing, inhibiting or preventing expression or activity of the polypeptides and/or polynucleotides. Suitable compounds may exert their effect by virtue of either a direct (for example binding) or indirect interaction.

Compounds which bind, or otherwise interact with the polypeptides and polynucleotides of the invention, and specifically compounds which modulate their activity, may be identified by a variety of suitable methods. Non limiting methods include the two-hybrid method, co-immunoprecipitation, affinity purification, mass spectroscopy, tandem affinity purification, phage display, label transfer, DNA microarrays/gene coexpression and protein microarrays.

For example, a two-hybrid assay may be used to determine whether a candidate agent or plurality of candidate agents interacts or binds with a polypeptide of the invention or a variant or fragment thereof. The yeast two-hybrid assay system is a yeast-based genetic assay typically used for detecting protein-protein interactions (Fields and Song., *Nature* 340: 245-246 (1989)). The assay makes use of the multi-domain nature of transcriptional activators. For example, the DNA-binding domain of a known transcriptional activator may be fused to a polypeptide of the invention or a variant or fragment thereof, and the activation domain of the transcriptional activator fused to the candidate agent. Interaction between the candidate agent and the polypeptide of the invention or a variant or fragment thereof, will bring the DNA-binding and activation domains of the transcriptional activator into close proximity. Subsequent transcription of a specific reporter gene activated by the transcriptional activator allows the detection of an interaction.

In a modification of the technique above, a fusion protein may be constructed by fusing the polypeptide of the invention or a variant or fragment thereof to a detectable tag, for example alkaline phosphatase, and using a modified form of immunoprecipitation as described by Flanagan and Leder (Flanagan and Leder, *Cell* 63:185-194 (1990))

Alternatively, co-immunoprecipation may be used to determine whether a candidate agent or plurality of candidate agents interacts or binds with polypeptide of the invention or a variant or fragment thereof. Using this technique, cyanotoxic organisms, cyanobacteria and/or dinoflagellates may be lysed under nondenaturing conditions suitable for the preservation of protein-protein interactions. The resulting solution can then be incubated with an antibody specific for a polypeptide of the invention or a variant or fragment thereof and immunoprecipitated from the bulk solution, for example by capture with an antibody-binding protein attached to a solid support. Immunoprecipitation of the polypeptide of the invention or a variant or fragment thereof by this method facilitates the co-immunoprecipation of an agent associated with that protein. The identification an associated agent can be established using a number of methods known in the art, including but not limited to SDS-PAGE, western blotting, and mass spectrometry.

Alternatively, the phage display method may be used to determine whether a candidate agent or plurality of candidate agents interacts or binds with a polypeptide of the invention or a variant or fragment thereof. Phage display is a test to screen for protein interactions by integrating multiple genes from a gene bank into phage. Under this method, recombinant DNA techniques are used to express numerous genes as fusions with the coat protein of a bacteriophage such the peptide or protein product of each gene is displayed on the surface of the viral particle. A whole library of phage-displayed peptides or protein products of interest can be produced in this way. The resulting libraries of phage-displayed peptides or protein products may then be screened for the ability to bind a polypeptide of the invention or a variant or fragment thereof. DNA extracted from interacting phage contains the sequences of interacting proteins.

Alternatively, affinity chromatography may be used to determine whether a candidate agent or plurality of candidate agents interacts or binds with a polypeptide of the invention or a variant or fragment thereof. For example, a polypeptide of the invention or a variant or fragment thereof, may be immobilised on a support (such as sepharose) and cell lysates passed over the column. Proteins binding to the immobilised polypeptide of the invention or a variant or fragment thereof may then be eluted from the column and identified, for example by N-terminal amino acid sequencing.

Potential modulators of the activity of the polypeptides of the invention may be generated for screening by the above methods by a number of techniques known to those skilled in the art. For example, methods such as X-ray crystallography and nuclear magnetic resonance spectroscopy may be used to model the structure of polypeptide of the invention or a variant or fragment thereof, thus facilitating the design of potential modulating agents using computer-based modeling. Various forms of combinatorial chemistry may also be used to generate putative modulators.

Polypeptides of the invention and appropriate variants or fragments thereof can be used in high-throughput screens to assay candidate compounds for the ability to bind to, or otherwise interact therewith. These candidate compounds can be further screened against functional polypeptides to determine the effect of the compound on polypeptide activity.

The present invention also contemplates compounds which may exert their modulatory effect on polypeptides of the invention by altering expression of the polypeptide. In this case, such compounds may be identified by comparing the level of expression of the polypeptide in the presence of a candidate compound with the level of expression in the absence of the candidate compound.

It will be appreciated that the methods described above are merely examples of the types of methods that may be utilised to identify agents that are capable of interacting with, or modulating the activity of polypeptides of the invention or variants or fragments thereof. Other suitable methods will be known by persons skilled in the art and are within the scope of this invention.

Using the methods described above, an agent may be identified that is an agonist of a polypeptide of the invention or a variant or fragment thereof. Agents which are agonists enhance one or more of the biological activities of the polypeptide. Alternatively, the methods described above may identify an agent that is an antagonist of a polypeptide of the invention or a variant or fragment thereof. Agents which are antagonists retard one or more of the biological activities of the polypeptide.

Antibodies may act as agonists or antagonists of a polypeptide of the invention or a variant or fragment thereof. Preferably suitable antibodies are prepared from discrete regions or fragments of the polypeptides of the invention or variants or fragments thereof. An antigenic portion of a polynucleotide of interest may be of any appropriate length, such as from about 5 to about 15 amino acids. Preferably, an antigenic portion contains at least about 5, 6, 7, 8, 9, 10, 11, 12, 13 or 14 amino acid residues.

Methods for the generation of suitable antibodies will be readily appreciated by those skilled in the art. For example, monoclonal antibody specific for a polypeptide of the invention or a variant or fragment thereof typically containing Fab portions, may be prepared using hybridoma technology described in *Antibodies-A Laboratory Manual*, Harlow and Lane, eds., Cold Spring Harbor Laboratory, N.Y. (1988).

In essence, in the preparation of monoclonal antibodies directed toward polypeptide of the invention or a variant or fragment thereof, any technique that provides for the production of antibody molecules by continuous cell lines in culture may be used. These include the hybridoma technique originally developed by Kohler et al., *Nature,* 256:495-497 (1975), as well as the trioma technique, the human B-cell hybridoma technique (Kozbor et al., *Immunology Today,* 4:72 (1983)), and the EBV-hybridoma technique to produce human monoclonal antibodies (Cole et al., in Monoclonal Antibodies and Cancer Therapy, pp. 77-96, Alan R. Liss, Inc., (1985)). Immortal, antibody-producing cell lines can be created by techniques other than fusion, such as direct transformation of B lymphocytes with oncogenic DNA, or transfection with Epstein-Barr virus. See, for example, M. Schreier et al., "*Hybridoma Techniques*" Cold Spring Harbor Laboratory, (1980); Hammerling et al., "*Monoclonal Antibodies and T-cell Hybridomas*" Elsevier/North-Holland Biochemical Press, Amsterdam (1981); and Kennett et al., "*Monoclonal Antibodies*", Plenum Press (1980).

In brief, a means of producing a hybridoma from which the monoclonal antibody is produced, a myeloma or other self-perpetuating cell line is fused with lymphocytes obtained from the spleen of a mammal hyperimmunised with a recognition factor-binding portion thereof, or recognition factor, or an origin-specific DNA-binding portion thereof. Hybridomas producing a monoclonal antibody useful in practicing this invention are identified by their ability to immunoreact with the present recognition factors and their ability to inhibit specified transcriptional activity in target cells.

A monoclonal antibody useful in practicing the invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Similarly, there are various procedures known in the art which may be used for the production of polyclonal antibodies. For the production of polyclonal antibodies against a polypeptide of the invention or a variant or fragment thereof, various host animals can be immunized by injection with a polypeptide of the invention, or a variant or fragment thereof, including but not limited to rabbits, chickens, mice, rats, sheep, goats, etc. Further, the polypeptide variant or fragment thereof can be conjugated to an immunogenic carrier (e.g., bovine serum albumin (BSA) or keyhole limpet hemocyanin (KLH)). Also, various adjuvants may be used to increase the immunological response, including but not limited to Freund's (complete and incomplete), mineral gels such as aluminium hydroxide, surface active substances such as rysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and Immunoelectrophoresis assays, and the like (see, for example, Ausubel et al., Current Protocols in Molecular Biology, Vol. 1, John Wiley & Sons, Inc., New York (1994)). Antibody binding may be detected by virtue of a detectable label on the primary antibody. Alternatively, the antibody may be detected by virtue of its binding with a secondary antibody or reagent which is appropriately labelled. A variety of methods are known in the art for detecting binding in an immunoassay and are included in the scope of the present invention.

The antibody (or fragment thereof) raised against a polypeptide of the invention or a variant or fragment thereof, has binding affinity for that protein. Preferably, the antibody (or fragment thereof) has binding affinity or avidity greater than about $10^5M^{-1}$, more preferably greater than about $10^6$ $M^{-1}$, more preferably still greater than about $10^7$ $M^{-1}$ and most preferably greater than about $10^8$ $M^{-1}$.

In terms of obtaining a suitable amount of an antibody according to the present invention, one may manufacture the antibody(s) using batch fermentation with serum free medium. After fermentation the antibody may be purified via a multistep procedure incorporating chromatography and viral inactivation/removal steps. For instance, the antibody may be first separated by Protein A affinity chromatography and then treated with solvent/detergent to inactivate any lipid enveloped viruses. Further purification, typically by anion and cation exchange chromatography may be used to remove residual proteins, solvents/detergents and nucleic acids. The purified antibody may be further purified and formulated into 0.9% saline using gel filtration columns. The formulated bulk preparation may then be sterilised and viral filtered and dispensed.

Embodiments of the invention may utilise antisense technology to inhibit the expression of a nucleic acid of the invention or a fragment or variant thereof by blocking translation of the encoded polypeptide. Antisense technology takes advantage of the fact that nucleic acids pair with complementary sequences. Suitable antisense molecules can be manufactured by chemical synthesis or, in the case of antisense RNA, by transcription in vitro or in vivo when linked to a promoter, by methods known to those skilled in the art.

For example, antisense oligonucleotides, typically of 18-30 nucleotides in length, may be generated which are at least substantially complementary across their length to a region of the nucleotide sequence of the polynucleotide of interest. Binding of the antisense oligonucleotide to their complementary cellular nucleotide sequences may interfere with transcription, RNA processing, transport, translation and/or mRNA stability. Suitable antisense oligonucleotides may be prepared by methods well known to those of skill in the art and may be designed to target and bind to regulatory regions of the nucleotide sequence or to coding (gene) or non-coding (intergenic region) sequences. Typically antisense oligonucleotides will be synthesized on automated synthesizers. Suitable antisense oligonucleotides may include modifications designed to improve their delivery into cells, their stability once inside a cell, and/or their binding to the appropriate target. For example, the antisense oligonucleotide may be modified by the addition of one or more phosphorothioate linkages, or the inclusion of one or morpholine rings into the backbone (so-called 'morpholino' oligonucleotides).

An alternative antisense technology, known as RNA interference (RNAi), may be used, according to known methods in the art (see for example WO 99/49029 and WO 01/70949), to inhibit the expression of a polynucleotide. RNAi refers to a means of selective post-transcriptional gene silencing by destruction of specific mRNA by small interfering RNA molecules (siRNA). The siRNA is generated by cleavage of double stranded RNA, where one strand is identical to the message to be inactivated. Double-stranded RNA molecules may be synthesised in which one strand is identical to a specific region of the p53 mRNA transcript and introduced directly. Alternatively corresponding dsDNA can be employed, which, once presented intracellularly is converted into dsRNA. Methods for the synthesis of suitable molecule for use in RNAi and for achieving post-transcriptional gene silencing are known to those of skill in the art.

A further means of inhibiting expression may be achieved by introducing catalytic antisense nucleic acid constructs, such as ribozymes, which are capable of cleaving mRNA transcripts and thereby preventing the production of wild type protein. Ribozymes are targeted to and anneal with a particular sequence by virtue of two regions of sequence complementarity to the target flanking the ribozyme catalytic site. After binding the ribozyme cleaves the target in a site-specific manner. The design and testing of ribozymes which specifically recognise and cleave sequences of interest can be achieved by techniques well known to those in the art (see for example Lieber and Strauss, 1995, *Molecular and Cellular Biology,* 15:540-551.

The invention will now be described with reference to specific examples, which should not be construed as in any way limiting the scope of the invention.

EXAMPLES

The invention will now be described with reference to specific examples, which should not be construed as in any way limiting the scope of the invention.

Example 1: Cyanobacterial Cultures and Characterisation of the SXT Gene Cluster Cyanobacterial strains used in the present study (FIG. 1) were grown in Jaworski medium in static batch culture at 26° C. under continuous illumination (10 μmol $m^{-2}$ $s^{-1}$). Total genomic DNA was extracted from cyanobacterial cells by lysozyme/SDS/proteinase K lysis following phenol-chloroform extraction as described in Neilan, B. A. 1995. Appl Environ Microbiol 61:2286-2291. DNA in the supernatant was precipitated with 2 volumes −20° C. ethanol, washed with 70% ethanol, dissolved in TE-buffer (10:1), and stored at −20° C. PCR primer sequences used for the amplification of sxt ORFs are shown in FIG. 1B).

PCR amplicons were separated by agarose gel electrophoresis in TAE buffer (40 mM Tris-acetate, 1 mM EDTA, pH 7.8), and visualised by UV translumination after staining in ethidium bromide (0.5 μg/ml). Sequencing of unknown regions of DNA was performed by adaptor-mediated PCR as described in Moffitt et al. (2004) Appl. Environ. Microbiol.

70:6353-6362. Automated DNA sequencing was performed using the PRISM Big Dye cycle sequencing system and a model 373 sequencer (Applied Biosystems). Sequence data were analysed using ABI Prism-Autoassembler software, and percentage similarity and identity to other translated sequences determined using BLAST in conjunction with the National Center for Biotechnology Information (NIH), Fugue blast was used to identify distant homologs via sequence-structure comparisons. The sxt gene clusters were assembled using the software Phred, Phrap, and Consed, and open reading frames manually identified. GenBank accession numbers for the sxt gene cluster from *C. raciborskii* T3 is DQ787200.

Example 2: Mass Spectrometric Analysis of SXT Intermediates

Bacterial extracts and SXT standards were analysed by HPLC (Thermo Finnigan Surveyor HPLC and autosampler) coupled to an ion trap mass spectrometer (Thermo Finnigan LCQ Deca XP Plus) fitted with an electrospray source. Separation of analytes was obtained on a 2.1 mm×150 mm Phenomenex Luna 3 micron C18 column at 100 mL/min. Analysis was performed using a gradient starting at 5% acetonitrile in 10 mM heptafluorobutyric acid (HFBA) This was maintained for 10 min, then ramped to 100% acetonitrile, over 30 min. Conditions were held at 100% acetonitrile for 10 min to wash the column and then returned to 5% acetonitrile in 10 mM HFBA and again held for 10 min to equilibrate the column for the next sample. This resulted in a runtime of 60 min per sample. Sample volumes of 10-100 mL were injected for each analysis. The HPLC eluate directly entered the electrospray source, which was programmed as follows: electrospray voltage 5 kV, sheath gas flow rate 30 arbitrary units, auxiliary gas flow rate 5 arbitrary units. The capillary temperature was 200° C. and had a voltage of 47 V. Ion optics were optimised for maximum sensitivity before sample analysis using the instruments autotune function with a standard toxin solution. Mass spectra were acquired in the centroid mode over the m/z range 145-650. Mass range setting was 'normal', with 200 ms maximum ion injection time and automatic gain control (AGC) on. Tandem mass spectra were obtained over a m/z range relevant to the precursor ion. Collision energy was typically 20-30 ThermoFinnigan arbitrary units, and was optimised for maximal information using standards where available.

Example 3: Identification and Sequencing of the SXT Gene Cluster in *Cylindrospermopsis raciborskii* T3

O-carbamoyltransferase was initially detected in *C. raciborskii* T3 via degenerate PCR, and later named sxtI. Further investigation showed that homologues of sxtI were exclusively present in SXT toxin-producing strains of four cyanobacterial genera (Table 1), thus representing a good candidate gene in SXT toxin biosynthesis. The sequence of the complete putative SXT biosynthetic gene cluster (sxt) was then obtained by genome walking up- and downstream of sxtI in *C. raciborskii* T3 (FIG. 3). In *C. raciborskii* T3, this sxt gene cluster spans approximately 35000 bp, encoding 31 open reading frames (FIG. 2). The cluster also included other genes encoding SXT-biosynthesis enzymes, including a methyltransferase (sxtA1), a class II aminotransferase (sxtA4), an amidinotransferase (sxtG), dioxygenases (sxtH), in addition to the Ocarbamoyltransferase (sxtI). PCR screening of selected sxt open reading frames in toxic and non-toxic cyanobacteria strains showed that they were exclusively present in SXT toxin-producing isolates (FIG. 1A), indicating the association of these genes with the toxic phenotype. In the following passages we describe the open reading frames in the putative sxt gene cluster and their predicted functions, based on bioinformatic analysis, LCMS/MS data on biosynthetic intermediates and in vitro biosynthesis, when applicable.

Example 4: Functional Prediction of the Parent Molecule SXT Biosynthetic Genes

Bioinformatic analysis of the sxt gene cluster revealed that it contains a previously undescribed example of a polyketide synthase (PKS) like structure, named sxtA. SxtA possesses four catalytic domains, SxtA1 to SxtA4. An iterated PSI-blast search revealed low sequence homology of SxtA1 to S-adenosylmethionine (SAM)-dependent methyltransferases. Further analysis revealed the presence of three conserved sequence motifs in SxtA1 (278-ITD-MGCGDG-286, 359-DPENILHI-366, and 424-VVNKH-GLMIL-433) that are specific for SAMdependent methyltransferases. SxtA2 is related to GCN5-related N-acetyl transferases (GNAT). GNAT catalyse the transfer of acetate from acetyl-CoA to various heteroatoms, and have been reported in association with other unconventional PKSs, such as PedI, where they load the acyl carrier protein (ACP) with acetate. SxtA3 is related to an ACP, and provides a phosphopantetheinyl-attachment site. SxtA4 is homologous to class II aminotransferases and was most similar to 8-amino-7-oxononanoate synthase (AONS). Class II aminotransferases are a monophyletic group of pyridoxal phosphate (PLP)-dependent enzymes, and the only enzymes that are known to perform Claisen-condensations of amino acids. We therefore reasoned that sxtA performs the first step in SXT biosynthesis, involving a Claisen-condensation.

Figure 4:
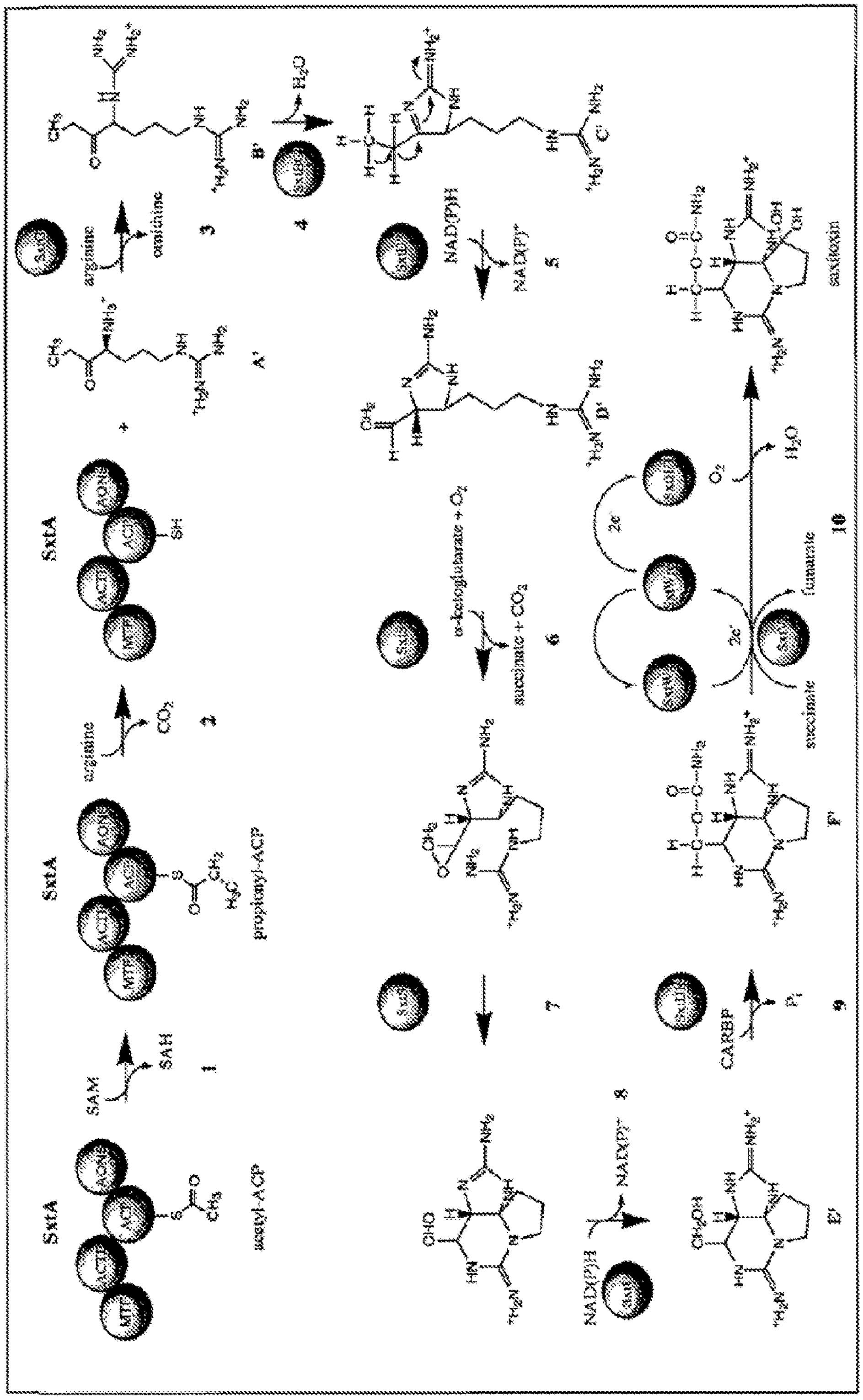
FIG. 4 is a flow diagram showing the pathway for SXT biosynthesis and the putative functions of sxt genes.
Figure 5A:
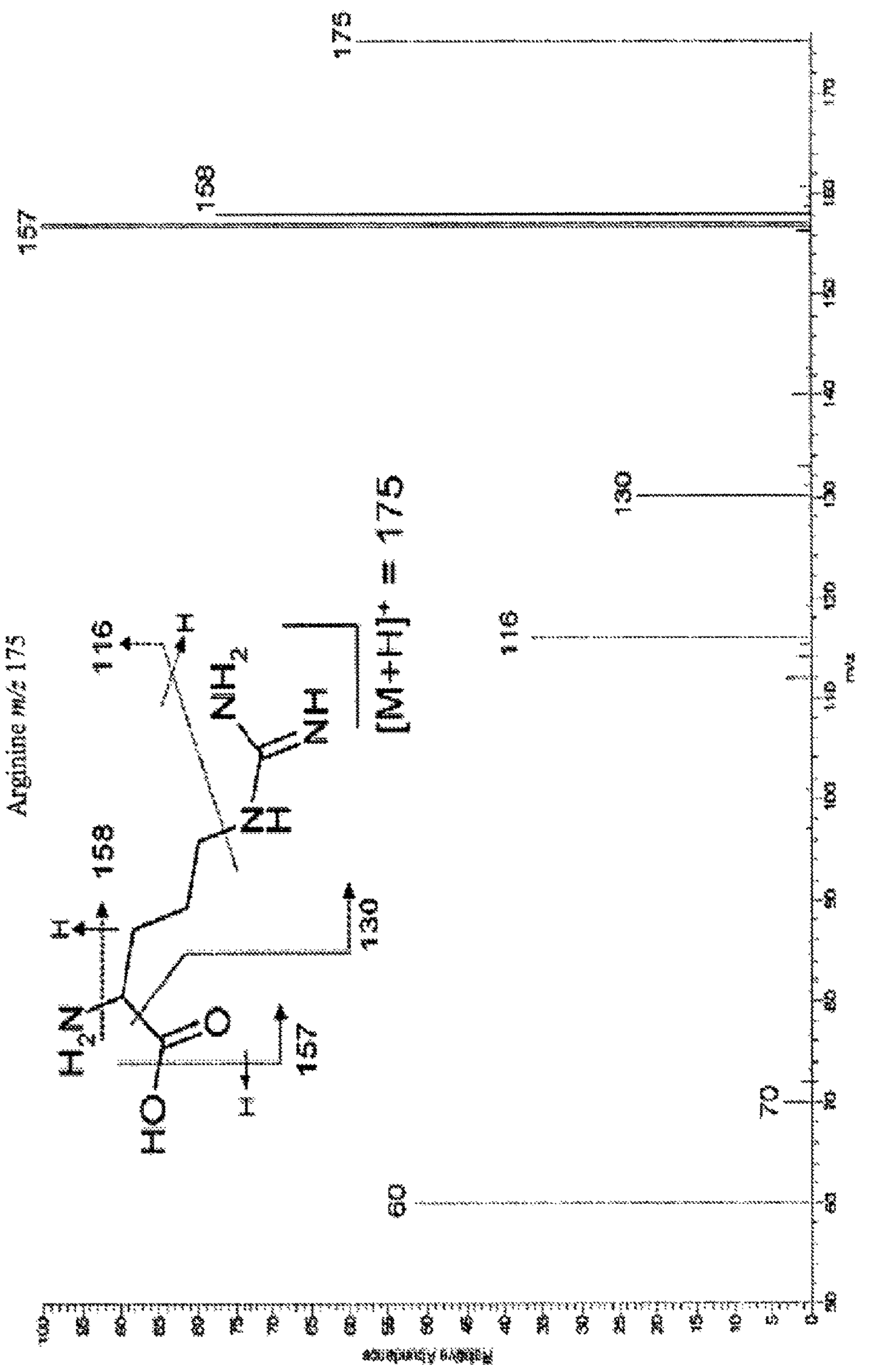
FIGS. 5A, 5B, 5C, 5D and 5E show MS/MS spectra of selected ions from cellular extracts of *Cylindrospermopsis raciborskii* T3. The predicted fragmentation of ions and the corresponding m/z values are indicated.
Figure 5B:
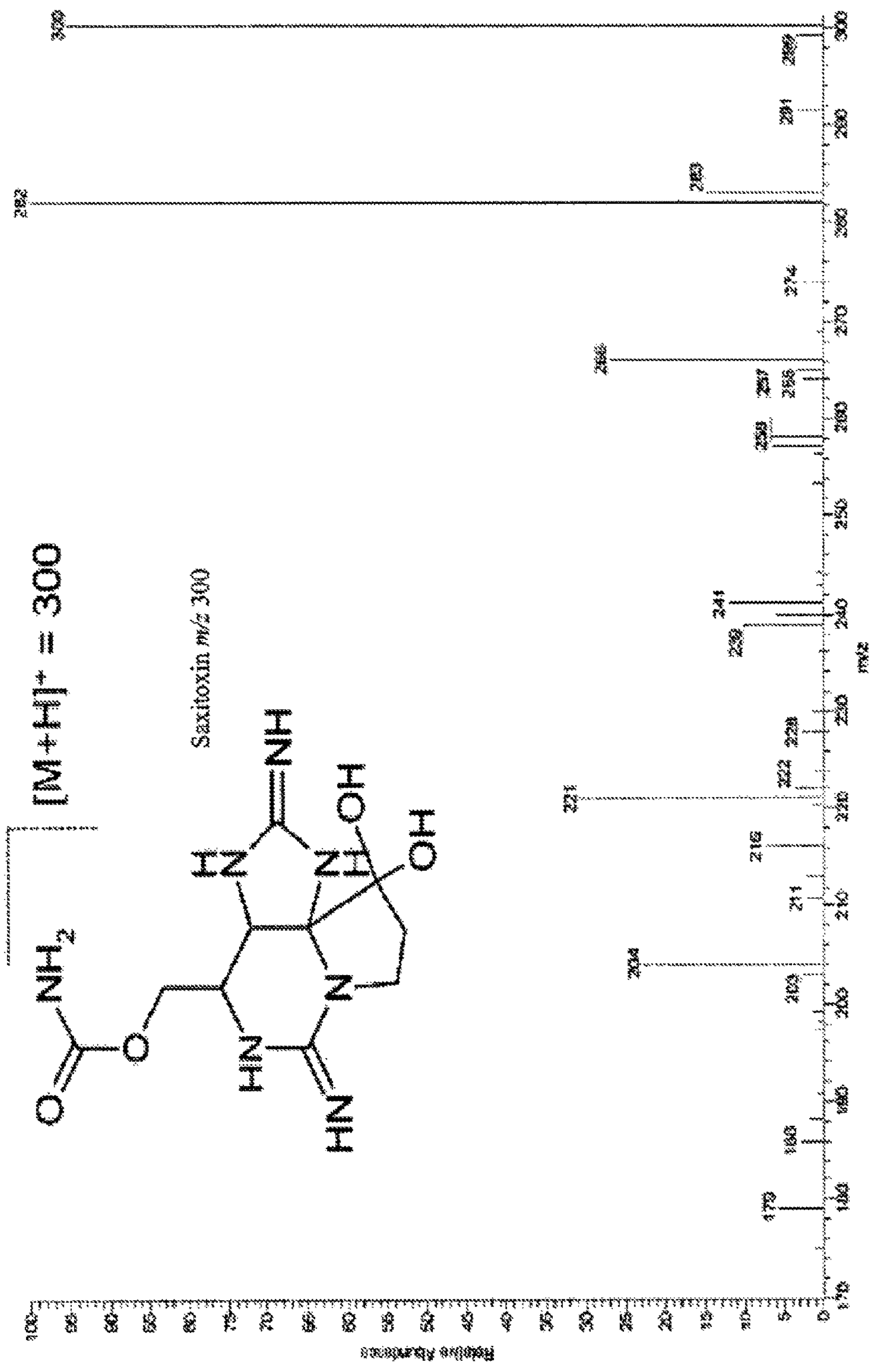
Figure 5C:
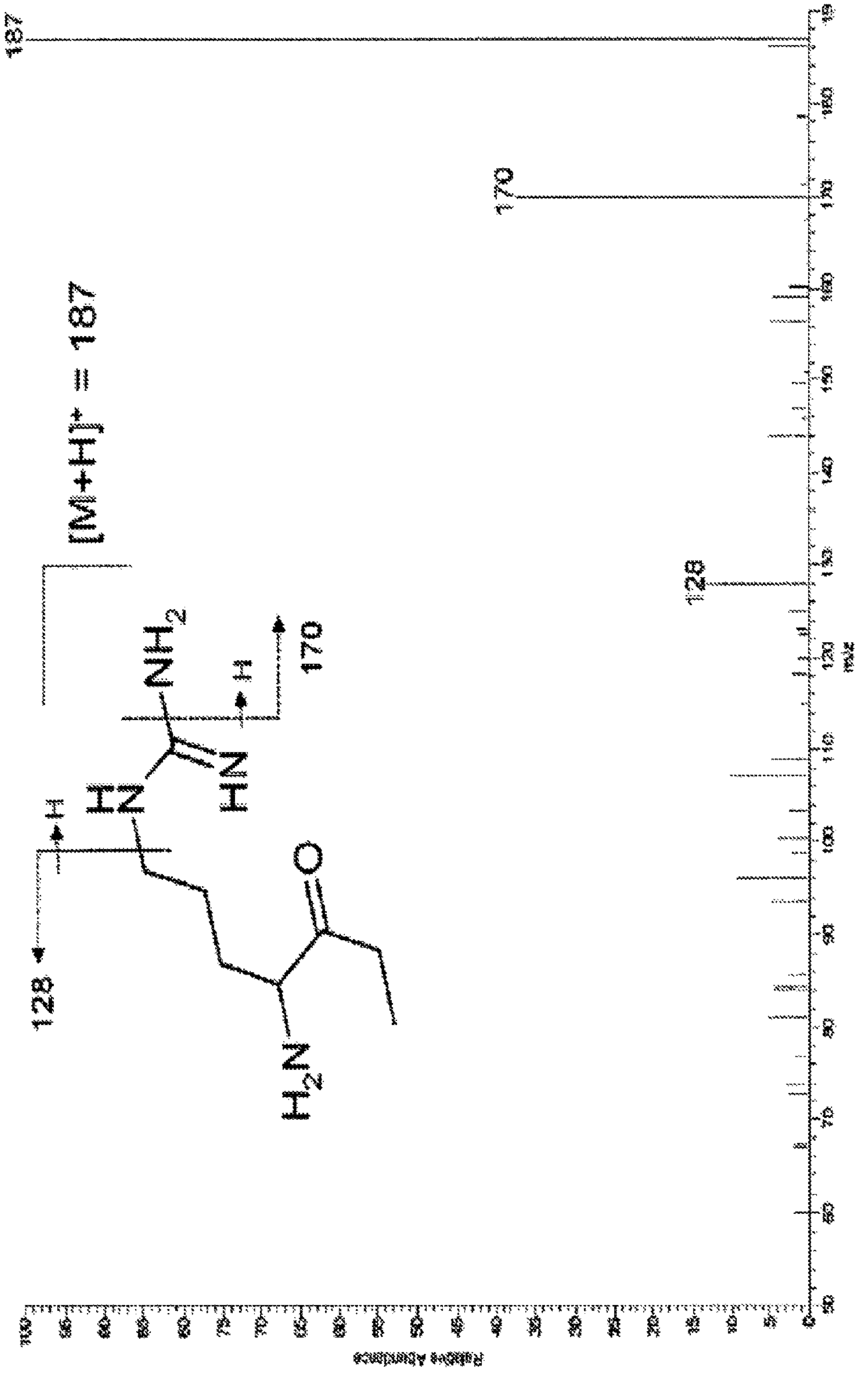
Figure 5D:
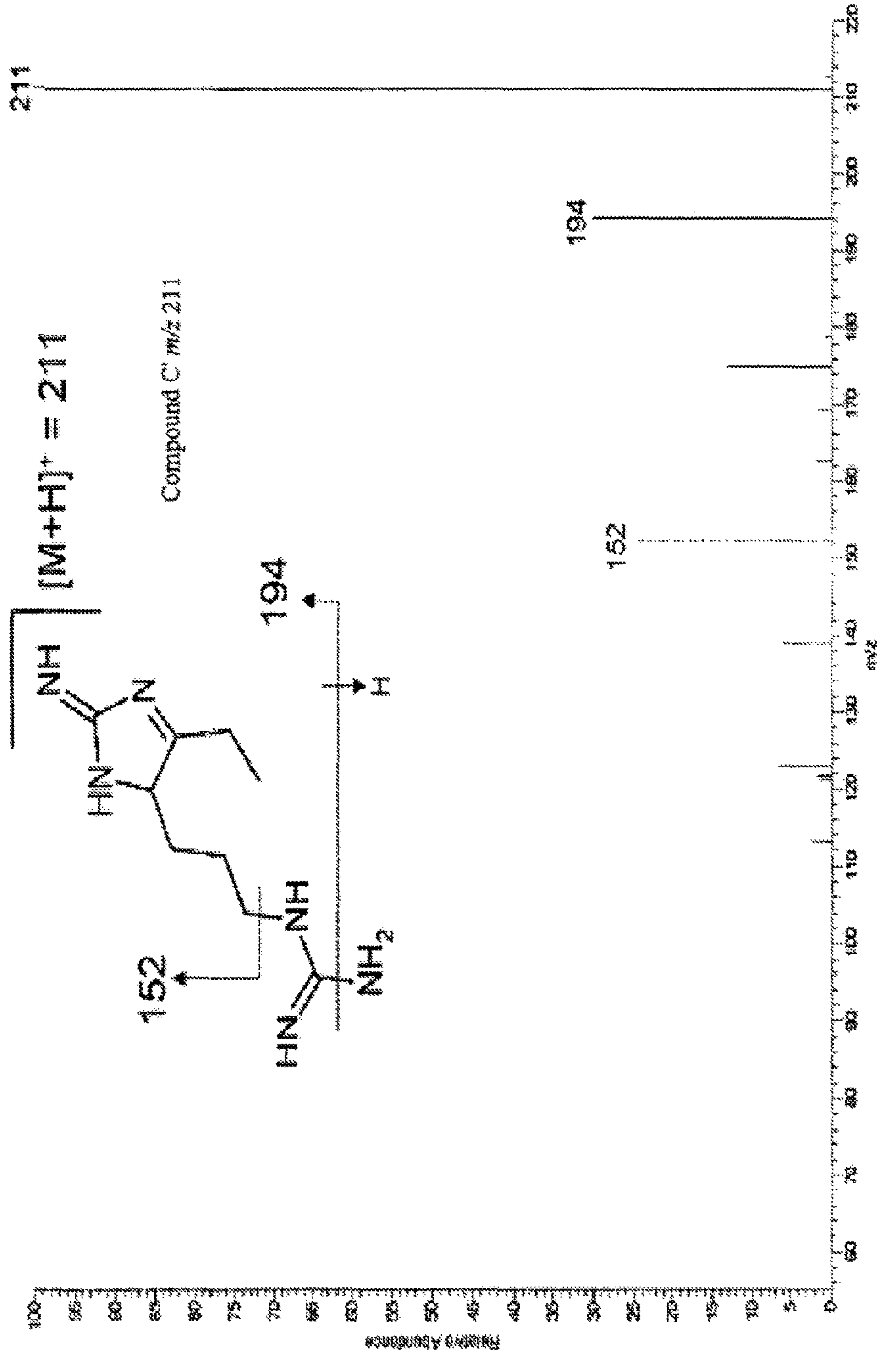
Figure 5E:
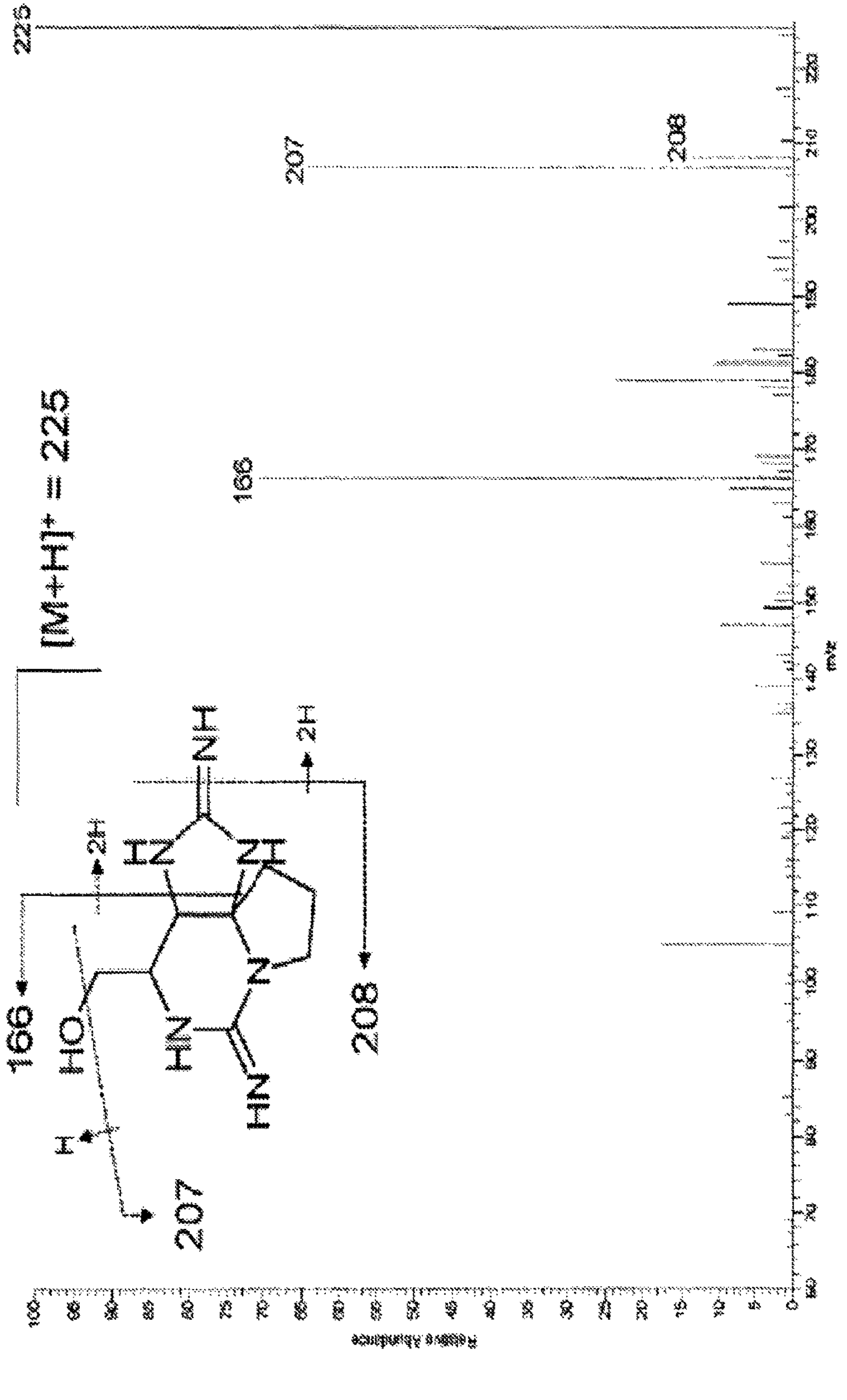

The predicted reaction sequence of SxtA, based on its primary structure, is the loading of the ACP (SxtA3) with acetate from acetyl-CoA, followed by the SxtA1-catalysed methylation of acetyl-ACP, converting it to propionyl-ACP. The class II aminotransferase domain, SxtA4, would then perform a Claisen-condensation between propionyl-ACP and arginine (FIG. 4). The putative product of SxtA is thus 4-amino-3-oxoguanidinoheptane which is here designated as Compound A', (FIG. 4). To verify this pathway for SXT biosynthesis based on comparative gene sequence analysis, cell extracts of *C. raciborskii* T3 were screened by LC-MS/MS for the presence of compound A' (FIG. 5) as well as arginine and SXT as controls. Arginine and SXT were readily detected (FIG. 5) and produced the expected fragment ions. On the other hand, LC-MS/MS data obtained from m/z 187 was consistent with the presence of structure A from *C. raciborskii* T3 (FIG. 5). MS/MS spectra showed the expected fragment ion (m/z 170, m/z 128) after the loss of ammonia and guanidine from A'. LC-MS/MS data strongly supported the predicted function of SxtA and thus a revised initiating reaction in the SXT biosynthesis pathway.

sxtG encodes a putative amidinotransferase, which had the highest amino acid sequence similarity to L-arginine: lysine amidinotransferases. It is proposed that the product of SxtA is the substrate for the amidinotransferase SxtG, which transfers an amidino group from arginine to the a-amino group A' (FIG. 4), thus producing 4,7-diguanidino-3-oxoheptane designated compound B' (FIG. 3). This hypothetical sequence of reactions was also supported by the detection of C' by LC-MS/MS (FIG. 4). Cell extracts from *C. raciborskii* T3, however, did not contain any measurable levels of B' (4,7-diguanidino-3-oxoheptane). A likely explanation for the failure to detect the intermediate B' is its rapid cyclisation to form C' via the action of SxtB.

The sxt gene cluster encodes an enzyme, sxtB, similar to the cytidine deaminase-like enzymes from g-proteobacteria. The catalytic mechanism of cytidine deaminase is a retro-aldol cleavage of ammonia from cytidine, which is the same reaction mechanism in the reverse direction as the formation of the first heterocycle in the conversion from B' to C' (FIG. 4). It is therefore suggested that SxtB catalyses this retroaldol-like condensation (step 4, FIG. 4).

The incorporation of methionine methyl into SXT, and its hydroxylation was studied. Only one methionine methyl-derived hydrogen is retained in SXT, and a 1,2-H shift has been observed between acetate-derived C-5 and C-6 of SXT. Hydroxylation of the methyl side-chain of the SXT precursor proceeds via epoxidation of a double-bond between the SAM-derived methyl group and the acetate derived C-6. This incorporation pattern may result from an electrophilic attack of methionine methyl on the double bond between C-5 and C-6, which would have formed during the preceding cyclisation. Subsequently, the new methylene side-chain would be epoxidated, followed by opening to an aldehyde, and subsequent reduction to a hydroxyl. Retention of only one methionine methyl-derived hydrogen, the 1,2-H shift between C-5 and C-6, and the lacking 1,2-H shift between C-1 and C-5 is entirely consistent with the results of this study, whereby the introduction of methionine methyl precedes the formation of the three heterocycles.

sxtD encodes an enzyme with sequence similarity to sterol desaturase and is the only candidate desaturase present in the sxt gene cluster, SxtD is predicted to introduce a double bond between C-1 and C-5 of C', and cause a 1,2-H shift between C-5 and C-6 (compound D', FIG. 3). The gene product of sxtS has sequence homology to non-heme iron 2-oxoglutaratedependent (2OG) dioxygenases. These are multifunctional enzymes that can perform hydroxylation, epoxidation, desaturation, cyclisation, and expansion reactions. 2OG dioxygenases have been reported to catalyse the oxidative formation of heterocycles. SxtS could therefore perform the consecutive epoxidation of the new double bond, and opening of the epoxide to an aldehyde with concomitant bicyclisation. This explains the retention of only one methionine methyl-derived hydrogen, and the lack of a 1,2-H shift between C-1 and C-5 of SXT (steps 5 to 7, FIG. 4). SxtU has sequence similarity to short-chain alcohol dehydrogenases. The most similar enzyme with a known function is clavaldehyde dehydrogenase (AAF86624), which reduces the terminal aldehyde of clavulanate-9-aldehyde to an alcohol. SxtU is therefore predicted to reduce the terminal aldehyde group of the SXT precursor in step 8 (FIG. 4), forming compound E'.

The concerted action of SxtD, SxtS and SxtU is therefore the hydroxylation and bicyclisation of compound C' to E' (FIG. 4). In support for this proposed pathway of SXT biosynthesis, LC-MS/MS obtained from m/z 211 and m/z 225 allowed the detection of compounds C' and E' from *C. raciborskii* T3 (FIG. 5). On the other hand, no evidence could be found by LC-MS/MS for intermediates B (m/z 216), and C (m/z 198). MS/MS spectra showed the expected fragment ions after the loss of ammonia and guanidine from C', as well as the loss of water in the case of E'.

The detection of E' indicated that the final reactions leading to the complete SXT molecule are the O-carbamoylation of its free hydroxyl group and a oxidation of C-12. The actual sequence of these final reactions, however, remains uncertain. The gene product of sxtI is most similar to a predicted Ocarbamoyltransferase from *Trichodesmium erythraeum* (accession ABG50968) and other predicted O-carbamoyltransferases from cyanobacteria. O-carbamoyltransferases invariably transfer a carbamoyl group from carbamoylphosphate to a free hydroxyl group. Our data indicate that SxtI may catalyse the transfer of a carbamoyl group from carbamoylphosphate to the free hydroxy group of E'. Homologues of sxtJ and sxtK with a known function were not found in the databases, however it was noted that sxtJ and sxtK homologues were often encoded adjacent to O-carbamoyltransferase genes.

The sxt gene cluster contains two genes, sxtH and sxtT, each encoding a terminal oxygenase subunit of bacterial phenyl-propionate and related ring-hydroxylating dioxygenases. The closest homologue with a predicted function was capreomycidine hydroxylase from *Streptomyces vinaceus*, which hydroxylates a ringcarbon (C-6) of capreomycidine. SxtH and SxtT may therefore perform a similar function in SXT biosynthesis, that is, the oxidation or hydroxylation and oxidation of C-12, converting F' into SXT.

Members belonging to bacterial phenylpropionate and related ring-hydroxylating dioxygenases are multi-component enzymes, as they require an oxygenase reductase for their regeneration after each catalytic cycle. The sxt gene cluster provides a putative electron transport system, which would fulfill this function. sxtV encodes a 4Fe-4S ferredoxin with high sequence homology to a ferredoxin from *Nostoc punctiforme*. sxtW was most similar to fumarate reductase/succinate dehydrogenase-like enzymes from *A. variabilis* and *Nostoc punctiforme*, followed by AsfA from *Pseudomonas putida*. AsfA and AsfB are enzymes involved in the transport of electrons resulting from the catabolism of aryl sulfonates. SxtV could putatively extract an electron pair from succinate, converting it to fumarate, and then transfer the electrons via ferredoxin (SxtW) to SxtH and SxtT.

Example 5: Comparative Sequence Analysis and Functional Assignment of SXT Tailoring Genes Following synthesis of the parent molecule SXT, modifying enzymes introduce various functional groups. In addition to SXT, *C. raciborskii* T3 produces N-1 hydroxylated (neoSXT), decarbamoylated (dcSXT), and N-sulfurylated (GTX-5) toxins, whereas *A. circinalis* AWQC131C produces decarbamoylated (dcSXT), O-sulfurylated (GTX-3/2, dcGTX-3/2), as well as both O- and N-sulfurylated toxins (C-1/2), but no N-1 hydroxylated toxins.

sxtX encodes an enzyme with homology to cephalosporin hydroxylase. sxtX was only detected in *C. raciborskii* T3, *A. flos-aquae* NH-5, and *Lyngbya wollei*, which produce N-1 hydroxylated analogues of SXT, such as neoSXT. This component of the gene cluster was not present in any strain of *A. circinalis*, and therefore probably the reason why this species does not produce N-1 hydroxylated PSP toxins (FIG. 1A). The predicted function of SxtX is therefore the N-1 hydroxylation of SXT.

*A. circinalis* AWQC131C and *C. raciborskii* T3 also produces N- and O-sulfated analogues of SXT (GTX-5, C-2/3, (dc)GTX-3/4). The activity of two 3'-phosphate 5'-phosphosulfate (PAPS)-dependent sulfotransferases, which were specific for the N-21 of SXT and GTX-3/2, and O-22 of 11-hydroxy SXT, respectively, has been described from the SXT toxin-producing dinoflagellate *Gymnodinium catenatum*. The sxt gene cluster from *C. raciborskii* T3 encodes a putative sulfotransferase, SxtN. A PSI-BLAST search with SxtN identified only 25 hypothetical proteins of unknown function with an E value above the threshold (0.005). A profile library search, however, revealed significant structural relatedness of SxtN to estrogen sulfotransferase (1AQU) (Z-score=24.02) and other sulfotransferases. SxtN has a conserved N-terminal region, which corresponds to the adenosine 3'-phosphate 5'-phosphosulfate (PAPS) binding region in 1AQU. It is not known, however, whether SxtN transfers a sulfate group to N-21 or O-22. Interestingly, the sxt gene cluster encodes an adenylylsulfate kinase (APSK), SxtO, homologues of which are involved in the formation of PAPS (FIG. 2). APKS phosphorylates the product of ATPsulfurylase, adenylylsulfate, converting it to PAPS. Other biosynthetic gene clusters that result in sulfated secondary metabolites also contain genes required for the production of PAPS.

Decarbamoylated analogues of SXT could be produced via either of two hypothetical scenarios. Enzymes that act downstream of the carbamoyltransferase, SxtI, in the biosynthesis of PSP toxins are proposed to have broad substrate specificity, processing both carbamoylated and decarbamoylated precursors of SXT. Alternatively, hydrolytic cleavage of the carbamoyl moiety from SXT or its precursors may occur. SxtL is related to GDSL-lipases, which are multifunctional enzymes with thioesterase, arylesterase, protease and lysophospholipase activities. The function of SxtL could therefore include the hydrolytic cleavage of the carbamoyl group from SXT analogues.

Example 6: Cluster-Associated SXT Genes Involved in Metabolite Transport sxtF and sxtM encoded two proteins with high sequence similarity to sodium-driven multidrug and toxic compound extrusion (MATE) proteins of the NorM family. Members of the NorM family of MATE proteins are bacterial sodium-driven antiporters, that export cationic substances. All of the PSP toxins are cationic substances, except for the C-toxins which are zwitterionic. It is therefore probable that SxtF and SxtM are also involved in the export of PSP toxins. A mutational study of NorM from *V. parahaematolyticus* identified three conserved negatively charged residues (D32, E251, and D367) that confer substrate specificity, however the mechanism of substrate recognition remains unknown. In SxtF, the residue corresponding to E251 of NorM is conserved, whereas those corresponding to D32 and D367 are replaced by the neutral amino acids asparagine and tyrosine, respectively. Residues corresponding to D32 and E251 are conserved in SxtM, but D367 is replaced by histidine. The changes in substrate-binding residues may reflect the differences in PSP toxin substrates transported by these proteins.

Example 7: Putative Transcriptional Regulators of Saxitoxin Synthase

Environmental factors, such as nitrogen and phosphate availability have been reported to regulate the production of PSP toxins in dinoflagellates and cyanobacteria. Two transcriptional factors, sxtY and sxtZ, related to PhoU and OmpR, respectively, as well as a two component regulator histidine kinase were identified proximal to the 3'-end of the sxt gene cluster in *C. raciborskii* T3. PhoU-related proteins are negative regulators of phosphate uptake whereas OmpR-like proteins are involved in the regulation of a variety of metabolisms, including nitrogen and osmotic balance. It is therefore likely that PSP toxin production in *C. raciborskii* T3 is regulated at the transcriptional level in response to the availability of phosphate, as well as, other environmental factors.

Example 8: Phylogenetic Origins of the SXT Genes

The sxt gene cluster from *C. raciborskii* T3 has a true mosaic structure. Approximately half of the sxt genes of *C. raciborskii* T3 were most similar to counterparts from other cyanobacteria, however the remaining genes had their closest matches with homologues from proteobacteria, actinomycetes, sphingobacteria, and firmicutes. There is an increasing body of evidence that horizontal gene transfer (HGT) is a major driving force behind the evolution of prokaryotic genomes, and cyanobacterial genomes are known to be greatly affected by HGT, often involving transposases and phages. The fact that the majority of sxt genes are most closely related to homologues from other cyanobacteria, suggests that SXT biosynthesis may have evolved in an ancestral cyanobacterium that successively acquired the remaining genes from other bacteria via HGT. The structural organisation of the investigated sxt gene cluster, as well as the presence of several transposases related to the IS4-family, suggests that small cassettes of sxt genes are mobile.

Example 9: Cyanobacterial Cultures and Characterisation of the CYR Gene Cluster Cyanobacterial strains were grown in Jaworski medium as described in Example 1 above. Total genomic DNA was extracted from cyanobacterial cells by lysozyme/SDS/proteinase K lysis following phenol-chloroform extraction as described previously Neilan, B. A. 1995. Appl Environ Microbiol 61:2286-2291. DNA in the supernatant was precipitated with 2 volumes −20° C. ethanol, washed with 70% ethanol, dissolved in TE-buffer (10:1), and stored at −20° C.

Characterization of unknown regions of DNA flanking the putative cylindrospermopsin biosynthesis genes was performed using an adaptor-mediated PCR as described in Moffitt et al. (2004) Appl. Environ. Microbiol. 70:6353-6362. PCRs were performed in 20 μl reaction volumes containing 1×Taq polymerase buffer 2.5 mM $MgCl_2$, 0.2 mM deoxynucleotide triphosphates, 10 pmol each of the forward and reverse primers, between 10 and 100 ng genomic DNA and 0.2 U of Taq polymerase (Fischer Biotech, Australia). Thermal cycling was performed in a GeneAmp PCR System 2400 Thermal cycler (Perkin Elmer Corporation, Norwalk, Conn.). Cycling began with a denaturing step at 94° C. for 3 min followed by 30 cycles of denaturation at 94° C. for 10 s, primer annealing between 55° and 65° C. for 20 s and a DNA strand extension at 72° C. for 1-3 min. Amplification was completed by a final extension step at 72° C. for 7 min. Amplified DNA was separated by agarose gel electrophoresis in TAE buffer (40 mM Tris-acetate, 1 mM EDTA, pH 7.8), and visualized by UV transillumination after staining with ethidium bromide (0.5 μg/ml).

Automated DNA sequencing was performed using the PRISM Big Dye cycle sequencing system and a model 373 sequencer (Applied Biosystems, Foster City, Calif.). Sequence data were analyzed using ABI Prism-Autoassembler software, while identity/similarity values to other translated sequences were determined using BLAST in conjunction with the National Center for Biotechnology Information (NIH, Bethesda, Md.). Fugue blast was used to identify distant homologs via sequence-structure comparisons. The gene clusters were assembled using the software Phred, Phrap, and Consed, open reading frames were manually identified. Polyketide synthase and non-ribosomal peptide synthetase domains were determined using the specialized databases based on crystal structures.

Example 10: Genetic Screening of Cylindrospermopsin-Producing and Non-Producing Cyanobacterial Strains Cylindrospermopsin-producing and non-producing cyanobacterial strains were screened for the presence of the sulfotransferase gene cyrJ using the primer set cynsulfF (5' ACTTCTCTCCTTTCCCTATC 3') (SEQ ID NO: 111) and cylnamR (5' GAGTGAAAATGCGTAGAACTTG 3') (SEQ ID NO: 112). Genomic DNA was tested for positive amplification using the 16S rRNA gene primers 27F and 809 as described in Neilan et al. (1997) Int. J. Syst. Bacteriol. 47:693-697. Amplicons were sequenced, as described in Example 9 above, to verify the identity of the gene fragment.

The biosynthesis of cylindrospermopsin involves an amidinotransferase, a NRPS, and a PKS (AoaA, AoaB and AoaC, respectively). In order to obtain the entire sequence of the cylindrospermopsin biosynthesis gene cluster, we used adaptor-mediated ‘gene-walking’ technology, initiating the process from a partial sequence of the amidinotransferase gene from *C. raciborskii* AWT205. Successive outward facing primers were designed and the entire gene cluster spanning 43 kb was sequenced, together with a further 3.5 kb on either side of the toxin gene cluster.

These flanking regions encode putative accessory genes (hyp genes), which include molecular chaperons involved in the maturation of hydrogenases. Due to the fact that these genes are flanking the cylindrospermopsin gene cluster at both ends, we postulate that the toxin gene cluster was inserted into this area of the genome thus interrupting the HYP gene cluster. This genetic rearrangement is mechanistically supported by the presence of transposase-like sequences within the cylindrospermopsin cluster.

Bioinformatic analysis of the toxin gene cluster was performed and based on gene function inference using sequence alignments (NCBI BLAST), predicted structural homologies (Fugue Blast), and analysis of PKS and NRPS domains using specialized blast servers based on crystal structures. The cylindrospermopsin biosynthesis cluster contains 15 ORFs, which encode all the functions required for the biosynthesis, regulation and export of the toxin cylindrospermopsin (FIG. 6).

Example 11: Formation of the CYR Carbon Skeleton

Figure 8:
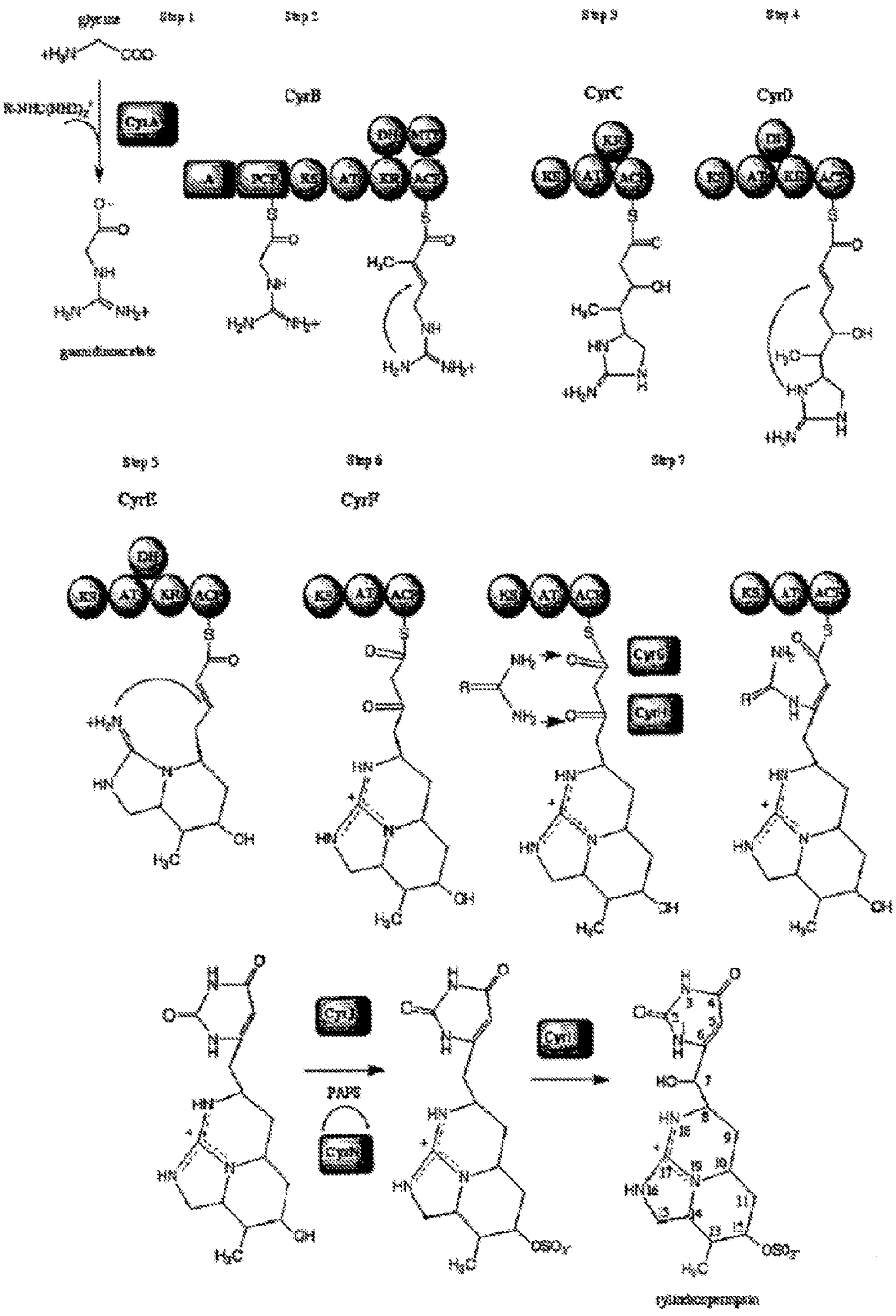
FIG. 8 is a flow diagram showing the biosynthetic pathway of cylindrospermopsin biosynthesis.
Figure 9:
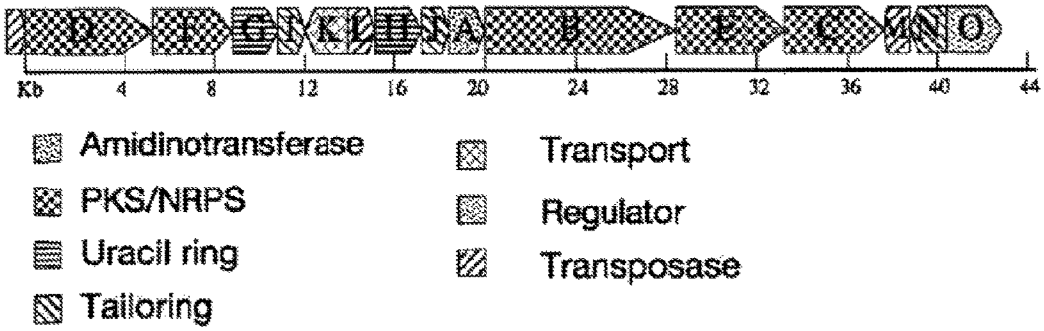
FIG. 9 is a diagram showing the structural organization of the cylindrospermopsin gene cluster from *C. raciborskii* AWT205. Scale indicates gene cluster length in base pairs.

The first step in formation of the carbon skeleton of cylindrospermopsin involves the synthesis of guanidinoacetate via transamidination of glycine. CyrA, the AoaA homolog, which encodes an amidinotransferase similar to the human arginine:glycine amidinotransferase GATM, transfers a guanidino group from a donor molecule, most likely arginine, onto an acceptor molecule of glycine thus forming guanidinoacetate (FIG. 8, step 1).

The next step (FIG. 8, step 2) in the biosynthesis is carried out by CyrB (AoaB homolog), a mixed NRPS-PKS. CyrB spans 8.7 kb and encodes the following domains; adenylation domain (A domain) and a peptidyl carrier protein (PCP) of an NRPS followed by a βketosynthase domain (KS), acyltransferase domain (AT), dehydratase domain (DH), methyltransferase domain (MT), ketoreductase domain (KR), and an acyl carrier protein (ACP) of PKS origin. CyrB therefore must catalyse the second reaction since it is the only gene containing an A domain that could recruit a starter unit for subsequent PKS extensions. The specific amino acid activated by the CyrB A domain cannot be predicted as its substrate specificity conferring residues do not match any in the available databases. So far, no other NRPS has been described that utilizes guanidinoacetate as a substrate. The A domain is thought to activate guanidinoacetate, which is then transferred via the swinging arm of the peptidyl carrier protein (PCP) to the KS domain. The AT domain activates malonyl-CoA and attaches it to the ACP. This is followed by a condensation reaction between the activated guanidinoacetate and malonyl-CoA in the KS domain. CyrB contains two reducing modules, KR and DH. Their concerted reaction reduces the keto group to a hydroxyl followed by elimination of $H_2O$, resulting in a double bond between C13 and C14. The methyl transferase (MT) domain identified in CyrB via the NRPS/PKS databases (Example 9 above), is homologous to S-adenosylmethionine (SAM) dependent MT. It is therefore suggested that the MT methylates C13. It is proposed that a nucleophilic attack of the amidino group at N19 onto the newly formed double bond between C13 and C14 occurs via a ‘Michael addition’. The cyclization follows Baldwin’s rules for ring closure (Baldwin et al. (1997) J. Org. Chem 42; 3846-3852), resulting in the formation of the first ring in cylindrospermopsin. This reaction could be spontaneous and may not require enzymatic catalysis, as it is energetically favourable. This is the first of three ring formations.

The third step (FIG. 8, step 3) in the biosynthesis involves CyrC (AoaC homolog), which encodes a PKS with KS, AT, KR, and ACP domains. The action of these domains results in the elongation of the growing chain by an acetate via activation of malonyl-CoA by the AT domain, its transfer to ACP and condensation at the KS domain with the product of CyrB. The elongated chain is bound to the ACP of CyrC and the KR domain reduces the keto group to a hydroxyl group on C12. The PKS module carrying out this step contains a KR domain and does not contain a DH domain, this corresponds only to CyrC.

Following the catalysis of enzyme CyrC is CyrD (FIG. 8, step 4), a PKS with five modules; KS, AT, DH, KR, and an ACP. The action of this PKS module on the product of CyrC results in the addition of one acetate and the reduction of the keto group on C10 to a hydroxyl and dehydration to a double bond between C9 and C10. This double bond is the site of a nucleophilic attack by the amidino group N19 via another Michael addition that again follows Baldwin’s rules of ring closure, resulting in the formation of the second ring, the first 6-membered ring made in cylindrospermopsin.

The product of CyrD is the substrate for CyrE (step 5 in FIG. 8), a PKS containing a KS, AT, DH, KR domains and an ACP. Since this sequence of domains is identical to that of CyrD, it is not possible at this stage to ascertain which PKS acts first, but as their action is proposed to be identical it is immaterial at this point. CyrE catalyzes the addition of one acetate and the formation of a double bond between C7 and C8. This double bond is attacked by N18 via a Michael addition and the third cyclisation occurs, resulting in the second 6-member ring.

CyrF is the final PKS module (step 6 of FIG. 8) and is a minimal PKS containing only a KS, AT, and ACP. CyrF acts on the product of CyrE and elongates the chain by an acetate, leaving C4 and C6 unreduced.

Step 7 in the pathway (FIG. 8) involves the formation of the uracil ring, a reaction that is required for the toxicity of the final cylindrospermopsin compound. The cylindrospermopsin gene cluster encodes two enzymes with high sequence similarity (87%) that have been denoted CyrG and CyrH. A Psi-blast search (NCBI) followed by a Fugue profile library search (see materials and methods) revealed that CyrG and CyrH are most similar to the enzyme family of amidohydrolases/ureases/dihydroorotases, whose members catalyze the formation and cleavage of N—C bonds. It is proposed that these enzymes transfer a second guanidino group from a donor molecule, such as arginine or urea, onto C6 and C4 of cylindrospermopsin resulting in the formation of the uracil ring. These enzymes carry out two or three reactions depending on the guanidino donor. The first reaction consists of the formation of a covalent bond between the N of the guanidino donor and C6 of cylindrospermopsin followed by an elimination of $H_2O$ forming a double bond between C5 and C6. The second reaction catalyses the formation of a bond between the second N on the guanidino donor and C4 of cylindrospermopsin, co-committently with the breaking of the thioester bond between the acyl carrier protein of CyrE and cylindrospermopsin, causing the release of the molecule from the enzyme complex. Feeding experiments with labeled acetate have shown that the oxygen at C4 is of acetate origin and is not lost during biosynthesis, therefore requiring the de novo formation of the uracil ring. The third reaction—if required—would catalyze the cleavage of the guanidino group from a donor molecule other than urea. The action of CyrG and CyrH in the formation of the uracil ring in cylindrospermopsin describes a novel biosynthesis pathway of a pyrimidine.

One theory suggest a linear polyketide which readily assumes a favorable conformation for the formation of the rings. Cyclization may thus be spontaneous and not under enzymatic control. These analyses show that this may happen step-wise, with successive ring formation of the appropriate intermediate as it is synthesized. This mechanism also explains the lack of a thioesterase or cyclization domain, which are usually associated with NRPS/PKS modules and catalyze the release and cyclization of the final product from the enzyme complex.

Example 12: CYR Tailoring Reactions

Cylindrospermopsin biosynthesis requires the action of tailoring enzymes in order to complete the biosynthesis, catalyzing the sulfation at C12 and hydroxylation at C7. Analysis of the cylindrospermopsin gene cluster revealed three candidate enzymes for the tailoring reactions involved in the biosynthesis of cylindrospermopsin, namely CyrI, CyrJ, and CyrN. The sulfation of cylindrospermopsin at C12 is likely to be carried out by the action of a sulfotransferase. CyrJ encodes a protein that is most similar to human 3'-phosphoadenylyl sulfate (PAPS) dependent sulfotransferases. The cylindrospermopsin gene cluster also encodes an adenylsulfate kinase (ASK), namely CyrN. ASKs are enzymes that catalyze the formation of PAPS, which is the sulfate donor for sulfotransferases. It is proposed that CyrJ sulfates cylindrospermopsin at C12 while CyrN creates the pool of PAPS required for this reaction. Screening of cylindrospermopsin producing and non-producing strains revealed that the sulfotransferase genes were only present in cylindrospermopsin producing strains, further affirming the involvement of this entire cluster in the biosynthesis of cylindrospermopsin (FIG. 7). The cyrJ gene might therefore be a good candidate for a toxin probe, as it is more unique than NRPS and PKS genes and would presumably have less cross-reactivity with other gene clusters containing these genes, which are common in cyanobacteria. The final tailoring reaction is carried out by CyrI. A Fugue search and an iterated Psi-Blast revealed that CyrI is similar to a hydroxylase belonging to the 2-oxoglutarate and Fe(II)-dependent oxygenase superfamily, which includes the mammalian Prolyl 4-hydroxylase alpha subunit that catalyze the hydroxylation of collagen. It is proposed that CyrI catalyzes the hydroxylation of C7, a residue that, along with the uracil ring, seems to confer much of the toxicity of cylindrospermopsin. The hydroxylation at C7 by CyrI is probably the final step in the biosynthesis of cylindrospermopsin.

Example 13: CYR Toxin Transport

Cylindrospermopsin and other cyanobacterial toxins appear to be exported out of the producing cells. The cylindrospermopsin gene cluster contains an ORF denoted CyrK, the product of which is most similar to sodium ion driven multi-drug and toxic compound extrusion proteins (MATE) of the NorM family. It is postulated that CyrK is a transporter for cylindrospermopsin, based on this homology and its central location in the cluster. Heterologous expression and characterization of the protein are currently being undertaken to verify its putative role in cylindrospermopsin export.

Example 14: Transcriptional Regulation of the Toxin Gene Cluster

Cylindrospermopsin production has been shown to be highest when fixed nitrogen is eliminated from the growth media (Saker et al. (1999) J. Phycol 35:599-606). Flanking the cylindrospermopsin gene cluster are "hyp" gene homologs involved in the maturation of hydrogenases. In the cyanobacterium Nostoc PCC73102 they are under the regulation of the global nitrogen regulator NtcA, that activates transcription of nitrogen assimilation genes. It is plausible that the cylindrospermopsin gene cluster is under the same regulation, as it is located wholly within the "hyp" gene cluster in *C. raciborskii* AWT205, and no obvious promoter region in the cylindrospermopsin gene cluster could be identified.

Finally, the cylindrospermopsin cluster also includes an ORF at its 3'-end designated CyrO. By homology, it encodes a hypothetical protein that appears to possess an ATP binding cassette, and is similar to WD repeat proteins, which have diverse regulatory and signal transduction roles. CyrO may also have a role in transcriptional regulation and DNA binding. It also shows homology to AAA family proteins that often perform chaperone-like functions and assist in the assembly, operation, or disassembly of protein complexes. Further insights into the role of CyrO are hindered due to low sequence homology with other proteins in databases.

The foregoing describes preferred forms of the present invention. It is to be understood that the present invention should not be restricted to the particular embodiment(s) shown above. Modifications and variations, obvious to those skilled in the art can be made thereto without departing from the scope of the present invention.

We claim:

1. A method for detecting cyanobacteria in a sample, the method comprising: (a) obtaining a sample for use in the method; and (b) detecting in the sample the presence of: (i) a polynucleotide comprising the sequence of SEQ ID NO: 14 and fragments of SEQ ID NO: 14 and variants having at least 90% sequence identity with SEQ ID NO: 14, wherein the fragment comprises a SXT open reading frame or (ii) complementary DNA (cDNA) encoded by the sequence of (i), and (c) amplifying said cDNA and/or polynucleotide of (i) and/or (ii) from the sample and detecting the amplified sequences.

2. A method for detecting cyanotoxic organisms in a sample, the method comprising: (a) obtaining a sample for use in the method; and (b) detecting in the sample the presence of: (i) a polynucleotide comprising the sequence of SEQ ID NO: 14 and fragments of SEQ ID NO: 14 and variants having at least 90% sequence identity with SEQ ID NO: 14, wherein the fragment comprises an open reading frame, or (ii) a cDNA encoded by the sequence according to (i), amplifying said cDNA and/or polynucleotide of (i) and/or (ii) from the sample by polymerase chain and detecting the amplified sequences.

3. The method according to claim 2, wherein said cyanotoxic organism is a cyanobacteria or a dinoflagellate.

4. The method according to any of claims 1-3, wherein said amplifying utilizes primers comprising a sequence selected from the group consisting of SEQ ID NO: 70 and SEQ ID NO: 71 and fragments thereof wherein the fragments are about 15 nucleotides to about 30 nucleotides in length.

5. The method according to claim any one of claims 1-3 or 4, further comprising detecting the presence of: (i) a polynucleotide comprising SEQ ID NO: 95, and fragments thereof wherein the fragments comprise a CYR open reading frame; or (ii) a ribonucleic acid or cDNA encoded by the sequence according to (i), or (iii) a polypeptide comprising the sequence of: SEQ ID NO: 96 and fragments thereof wherein the fragments are between about 5 amino acids to about 780 amino acids in length; or (iv) a polypeptide comprising the sequence of SEQ ID NO: 15 and fragments thereof wherein the fragments are between about 5 amino acids to about 1000 amino acids in length.

6. The method according to claim 5, wherein said detecting of the polynucleotides of (i) or the cDNA of (ii) comprises amplification of said polynucleotides or cDNA.

7. The method according to claim 6, wherein said polymerase chain reaction utilizes one or more primers comprising a sequence selected from the group consisting of SEQ ID NO: 111, SEQ ID NO: 112, and variants that have at least 90% sequence identity with SEQ ID NO: 111, or SEQ ID NO: 112 and fragments thereof wherein the fragments are 15 nucleotides to 22 nucleotides in length.

8. A method for detecting dinoflagellates in a sample, the method comprising: (a) obtaining a sample for use in the method and (b) detecting in the sample the presence of (i) a polynucleotide comprising the sequence of SEQ ID NO: 14 and variants having at least 90% sequence identity with SEQ ID NO: 14 and fragments thereof wherein the fragments comprise a SXT open reading frame, (ii) cDNA encoded by the sequence of part (i), (iii) amplifying the DNA from the sample and detecting the amplified sequences.

9. The method according to any one of claims 1-3 or 8, wherein said sample comprises one or more isolated or cultured organisms.

10. The method according to any one of claims 1-3 or 8 wherein said sample is an environmental sample.

11. The method according to claim 10, wherein said environmental sample is derived from salt water, fresh water or a blue-green algal bloom.

12. The method of claim 1, wherein the primers may be optionally labelled or the amplified products may be optionally labelled.

13. The method of claim 2, wherein the primers may be optionally labelled or the amplified products may be optionally labelled.

14. The method of claim 8, wherein the primers may be optionally labelled or the amplified products may be optionally labelled.

15. The method according to claim 1, further comprising detecting in the sample the presence of one or more of a polynucleotide comprising a sequence selected from the group consisting of SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68.

16. The method according to claim 2, further comprising detecting in the sample the presence of one or more of a polynucleotide comprising a sequence selected from the group consisting of: SEQ ID NO: 20, SEQ ID NO: 22, SEQ ID NO: 24 and SEQ ID NO: 36.

17. The method according to claim 4, wherein said amplifying further utilizes one or more primers comprising a sequence selected from the group consisting of SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ 11) NO: 133, SEQ ID NO: 134, and fragments thereof wherein the fragments are about 15 nucleotides to about 30 nucleotides in length.

18. The method according to claim 5, further comprising detecting the presence of one or more of: (i) a polynucleotide comprising a sequence selected from the group consisting of: SEQ ID NO: 80, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 97, SEQ ID NO: 99, SEQ ID NO: 101, SEQ ID NO: 103, SEQ ID NO: 105, SEQ ID NO: 107, SEQ ID NO: 109, or (ii) a ribonucleic acid or cDNA encoded by a sequence according to (i), or (iii) a polypeptide comprising a sequence selected from the group consisting of: SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 98, SEQ ID NO: 100, SEQ ID NO: 102, SEQ ID NO: 104, SEQ ID NO: 106, SEQ ID NO: 108, and SEQ ID NO:110; or (iv) a polypeptide comprising a sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67 and SEQ ID NO: 69.

19. The method according to claim 8, further comprising detecting in the sample the presence of one or more of a polynucleotide comprising a sequence selected from the group consisting of SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66 and SEQ ID NO: 68.

* * * * *

SEQUENCE LISTING

<160> NUMBER OF SEQ ID NOS: 186

<210> SEQ ID NO 1
<211> LENGTH: 37606
<212> TYPE: DNA
<213> ORGANISM: Cylindrospermopsis raciborskii T3

<400> SEQUENCE: 1

```
atgatcccag ctaaaaaagt ttattttta ttgagtttag caatagttat ttcacccttt     60
ttatccatga ttgtgggtat ttacgaaaat attaaattta gggtattatt tgatttggtg    120
gtcagggcac taatggtggt tgactgcttc aatatcaaaa aacatcgggt caaaattagt    180
cgtcaattac ctctacgttt atctattgga cgtgagaatt tagtaatatt gaaggtagag    240
tctgggaatg tcaatagtgc tattcaaatt cgtgattact atcccacaga atttcccgta    300
tccacatcta acctgatagt taaccttccc cctaatcata ctcaggaagt aaagtacacc    360
attcgaccta atcaacgggg agaattttgg tggggaaata ttcaagttcg acagctggga    420
aattggtctc tagggtggga caattggcaa attccccaaa aaactgtggc taaggtgtat    480
cctgatttgt taggactcag atccctcgct attcgtttaa ccctacaatc ttctggatct    540
atcactaaat tgcgtcaacg gggaatggga acggaatttg ccgaactccg taattactgc    600
atgggggatg atctacggtt aattgattgg aaagctacag ctagacgtgc ttatggaaat    660
ctgagtcccc tagtaagagt tttagagcct caacaggaac aaactctgct tatattatta    720
gatcgtggta gactaatgac agctaatgta caagggttaa aacgatatga ttggggttta    780
aataccacct tgtctttggc attagcagga ttacataggg gcgatcgcgt aggagtaggg    840
gtatttgact cccagctgca tacctggata cctccagagc gaggacaaaa tcatctcaat    900
cggcttatag acagacttac acctattgaa ccagtgttag tggagtctga ttatttaaat    960
gccattacct atgtagtaaa acaacagact cgtagatctc tagtagtgtt aattactgat   1020
ttagtcgatg ttactgcttc ccatgaacta ctagtagcgc tgtgtaaatt agtgcctcga   1080
tatctacctt tttgtgtaac actcagggat cctgggattg ataaaatagc tcataatttt   1140
agtcaagact taacacaggc ttataatcga gcagtttctt tggacttgat atcacaaaga   1200
gaaattgctt ttgctcagtt gaaacaacag ggagttttgg tgttggatgc accagcaaat   1260
caaatttccg agcagttggt agaaaggtac ttacaaatca aagccaaaaa tcagatttga   1320
ctccctgtcg agataattga gaacttctgg aaagaatagc ccaataaact cgacaaagaa   1380
cgtggttaga agttctttaa agagtctatc atgccgaatc atattttaac agaagagcga   1440
tcgctcttcc taagggatag agtctgaaag ccacttcaac ggacgataat gcaactcttg   1500
ttccagctgg agtgcggaga attaccacat ccgaaataga caaaaagaaa taattggagt   1560
taagaagata agtacataaa tagtgataat atacaaaact agtcagcacg gattaaattt   1620
actaatgata gatacaatat cagtactatt aagagagtgg actgtaattt cccttacagg   1680
tttagccttc tggctttggg aaattcgctc tcccttccat caaattgaat acaaagctaa   1740
attcttcaag gaattgggat gggcgggaat atcattcgtc tttagaaatg tttatgcata   1800
tgtttctgtg gcaattataa aactattgag ttctctattt atgggagagt cagcaaattt   1860
tgcaggagta atgtatgtgc ccctctggct gaggatcatc actgcatata tattacagga   1920
cttaactgac tatctattac acaggacaat gcatagtaat cagtttcttt ggttgacgca   1980
caaatggcat cattcaacaa agcaatcatg gtggctgagt ggaaacaaag atagctttac   2040
cggcggactt ttatatactg ttacagcttt gtggtttcca ctgctggaca ttccctcaga   2100
```

ggttatgtct gtagtggcag tacatcaagt gattcataac aattggatac acctcaatgt 2160
aaagtggaac tcctggttag gaataattga atggatttat gttacgcccc gtattcacac 2220
tttgcatcat cttgatacag ggggaagaaa tttgagttct atgtttactt tcatcgaccg 2280
attatttgga acctatgtgt ttccagaaaa ctttgatata gaaaaatcta aaaatagatt 2340
ggatgatcaa tcagtaacgg tgaagacaat tttgggtttt taatagactt gggttctaag 2400
tggaatggac ggaaaaaatg gcggttaccc gcatctttaa tatatcctct ttttggggtt 2460
gagatttgga taaagcggct tgtactctgt cattattcaa atagccatgg cgttgcatat 2520
ttgcgggatg atttaagatt ttctcctaat ttgaaaaatt tctcttgtag gacgattgcg 2580
aagcactcgc gagattgcat tattaataaa accctgatag tcacccccaa cttattgcag 2640
aaaaactttt ttctcttagg taataaatta gtagtttaat tgaaaagcat agcatctctt 2700
ttgacttgga ataacaaaat gtcttacgat gtagtctagc taaatagtga cgcaaacgac 2760
tgttttctcc ctcaactcta gtcattgatg ttttactaat aatttggtct ccatcgggaa 2820
taaattttgg gtaaacttta tagccatccg taatccaaaa ataggatttc caatgctcta 2880
tctttttcca taatttggca aatgttttgg cacttctatc tcccactaca tattgaataa 2940
ttcccgaacg tttgttatct acaactgtcc agacccatat cttgtttttt tttaccaata 3000
aatgtttcca actcatccag ttgacaaact tcaggtgttt gggaattatt attactatct 3060
gataactgac gacctagctt tttgacccaa cgaatgactg tattgtgatt tactttagtc 3120
attctttcaa ttgccctaaa tccattccca tttacataca tggttaaaca tgcttccttt 3180
acttcttggg aataacctct aggagaataa gattcaataa attgacgacc acaattcttg 3240
cattgataat tttgttttcc ccttctctgg ccattttttc taatattatt ggaatcacag 3300
tttgaacagt tcatcttgat ttcttcctcg cggcgatcgc ctgctaaaaa ttcttcccct 3360
tattatacat catcccgtgc aggtgcaacg cccaaatagc catagtttat gatcggtatc 3420
gaattcgcta ttgtttttttc tgccatatcc cttacctaag atgggacgat attcgctcat 3480
aataccactg tcaattagat catcagcaac atggtgagtg tatcctgacg accatcgata 3540
tggccaccaa gatcactagc taccccactg ggcaacaatt cgagtaaaag cgagtagccc 3600
tactgtagca ttgaaaccat ccaagtttga agttaaatac ctaaaattat gacctcattt 3660
tcatttctag acgttcagca acgggcatta actcacgtat cagatcaaag tttcctacgt 3720
tccgtctcat ccagtctaat aagaattttt ctccttcatc tagcttacct ttatcatcaa 3780
caaaaaccat ctgctcgcac caatctacaa atccggaatt agtcatctca tagactaaaa 3840
tgatgggagg aaagtgtgcg aatcccattt tttcaatgac ttccatacaa accagcttaa 3900
atacttgttc gtttgtcaat tcattagaca taaagaattt tcctttaatc aattctgttt 3960
ctaatcctac cacagagtaa taactcttgg tctggaacat aaattattct gtttttatca 4020
atgcgtaagt cataacttat tacttgacgg agttgcaggg gcatacctta acttgacctt 4080
gggagcgata gaagaaagga aggcttcagt gacgggtctt tgactaatcc cagtttccac 4140
ttcaactaaa acagcatcac aaatgtcgaa tagtgattga gaatatctat tcatattcat 4200
gaaagtcaga gcagattcca tcggagacat ggatgaatta aaggcagcgt tttcagcgta 4260
tcgacctgta aatatattcc cgtgggaatc ttttaacgct acccctgcaa aatttttcgt 4320
gtagggagca taactttgat tggcagcgga tagagcagca agcacaacat catcggtaga 4380
ataggtctcc agatcatgaa atactgtttg cattaatcca cctgtgagtc ctagatccgc 4440

-continued

```
tggtccaaat ggctcgggta gaaaatgtgg gagtttattt gaggtataag tttgctcagg   4500
ctgtgattca ttagacttca caagaagaac aaaattttga tttacagttg ccatctcgta   4560
taaaaattgt cggcagtatc cacatggtgc ttcgtggatt gctaatgctt gtaaaccggt   4620
ttctccgtgc aaccacgcat ttatggtggc ggattgttct gcgtgaactg agaaactaag   4680
tgcctgtcct acaaattcca tgtcggcacc aaaataaaga gttccagaac ccagttgatt   4740
cttagattgt ggtttaccaa gagcgatcgc ccctacataa aactgcgata ttggtaccct   4800
agcataagtt gcggctacgg gtagtaattg aatcattaac gtactaatat tagtaccaag   4860
tcgatcaatc caagatgcga caacacttga gtcaattaca gcatgttggg caagaattgt   4920
ccttaactct gattgaatgg aacgtggaac cttggcaatc gcctgttcta atgctacatg   4980
ggtcatttgg gttattcttg gacagagaga taaagatata ttagttttta tgaatcaatt   5040
tcccacttaa tgcttgagta tgttttcctc ctgcttacaa ggcaaagctt tccttttttg   5100
tagcaaatcc caaactgctt tgagagattt aattgcttgg tctatctcct cttcggtatt   5160
ggcggctgta atcgaaaacc ttaaagcact tttatttaaa ggtacgattg gaaaaatagc   5220
aggagtaatt aaaataccat attcccaaag gagttgacac acatcaatca tgtgttgagc   5280
atctcccact aacacgccta cgatgggaac gtaaccatag ttatccactt cgaatccaat   5340
ggctcttgct tgtgtaacca atttgtgagt taggtgataa atttgttttc ttaactgctc   5400
cccctcctga cgattcacct gtaatccggc taaggcactt gccaaactcg caacaggaga   5460
aggaccagaa aatatggcag tccaagcgtt gcggaagttg gttttgatcc ggcgatcgcc   5520
acaagttaag aatgctgcgt aagaagaata ggctttggac aaaccagcta catagatgat   5580
attatcctct gcaaaccgca ggtcaaaata attcaccatc ccgtttcctt tgtaaccgta   5640
aggcatatcg ctgctgggat tttcgcccaa aatgccaaaa ccatgagcat catccatgta   5700
aattaaggca ttgtactctt ttgccagatg cacgtaagct ggcagatcgg gaaaatctgc   5760
cgacatggaa tacacgccat caatgacaat aatctttact tgttcaggcg gatattttgc   5820
tagtttttcg gctaaatcgt tcaaatcatt atgtcgatat tggatgaact gggctccttt   5880
gtgctgagcc agacagcacg cttcataaat acaacgatgt gcagctatgt caccaaagat   5940
gacaccatta ttcccagtta atagtggtaa aattcctatc tgaagcagtg ttacagctgg   6000
aaatactaaa acatcaggta cgcctaaaag tttggacaat tcttcctcca attcctcata   6060
aattgctggg gaagcaacaa gccgagtcca gcttggatgt gtgccccatt tatccaaagc   6120
tggtggaatt gcttccttaa cttttggatg caagtcaaga cctaaatagt tgcaagaagc   6180
aaagtctatc acccaatgtc cgtcaattag caccttgcga ccttgttgtt ctgtgacgac   6240
tcttgtgact tgaggaattt tttgttggtt aactacgttt tccagagtgt tgatttcgtt   6300
ggctgagtca acaggtggag ctagatcaga ttgtttctct tgtaccactt ggttttggaa   6360
ataagtgatg atggcagttg gagtgttctt ttgtaaaaag aacgttccag acagattgat   6420
ccctaaacgt tcctctagga gcgtttgcag ttctaataaa tctaaagaat ctaatcccat   6480
atccagcagt ttttgttgtg gagcgtaggc tgcctgacgt tgggaaccca ttacttttaa   6540
gatgcattct ttaacgagat ccgctacagt tttgttttcc ttagttgcag atgttgcttt   6600
tggtaccaat gaaccaattg ctgagttaat atacggtcct ttgcgatcac caggcgagtg   6660
caaagcactg tcgcgcaggt tatattcaat caaaataccc atgccgagat tatctgtatc   6720
ttccggacga taattagcaa taattcccct aatttcggct cctcccgaca catggaaacc   6780
cacaattgga tccagaagct gtcgttgctc attgtgtagc tttaaatact ccatcatcgg   6840
```

-continued

```
catttgggaa taattgacat aatttcgaca gcgagttaca cccaccacgc tctcaatgcc   6900
gcctttcagg gtacagtagt aaagcataaa gtcccgcaat tcatttccta acccccgcgc   6960
ctgaaactca ggtagaatat ttagtgcgag cagttgaata actgaccctt ggggagtatg   7020
taacgtcggc acttgcgcat attttacatt ctctaatgcc tcagtgctgg taattgtttg   7080
ggaataaatc gcaccaataa tttgatcttc tataatcagc actaaattac cttgcgggtt   7140
tagctcaagt cttcgccgaa tttcatgagt agatgcccgt aaattttctg gccaacactt   7200
gacctccaag tcaactaagg caggtaaatc tgacaaatag gcatgactaa ttttgtaagg   7260
tcttttctcg aagtaattaa gcgtaatgcg agtaaaagga aatgtttttg ggtatctttt   7320
agaaagctct agttttggaa atagacctac ttgtgcagca gacatgagaa aaacctcagc   7380
ttccacaaga tactgctgag aaaatccctg aaacgcatcg aaatgtaagt tttcgctttt   7440
gtctaaaaac tgatagacta cccttggttc caaacaatgg acctccaaaa tcattaaacc   7500
gtgtttattg accacttgag accatctttc taagtgttcc accaaacttt gcaccataac   7560
atgaggagga ataagctctc cttgatcatc gacacagact gattggtaag gtaagtgagc   7620
acgttctttc aattcgtttc ttttctgagg aggaataaag agacgatcat ggtcgaggaa   7680
cgaacggatg tgcaggatat tttcgggatc atgaatgcca tgagcttcta aagaacgcac   7740
catttgttct gggttcccaa tatctccctg taaaactaag tggggaaggc tagcaagggt   7800
gcgtgtggta gcttttaaag aagcttcgtt ataatctaca cctataagac gcaggggata   7860
ctgttcgagt gcttttcccc tagcagactt aaattgaatg gtttcccaga ctcgtttcag   7920
gagagttcca tcgccacacc ccatgtcagt aatgtatttg ggttgttctt ctaatggcaa   7980
ctgattgaat actgagagga tactttcttc taaatcggca aaatatttct ggtgttgaaa   8040
tccactcccg atcacgttaa gggtgcgatc aatgtgcctt tcgtgaccgg aagcatctct   8100
ttggaatacg gagagacaat tgccaaacaa tacatcatga atgcgggaca acataggagt   8160
gtaggacgcc actatggctg tattcaaggc tcgctctccc ataaatcgac caagttcggt   8220
tatggtcaaa cgacctgctg taaggtcagc ccagccaagg tggagaaata acttacccaa   8280
ctcttcttgc actgttgagc ttaatgagga gagcaaaggt ttgtcctccg aatctgcaag   8340
caagttgtgt ttgtgcagtg ccagcaggag tgggatgacc agtaatccat ctaaaaaatc   8400
tgccattagg ggattgtcca ggttccacaa ttggcaagaa cgctcaatcc atcttcccag   8460
caaatttcct tgtttccctt ctaaataaga ctgaattggt aggttgtaca attgaagaat   8520
gtcttccgaa attttgttgt gaatcgctgc ttctgcggtt agagagtatt taagctcctt   8580
atttcgggaa agccaatgta aagactcgag catcctcaaa gcaacttgaa aatgtccgct   8640
gttagctccc agatgttcca ccatttggtt taaagagaga ggactttcat cggcgagtaa   8700
ttcaaaaaca ccttttctc gacacgcaag aataacggga accgccacaa agccgtgagt   8760
ataacgatta atcttttgta acatttagac gattattgat taatttatga ggaatgcatt   8820
tttagtgcat accacgagat tttgattgtc tcagaagttg tgtgaaaaag caagacaagt   8880
agaccaaaaa aataagctaa ataagtgtag tagcaataaa aagacgaatc gcaattgtac   8940
gtgtcttgac taacaagcca agtctctcta gataataatc gccctctacc agttgcgtaa   9000
gtcccattgt tgttttaaac tttaattgct aattaaacag ttatcaaatc ctgttcataa   9060
cggatattta cagcaatttt cggttatata aaattgcata tactgtaagt aatagcagaa   9120
aattaattta ggtaggaaaa tgttgaaaga tttcaaccag tttttaatca gaacactagc   9180
```

-continued

```
attcgtattc gcatttggta ttttcttaac cactggagtt ggcattgcta aagctgacta    9240
cctagttaaa ggtggaaaga ttaccaatgt tcaaaatact tcttctaacg gtgataatta    9300
tgccgttagt atcagcggtg ggtttggtcc ttgcgcagat agagtgatta tcctaccaac    9360
ttcaggagtg ataaatcgag acattcatat gcgtggctat gaagccgcat taactgcact    9420
atccaatggc tttttagtag atatttacga ctatactggc tcttcttgca gcaatggtgg    9480
ccaactaact attaccaacc aattaggtaa gctaatcagc aattaggttg tatcatgata    9540
agatgaagta gtttaaccat ggcaccacca gccaaaaact ttttaacgct agggtgtaac    9600
agttatgggt gtggaatgta ggttgtatcc agtgcatgaa acagccataa ttttagtata    9660
agcaaacact aagattggag aattcatgga aacaacctca aaaaaattta agtcagatct    9720
gatattagaa gcacgagcaa gcctaaagtt gggaatcccc ttagtcattt cacaaatgtg    9780
cgaaacgggt atttatacag cgaatgcagt catgatgggt ttacttggta cgcaagtttt    9840
ggccgccggt gctttgggcg cgctcgcttt tttgacctta ttatttgcct gccatggtat    9900
tctctcagta ggaggatcac tagcagccga agcttttggg gcaaataaaa tagatgaagt    9960
tagtcgtatt gcttccgggc aaatatggct agcagttacc ttgtctttac ctgcaatgct   10020
tctgctttgg catggcgata ctatcttgct gctattcggt caagaggaaa gcaatgtgtt   10080
attgacaaaa acgtatttac actcaatttt atggggcttt cccgctgcgc ttagtatttt   10140
gacattaaga ggcattgcct ctgctctcaa cgttccccga ttgataacta ttactatgct   10200
cactcagctg atattgaata ccgccgccga ttatgtgtta atattcggta aatttggtct   10260
tcctcaactt ggtttggctg gaataggctg ggcaactgct ctgggttttt gggttagttt   10320
tacattgggg cttatcttgc tgattttctc cctgaaagtt agagattata aacttttccg   10380
ctacttgcat cagtttgata aacagatctt tgtcaaaatt tttcaaactg gatggcccat   10440
ggggtttcaa tggggggcgg aaacggcact atttaacgtc accgcttggg tagcagggta   10500
tttaggaacg gtaacattag cagcccatga tattggcttc caaacggcag aactggcgat   10560
ggttatacca ctcggagtcg gcaatgtcgc tatgacaaga gtaggtcaga gtataggaga   10620
aaaaaaccct ttgggtgcaa gaagggtagc atcgattgga attacaatag ttggcattta   10680
tgccagtatt gtagcacttg ttttctggtt gtttccatat caaattgccg gaatttattt   10740
aaatataaac aatcccgaga atatcgaagc aattaagaaa gcaactactt ttatcccctt   10800
ggcgggacta ttccaaatgt tttacagtat tcaaataatt attgttgggg ctttggtcgg   10860
tctgcgggat acatttgttc cagtatcaat gaacttaatt gtctggggtc ttggattggc   10920
aggaagctat ttcatggcaa tcattttagg atgggggggg atcgggattt ggttggctat   10980
ggttttgagt ccactcctct cggcagttat tttaactgtt cgtttttatc gagtgattga   11040
caatcttctt gccaacagtg atgatatgtt acagaatgcg tctgttacta ctctaggctg   11100
agaaaagcta tatgaccaat caaaataacc aagaattaga gaacgattta ccaatcgcca   11160
agcagccttg tccggtcaat tcttataatg agtgggacac acttgaggag gtcattgttg   11220
gtagtgttga aggtgcaatg ttaccggccc tagaaccaat caacaaatgg acattccctt   11280
ttgaagaatt ggaatctgcc caaaagatac tctctgagag gggaggagtt ccttatccac   11340
cagagatgat tacattagca cacaaagaac taaatgaatt tattcacatt cttgaagcag   11400
aaggggtcaa agttcgtcga gttaaacctg tagatttctc tgtccccttc tccacaccag   11460
cttggcaagt aggaagtggt ttttgtgccg ccaatcctcg cgatgttttt ttggtgattg   11520
ggaatgagat tattgaagca ccaatggcag atcgcaaccg ctattttgaa acttgggcgt   11580
```

-continued

```
atcgagagat gctcaaggaa tattttcagg caggagctaa gtggactgca gcgccgaagc  11640
cacaattatt cgacgcacag tatgacttca atttccagtt tcctcaactg ggggagccgc  11700
cgcgtttcgt cgttacagag tttgaaccga cttttgatgc ggcagatttt gtgcgctgtg  11760
gacgagatat ttttggtcaa aaaagtcatg tgactaatgg tttgggcata gaatggttac  11820
aacgtcactt ggaagacgaa taccgtattc atattattga atcgcattgt ccggaagcac  11880
tgcacatcga taccacctta atgcctcttg cacctggcaa aatactagta aatccagaat  11940
ttgtagatgt taataaattg ccaaaaaatcc tgaaaagctg ggacattttg gttgcacctt  12000
accccaacca tatacctcaa aaccagctga gactggtcag tgaatgggca ggtttgaatg  12060
tactgatgtt agatgaagag cgagtcattg tagaaaaaaa ccaggagcag atgattaaag  12120
cactgaaaga ttggggattt aagcctattg tttgccattt tgaaagctac tatccatttt  12180
taggatcatt tcactgtgca acattagacg ttcgccgacg cggaactctt cagtcctatt  12240
tttaagattt atttcgatta tcctttatcc tgatcatcca gagtgataag agcattacaa  12300
ctaggagaca attatgacaa ctgctgacct aatcttaatt aacaactggt acgtagtcgc  12360
aaaggtggaa gattgtaaac caggaagtat caccacggct cttttattgg gagttaagtt  12420
ggtactatgg cgcagtcgtg aacagaattc cccatacag atatggcaag actactgccc  12480
tcaccgaggt gtggctctgt ctatgggaga aattgttaat aatactttgg tttgtccgta  12540
tcacggatgg agatataatc aagcaggtaa atgcgtacat atcccggctc accctgacat  12600
gacaccccca gcaagtgccc aagccaagat ctatcattgc caggagcgat acggattagt  12660
atgggtgtgc ttaggtgatc ctgtcaatga tatacttca ttacccgaat gggacgatcc  12720
gaattatcat aatacttgta ctaaatctta ttttattcaa gctagtgcgt ttcgtgtaat  12780
ggataatttc atagatgtat ctcattttcc ttttgtccac gacggtgggt taggtgatcg  12840
caaccacgca caaattgaag aatttgaggt aaaagtagac aaagatggca ttagcatagg  12900
taaccttaaa ctccagatgc caaggtttaa cagcagtaac gaagatgact catggactct  12960
ttaccaaagg attagtcatc ccttgtgtca atactatatt actgaatcct ctgaaattcg  13020
gactgcggat ttgatgctgg taacaccgat tgatgaagac aacagcttag tgcgaatgtt  13080
agtaacgtgg aaccgctccg aaatattaga gtcaacggta ctagaggaat ttgacgaaac  13140
aatagaacaa gatattccga ttatacactc tcaacagcca gcgcgtttac cactgttacc  13200
ttcaaagcag ataaacatgc aatggttgtc acaggaaata catgtaccgt cagatcgatg  13260
cacagttgcc tatcgtcgat ggctaaagga actgggcgtt acctatggtg tttgttaatt  13320
tcagggttgt tggtatctgg ataggtatgg ttttgagtcc actgctatct ggagggattt  13380
taatggttgg tttttatcaa cagcttgcca ataagtatta ctaatagtga tgatggggaa  13440
gagaatcaaa ctatactcac caacaaggtg ttaaaatgca gatcttagga atttcagctt  13500
actaccacga tagtgctgcc gcgatggtta tcgatggcga aattgttgct gcagctcagg  13560
aagaacgttt ctcaagacga aagcacgatg ctgggtttcc gactggagcg attacttact  13620
gtctaaaaca agtaggaacc aagttacaat atatcgatca aattgttttt tacgacaagc  13680
cattagtcaa atttgagcgg ttgctagaaa catatttagc atatgcccca aagggatttg  13740
gctcgtttat tactgctatg cccgtttggc tcaaagaaaa gctttaccta aaaacacttt  13800
taaaaaaaga attggcgctt ttgggggagt gcaaagcttc tcaattgcct cctctactgt  13860
ttacctcaca tcaccaagcc catgcggccg ctgctttttt tcccagtcct tttcagcgtg  13920
```

ctgccgttct gtgcttagat ggtgtaggag agtgggcaac tacttctgtc tggttgggag 13980
aaggaaataa actcacacca caatgggaaa ttgattttcc ccattccctc ggtttgcttt 14040
actcagcgtt tacctactac actgggttca aagttaactc aggtgagtac aaactcatgg 14100
gtttagcacc ctacggggaa cccaaatatg tggaccaaat tctcaagcat ttgttggatc 14160
tcaaagaaga tggtactttt aggttgaata tggactactt caactacacg gtggggctaa 14220
ccatgaccaa tcataagttc catagtatgt ttggaggacc accacgccag gcggaaggaa 14280
aaatctccca aagagacatg gatctggcaa gttcgatcca aaaggtgact gaagaagtca 14340
tactgcgtct ggctagaact atcaaaaaag aactgggtgt agagtatcta tgtttagcag 14400
gtggtgtcgg tctcaattgc gtggctaacg gacgaattct ccgagaaagt gatttcaaag 14460
atatttggat tcaacccgca gcaggagatg ccggtagtgc agtgggagca gctttagcga 14520
tttggcatga ataccataag aaacctcgca cttcaacagc aggcgatcgc atgaaaggtt 14580
cttatctggg acctagcttt agcgaggcgg agattctcca gtttcttaat tctgttaaca 14640
taccctacca tcgatgcgtt gataacgaac ttatggctcg tcttgcagaa attttagacc 14700
agggaaatgt tgtaggctgg ttttctggac gaatggagtt tggtccgcgt gctttgggtg 14760
gccgttcgat tattggcgat tcacgcagtc caaaaaatgca atcggtcatg aacctgaaaa 14820
ttaaatatcg tgagtccttc cgtccatttg ctccttcagt cttggctgaa cgagtctccg 14880
actacttcga tcttgatcgt cctagtcctt atatgctttt ggtagcacaa gtcaaagaga 14940
atctgcacat tcctatgaca caagagcaac acgagctatt tgggatcgag aagctgaatg 15000
ttcctcgttc ccaaattccc gcagtcactc acgttgatta ctcagctcgt attcagacag 15060
ttcacaaaga aacgaatcct cgttactacg agttaattcg tcattttgag gcacgaactg 15120
gttgtgctgt cttggtcaat acttcgttta atgtccgcgg cgaaccaatt gtttgtactc 15180
ccgaagacgc ttatcgatgc tttatgagaa ctgaaatgga ctatttggtt atggagaatt 15240
tcttgttggt caaatctgaa cagccacggg gaaatagtga tgagtcatgg caaaaagaat 15300
tcgagttaga ttaacttatg agtgaatttt tcccacaaaa aagtggtaaa ttaaagatgg 15360
aacagataaa agaacttgac aaaaaaggat tgcgtgagtt tggactgatt ggcggttcta 15420
tagtggcggt tttattcggc tttttactgc cagttatacg ccatcattcc ttatcagtta 15480
tcccttgggt tgttgctgga tttctctgga tttgggcaat aatcgcacct acgactttaa 15540
gttttattta ccaaatatgg atgaggattg gacttgtttt aggatggata caaacacgaa 15600
ttattttggg agttttattt tatataatga tcacaccaat aggattcata agacggctgt 15660
tgaatcaaga tccaatgacg cgaatcttcg agccagagtt gccaacttat cgccaattga 15720
gtaagtcaag aactacacaa agtatggaga aaccattcta atgctaaaag acacttggga 15780
ttttattaaa gacattgccg gatttattaa agaacaaaaa aactatttgt tgattcccct 15840
aattatcacc ctggtatcct tgggggcgct gattgtcttt gctcaatctt ctgcgatcgc 15900
acctttcatt tacactcttt tttaaattgc catattatga gtaacttcaa gggttcggta 15960
aagatagcat tgatgggaat attgattttt tgtgggctaa tctttggcgt agcatttgtt 16020
gaaattgggt tacgtattgc cgggatcgaa cacatagcat tccatagcat tgatgaacac 16080
agggggtggg tagggcgacc tcatgtttcc gggtggtata gaaccgaagg tgaagctcac 16140
atccaaatga atagtgatgg ctttcgagat cgagaacaca tcaaggtcaa accagaaaat 16200
accttcagga tagcgctgtt gggagattcc tttgtagagt ccatgcaagt accgttggag 16260
caaaatttgg cagcagttat agaaggagaa atcagtagtt gtatagcttt agctggacga 16320

-continued

```
aaggcggaag tgattaattt tggagtgact ggttatggaa cagaccaaga actaattact  16380
ctacgggaga aagtttggga ctattcacct gatatagtag tgctagattt ttatactggc  16440
aacgacattg ttgataactc ccgtgcgctg agtcagaaat tctatcctaa tgaactaggt  16500
tcactaaagc cgttttttat acttagagat ggtaatctgg tggttgatgc ttcgtttatc  16560
aatacggata attatcgctc aaagctgaca tggtggggca aaacttatat gaaaataaaa  16620
gaccactcac ggattttaca ggttttaaac atggtacggg atgctcttaa caactctagt  16680
agagggtttt cttctcaagc tatagaggaa ccgttattta gtgatggaaa acaggataca  16740
aaattgagcg ggtttttga tatctacaaa ccacctactg accctgaatg gcaacaggca  16800
tggcaagtca cagagaaact gattagctca atgcaacacg aggtgactgc gaagaaagca  16860
gatttttag ttgttacttt tggcggtccc tttcaacgag aacctttagt gcgtcaaaaa  16920
gaaatgcaag aattgggtct gactgattgg ttttacccag agaagcgaat tacacgtttg  16980
ggtgaggatg aggggttcag tgtactcaat ctcagcccaa atttgcaggt ttattctgag  17040
cagaacaatg cttgcctata tgggtttgat gatactcaag gctgtgtagg gcattggaat  17100
gctttaggac atcaggtagc aggaaaaatg attgcatcga agatttgtca acagcagatg  17160
agagaaagta tattgcctca taagcacgac ccttcaagcc aaagctcacc tattacccaa  17220
tcagtgatcc aataaagaac tgggcatcac ttatgatgtt tactaatttc agttccgttg  17280
atgttaatgc gtaactttta ttactagttg taaagctgag atatgacaaa taccgaaaga  17340
ggattagcag aaataacatc aacaggatat aagtcagagc ttagatcgga ggcacgagtt  17400
agcctccaac tggcaattcc cttagtcctt gtcgaaatat gcggaacgag tattaatgtg  17460
gtggatgtag tcatgatggg cttacttggt actcaagttt tggctgctgg tgccttgggt  17520
gcgatcgctt ttttatctgt atcgaatact tgttataata tgcttttgtc gggggtagca  17580
aaggcatctg aggcttttgg ggcaaacaaa atagatcagg ttagtcgtat tgcttctggg  17640
caaatatggc tggcactcac cttgtctttg cctgcaatgc ttttgctttg gtatatggat  17700
actatattgg tgctatttgg tcaagttgaa agcaacacat taattgcaaa aacgtattta  17760
cactcaattg tgtggggatt tccggcggca gttggtattt tgatattaag aggcattgcc  17820
tctgctgtga acgtccccca attggtaact gtgacgatgc tagtagggct ggtcttgaat  17880
gccccggcca attatgtatt aatgttcggt aaatttggtc ttcctgaact tggtttagct  17940
ggaataggct gggcaagtac tttggttttt tggattagtt ttctagtggg ggttgtcttg  18000
ctgattttct ccccaaaagt tagagattat aaacttttcc gctacttgca tcagtttgat  18060
cgacagacgg ttgtggaaat ttttcaaact ggatggccta tgggttttct actgggagtg  18120
gaatcagtag tattgagcct caccgcttgg ttaacaggct atttgggaac agtaacatta  18180
gcagctcatg agatcgcgat ccaaacagca gaactggcga tagtgatacc actcggaatc  18240
gggaatgttg ccgtcacgag agtaggtcag actataggag aaaaaaaccc tttgggtgct  18300
agaagggcag cattgattgg gattatgatt ggtggcattt atgccagtct tgtggcagtc  18360
attttctggt tgtttccata tcagattgcg ggactttatt taaaaataaa cgatccagag  18420
agtatggaag cagttaagac agcaactaat tttctcttct tggcgggatt attccaattt  18480
tttcatagcg ttcaaataat tgttgttggg gttttaatag ggttgcagga tacgtttatc  18540
ccattgttaa tgaatttggt aggctggggt cttggcttgg cagtaagcta ttacatggga  18600
atcattttat gttggggagg tatgggtatc tggttaggtc tggttttgag tccactcctg  18660
```

-continued

```
tccggactta ttttaatggt tcgtttttat caagagattg ccaataggat tgccaatagt  18720
gatgatgggc aagagagtat atctattgac aacgttgaag aactctcctg acgaacagat  18780
tgaattgcct tggtcttgac acttcgttaa cctaagcatg agagtatagg ctatactctg  18840
ccgtggttaa ctgagtgttg tcctggatcg aggacgcagc ctggctgagc aacaaaaaag  18900
actggaatct tgacctgtca atggttttaa ctgctagttt gcggctggtg tcagcagctt  18960
cgccatttct gcgcctaaga cttgacctag ccataatatt ttagtattat gatgagcgat  19020
cttaatcaaa ggcaaaaaat ttacaattaa tctattgtta cattaatttt gctcctcatt  19080
ctgtttaaat tttcagtgac attgtaatct aactcaaaat gaaaacaaac aaacatatag  19140
ctatgtgggc ttgtcctaga agtcgttcta ctgtaattac ccgtgctttt gagaacttag  19200
atgggtgtgt tgtttatgat gagcctctag aggctccgaa tgtcttgatg acaacttaca  19260
cgatgagtaa cagtcgtacg ttagcagaag aagacttaaa gcaattaata ctgcaaaata  19320
atgtagaaac agacctcaag aaagttatag aacaattgac tggagattta ccggacggaa  19380
aattattctc atttcaaaaa atgataacag gtgactatag atctgaattt ggaatagatt  19440
gggcaaaaaa gctaactaac ttctttttaa taaggcatcc ccaagatatt atttttttctt  19500
tcgatatagc ggagagaaag acaggtatca cagaaccatt cacacaacaa aatcttggca  19560
tgaaaacact ttatgaagtt ttccaacaaa ttgaagttat tacagggcaa acacctttag  19620
ttattcactc agatgatata attaaaaacc ctccttctgc tttgaaatgg ctgtgtaaaa  19680
acttagggct tgcatttgat gaaaagatgc tgacatggaa agcaaatcta gaagactcca  19740
atttaaagta tacaaaatta tatgctaatt ctgcgtctgg cagttcagaa ccttggtttg  19800
aaactttaag atcgaccaaa acatttctcg cctatgaaaa gaaggagaaa aaattaccag  19860
ctcggttaat acctctacta gatgaatcta ttccttacta tgaaaaactc ttacagcatt  19920
gtcatatttt tgaatggtca gaacactgag tttgatcgta accgttcaga gggggggatag  19980
aagcgcgatt agggagatcc aaaaaataaa atatctagcc gtctaacctc tttattttca  20040
tcgattcttc ttaccgttcc ctattccctc ccttcaccag ttcgtttttg ggtaggtgca  20100
agatctgagc ctcccaccta gggccgatct ggcagtgcgc gatcgccact agcccatgga  20160
aaactagcac tttttgggga acagccaaaa cctttattga gtaagaattt gaaaaagtgc  20220
aagttaagag gcaatgacta aaaatttttt tctactcttt tcaggataga attccagttt  20280
ctagagccgt tgtaaccgta catatcttga tagtacgtat cgatgaggta ctcattttcg  20340
tggagcatta accagctttt taactccgct aatttctgct ctcctttttc tattaattct  20400
tgctcatcca aatcatccct gtccaactcc tccctgtcca actcccacat agttttgttg  20460
gtatcttcga caatcaagta gtctccactt tttagaccgt tttcgtgaaa atattcaact  20520
actcccaccg cattagcatg ggcatcttct acgatcaacc agggatgagc aagcccagaa  20580
agcagttccg acgacattat tgcacccata ttgttacaat ccccctctaa aaaatgaacg  20640
cgagagtcag tttttgcttt ctcgtcgagt agggaaagat cgatatcgat acagtagaca  20700
caaccttcta tttggaacag ttctaagtga tcggctagcc aaatcgcgct gccaccgctt  20760
aatgctccta tttcgattat tgttttcggg cgaagctcat acaggagcat tgaataaaga  20820
gctatttcgg tgcacccttt caggaagggt atccctttcc aagtgaacaa atcgcggttt  20880
gccaagagcg ctctccaagc tggcactgga atagcacatt tatcttctct ttcagaaatt  20940
ttggcaaacc gattaggttt gaaaggtgca actttatagg cggcttcttg aacaaatttt  21000
tggaagctca tctaattttc ctcttaggtg ttagaacatt tgtaaaatct tggcgatttt  21060
```

```
ttgttttctt tcttgaatat agcaaccgcc aaggcggttt gagcataaac tggatgtagt  21120
ccccgtgttt tacggttgag acttaggtaa agcggctttg tttgtactct cccattattc  21180
aaatagccgt agtttatgat cggtatccaa ttcgctattg tttttctgc catatcccca  21240
acctaagatg cgacgatatt cacccataat gccactgtca attaaatcat cctcgttgac  21300
tgcaacattg gtatgagatt gcggcgcaac atagagcgca tccgcaggac aatatgcttc  21360
acagatgaaa caagtttgac agtcttcctg tcgggcgatc gcaggcggtt ggttgggaac  21420
tgcatcaaag acattggtag ggcatacttg gacgcaaaca ttacaattaa tacagagttt  21480
atggctgaca agctcgatca tcatactgct cctgctacaa ctttaatact ggggctgtgg  21540
tttaagtggt taatactggt ggtgtagcgc tcgcatcctt cacccaatcc cgtctcaccc  21600
aaagcctttc taagccgccc gtggcttggt aataaagctg atttggatcg gtttcaggat  21660
agtctatgcg aatatgttcg ctacgcgttt ccttgcgatg taaagcgcta aaatatgccc  21720
atcgtgctac agacacaaga gcagccgctc gacgagaaaa ttccagatcg cgcactgtat  21780
cttgtttcgg gttcccttgt acttgctgcc acagcatttc taatttggcg agggaatcca  21840
aaagtccctg ctcacagcgc aagtaattct tctctaatgg gaacatctcg gcttgtacac  21900
cgcggacaac tgcctcgcta tcgaatgttt cggaaccagg gtactgggaa cgtaatccgg  21960
cttgacctgc tggacgcaca acccgttcat ggacatgagc gcccaaactc ttggcaaagg  22020
cggctgcacc ttcccctgcc cattgtcctg tagagattgc ccaagcagca ttaggaccat  22080
caccccc aga agctatccca gctaaaaact cccgcgatgc tgcatctccg gcggcataca  22140
gtccaggaac ttttgtacca caactatcat tcacaatccg aattccacct gtaccacgga  22200
ctgtaccttc taaaaccagt gttacaggta ctcgttctgt ataagggtca atgccagctt  22260
ttttataggg tagaaaggcg atgaagtgag acttttcaac caatgcttgg atttcaggtg  22320
tggctcgatc caaacgagca taaacgggac ctttcaggag ggcattgggc aggaacgatg  22380
gatcgcgacg accattgata tagccaccaa gatcgttacc tgcctcatcg gtgtaactag  22440
cccagtaaaa gggagcagcc cttgtcactg tggcattgaa agcggtcgag atggtatagt  22500
gactggaagc ttccatactg gagagttcgc cgccagcttc caccgccatc agcagtccat  22560
cgcctgtatt ggtattgcaa cctaaagctt tacttaggaa tgcacaaccg ccattcgcta  22620
gaactactgc accagcgcga acggtatagg tgcgatgatt ttgcctctgt acacctctag  22680
ctccagccac ggagccgtcc tgggctaata acagttctag agccggactt tggtcgaaaa  22740
tttgcacacc cacacgcaac aggttcttgc gaagtacccg catatattcc ggaccataat  22800
aactctggcg cacggattcc ccattttctt tggggaaacg atagccccaa tcttccacta  22860
agggcaaact cagccaagct ttttcaatta cacgttcaat ccaacgtaag ttagcgaggt  22920
tatttccttt gctgtaacat tcggatacat ctttctccca attctctgga gaaggtgcca  22980
tgacgctatt gccactggca gcagctgcac cgctcgtacc tagaaaacct ttatcaacaa  23040
tgatgacttt gacaccttgg gctccagccg cccatgctgc ccatgcggcg gcaggaccac  23100
caccaattac cagcacgtca gcagttaatt gtagttcagt gccgctatag gctgtaagca  23160
attgcttttc ctccttgttt aaagtcaagt tcatactttt aattatcttc tgcagtcggt  23220
cgaatcaaaa tttcatttac atttacatga tcgggttgtg tcactgcata aattatagct  23280
cttgcaatat cctcactttg taaaggtgtt attgtactaa gttgttcttt actaagctgt  23340
ttcgtgatcg ggtcagaaat taagtcatta aatggcgtat cgactaaacc tggctcaatg  23400
```

atggtaacgc gaatgttgtc taaagatacc tcctggcgta atgcttctga aagagcattg 23460
acgcctgatt tggcagcact ataaacgacc gcaccggact gcgctatcct gccatcgaca 23520
gaagatatat tgactatatg accggatttt tgggccttca gaagaggcaa aactgcgtgg 23580
atagcatata aaactcccag aacattcaca tcgaatgctc gcctccagtc tgcgggattt 23640
ccagtatcaa ttgcaccaaa cacaccaatt cctgcattat tcaccaaaat atctacatgt 23700
cctagctcaa ccttggtctt ttggactaga tgatttactt gagattcgtc tgtaatatct 23760
gtaacaatag gcaatgcttg accaccactg gcttcaatcc gttttgctag tgcatgcaaa 23820
agctcagcac gtcttgcggc gatcgcaact tttgcccccct ccgcagctaa agcaaatgct 23880
gtagcctctc caatcccaga ggaagctcca gtaataatcg ccacttttcc atccaattta 23940
cctgccatca gtcactcctt agttttcgtt ttgctggtgc aatatgtaat aagtgcgttt 24000
tgtacttgat tttgttcttt ggtgattttt atataggagc gcataaagtg cttagtgatc 24060
actttatttt ttagtgccat tcaacttaaa ttaacaaacc ccataagtaa cacctagttg 24120
ctttagccat cgacgatagg caagtgtgca tctatctgat ggtacgtgga tttcgtgtga 24180
aaacaattgt gtatttatct gctttggagt taacagtggt aaacgtaccg gctgttgtgc 24240
atgtaagatc cgaatatctt gttctattgt ttcgtcatat tcagttagca tctttgactc 24300
taacgtttca tacccgttcc acattatcaa catacgcaat acactatttt cctcatcaat 24360
cggtgtgatc gtcattaaat ccacaatcct catttcaggg gattctgaaa cgcagtattg 24420
acataaagga tgactaagcc tgaaccaatt aacccaagag tcatcttcga tatggctgac 24480
aatccttgat gtctggaatt gatacttacc catagtaagg ccatctttat ctaatttcac 24540
ctcaaattct tccacttttg tataattgcg atcacctaac caaccgtcat ggataaaagg 24600
aaaatgagac acgtctaagg aattatccat cacacgaaac gcactagctt taatcaagta 24660
agacttggta taagtcttgt gataattcgg atcatcccat tcaggaaatg aaggtatatc 24720
attaacagga tcgcccaagc acacccacac taagccatag cgctcctggg agtgatatgt 24780
cctggcttca gcacttgccg gtggtaccat gccagggtga gctgggatct gtatgcattt 24840
accagcctca ttgtatctcc atccgtgata cggacaaact aaagtattat tcgtaatttc 24900
tcccatagac agaggaacac ctcggtgggg gcagtagtca agccatacct gtatgggtga 24960
attttgttca taactgcgcc ataataccaa cttcactccc aacaaacgag atctggtgat 25020
acttccaggt ttacagtctt ctacattggc gactacgtgc cagttattga ttaagattgg 25080
gtcggtagtt gtcataattg tctcctagtt ttgccagcca gcgaggcgta agtcagaatt 25140
taagtttatg cttgtgtttg agcctgcgat cgctaaatta tccttttcaa ggcatccacc 25200
aacagtggtt tgatgttgtt ttttgtaaaa atcagagtta gcatcctgta atcggtaatt 25260
gaagtgttgg cagctgcggt atgccataca gttggtgtat aaaacattgc tgcccctcct 25320
ggaagtgaaa gacatatttc tgcatttagt gaattggcag aagatgaatc taatgagtgt 25380
tcccattggt ggctacttgg tataactcgc attgtaccca tagtattatc tgtatcctgt 25440
aagtatatag ttatgaatac catggcttga ttggctactg gaaccaacaa ccgaagcgcg 25500
tcgtcattta actcgttttt tgacatggat gcaagtgcgt tcaatacttc aactacatat 25560
ccatggtctt gatgccaagc aatgtatcct gtacctgcac gaattatggc tagatcggtg 25620
atcaatagga agatatcaga cccaattaga gcctgtactg gtcccatcac agttggaagc 25680
tctaaaagcc tctgaattat cttttgatac ctaactggat ctgggatagt atgctcagac 25740
caccactcat agtcacccgc caatactccc ccacgttttt gttcggtaat aagttctact 25800

-continued

```
tcatgccgta tttcttcaat taacgctttt ggtacagctt cttcaactgt gaaataacca  25860
tcatttgtgt aagcttgttt ttgttccgct gtgagcatct ctcttattct cttgcaattc  25920
aaaggattta gtggatcgtc tggacataat taaggtcaat actgctgtaa ctatcaatgg  25980
ttagtaggaa ttatcctata gctgttcttt ctctggatag aagaaaggtt gtgagaagct  26040
cgctccgact tcatttcagc caatttttct gcagaccaat actgaaaata tcccaatctt  26100
aataattcat cactagcctc ttgtaactgg ctgaatgact gtactgatgc taaaacatac  26160
ttagggtgag ttatgattac gttattcaca ttctccgcgt catcaccaac atattgtttg  26220
tctggatgcg atcctaaagc taccaaatcg tattctggta atacataatt cgccttggta  26280
atgtaccttt ccaacctctg tgcatctagg ttttgagggt cgcagccaaa aatcaccatt  26340
tcaaagtcat tattccatgt tcttatctgt tccattagaa gctctggcag ttcaggtcca  26400
tgaaaccaac gaacactaac acggttattt aaccaagctg ccttcgcgta aggacagggt  26460
ggaaaatttc ctgttagagg attgggaatg ctgacaacat tgataatcca atcctctatt  26520
tcttggcgaa attgttcgat atttatcata actgttgatt tttcctcctt tgtagtaatt  26580
agtagttaaa ggatttagtg gatattaatc taggtcatag tataaccata tattaggctc  26640
gatgtatatt cccatattgt tgggatagtc aattttgaca ggtactaagc ctttgggaat  26700
aatatagtca ccagtttctg gaaaacgcat cccaactcta tcttcccaac cgtcaatagt  26760
atcattaatt gttgtggatt taaaacagat ccctgcaatt ttagccccat gtttgacatt  26820
aactcgtaac caagggtcaa atataagacc atttttatct cgccaggtaa tataccgctc  26880
tatgggtata agtgggtaaa gatattttag gcttggacgt gcagccatga tcaaagaatt  26940
aagaccgtgg tattgagcaa gttctttcat gtatccaatc agatactgac tcaagttttt  27000
gccttgatac tctggtagga ttgaaatcga tactacacat aacgcattag gcaggcggtt  27060
ctgttctcgg tcttcaagcc acttggctaa agcccagtca caaccttcgt ccggtaactc  27120
atcaaaacgg ctttcataag ttaaagggat acagtttcct tgcgctatca taagctgtgt  27180
ggtagcttct actaacccaa actggaattc tggataaatt tcaaatagag ctaaggaagc  27240
tggatctgcc cagacatcat gtatcaaaaa ttttgggtat gcttgatcaa agacactcat  27300
cgtcctttcc acaaaatcag aagtttcttt tggggttaca aagctatact ctaaattatg  27360
ctgtacaatt tgaatggtca ttggttattg gctaatcctt aaatttatac tggaagtcaa  27420
atgagatctc actatcgtta ttatctggaa gtacttgcac tgtcaattca ttaccgactt  27480
tcccattccc aggcataatt aataagttag ggtgaggtgg aatgccgtcg tactgtcgga  27540
cgcggcgaaa aatgctcgaa ttctcgccac catgtttatt caagaggact tcaactggtg  27600
tgatgacaaa agtcattcct gacccaaggt ggcgcgatcg ccgcttttga tttgctggag  27660
tggaaacact aacaaataag gcacaccctc ctagagaata agaccagtta gcagactgcg  27720
gatcggcaga ccaatggcag ggacaagaca ccgcatcaag gctatgtaac gcattcaaaa  27780
aatcaaatgc ttgacctgca tattcctcta ctgtaagaac tgttggttca ggtgggaaaa  27840
agatgacaag tgtcagaaga tccgcatttt cgtgctgaag caattcgttt tcattaactt  27900
catcaatgta tttgtagata ccctcaagcg tatgctcaac caagatcggg tcagttaaag  27960
atgagactat caggtatcta atcattccct tctgttcccc gatagttccc cagaagcaag  28020
ggaaggcaga atcgctgatt gtttcaacaa atgttgagta gctagtgcgt acccaagcag  28080
gaaggcactc ctctagaaga gaggattcca tctggctttt gttccagatt ggtgtaactc  28140
```

-continued

```
cgtcaggaca taaattcttg attaccatag ctgagttgaa aagtgagctt atttatacaa  28200
aaacgatgga agtgacacct gatggatggg acttcaaccc cctacacata attattatca  28260
ttactatgtg gcaggtcctt ctatatctta ttttttggaa gtccctgaaa attattcaac  28320
aagatcgaga cgttgttgtt gccagaattt gtgacagcca ggtcaagctt gctgtcgccg  28380
ttgaaatccg caattgctat agattcagga ttagtaccga ctggaaagtt agtagctatg  28440
ccaaaagacc cattaccatt tcctggtaag accgagacgt tattgctact ataatttgta  28500
acagccaggt caagtttact gtcgccattc acatctctaa tcgctacaga gtagggatta  28560
gtaccggctg gaaagttagt ggctgcgcca aaagacccat taccatttcc cagtaagacc  28620
gagacgttat tgctgctagt atttgcaaca gccaggtcaa gcttgctgtc gccatttaca  28680
tccccagttg ctacaaatat gggattagta ccgactggaa agttagtggc tgcgccaaaa  28740
gacccattac catttcccag taagaccgag acgttattgc tgacccaatt tgtaatagca  28800
aggtcgagct tactgtcgct attaaaatcc gcaatcgcta cggaaatcga ataagtatcg  28860
acagggaagc tgctggctgc gccaaaagac ccattaccat ttcccagtaa aaccaagacc  28920
ttattgtcga accaatttgt aaaagcaagg tcaagctcac tatcgttatt cacatctcca  28980
atggctacag aataagggtt agtaccaact gaaaagttag tggctgcgcc aaaagaccca  29040
ttaccatttc ctagtaagac cgagacgtta ttgctactaa aatttgcaac agccaggtca  29100
agcttgctgt cgccatttac atccccagtc actacaaaga cgggattagt accgactgga  29160
aagttagtgg ctgcgccaaa agacccatta ccatttccca gtaagaccga gacgttattg  29220
tcgaaccaat ttgtaacagc caggtcgagc ttactatcgc tattgaaatc cccaactgct  29280
acagagtcag catcaagacc agttgggaag ttaatagcag tagcataact actcctgtgg  29340
gcaaatctca ctcctacgga caaattaacc ggaacactaa attgcccaga aagcttttca  29400
ttcttcagat aatagtcagt tatatttgct aatgcaacag gagttataca taaaaatgta  29460
ctaacagata atatccccgc tataattagt aaagtgagcc ttttcacgag ttgtatagtt  29520
caaatgtatt aacaatgttt gtagccatac accatcgtgt atgaagaaag gtattgatcg  29580
caaaatatct atccttgatc tagcctatca cctaagttaa gccatattga gttctattta  29640
gattttcttt ataaatcagc tataatctat tgtttgaaaa ttgtgaattt gttttccacg  29700
tatttgagta gttgttctag gctttcctcg acggtgagtt cggatgtttc cacccataaa  29760
tctgggctat tgggtggttc ataaggggcg ctgattcccg taaatccatc tatttcccca  29820
ctgcgtgctt ttagataaag acctttcgga tcacgctgct cacaaagttc cagtggagtt  29880
gcaatgtata cttcatgaaa tagatctcca gctagtctac gcacctgttc tcggtcattc  29940
ctgtagggtg agatgaaggc agtgatcact aggcatcctg actccgcaaa gagtttggca  30000
acctcaccca aacgacggat attttctgag cgatcactag cagaaaatcc taaatcggaa  30060
cacagtccat gacgaacact atcaccatct aaaacaaagg tagaccatcc tttctcgaac  30120
aaagtctgct ctaattttaa agccaatgtt gttttaccag ccccggacag tccagtaaac  30180
catagaatcc cgcttttatg accattcttt agataacgat catatggaga tataagatgt  30240
tttgtatagt gaatattagt tgatttcata ttgctggagt ttagactaaa cagaagagcg  30300
atcgctccat gcctgagatt ttagtcagta tttccactcc tgtcaaacca ccaaaaacac  30360
ggggtaacct ggaaaattcc cctggggatc agctgaaaac tgctgtttaa cctgcattat  30420
tcatgaaggc aaaaacagga aaaacaaaac ctaacattta taccccaatt tatggcggaa  30480
ctaacttaat aagtaaaaag taaattaaac ctaattaaaa tccctgattt taaccccaaa  30540
```

-continued

```
atcaatattt taaacctcaa aacttctctt aatcccccat ttagacacac ctatcctatc  30600
aaggcttaat tttaagaaaa aattatttca aactcgctcg ccaaacgctc cataatcaaa  30660
ttaatttcag acgaaaaagg acagtaatat ggtagctcta ccaacaccct tcttgcggaa  30720
actgtcacct tcgctgctat tttgataatc gtttccctta acctaggaac ctgggcttta  30780
gccagttttg ttccctgtgc tgcttgccga attcccaaca ttaaaatgta agctgcttga  30840
gataaaaata accgaaactg attgacaata aatttctcac agctgagtct atctgatttt  30900
atccccagtt ttaattcctt aattctatgc tctgaagtag ctcctctttg aacataaaat  30960
ttatcgtata aatcctgagc ttctgtttcc aagctagtaa ttataaatct aggattgggt  31020
ccttttttcta gccattctgc tttcataatt actcgccgag gttctgacca actccgagct  31080
gcgtaataca catcatcaaa taaacgaact ttttctcctg tgcgacaata ttccagtctg  31140
gctcggtcaa gaaggtaatt aatttttcgt tttaagacat cattattgct gaatccaaaa  31200
acatatccaa ccccgctttt ttcacaaacc tcaatgattt ctggtaacga gaaacccccg  31260
tctcccctca gaacaattct aatttcaggt aaggctcttt tgattcgcaa aaataaccat  31320
tttagaatgc cagctactcc tttaccagag tgagaatttc ccgcccttag ttgtagaact  31380
aatggataac cactggaagc ttcattaatc agaactggaa agtagatatc atgcctatgg  31440
taaccattaa ataagctcag ttgttgatga ccatgagtta gagcatccca cgcatctatg  31500
tccaggacaa tctcttttga ttcccgagga taggattcta ggaatttatc aacaaataac  31560
cgacgaattt gtttgatatc tttttgagtc acctgatttt ctaaacgact catagttggt  31620
tgactagcta ataagttttc tcctactgtg ggaacttgat tacaaactag cttaaaaatt  31680
ggatcttggc gcaatttatt actatcgttg ctatcttcat agccagcaat tatttgataa  31740
attcgttggc taattaattg agaaagagaa tgtttgactt tagtttggtc ccgattatcc  31800
gtcaaacaat ctgccatatc ttgacaaatt tttacctttt cttctacttg tcgtgccaga  31860
ataattccgc catcactact taaactcata tcagaaaaag tcagatctaa agttttttta  31920
tcgaagaaat ttaaagataa tcttgaggaa gatttagtca tatatagtgg ataggtttaa  31980
tttttaaaat cctgatttat tatagctgtt tttattcctt tttttcagtt tataactaaa  32040
gttagttatt atttaatttg gtgacggata ggaattacag agtgttggga tgacaaaatt  32100
gccgtagctg ttgcagtata acccttttcag cgatttttat tctactctga tgaataatcc  32160
aggataggct tgccatcact ttctgggtag acaatgtcag gcgcgattgt ctccccaccc  32220
tgattaacgt tagattttat cacccccagt tgagttttttg gtgcaatttc cctcaccata  32280
tctatacctc ccattcactt tggtattgac tcaatcggtt caatttacta taacatgact  32340
tatgtggggg tgtgtgcata ccctcactta aaattaatgg atttgaatct cctcgcactg  32400
ctgcaacttg aaaaactctg agagtcagtt gagagctaac tctaccagga ggagagtttt  32460
taaaaacccc cttcccgagc gatcgcataa tttatggtat acaagaatag tgggtgaaaa  32520
actaactggc gatcgctctt ttcatttaag agacacccct tagttttttt tgcagtctca  32580
tgaatttaaa cgatatctaa ttattttcaa cctatctttg ccctgtaaca atgtatgcta  32640
ccctttgacc aatattagta gcatgatctg ccattctctc taaacactga attgctaatg  32700
ttaatagtaa aatgggctcc actaccccgg gaacatcttt ctgctgcgcc aaattacgat  32760
ataacttttt gtaagcatca tctactgtat catctaataa tttaatcctt ctaccactaa  32820
tctcgtctaa atccgctaaa gctactaggc tggtagccaa catagattgg gcatgatcgg  32880
```

-continued

```
acataatggc aacctccccc aaagtaggat gggggggata gggaaatatt ttcattgcta  32940
tttctgccaa atctttggca tagtccccaa tacgttccaa gtctctaact aattgcatga  33000
atgagcttaa acaccgagat tcttggtctg tgggagcttg actgctcata attgtggcac  33060
aatcgacttc tatttgtctg tagaagcgat caattttttt gtctaatctc cgtatttgct  33120
cagctgctgt taaatcccga ttgaatagag cttggtgact cagacggaat gactgctcta  33180
ctaaagcacc catacgcaaa acatctcgtt ccagtctttt aatggcacgt ataggttgag  33240
gtttttcaaa aattgtatat ttcacaacag ctttcatatt tttaatctcg ggtttaatat  33300
atttctagct attatagtct tgattcagaa atatccgcca tcatgttgaa ccacctgggg  33360
aagatgaatt tgtatccaag caccaccggt atcaggatgg ttcatggccc tgattttgcc  33420
accatgagct ataattattt ggcggacaat ggataaccct aaaccactac cagtaatttc  33480
tactgtttca ttctcagagc gggactcgcg gtgtctagct ttgtcccccc gataaaatct  33540
ttgaaagaca tggggtagat ccatgggagc aaatccaacc ccggaatcaa taatgttaat  33600
ttctaaaatc tgatttgata cttggtttaa tattgtatct gcttctggat caaccccatt  33660
aatagacttc tccccacaaa ctggattcat ttcaatgaaa atagtaccgt tcaggttgct  33720
gtatttaata cagttatcta acagattaag aaacacttga taaattctgg acttatcagc  33780
acatatatag accttttccg ggccggagta agaaatacta agatgctgat tagcggctag  33840
gggctctaaa ttctcccaga ctgaaaaaat tagggagcgg acttctagca tttccaaatt  33900
cagttgtatg gaggaggtta tttccatctg ggtcaggtct aaccaatttt ggactaaatt  33960
aattagtctg tcaacctcct gcatcaagcg gatgacccaa cggtttagag gggggatctaa  34020
gcgagtttgc agggtttctg cgaccagacg aatggaagtc agaggtgttc tcagttcatg  34080
ggccaggtct gaaaaagagc ggtcacgttg ctgatgaatg tctacaaatt gttggtgact  34140
ttctagaaac acacccactt gtcccccggg taggggaaaa ctgttagctg ctaaagacaa  34200
tggctttaat cctaaaatac cctgaccatg atctcgggaa gggtgaaaaa tccactcttg  34260
catttgcggt ttttgccaat cccgggtttg ctcaattaac tgatccagct cataggatct  34320
cactaattcc agtagcaggc gcacttgacc cggttgccat ctttgtaaat acagcatttc  34380
ccgcgcgcac tgattacacc atagtagttg gttttcttca tctacttgta aatatcccaa  34440
aggcgcagca tccagcaact gttcataagc tttgagtgac aagcgtaagt tttgttgctc  34500
atctctaacg gtagatattt tacgatgtaa tccagctaat aggggtaata atatcttttc  34560
agcgtgaggg tttaagggtt gggttaactg ctccaaatga ctgttaagtt gaaattgttg  34620
ccaaagccaa aaaccaaaac cgactgccaa acccagaaga aatcccaata agaacatttg  34680
atcgtaagtg tgctatttga ccggaattaa agggggagga tccaagcacg gtctttacag  34740
gacggctttt tctaattgtt aaattataat tataatcggt agggactgct ttgggaaaat  34800
gcgatcgccc aggtatctgt aaccatttct gtaccacagg ttagactgga tcaggtaact  34860
gatacacttc ttgctgaatt ttatgtccaa tcaaaatgac aactcccaaa atgataactc  34920
ccgtgacaag agccaaaaac ccgaatccag cagatggttt aaaataaaaa gaccacgacc  34980
acctaaagga ataggaaaac caaaaacaga atagcccaca tatagaaatc aaccaaatct  35040
atagccaaaa cccctaactg tgacaatata ttctggatgg ctagggtcta actctaattt  35100
ttccctcagc catcgaatgt gaacatccac cgttttactg tcaccaacaa aatcaggacc  35160
ccaaacctgg tctaataact gttcccgtga ccacaccctg cgagcataac tcataaatag  35220
ttctagtaac cggaattctt tcggtgacaa gctcacctcc ctccctctca ctaacacccg  35280
```

```
acattcctga ggatttaaac tgatatcctt atattttaaa gtgggtatca agggcaaatt  35340
agaaaaccgc tgacgacgta acagggcgcg acacctagcc accatttccc gtacgctaaa  35400
aggcttagtt aggtaatcat ccgcccctac ctctaaaccc agcacccggt cagtttcact  35460
acctttcgca ctcagaatta aaatcggtat ggaattaccc tggtgacgta acaaacgaca  35520
aatatctaat ccgttgattt gtggcaacat caagtctagc acaagcaggt cgaaggataa  35580
ctcaccaggt tgggtctcta aattcctgat taattccaca gcacaacgac catccttagc  35640
agtcacaact tcataacctt caccctctaa ggctactaca agcatctctc ggatcagttc  35700
ttcgtcttcc actattaaaa cgcgactaac tggttcaata tccgatttag tgaagtatct  35760
agggtaattc agtagtatac attgataaca aaaatttgta agaatgtact ggtctgggtt  35820
tcccactagt atatgatcct cactcattga tgccacatat tggggaacac ggaattcttg  35880
tattcaatac aacaatttgc ttaaatttat aattcaaata ggtgttttat agaaaatttt  35940
gtcgaatatt tccacatttg tggcttttag ttcaggcaaa acgagagaag tctaaagtgg  36000
gtggaatatc ctgaattctt ccaggaccta tagcccgtag tgcttctggt aaactaatat  36060
ccccagtata tagggcttta cccacaatta ctcctgtaac cccctgatgt tctaaagata  36120
ataaggttaa taggtcagta acagaaccca cacccccaga ggcaatcacg ggtatggaaa  36180
tagcagatac caagtctctt aatgctcgca agtttggtcc ctgaagcgta ccatcacggt  36240
ttatatccgt ataaataata gctgccgcac ccaattcctg catttgggtt gctagttggg  36300
gggccaaaat ttgagaagtt tctaaccaac ccctggtagc aactagacca ttccgcgcat  36360
caatcccaat tataatttgc tgggggaatt gttcacacag tccttgaacc agatctggtt  36420
gctctactgc tacagttccc agaattgccc actgtacccc aagattaaat aactgtataa  36480
cgctggagct atcacgtatt cctccgccaa cttcaatagg tatggaaata gcattggtaa  36540
tagcttctat agtagataaa ttaactattt taccagtttt tgctccatct aaatctacta  36600
aatgtagtct tgttgctcct tggtctgccc acattttagc ggtttccaca gggttatggc  36660
tgtaaacctg ggattgtgca tagtcacctt tgtagagtct tacacaacgc ccctctaata  36720
gatctattgc tgggataact tccatgacta attagtgaat aggttaattt cagttgagct  36780
aaatggagaa ggagggattc gaaccctcgg atggacctta cgattccatc aacagattag  36840
caatctgccg ctttcgacca ctcagccacc tctccaggtt tgttataaat tatgatgggt  36900
caatcctaac agacaatttt tggcttgtca agagattttt tgcaagtgga ggaggaaatc  36960
cgtcagggat ttcaatcctg gtcaactttt ttttgatttt gaatataaag ttaagtttaa  37020
caatttctag tggcgctcct ccaacagtag atataaaata tgagttggtc cacaatgaag  37080
gacgtcttga ttttaatagt caaatccctc caaatccatt ataatcccat gaatgctctt  37140
tcaattccta cctggattat ccatatttct agtgtcattg aatgggtagt tgccatttcc  37200
ctcatctgga aatatggcga actgacccaa aaccatagtt ggaggggatt tgccttaggt  37260
atgatacccg ccttaattag cgccctatcc gcttgtacct ggcattattt cgataatccc  37320
cagtccctag aatggttagt caccctccag gctactacta cgttaatagg taattttact  37380
ctttgggcag cagcagtctg ggtttggcgt tctactcgac cgaatgaggt tctcagtatc  37440
tcaaataagg agtagaccgt tatgatgtca aaagaaactc tctttgctct ctccctgttc  37500
ccctatttgg gaatgttgtg gtttctcagt cgcagtcccc aaatgccccc ttaagggctc  37560
tatggattct atggcacttt agtatttgtt ggtgttacca ttccag                 37606
```

<210> SEQ ID NO 2
<211> LENGTH: 1320
<212> TYPE: DNA
<213> ORGANISM: Cylindrospermopsis raciborskii T3

<400> SEQUENCE: 2
atgatcccag ctaaaaaagt ttattttta ttgagtttag caatagttat ttcacccttt 60
ttatccatga ttgtgggtat ttacgaaaat attaaattta gggtattatt tgatttggtg 120
gtcagggcac taatggtggt tgactgcttc aatatcaaaa aacatcgggt caaaattagt 180
cgtcaattac ctctacgttt atctattgga cgtgagaatt tagtaatatt gaaggtagag 240
tctgggaatg tcaatagtgc tattcaaatt cgtgattact atcccacaga atttcccgta 300
tccacatcta acctgatagt taaccttccc cctaatcata ctcaggaagt aaagtacacc 360
attcgaccta atcaacgggg agaattttgg tggggaaata ttcaagttcg acagctggga 420
aattggtctc tagggtggga caattggcaa attccccaaa aaactgtggc taaggtgtat 480
cctgatttgt taggactcag atccctcgct attcgtttaa ccctacaatc ttctggatct 540
atcactaaat tgcgtcaacg gggaatggga acggaatttg ccgaactccg taattactgc 600
atgggggatg atctacggtt aattgattgg aaagctacag ctagacgtgc ttatggaaat 660
ctgagtcccc tagtaagagt tttagagcct caacaggaac aaactctgct tatattatta 720
gatcgtggta gactaatgac agctaatgta caagggttaa aacgatatga ttggggttta 780
aataccacct tgtctttggc attagcagga ttacataggg gcgatcgcgt aggagtaggg 840
gtatttgact cccagctgca tacctggata cctccagagc gaggacaaaa tcatctcaat 900
cggcttatag acagacttac acctattgaa ccagtgttag tggagtctga ttatttaaat 960
gccattacct atgtagtaaa acaacagact cgtagatctc tagtagtgtt aattactgat 1020
ttagtcgatg ttactgcttc ccatgaacta ctagtagcgc tgtgtaaatt agtgcctcga 1080
tatctacctt tttgtgtaac actcagggat cctgggattg ataaaatagc tcataatttt 1140
agtcaagact taacacaggc ttataatcga gcagtttctt tggacttgat atcacaaaga 1200
gaaattgctt ttgctcagtt gaaacaacag ggagttttgg tgttggatgc accagcaaat 1260
caaatttccg agcagttggt agaaaggtac ttacaaatca aagccaaaaa tcagatttga 1320

<210> SEQ ID NO 3
<211> LENGTH: 439
<212> TYPE: PRT
<213> ORGANISM: Cylindrospermopsis raciborskii T3

<400> SEQUENCE: 3

Met Ile Pro Ala Lys Lys Val Tyr Phe Leu Leu Ser Leu Ala Ile Val
1 5 10 15

Ile Ser Pro Phe Leu Ser Met Ile Val Gly Ile Tyr Glu Asn Ile Lys
20 25 30

Phe Arg Val Leu Phe Asp Leu Val Val Arg Ala Leu Met Val Val Asp
35 40 45

Cys Phe Asn Ile Lys Lys His Arg Val Lys Ile Ser Arg Gln Leu Pro
50 55 60

Leu Arg Leu Ser Ile Gly Arg Glu Asn Leu Val Ile Leu Lys Val Glu
65 70 75 80

Ser Gly Asn Val Asn Ser Ala Ile Gln Ile Arg Asp Tyr Tyr Pro Thr
85 90 95

Glu Phe Pro Val Ser Thr Ser Asn Leu Ile Val Asn Leu Pro Pro Asn

-continued

```
            100                 105                 110

His Thr Gln Glu Val Lys Tyr Thr Ile Arg Pro Asn Gln Arg Gly Glu
        115                 120                 125

Phe Trp Trp Gly Asn Ile Gln Val Arg Gln Leu Gly Asn Trp Ser Leu
    130                 135                 140

Gly Trp Asp Asn Trp Gln Ile Pro Gln Lys Thr Val Ala Lys Val Tyr
145                 150                 155                 160

Pro Asp Leu Leu Gly Leu Arg Ser Leu Ala Ile Arg Leu Thr Leu Gln
                165                 170                 175

Ser Ser Gly Ser Ile Thr Lys Leu Arg Gln Arg Gly Met Gly Thr Glu
            180                 185                 190

Phe Ala Glu Leu Arg Asn Tyr Cys Met Gly Asp Asp Leu Arg Leu Ile
        195                 200                 205

Asp Trp Lys Ala Thr Ala Arg Arg Ala Tyr Gly Asn Leu Ser Pro Leu
    210                 215                 220

Val Arg Val Leu Glu Pro Gln Gln Glu Gln Thr Leu Leu Ile Leu Leu
225                 230                 235                 240

Asp Arg Gly Arg Leu Met Thr Ala Asn Val Gln Gly Leu Lys Arg Tyr
                245                 250                 255

Asp Trp Gly Leu Asn Thr Thr Leu Ser Leu Ala Leu Ala Gly Leu His
            260                 265                 270

Arg Gly Asp Arg Val Gly Val Gly Val Phe Asp Ser Gln Leu His Thr
        275                 280                 285

Trp Ile Pro Pro Glu Arg Gly Gln Asn His Leu Asn Arg Leu Ile Asp
    290                 295                 300

Arg Leu Thr Pro Ile Glu Pro Val Leu Val Glu Ser Asp Tyr Leu Asn
305                 310                 315                 320

Ala Ile Thr Tyr Val Val Lys Gln Gln Thr Arg Arg Ser Leu Val Val
                325                 330                 335

Leu Ile Thr Asp Leu Val Asp Val Thr Ala Ser His Glu Leu Leu Val
            340                 345                 350

Ala Leu Cys Lys Leu Val Pro Arg Tyr Leu Pro Phe Cys Val Thr Leu
        355                 360                 365

Arg Asp Pro Gly Ile Asp Lys Ile Ala His Asn Phe Ser Gln Asp Leu
    370                 375                 380

Thr Gln Ala Tyr Asn Arg Ala Val Ser Leu Asp Leu Ile Ser Gln Arg
385                 390                 395                 400

Glu Ile Ala Phe Ala Gln Leu Lys Gln Gln Gly Val Leu Val Leu Asp
                405                 410                 415

Ala Pro Ala Asn Gln Ile Ser Glu Gln Leu Val Glu Arg Tyr Leu Gln
            420                 425                 430

Ile Lys Ala Lys Asn Gln Ile
        435


<210> SEQ ID NO 4
<211> LENGTH: 759
<212> TYPE: DNA
<213> ORGANISM: Cylindrospermopsis raciborskii T3

<400> SEQUENCE: 4

atgatagata caatatcagt actattaaga gagtggactg taatttccct tacaggttta      60

gccttctggc tttgggaaat tcgctctccc ttccatcaaa ttgaatacaa agctaaattc     120

ttcaaggaat tgggatgggc gggaatatca ttcgtcttta gaaatgttta tgcatatgtt     180
```

```
tctgtggcaa ttataaaact attgagttct ctatttatgg gagagtcagc aaattttgca    240

ggagtaatgt atgtgcccct ctggctgagg atcatcactg catatatatt acaggactta    300

actgactatc tattacacag gacaatgcat agtaatcagt ttctttggtt gacgcacaaa    360

tggcatcatt caacaaagca atcatggtgg ctgagtggaa acaaagatag ctttaccggc    420

ggacttttat atactgttac agctttgtgg tttccactgc tggacattcc ctcagaggtt    480

atgtctgtag tggcagtaca tcaagtgatt cataacaatt ggatacacct caatgtaaag    540

tggaactcct ggttaggaat aattgaatgg atttatgtta cgccccgtat tcacactttg    600

catcatcttg atacaggggg aagaaatttg agttctatgt ttactttcat cgaccgatta    660

tttggaacct atgtgtttcc agaaaacttt gatatagaaa aatctaaaaa tagattggat    720

gatcaatcag taacggtgaa gacaattttg ggtttttaa                           759


<210> SEQ ID NO 5
<211> LENGTH: 252
<212> TYPE: PRT
<213> ORGANISM: Cylindrospermopsis raciborskii T3

<400> SEQUENCE: 5

Met Ile Asp Thr Ile Ser Val Leu Leu Arg Glu Trp Thr Val Ile Ser
1               5                   10                  15

Leu Thr Gly Leu Ala Phe Trp Leu Trp Glu Ile Arg Ser Pro Phe His
            20                  25                  30

Gln Ile Glu Tyr Lys Ala Lys Phe Phe Lys Glu Leu Gly Trp Ala Gly
        35                  40                  45

Ile Ser Phe Val Phe Arg Asn Val Tyr Ala Tyr Val Ser Val Ala Ile
    50                  55                  60

Ile Lys Leu Leu Ser Ser Leu Phe Met Gly Glu Ser Ala Asn Phe Ala
65                  70                  75                  80

Gly Val Met Tyr Val Pro Leu Trp Leu Arg Ile Ile Thr Ala Tyr Ile
                85                  90                  95

Leu Gln Asp Leu Thr Asp Tyr Leu Leu His Arg Thr Met His Ser Asn
            100                 105                 110

Gln Phe Leu Trp Leu Thr His Lys Trp His His Ser Thr Lys Gln Ser
        115                 120                 125

Trp Trp Leu Ser Gly Asn Lys Asp Ser Phe Thr Gly Gly Leu Leu Tyr
    130                 135                 140

Thr Val Thr Ala Leu Trp Phe Pro Leu Leu Asp Ile Pro Ser Glu Val
145                 150                 155                 160

Met Ser Val Val Ala Val His Gln Val Ile His Asn Asn Trp Ile His
                165                 170                 175

Leu Asn Val Lys Trp Asn Ser Trp Leu Gly Ile Ile Glu Trp Ile Tyr
            180                 185                 190

Val Thr Pro Arg Ile His Thr Leu His His Leu Asp Thr Gly Gly Arg
        195                 200                 205

Asn Leu Ser Ser Met Phe Thr Phe Ile Asp Arg Leu Phe Gly Thr Tyr
    210                 215                 220

Val Phe Pro Glu Asn Phe Asp Ile Glu Lys Ser Lys Asn Arg Leu Asp
225                 230                 235                 240

Asp Gln Ser Val Thr Val Lys Thr Ile Leu Gly Phe
                245                 250


<210> SEQ ID NO 6
<211> LENGTH: 396
```

```
<212> TYPE: DNA
<213> ORGANISM: Cylindrospermopsis raciborskii T3

<400> SEQUENCE: 6

tcacccccaa cttattgcag aaaaactttt ttctcttagg taataaatta gtagtttaat      60

tgaaaagcat agcatctctt ttgacttgga ataacaaaat gtcttacgat gtagtctagc     120

taaatagtga cgcaaacgac tgttttctcc ctcaactcta gtcattgatg ttttactaat     180

aatttggtct ccatcgggaa taaattttgg gtaaacttta tagccatccg taatccaaaa     240

ataggatttc caatgctcta tctttttcca taatttggca aatgttttgg cacttctatc     300

tcccactaca tattgaataa ttcccgaacg tttgttatct acaactgtcc agacccatat     360

cttgtttttt tttaccaata aatgtttcca actcat                               396


<210> SEQ ID NO 7
<211> LENGTH: 131
<212> TYPE: PRT
<213> ORGANISM: Cylindrospermopsis raciborskii T3

<400> SEQUENCE: 7

Met Ser Trp Lys His Leu Leu Val Lys Lys Asn Lys Ile Trp Val Trp
1               5                   10                  15

Thr Val Val Asp Asn Lys Arg Ser Gly Ile Ile Gln Tyr Val Val Gly
            20                  25                  30

Asp Arg Ser Ala Lys Thr Phe Ala Lys Leu Trp Lys Lys Ile Glu His
        35                  40                  45

Trp Lys Ser Tyr Phe Trp Ile Thr Asp Gly Tyr Lys Val Tyr Pro Lys
    50                  55                  60

Phe Ile Pro Asp Gly Asp Gln Ile Ile Ser Lys Thr Ser Met Thr Arg
65                  70                  75                  80

Val Glu Gly Glu Asn Ser Arg Leu Arg His Tyr Leu Ala Arg Leu His
                85                  90                  95

Arg Lys Thr Phe Cys Tyr Ser Lys Ser Lys Glu Met Leu Cys Phe Ser
            100                 105                 110

Ile Lys Leu Leu Ile Tyr Tyr Leu Arg Glu Lys Ser Phe Ser Ala Ile
        115                 120                 125

Ser Trp Gly
    130


<210> SEQ ID NO 8
<211> LENGTH: 360
<212> TYPE: DNA
<213> ORGANISM: Cylindrospermopsis raciborskii T3

<400> SEQUENCE: 8

ttatctacaa ctgtccagac ccatatcttg ttttttttta ccaataaatg tttccaactc      60

atccagttga caaacttcag gtgtttggga attattatta ctatctgata actgacgacc     120

tagctttttg acccaacgaa tgactgtatt gtgatttact ttagtcattc tttcaattgc     180

cctaaatcca ttcccattta catacatggt taaacatgct tcctttactt cttgggaata     240

acctctagga gaataagatt caataaattg acgaccacaa ttcttgcatt gataattttg     300

ttttcccctt ctctggccat tttttctaat attattggaa tcacagtttg aacagttcat     360


<210> SEQ ID NO 9
<211> LENGTH: 119
<212> TYPE: PRT
<213> ORGANISM: Cylindrospermopsis raciborskii T3
```

<400> SEQUENCE: 9

Met Asn Cys Ser Asn Cys Asp Ser Asn Asn Ile Arg Lys Asn Gly Gln
1 5 10 15

Arg Arg Gly Lys Gln Asn Tyr Gln Cys Lys Asn Cys Gly Arg Gln Phe
20 25 30

Ile Glu Ser Tyr Ser Pro Arg Gly Tyr Ser Gln Glu Val Lys Glu Ala
35 40 45

Cys Leu Thr Met Tyr Val Asn Gly Asn Gly Phe Arg Ala Ile Glu Arg
50 55 60

Met Thr Lys Val Asn His Asn Thr Val Ile Arg Trp Val Lys Lys Leu
65 70 75 80

Gly Arg Gln Leu Ser Asp Ser Asn Asn Asn Ser Gln Thr Pro Glu Val
85 90 95

Cys Gln Leu Asp Glu Leu Glu Thr Phe Ile Gly Lys Lys Lys Gln Asp
100 105 110

Met Gly Leu Asp Ser Cys Arg
115

<210> SEQ ID NO 10
<211> LENGTH: 354
<212> TYPE: DNA
<213> ORGANISM: Cylindrospermopsis raciborskii T3

<400> SEQUENCE: 10
ttatgacctc attttcattt ctagacgttc agcaacgggc attaactcac gtatcagatc 60
aaagtttcct acgttccgtc tcatccagtc taataagaat ttttctcctt catctagctt 120
acctttatca tcaacaaaaa ccatctgctc gcaccaatct acaaatccgg aattagtcat 180
ctcatagact aaaatgatgg gaggaaagtg tgcgaatccc attttttcaa tgacttccat 240
acaaaccagc ttaaatactt gttcgtttgt caattcatta gacataaaga attttccttt 300
aatcaattct gtttctaatc ctaccacaga gtaataactc ttggtctgga acat 354

<210> SEQ ID NO 11
<211> LENGTH: 117
<212> TYPE: PRT
<213> ORGANISM: Cylindrospermopsis raciborskii T3

<400> SEQUENCE: 11

Met Phe Gln Thr Lys Ser Tyr Tyr Ser Val Val Gly Leu Glu Thr Glu
1 5 10 15

Leu Ile Lys Gly Lys Phe Phe Met Ser Asn Glu Leu Thr Asn Glu Gln
20 25 30

Val Phe Lys Leu Val Cys Met Glu Val Ile Glu Lys Met Gly Phe Ala
35 40 45

His Phe Pro Pro Ile Ile Leu Val Tyr Glu Met Thr Asn Ser Gly Phe
50 55 60

Val Asp Trp Cys Glu Gln Met Val Phe Val Asp Asp Lys Gly Lys Leu
65 70 75 80

Asp Glu Gly Glu Lys Phe Leu Leu Asp Trp Met Arg Arg Asn Val Gly
85 90 95

Asn Phe Asp Leu Ile Arg Glu Leu Met Pro Val Ala Glu Arg Leu Glu
100 105 110

Met Lys Met Arg Ser
115

<210> SEQ ID NO 12
<211> LENGTH: 957
<212> TYPE: DNA
<213> ORGANISM: Cylindrospermopsis raciborskii T3

<400> SEQUENCE: 12
tcataactta ttacttgacg gagttgcagg ggcatacctt aacttgacct tgggagcgat 60
agaagaaagg aaggcttcag tgacgggtct ttgactaatc ccagtttcca cttcaactaa 120
aacagcatca caaatgtcga atagtgattg agaatatcta ttcatattca tgaaagtcag 180
agcagattcc atcggagaca tggatgaatt aaaggcagcg ttttcagcgt atcgacctgt 240
aaatatattc ccgtgggaat cttttaacgc tacccctgca aaatttttcg tgtagggagc 300
ataactttga ttggcagcgg atagagcagc aagcacaaca tcatcggtag aataggtctc 360
cagatcatga aatactgttt gcattaatcc acctgtgagt cctagatccg ctggtccaaa 420
tggctcgggt agaaaatgtg ggagtttatt tgaggtataa gtttgctcag gctgtgattc 480
attagacttc acaagaagaa caaaattttg atttacagtt gccatctcgt ataaaaattg 540
tcggcagtat ccacatggtg cttcgtggat tgctaatgct tgtaaaccgg tttctccgtg 600
caaccacgca tttatggtgg cggattgttc tgcgtgaact gagaaactaa gtgcctgtcc 660
tacaaattcc atgtcggcac caaaataaag agttccagaa cccagttgat tcttagattg 720
tggtttacca agagcgatcg cccctacata aaactgcgat attggtaccc tagcataagt 780
tgcggctacg ggtagtaatt gaatcattaa cgtactaata ttagtaccaa gtcgatcaat 840
ccaagatgcg acaacacttg agtcaattac agcatgttgg gcaagaattg tccttaactc 900
tgattgaatg gaacgtggaa ccttggcaat cgcctgttct aatgctacat gggtcat 957

<210> SEQ ID NO 13
<211> LENGTH: 318
<212> TYPE: PRT
<213> ORGANISM: Cylindrospermopsis raciborskii T3

<400> SEQUENCE: 13

Met Thr His Val Ala Leu Glu Gln Ala Ile Ala Lys Val Pro Arg Ser
1 5 10 15

Ile Gln Ser Glu Leu Arg Thr Ile Leu Ala Gln His Ala Val Ile Asp
20 25 30

Ser Ser Val Val Ala Ser Trp Ile Asp Arg Leu Gly Thr Asn Ile Ser
35 40 45

Thr Leu Met Ile Gln Leu Leu Pro Val Ala Ala Thr Tyr Ala Arg Val
50 55 60

Pro Ile Ser Gln Phe Tyr Val Gly Ala Ile Ala Leu Gly Lys Pro Gln
65 70 75 80

Ser Lys Asn Gln Leu Gly Ser Gly Thr Leu Tyr Phe Gly Ala Asp Met
85 90 95

Glu Phe Val Gly Gln Ala Leu Ser Phe Ser Val His Ala Glu Gln Ser
100 105 110

Ala Thr Ile Asn Ala Trp Leu His Gly Glu Thr Gly Leu Gln Ala Leu
115 120 125

Ala Ile His Glu Ala Pro Cys Gly Tyr Cys Arg Gln Phe Leu Tyr Glu
130 135 140

Met Ala Thr Val Asn Gln Asn Phe Val Leu Leu Val Lys Ser Asn Glu
145 150 155 160

Ser Gln Pro Glu Gln Thr Tyr Thr Ser Asn Lys Leu Pro His Phe Leu

-continued

```
                165                 170                 175

Pro Glu Pro Phe Gly Pro Ala Asp Leu Gly Leu Thr Gly Gly Leu Met
            180                 185                 190

Gln Thr Val Phe His Asp Leu Glu Thr Tyr Ser Thr Asp Asp Val Val
        195                 200                 205

Leu Ala Ala Leu Ser Ala Ala Asn Gln Ser Tyr Ala Pro Tyr Thr Lys
    210                 215                 220

Asn Phe Ala Gly Val Ala Leu Lys Asp Ser His Gly Asn Ile Phe Thr
225                 230                 235                 240

Gly Arg Tyr Ala Glu Asn Ala Ala Phe Asn Ser Ser Met Ser Pro Met
                245                 250                 255

Glu Ser Ala Leu Thr Phe Met Asn Met Asn Arg Tyr Ser Gln Ser Leu
            260                 265                 270

Phe Asp Ile Cys Asp Ala Val Leu Val Glu Val Glu Thr Gly Ile Ser
        275                 280                 285

Gln Arg Pro Val Thr Glu Ala Phe Leu Ser Ser Ile Ala Pro Lys Val
    290                 295                 300

Lys Leu Arg Tyr Ala Pro Ala Thr Pro Ser Ser Asn Lys Leu
305                 310                 315


<210> SEQ ID NO 14
<211> LENGTH: 3738
<212> TYPE: DNA
<213> ORGANISM: Cylindrospermopsis raciborskii T3

<400> SEQUENCE: 14

ttaatgcttg agtatgtttt cctcctgctt acaaggcaaa gctttccttt tttgtagcaa     60

atcccaaact gctttgagag atttaattgc ttggtctatc tcctcttcgg tattggcggc    120

tgtaatcgaa aaccttaaag cacttttatt taaaggtacg attggaaaaa tagcaggagt    180

aattaaaata ccatattccc aaaggagttg acacacatca atcatgtgtt gagcatctcc    240

cactaacacg cctacgatgg gaacgtaacc atagttatcc acttcgaatc caatggctct    300

tgcttgtgta accaatttgt gagttaggtg ataaatttgt tttcttaact gctccccctc    360

ctgacgattc acctgtaatc cggctaaggc acttgccaaa ctcgcaacag gagaaggacc    420

agaaaatatg gcagtccaag cgttgcggaa gttggttttg atccggcgat cgccacaagt    480

taagaatgct gcgtaagaag aataggcttt ggacaaacca gctacataga tgatattatc    540

ctctgcaaac cgcaggtcaa aataattcac catcccgttt cctttgtaac cgtaaggcat    600

atcgctgctg ggattttcgc ccaaaatgcc aaaaccatga gcatcatcca tgtaaattaa    660

ggcattgtac tcttttgcca gatgcacgta agctggcaga tcgggaaaat ctgccgacat    720

ggaatacacg ccatcaatga caataatctt tacttgttca ggcggatatt ttgctagttt    780

ttcggctaaa tcgttcaaat cattatgtcg atattggatg aactgggctc ctttgtgctg    840

agccagacag cacgcttcat aaatacaacg atgtgcagct atgtcaccaa agatgacacc    900

attattccca gttaatagtg gtaaaattcc tatctgaagc agtgttacag ctggaaatac    960

taaaacatca ggtacgccta aaagtttgga caattcttcc tccaattcct cataaattgc   1020

tggggaagca acaagccgag tccagcttgg atgtgtgccc catttatcca aagctggtgg   1080

aattgcttcc ttaacttttg gatgcaagtc aagacctaaa tagttgcaag aagcaaagtc   1140

tatcacccaa tgtccgtcaa ttagcacctt gcgaccttgt tgttctgtga cgactcttgt   1200

gacttgagga attttttgtt ggttaactac gttttccaga gtgttgattt cgttggctga   1260
```

-continued

```
gtcaacaggt ggagctagat cagattgttt ctcttgtacc acttggtttt ggaaataagt   1320
gatgatggca gttggagtgt tcttttgtaa aaagaacgtt ccagacagat tgatccctaa   1380
acgttcctct aggagcgttt gcagttctaa taaatctaaa gaatctaatc ccatatccag   1440
cagtttttgt tgtggagcgt aggctgcctg acgttgggaa cccattactt ttaagatgca   1500
ttctttaacg agatccgcta cagttttgtt ttccttagtt gcagatgttg cttttggtac   1560
caatgaacca attgctgagt taatatacgg tcctttgcga tcaccaggcg agtgcaaagc   1620
actgtcgcgc aggttatatt caatcaaaat acccatgccg agattatctg tatcttccgg   1680
acgataatta gcaataattc ccctaatttc ggctcctccc gacacatgga aacccacaat   1740
tggatccaga agctgtcgtt gctcattgtg tagctttaaa tactccatca tcggcatttg   1800
ggaataattg acataatttc gacagcgagt tacacccacc acgctctcaa tgccgccttt   1860
cagggtacag tagtaaagca taaagtcccg caattcattt cctaaccccc gcgcctgaaa   1920
ctcaggtaga atatttagtg cgagcagttg aataactgac ccttggggag tatgtaacgt   1980
cggcacttgc gcatatttta cattctctaa tgcctcagtg ctggtaattg tttgggaata   2040
aatcgcacca ataatttgat cttctataat cagcactaaa ttaccttgcg ggtttagctc   2100
aagtcttcgc cgaatttcat gagtagatgc ccgtaaattt tctggccaac acttgacctc   2160
caagtcaact aaggcaggta aatctgacaa ataggcatga ctaattttgt aaggtctttt   2220
ctcgaagtaa ttaagcgtaa tgcgagtaaa aggaaatgtt tttgggtatc ttttagaaag   2280
ctctagtttt ggaaatagac ctacttgtgc agcagacatg agaaaaacct cagcttccac   2340
aagatactgc tgagaaaatc cctgaaacgc atcgaaatgt aagttttcgc ttttgtctaa   2400
aaactgatag actacccttg gttccaaaca atggacctcc aaaatcatta aaccgtgttt   2460
attgaccact tgagaccatc tttctaagtg ttccaccaaa ctttgcacca taacatgagg   2520
aggaataagc tctccttgat catcgacaca gactgattgg taaggtaagt gagcacgttc   2580
tttcaattcg tttcttttct gaggaggaat aaagagacga tcatggtcga ggaacgaacg   2640
gatgtgcagg atattttcgg gatcatgaat gccatgagct tctaaagaac gcaccatttg   2700
ttctgggttc ccaatatctc cctgtaaaac taagtgggga aggctagcaa gggtgcgtgt   2760
ggtagctttt aaagaagctt cgttataatc tacacctata agacgcaggg gatactgttc   2820
gagtgctttt cccctagcag acttaaattg aatggtttcc cagactcgtt tcaggagagt   2880
tccatcgcca caccccatgt cagtaatgta tttgggttgt tcttctaatg gcaactgatt   2940
gaatactgag aggatacttt cttctaaatc ggcaaaatat ttctggtgtt gaaatccact   3000
cccgatcacg ttaagggtgc gatcaatgtg cctttcgtga ccggaagcat ctctttggaa   3060
tacggagaga caattgccaa acaatacatc atgaatgcgg gacaacatag gagtgtagga   3120
cgccactatg gctgtattca aggctcgctc tcccataaat cgaccaagtt cggttatggt   3180
caaacgacct gctgtaaggt cagcccagcc aaggtggaga aataacttac ccaactcttc   3240
ttgcactgtt gagcttaatg aggagagcaa aggtttgtcc tccgaatctg caagcaagtt   3300
gtgtttgtgc agtgccagca ggagtgggat gaccagtaat ccatctaaaa aatctgccat   3360
taggggattg tccaggttcc acaattggca agaacgctca atccatcttc ccagcaaatt   3420
tccttgtttc ccttctaaat aagactgaat tggtaggttg tacaattgaa gaatgtcttc   3480
cgaaattttg ttgtgaatcg ctgcttctgc ggttagagag tatttaagct ccttatttcg   3540
ggaaagccaa tgtaaagact cgagcatcct caaagcaact tgaaaatgtc cgctgttagc   3600
tcccagatgt tccaccattt ggtttaaaga gagaggactt tcatcggcga gtaattcaaa   3660
```

-continued

```
aacacctttt tctcgacacg caagaataac gggaaccgcc acaaagccgt gagtataacg    3720

attaatcttt tgtaacat                                                  3738
```

<210> SEQ ID NO 15
<211> LENGTH: 1245
<212> TYPE: PRT
<213> ORGANISM: Cylindrospermopsis raciborskii T3

<400> SEQUENCE: 15

Met Leu Gln Lys Ile Asn Arg Tyr Thr His Gly Phe Val Ala Val Pro
1 5 10 15

Val Ile Leu Ala Cys Arg Glu Lys Gly Val Phe Glu Leu Leu Ala Asp
20 25 30

Glu Ser Pro Leu Ser Leu Asn Gln Met Val Glu His Leu Gly Ala Asn
35 40 45

Ser Gly His Phe Gln Val Ala Leu Arg Met Leu Glu Ser Leu His Trp
50 55 60

Leu Ser Arg Asn Lys Glu Leu Lys Tyr Ser Leu Thr Ala Glu Ala Ala
65 70 75 80

Ile His Asn Lys Ile Ser Glu Asp Ile Leu Gln Leu Tyr Asn Leu Pro
85 90 95

Ile Gln Ser Tyr Leu Glu Gly Lys Gln Gly Asn Leu Leu Gly Arg Trp
100 105 110

Ile Glu Arg Ser Cys Gln Leu Trp Asn Leu Asp Asn Pro Leu Met Ala
115 120 125

Asp Phe Leu Asp Gly Leu Leu Val Ile Pro Leu Leu Leu Ala Leu His
130 135 140

Lys His Asn Leu Leu Ala Asp Ser Glu Asp Lys Pro Leu Leu Ser Ser
145 150 155 160

Leu Ser Ser Thr Val Gln Glu Glu Leu Gly Lys Leu Phe Leu His Leu
165 170 175

Gly Trp Ala Asp Leu Thr Ala Gly Arg Leu Thr Ile Thr Glu Leu Gly
180 185 190

Arg Phe Met Gly Glu Arg Ala Leu Asn Thr Ala Ile Val Ala Ser Tyr
195 200 205

Thr Pro Met Leu Ser Arg Ile His Asp Val Leu Phe Gly Asn Cys Leu
210 215 220

Ser Val Phe Gln Arg Asp Ala Ser Gly His Glu Arg His Ile Asp Arg
225 230 235 240

Thr Leu Asn Val Ile Gly Ser Gly Phe Gln His Gln Lys Tyr Phe Ala
245 250 255

Asp Leu Glu Glu Ser Ile Leu Ser Val Phe Asn Gln Leu Pro Leu Glu
260 265 270

Glu Gln Pro Lys Tyr Ile Thr Asp Met Gly Cys Gly Asp Gly Thr Leu
275 280 285

Leu Lys Arg Val Trp Glu Thr Ile Gln Phe Lys Ser Ala Arg Gly Lys
290 295 300

Ala Leu Glu Gln Tyr Pro Leu Arg Leu Ile Gly Val Asp Tyr Asn Glu
305 310 315 320

Ala Ser Leu Lys Ala Thr Thr Arg Thr Leu Ala Ser Leu Pro His Leu
325 330 335

Val Leu Gln Gly Asp Ile Gly Asn Pro Glu Gln Met Val Arg Ser Leu
340 345 350

-continued

```
Glu Ala His Gly Ile His Asp Pro Glu Asn Ile Leu His Ile Arg Ser
        355                 360                 365

Phe Leu Asp His Asp Arg Leu Phe Ile Pro Pro Gln Lys Arg Asn Glu
    370                 375                 380

Leu Lys Glu Arg Ala His Leu Pro Tyr Gln Ser Val Cys Val Asp Asp
385                 390                 395                 400

Gln Gly Glu Leu Ile Pro Pro His Val Met Val Gln Ser Leu Val Glu
                405                 410                 415

His Leu Glu Arg Trp Ser Gln Val Val Asn Lys His Gly Leu Met Ile
            420                 425                 430

Leu Glu Val His Cys Leu Glu Pro Arg Val Val Tyr Gln Phe Leu Asp
        435                 440                 445

Lys Ser Glu Asn Leu His Phe Asp Ala Phe Gln Gly Phe Ser Gln Gln
    450                 455                 460

Tyr Leu Val Glu Ala Glu Val Phe Leu Met Ser Ala Ala Gln Val Gly
465                 470                 475                 480

Leu Phe Pro Lys Leu Glu Leu Ser Lys Arg Tyr Pro Lys Thr Phe Pro
                485                 490                 495

Phe Thr Arg Ile Thr Leu Asn Tyr Phe Glu Lys Arg Pro Tyr Lys Ile
            500                 505                 510

Ser His Ala Tyr Leu Ser Asp Leu Pro Ala Leu Val Asp Leu Glu Val
        515                 520                 525

Lys Cys Trp Pro Glu Asn Leu Arg Ala Ser Thr His Glu Ile Arg Arg
    530                 535                 540

Arg Leu Glu Leu Asn Pro Gln Gly Asn Leu Val Leu Ile Ile Glu Asp
545                 550                 555                 560

Gln Ile Ile Gly Ala Ile Tyr Ser Gln Thr Ile Thr Ser Thr Glu Ala
                565                 570                 575

Leu Glu Asn Val Lys Tyr Ala Gln Val Pro Thr Leu His Thr Pro Gln
            580                 585                 590

Gly Ser Val Ile Gln Leu Leu Ala Leu Asn Ile Leu Pro Glu Phe Gln
        595                 600                 605

Ala Arg Gly Leu Gly Asn Glu Leu Arg Asp Phe Met Leu Tyr Tyr Cys
    610                 615                 620

Thr Leu Lys Gly Gly Ile Glu Ser Val Val Gly Val Thr Arg Cys Arg
625                 630                 635                 640

Asn Tyr Val Asn Tyr Ser Gln Met Pro Met Met Glu Tyr Leu Lys Leu
                645                 650                 655

His Asn Glu Gln Arg Gln Leu Leu Asp Pro Ile Val Gly Phe His Val
            660                 665                 670

Ser Gly Gly Ala Glu Ile Arg Gly Ile Ile Ala Asn Tyr Arg Pro Glu
        675                 680                 685

Asp Thr Asp Asn Leu Gly Met Gly Ile Leu Ile Glu Tyr Asn Leu Arg
    690                 695                 700

Asp Ser Ala Leu His Ser Pro Gly Asp Arg Lys Gly Pro Tyr Ile Asn
705                 710                 715                 720

Ser Ala Ile Gly Ser Leu Val Pro Lys Ala Thr Ser Ala Thr Lys Glu
                725                 730                 735

Asn Lys Thr Val Ala Asp Leu Val Lys Glu Cys Ile Leu Lys Val Met
            740                 745                 750

Gly Ser Gln Arg Gln Ala Ala Tyr Ala Pro Gln Gln Lys Leu Leu Asp
        755                 760                 765

Met Gly Leu Asp Ser Leu Asp Leu Leu Glu Leu Gln Thr Leu Leu Glu
```

-continued

```
    770                 775                 780

Glu Arg Leu Gly Ile Asn Leu Ser Gly Thr Phe Phe Leu Gln Lys Asn
785                 790                 795                 800

Thr Pro Thr Ala Ile Ile Thr Tyr Phe Gln Asn Gln Val Val Gln Glu
                805                 810                 815

Lys Gln Ser Asp Leu Ala Pro Pro Val Asp Ser Ala Asn Glu Ile Asn
            820                 825                 830

Thr Leu Glu Asn Val Val Asn Gln Gln Lys Ile Pro Gln Val Thr Arg
        835                 840                 845

Val Val Thr Glu Gln Gln Gly Arg Lys Val Leu Ile Asp Gly His Trp
    850                 855                 860

Val Ile Asp Phe Ala Ser Cys Asn Tyr Leu Gly Leu Asp Leu His Pro
865                 870                 875                 880

Lys Val Lys Glu Ala Ile Pro Pro Ala Leu Asp Lys Trp Gly Thr His
                885                 890                 895

Pro Ser Trp Thr Arg Leu Val Ala Ser Pro Ala Ile Tyr Glu Glu Leu
            900                 905                 910

Glu Glu Glu Leu Ser Lys Leu Leu Gly Val Pro Asp Val Leu Val Phe
        915                 920                 925

Pro Ala Val Thr Leu Leu Gln Ile Gly Ile Leu Pro Leu Leu Thr Gly
    930                 935                 940

Asn Asn Gly Val Ile Phe Gly Asp Ile Ala Ala His Arg Cys Ile Tyr
945                 950                 955                 960

Glu Ala Cys Cys Leu Ala Gln His Lys Gly Ala Gln Phe Ile Gln Tyr
                965                 970                 975

Arg His Asn Asp Leu Asn Asp Leu Ala Glu Lys Leu Ala Lys Tyr Pro
            980                 985                 990

Pro Glu Gln Val Lys Ile Ile Val  Ile Asp Gly Val Tyr  Ser Met Ser
        995                 1000                1005

Ala Asp  Phe Pro Asp Leu Pro  Ala Tyr Val His Leu  Ala Lys Glu
    1010                1015                1020

Tyr Asn  Ala Leu Ile Tyr Met  Asp Asp Ala His Gly  Phe Gly Ile
    1025                1030                1035

Leu Gly  Glu Asn Pro Ser Ser  Asp Met Pro Tyr Gly  Tyr Lys Gly
    1040                1045                1050

Asn Gly  Met Val Asn Tyr Phe  Asp Leu Arg Phe Ala  Glu Asp Asn
    1055                1060                1065

Ile Ile  Tyr Val Ala Gly Leu  Ser Lys Ala Tyr Ser  Ser Tyr Ala
    1070                1075                1080

Ala Phe  Leu Thr Cys Gly Asp  Arg Arg Ile Lys Thr  Asn Phe Arg
    1085                1090                1095

Asn Ala  Trp Thr Ala Ile Phe  Ser Gly Pro Ser Pro  Val Ala Ser
    1100                1105                1110

Leu Ala  Ser Ala Leu Ala Gly  Leu Gln Val Asn Arg  Gln Glu Gly
    1115                1120                1125

Glu Gln  Leu Arg Lys Gln Ile  Tyr His Leu Thr His  Lys Leu Val
    1130                1135                1140

Thr Gln  Ala Arg Ala Ile Gly  Phe Glu Val Asp Asn  Tyr Gly Tyr
    1145                1150                1155

Val Pro  Ile Val Gly Val Leu  Val Gly Asp Ala Gln  His Met Ile
    1160                1165                1170

Asp Val  Cys Gln Leu Leu Trp  Glu Tyr Gly Ile Leu  Ile Thr Pro
    1175                1180                1185
```

```
Ala Ile Phe Pro Ile Val Pro Leu Asn Lys Ser Ala Leu Arg Phe
    1190                1195                1200

Ser Ile Thr Ala Ala Asn Thr Glu Glu Glu Ile Asp Gln Ala Ile
    1205                1210                1215

Lys Ser Leu Lys Ala Val Trp Asp Leu Leu Gln Lys Arg Lys Ala
    1220                1225                1230

Leu Pro Cys Lys Gln Glu Glu Asn Ile Leu Lys His
    1235                1240                1245
```

<210> SEQ ID NO 16
<211> LENGTH: 387
<212> TYPE: DNA
<213> ORGANISM: Cylindrospermopsis raciborskii T3

<400> SEQUENCE: 16

```
atgttgaaag atttcaacca gtttttaatc agaacactag cattcgtatt cgcatttggt     60

attttcttaa ccactggagt tggcattgct aaagctgact acctagttaa aggtggaaag    120

attaccaatg ttcaaaatac ttcttctaac ggtgataatt atgccgttag tatcagcggt    180

gggtttggtc cttgcgcaga tagagtgatt atcctaccaa cttcaggagt gataaatcga    240

gacattcata tgcgtggcta tgaagccgca ttaactgcac tatccaatgg ctttttagta    300

gatatttacg actatactgg ctcttcttgc agcaatggtg gccaactaac tattaccaac    360

caattaggta agctaatcag caattag                                        387
```

<210> SEQ ID NO 17
<211> LENGTH: 128
<212> TYPE: PRT
<213> ORGANISM: Cylindrospermopsis raciborskii T3

<400> SEQUENCE: 17

```
Met Leu Lys Asp Phe Asn Gln Phe Leu Ile Arg Thr Leu Ala Phe Val
1               5                   10                  15

Phe Ala Phe Gly Ile Phe Leu Thr Thr Gly Val Gly Ile Ala Lys Ala
            20                  25                  30

Asp Tyr Leu Val Lys Gly Gly Lys Ile Thr Asn Val Gln Asn Thr Ser
        35                  40                  45

Ser Asn Gly Asp Asn Tyr Ala Val Ser Ile Ser Gly Gly Phe Gly Pro
    50                  55                  60

Cys Ala Asp Arg Val Ile Ile Leu Pro Thr Ser Gly Val Ile Asn Arg
65                  70                  75                  80

Asp Ile His Met Arg Gly Tyr Glu Ala Ala Leu Thr Ala Leu Ser Asn
                85                  90                  95

Gly Phe Leu Val Asp Ile Tyr Asp Tyr Thr Gly Ser Ser Cys Ser Asn
            100                 105                 110

Gly Gly Gln Leu Thr Ile Thr Asn Gln Leu Gly Lys Leu Ile Ser Asn
        115                 120                 125
```

<210> SEQ ID NO 18
<211> LENGTH: 1416
<212> TYPE: DNA
<213> ORGANISM: Cylindrospermopsis raciborskii T3

<400> SEQUENCE: 18

```
atggaaacaa cctcaaaaaa atttaagtca gatctgatat tagaagcacg agcaagccta     60

aagttgggaa tccccttagt catttcacaa atgtgcgaaa cgggtattta tacagcgaat    120
```

-continued

```
gcagtcatga tgggtttact tggtacgcaa gttttggccg ccggtgcttt gggcgcgctc    180

gctttttga ccttattatt tgcctgccat ggtattctct cagtaggagg atcactagca    240

gccgaagctt tggggcaaa taaaatagat gaagttagtc gtattgcttc cgggcaaata    300

tggctagcag ttaccttgtc tttacctgca atgcttctgc tttggcatgg cgatactatc    360

ttgctgctat tcggtcaaga ggaaagcaat gtgttattga caaaaacgta tttacactca    420

attttatggg gctttcccgc tgcgcttagt attttgacat taagaggcat tgcctctgct    480

ctcaacgttc cccgattgat aactattact atgctcactc agctgatatt gaataccgcc    540

gccgattatg tgttaatatt cggtaaattt ggtcttcctc aacttggttt ggctggaata    600

ggctgggcaa ctgctctggg tttttgggtt agttttacat tggggcttat cttgctgatt    660

ttctccctga aagttagaga ttataaactt ttccgctact tgcatcagtt tgataaacag    720

atctttgtca aaatttttca aactggatgg cccatggggt ttcaatgggg ggcggaaacg    780

gcactattta acgtcaccgc ttgggtagca gggtatttag gaacggtaac attagcagcc    840

catgatattg gcttccaaac ggcagaactg gcgatggtta taccactcgg agtcggcaat    900

gtcgctatga caagagtagg tcagagtata ggagaaaaaa acccctttggg tgcaagaagg    960

gtagcatcga ttggaattac aatagttggc atttatgcca gtattgtagc acttgttttc   1020

tggttgtttc catatcaaat tgccggaatt tatttaaata taaacaatcc cgagaatatc   1080

gaagcaatta agaaagcaac tacttttatc cccttggcgg gactattcca aatgttttac   1140

agtattcaaa taattattgt tggggctttg gtcggtctgc gggatacatt tgttccagta   1200

tcaatgaact taattgtctg ggtcttgga ttggcaggaa gctatttcat ggcaatcatt   1260

ttaggatggg gggggatcgg gatttggttg gctatggttt tgagtccact cctctcggca   1320

gttattttaa ctgttcgttt ttatcgagtg attgacaatc ttcttgccaa cagtgatgat   1380

atgttacaga atgcgtctgt tactactcta ggctga                             1416
```

<210> SEQ ID NO 19
<211> LENGTH: 471
<212> TYPE: PRT
<213> ORGANISM: Cylindrospermopsis raciborskii T3

<400> SEQUENCE: 19

```
Met Glu Thr Thr Ser Lys Lys Phe Lys Ser Asp Leu Ile Leu Glu Ala
1               5                   10                  15

Arg Ala Ser Leu Lys Leu Gly Ile Pro Leu Val Ile Ser Gln Met Cys
            20                  25                  30

Glu Thr Gly Ile Tyr Thr Ala Asn Ala Val Met Met Gly Leu Leu Gly
        35                  40                  45

Thr Gln Val Leu Ala Ala Gly Ala Leu Gly Ala Leu Ala Phe Leu Thr
    50                  55                  60

Leu Leu Phe Ala Cys His Gly Ile Leu Ser Val Gly Gly Ser Leu Ala
65                  70                  75                  80

Ala Glu Ala Phe Gly Ala Asn Lys Ile Asp Glu Val Ser Arg Ile Ala
                85                  90                  95

Ser Gly Gln Ile Trp Leu Ala Val Thr Leu Ser Leu Pro Ala Met Leu
            100                 105                 110

Leu Leu Trp His Gly Asp Thr Ile Leu Leu Leu Phe Gly Gln Glu Glu
        115                 120                 125

Ser Asn Val Leu Leu Thr Lys Thr Tyr Leu His Ser Ile Leu Trp Gly
    130                 135                 140
```

-continued

```
Phe Pro Ala Ala Leu Ser Ile Leu Thr Leu Arg Gly Ile Ala Ser Ala
145                 150                 155                 160

Leu Asn Val Pro Arg Leu Ile Thr Ile Thr Met Leu Thr Gln Leu Ile
                165                 170                 175

Leu Asn Thr Ala Ala Asp Tyr Val Leu Ile Phe Gly Lys Phe Gly Leu
            180                 185                 190

Pro Gln Leu Gly Leu Ala Gly Ile Gly Trp Ala Thr Ala Leu Gly Phe
        195                 200                 205

Trp Val Ser Phe Thr Leu Gly Leu Ile Leu Leu Ile Phe Ser Leu Lys
    210                 215                 220

Val Arg Asp Tyr Lys Leu Phe Arg Tyr Leu His Gln Phe Asp Lys Gln
225                 230                 235                 240

Ile Phe Val Lys Ile Phe Gln Thr Gly Trp Pro Met Gly Phe Gln Trp
                245                 250                 255

Gly Ala Glu Thr Ala Leu Phe Asn Val Thr Ala Trp Val Ala Gly Tyr
            260                 265                 270

Leu Gly Thr Val Thr Leu Ala Ala His Asp Ile Gly Phe Gln Thr Ala
        275                 280                 285

Glu Leu Ala Met Val Ile Pro Leu Gly Val Gly Asn Val Ala Met Thr
    290                 295                 300

Arg Val Gly Gln Ser Ile Gly Glu Lys Asn Pro Leu Gly Ala Arg Arg
305                 310                 315                 320

Val Ala Ser Ile Gly Ile Thr Ile Val Gly Ile Tyr Ala Ser Ile Val
                325                 330                 335

Ala Leu Val Phe Trp Leu Phe Pro Tyr Gln Ile Ala Gly Ile Tyr Leu
            340                 345                 350

Asn Ile Asn Asn Pro Glu Asn Ile Glu Ala Ile Lys Lys Ala Thr Thr
        355                 360                 365

Phe Ile Pro Leu Ala Gly Leu Phe Gln Met Phe Tyr Ser Ile Gln Ile
    370                 375                 380

Ile Ile Val Gly Ala Leu Val Gly Leu Arg Asp Thr Phe Val Pro Val
385                 390                 395                 400

Ser Met Asn Leu Ile Val Trp Gly Leu Gly Leu Ala Gly Ser Tyr Phe
                405                 410                 415

Met Ala Ile Ile Leu Gly Trp Gly Gly Ile Gly Ile Trp Leu Ala Met
            420                 425                 430

Val Leu Ser Pro Leu Leu Ser Ala Val Ile Leu Thr Val Arg Phe Tyr
        435                 440                 445

Arg Val Ile Asp Asn Leu Leu Ala Asn Ser Asp Asp Met Leu Gln Asn
    450                 455                 460

Ala Ser Val Thr Thr Leu Gly
465                 470
```

<210> SEQ ID NO 20
<211> LENGTH: 1134
<212> TYPE: DNA
<213> ORGANISM: Cylindrospermopsis raciborskii T3

<400> SEQUENCE: 20

```
atgaccaatc aaaataacca agaattagag aacgatttac caatcgccaa gcagccttgt      60

ccggtcaatt cttataatga gtgggacaca cttgaggagg tcattgttgg tagtgttgaa     120

ggtgcaatgt taccggccct agaaccaatc aacaaatgga cattcccttt tgaagaattg     180

gaatctgccc aaaagatact ctctgagagg ggaggagttc cttatccacc agagatgatt     240
```

-continued

```
acattagcac acaaagaact aaatgaattt attcacattc ttgaagcaga aggggtcaaa    300

gttcgtcgag ttaaacctgt agatttctct gtccccttct ccacaccagc ttggcaagta    360

ggaagtggtt tttgtgccgc caatcctcgc gatgtttttt tggtgattgg gaatgagatt    420

attgaagcac caatggcaga tcgcaaccgc tattttgaaa cttgggcgta tcgagagatg    480

ctcaaggaat attttcaggc aggagctaag tggactgcag cgccgaagcc acaattattc    540

gacgcacagt atgacttcaa tttccagttt cctcaactgg gggagccgcc gcgtttcgtc    600

gttacagagt ttgaaccgac ttttgatgcg gcagattttg tgcgctgtgg acgagatatt    660

tttggtcaaa aaagtcatgt gactaatggt ttgggcatag aatggttaca acgtcacttg    720

gaagacgaat accgtattca tattattgaa tcgcattgtc cggaagcact gcacatcgat    780

accaccttaa tgcctcttgc acctggcaaa atactagtaa atccagaatt tgtagatgtt    840

aataaattgc caaaaatcct gaaaagctgg gacattttgg ttgcacctta ccccaaccat    900

atacctcaaa accagctgag actggtcagt gaatgggcag gtttgaatgt actgatgtta    960

gatgaagagc gagtcattgt agaaaaaaac caggagcaga tgattaaagc actgaaagat   1020

tggggattta agcctattgt ttgccatttt gaaagctact atccattttt aggatcattt   1080

cactgtgcaa cattagacgt tcgccgacgc ggaactcttc agtcctattt ttaa         1134
```

```
<210> SEQ ID NO 21
<211> LENGTH: 377
<212> TYPE: PRT
<213> ORGANISM: Cylindrospermopsis raciborskii T3

<400> SEQUENCE: 21

Met Thr Asn Gln Asn Asn Gln Glu Leu Glu Asn Asp Leu Pro Ile Ala
1               5                   10                  15

Lys Gln Pro Cys Pro Val Asn Ser Tyr Asn Glu Trp Asp Thr Leu Glu
            20                  25                  30

Glu Val Ile Val Gly Ser Val Glu Gly Ala Met Leu Pro Ala Leu Glu
        35                  40                  45

Pro Ile Asn Lys Trp Thr Phe Pro Phe Glu Glu Leu Glu Ser Ala Gln
    50                  55                  60

Lys Ile Leu Ser Glu Arg Gly Gly Val Pro Tyr Pro Pro Glu Met Ile
65                  70                  75                  80

Thr Leu Ala His Lys Glu Leu Asn Glu Phe Ile His Ile Leu Glu Ala
                85                  90                  95

Glu Gly Val Lys Val Arg Arg Val Lys Pro Val Asp Phe Ser Val Pro
            100                 105                 110

Phe Ser Thr Pro Ala Trp Gln Val Gly Ser Gly Phe Cys Ala Ala Asn
        115                 120                 125

Pro Arg Asp Val Phe Leu Val Ile Gly Asn Glu Ile Ile Glu Ala Pro
    130                 135                 140

Met Ala Asp Arg Asn Arg Tyr Phe Glu Thr Trp Ala Tyr Arg Glu Met
145                 150                 155                 160

Leu Lys Glu Tyr Phe Gln Ala Gly Ala Lys Trp Thr Ala Ala Pro Lys
                165                 170                 175

Pro Gln Leu Phe Asp Ala Gln Tyr Asp Phe Asn Phe Gln Phe Pro Gln
            180                 185                 190

Leu Gly Glu Pro Pro Arg Phe Val Val Thr Glu Phe Glu Pro Thr Phe
        195                 200                 205

Asp Ala Ala Asp Phe Val Arg Cys Gly Arg Asp Ile Phe Gly Gln Lys
    210                 215                 220
```

Ser His Val Thr Asn Gly Leu Gly Ile Glu Trp Leu Gln Arg His Leu
225 230 235 240

Glu Asp Glu Tyr Arg Ile His Ile Ile Glu Ser His Cys Pro Glu Ala
245 250 255

Leu His Ile Asp Thr Thr Leu Met Pro Leu Ala Pro Gly Lys Ile Leu
260 265 270

Val Asn Pro Glu Phe Val Asp Val Asn Lys Leu Pro Lys Ile Leu Lys
275 280 285

Ser Trp Asp Ile Leu Val Ala Pro Tyr Pro Asn His Ile Pro Gln Asn
290 295 300

Gln Leu Arg Leu Val Ser Glu Trp Ala Gly Leu Asn Val Leu Met Leu
305 310 315 320

Asp Glu Glu Arg Val Ile Val Glu Lys Asn Gln Glu Gln Met Ile Lys
325 330 335

Ala Leu Lys Asp Trp Gly Phe Lys Pro Ile Val Cys His Phe Glu Ser
340 345 350

Tyr Tyr Pro Phe Leu Gly Ser Phe His Cys Ala Thr Leu Asp Val Arg
355 360 365

Arg Arg Gly Thr Leu Gln Ser Tyr Phe
370 375

<210> SEQ ID NO 22
<211> LENGTH: 1005
<212> TYPE: DNA
<213> ORGANISM: Cylindrospermopsis raciborskii T3

<400> SEQUENCE: 22
atgacaactg ctgacctaat cttaattaac aactggtacg tagtcgcaaa ggtggaagat 60
tgtaaaccag gaagtatcac cacggctctt ttattgggag ttaagttggt actatggcgc 120
agtcgtgaac agaattcccc catacagata tggcaagact actgccctca ccgaggtgtg 180
gctctgtcta tgggagaaat tgttaataat actttggttt gtccgtatca cggatggaga 240
tataatcaag caggtaaatg cgtacatatc ccggctcacc ctgacatgac acccccagca 300
agtgcccaag ccaagatcta tcattgccag gagcgatacg gattagtatg ggtgtgctta 360
ggtgatcctg tcaatgatat accttcatta cccgaatggg acgatccgaa ttatcataat 420
acttgtacta aatcttattt tattcaagct agtgcgtttc gtgtaatgga taatttcata 480
gatgtatctc attttccttt tgtccacgac ggtgggttag gtgatcgcaa ccacgcacaa 540
attgaagaat ttgaggtaaa agtagacaaa gatggcatta gcataggtaa ccttaaactc 600
cagatgccaa ggtttaacag cagtaacgaa gatgactcat ggactcttta ccaaaggatt 660
agtcatccct tgtgtcaata ctatattact gaatcctctg aaattcggac tgcggatttg 720
atgctggtaa caccgattga tgaagacaac agcttagtgc gaatgttagt aacgtggaac 780
cgctccgaaa tattagagtc aacggtacta gaggaatttg acgaaacaat agaacaagat 840
attccgatta tacactctca acagccagcg cgtttaccac tgttaccttc aaagcagata 900
aacatgcaat ggttgtcaca ggaaatacat gtaccgtcag atcgatgcac agttgcctat 960
cgtcgatggc taaaggaact gggcgttacc tatggtgttt gttaa 1005

<210> SEQ ID NO 23
<211> LENGTH: 334
<212> TYPE: PRT
<213> ORGANISM: Cylindrospermopsis raciborskii T3

<400> SEQUENCE: 23

Met Thr Thr Ala Asp Leu Ile Leu Ile Asn Asn Trp Tyr Val Val Ala
1 5 10 15

Lys Val Glu Asp Cys Lys Pro Gly Ser Ile Thr Thr Ala Leu Leu Leu
20 25 30

Gly Val Lys Leu Val Leu Trp Arg Ser Arg Glu Gln Asn Ser Pro Ile
35 40 45

Gln Ile Trp Gln Asp Tyr Cys Pro His Arg Gly Val Ala Leu Ser Met
50 55 60

Gly Glu Ile Val Asn Asn Thr Leu Val Cys Pro Tyr His Gly Trp Arg
65 70 75 80

Tyr Asn Gln Ala Gly Lys Cys Val His Ile Pro Ala His Pro Asp Met
85 90 95

Thr Pro Pro Ala Ser Ala Gln Ala Lys Ile Tyr His Cys Gln Glu Arg
100 105 110

Tyr Gly Leu Val Trp Val Cys Leu Gly Asp Pro Val Asn Asp Ile Pro
115 120 125

Ser Leu Pro Glu Trp Asp Asp Pro Asn Tyr His Asn Thr Cys Thr Lys
130 135 140

Ser Tyr Phe Ile Gln Ala Ser Ala Phe Arg Val Met Asp Asn Phe Ile
145 150 155 160

Asp Val Ser His Phe Pro Phe Val His Asp Gly Gly Leu Gly Asp Arg
165 170 175

Asn His Ala Gln Ile Glu Glu Phe Glu Val Lys Val Asp Lys Asp Gly
180 185 190

Ile Ser Ile Gly Asn Leu Lys Leu Gln Met Pro Arg Phe Asn Ser Ser
195 200 205

Asn Glu Asp Asp Ser Trp Thr Leu Tyr Gln Arg Ile Ser His Pro Leu
210 215 220

Cys Gln Tyr Tyr Ile Thr Glu Ser Ser Glu Ile Arg Thr Ala Asp Leu
225 230 235 240

Met Leu Val Thr Pro Ile Asp Glu Asp Asn Ser Leu Val Arg Met Leu
245 250 255

Val Thr Trp Asn Arg Ser Glu Ile Leu Glu Ser Thr Val Leu Glu Glu
260 265 270

Phe Asp Glu Thr Ile Glu Gln Asp Ile Pro Ile Ile His Ser Gln Gln
275 280 285

Pro Ala Arg Leu Pro Leu Leu Pro Ser Lys Gln Ile Asn Met Gln Trp
290 295 300

Leu Ser Gln Glu Ile His Val Pro Ser Asp Arg Cys Thr Val Ala Tyr
305 310 315 320

Arg Arg Trp Leu Lys Glu Leu Gly Val Thr Tyr Gly Val Cys
325 330

<210> SEQ ID NO 24
<211> LENGTH: 1839
<212> TYPE: DNA
<213> ORGANISM: Cylindrospermopsis raciborskii T3

<400> SEQUENCE: 24
atgcagatct taggaatttc agcttactac cacgatagtg ctgccgcgat ggttatcgat 60
ggcgaaattg ttgctgcagc tcaggaagaa cgtttctcaa gacgaaagca cgatgctggg 120
tttccgactg gagcgattac ttactgtcta aaacaagtag gaaccaagtt acaatatatc 180

```
gatcaaattg tttttacga caagccatta gtcaaatttg agcggttgct agaaacatat    240
ttagcatatg ccccaaaggg atttggctcg tttattactg ctatgcccgt ttggctcaaa    300
gaaaagcttt acctaaaaac acttttaaaa aaagaattgg cgcttttggg ggagtgcaaa    360
gcttctcaat tgcctcctct actgtttacc tcacatcacc aagcccatgc ggccgctgct    420
tttttccca gtccttttca gcgtgctgcc gttctgtgct tagatggtgt aggagagtgg    480
gcaactactt ctgtctggtt gggagaagga aataaactca caccacaatg ggaaattgat    540
tttccccatt ccctcggttt gctttactca gcgtttacct actacactgg gttcaaagtt    600
aactcaggtg agtacaaact catgggttta gcaccctacg gggaacccaa atatgtggac    660
caaattctca agcatttgtt ggatctcaaa gaagatggta cttttaggtt gaatatggac    720
tacttcaact acacggtggg gctaaccatg accaatcata agttccatag tatgtttgga    780
ggaccaccac gccaggcgga aggaaaaatc tcccaaagag acatggatct ggcaagttcg    840
atccaaaagg tgactgaaga agtcatactg cgtctggcta gaactatcaa aaaagaactg    900
ggtgtagagt atctatgttt agcaggtggt gtcggtctca attgcgtggc taacggacga    960
attctccgag aaagtgattt caaagatatt tggattcaac ccgcagcagg agatgccggt   1020
agtgcagtgg gagcagcttt agcgatttgg catgaatacc ataagaaacc tcgcacttca   1080
acagcaggcg atcgcatgaa aggttcttat ctgggaccta gctttagcga ggcggagatt   1140
ctccagtttc ttaattctgt taacataccc taccatcgat gcgttgataa cgaacttatg   1200
gctcgtcttg cagaaatttt agaccaggga aatgttgtag gctggttttc tggacgaatg   1260
gagtttggtc cgcgtgcttt gggtggccgt tcgattattg gcgattcacg cagtccaaaa   1320
atgcaatcgg tcatgaacct gaaaattaaa tatcgtgagt ccttccgtcc atttgctcct   1380
tcagtcttgg ctgaacgagt ctccgactac ttcgatcttg atcgtcctag tccttatatg   1440
cttttggtag cacaagtcaa agagaatctg cacattccta tgacacaaga gcaacacgag   1500
ctatttggga tcgagaagct gaatgttcct cgttcccaaa ttcccgcagt cactcacgtt   1560
gattactcag ctcgtattca gacagttcac aaagaaacga atcctcgtta ctacgagtta   1620
attcgtcatt ttgaggcacg aactggttgt gctgtcttgg tcaatacttc gtttaatgtc   1680
cgcggcgaac caattgtttg tactcccgaa gacgcttatc gatgctttat gagaactgaa   1740
atggactatt tggttatgga gaatttcttg ttggtcaaat ctgaacagcc acggggaaat   1800
agtgatgagt catggcaaaa agaattcgag ttagattaa                          1839
```

<210> SEQ ID NO 25
<211> LENGTH: 612
<212> TYPE: PRT
<213> ORGANISM: Cylindrospermopsis raciborskii T3

<400> SEQUENCE: 25

```
Met Gln Ile Leu Gly Ile Ser Ala Tyr Tyr His Asp Ser Ala Ala Ala
1               5                   10                  15

Met Val Ile Asp Gly Glu Ile Val Ala Ala Ala Gln Glu Glu Arg Phe
            20                  25                  30

Ser Arg Arg Lys His Asp Ala Gly Phe Pro Thr Gly Ala Ile Thr Tyr
        35                  40                  45

Cys Leu Lys Gln Val Gly Thr Lys Leu Gln Tyr Ile Asp Gln Ile Val
    50                  55                  60

Phe Tyr Asp Lys Pro Leu Val Lys Phe Glu Arg Leu Leu Glu Thr Tyr
65                  70                  75                  80
```

-continued

```
Leu Ala Tyr Ala Pro Lys Gly Phe Gly Ser Phe Ile Thr Ala Met Pro
                85                  90                  95

Val Trp Leu Lys Glu Lys Leu Tyr Leu Lys Thr Leu Leu Lys Lys Glu
            100                 105                 110

Leu Ala Leu Leu Gly Glu Cys Lys Ala Ser Gln Leu Pro Pro Leu Leu
        115                 120                 125

Phe Thr Ser His His Gln Ala His Ala Ala Ala Ala Phe Phe Pro Ser
    130                 135                 140

Pro Phe Gln Arg Ala Ala Val Leu Cys Leu Asp Gly Val Gly Glu Trp
145                 150                 155                 160

Ala Thr Thr Ser Val Trp Leu Gly Glu Gly Asn Lys Leu Thr Pro Gln
                165                 170                 175

Trp Glu Ile Asp Phe Pro His Ser Leu Gly Leu Leu Tyr Ser Ala Phe
            180                 185                 190

Thr Tyr Tyr Thr Gly Phe Lys Val Asn Ser Gly Glu Tyr Lys Leu Met
        195                 200                 205

Gly Leu Ala Pro Tyr Gly Glu Pro Lys Tyr Val Asp Gln Ile Leu Lys
    210                 215                 220

His Leu Leu Asp Leu Lys Glu Asp Gly Thr Phe Arg Leu Asn Met Asp
225                 230                 235                 240

Tyr Phe Asn Tyr Thr Val Gly Leu Thr Met Thr Asn His Lys Phe His
                245                 250                 255

Ser Met Phe Gly Gly Pro Pro Arg Gln Ala Glu Gly Lys Ile Ser Gln
            260                 265                 270

Arg Asp Met Asp Leu Ala Ser Ser Ile Gln Lys Val Thr Glu Glu Val
        275                 280                 285

Ile Leu Arg Leu Ala Arg Thr Ile Lys Lys Glu Leu Gly Val Glu Tyr
    290                 295                 300

Leu Cys Leu Ala Gly Gly Val Gly Leu Asn Cys Val Ala Asn Gly Arg
305                 310                 315                 320

Ile Leu Arg Glu Ser Asp Phe Lys Asp Ile Trp Ile Gln Pro Ala Ala
                325                 330                 335

Gly Asp Ala Gly Ser Ala Val Gly Ala Ala Leu Ala Ile Trp His Glu
            340                 345                 350

Tyr His Lys Lys Pro Arg Thr Ser Thr Ala Gly Asp Arg Met Lys Gly
        355                 360                 365

Ser Tyr Leu Gly Pro Ser Phe Ser Glu Ala Glu Ile Leu Gln Phe Leu
    370                 375                 380

Asn Ser Val Asn Ile Pro Tyr His Arg Cys Val Asp Asn Glu Leu Met
385                 390                 395                 400

Ala Arg Leu Ala Glu Ile Leu Asp Gln Gly Asn Val Val Gly Trp Phe
                405                 410                 415

Ser Gly Arg Met Glu Phe Gly Pro Arg Ala Leu Gly Gly Arg Ser Ile
            420                 425                 430

Ile Gly Asp Ser Arg Ser Pro Lys Met Gln Ser Val Met Asn Leu Lys
        435                 440                 445

Ile Lys Tyr Arg Glu Ser Phe Arg Pro Phe Ala Pro Ser Val Leu Ala
    450                 455                 460

Glu Arg Val Ser Asp Tyr Phe Asp Leu Asp Arg Pro Ser Pro Tyr Met
465                 470                 475                 480

Leu Leu Val Ala Gln Val Lys Glu Asn Leu His Ile Pro Met Thr Gln
                485                 490                 495

Glu Gln His Glu Leu Phe Gly Ile Glu Lys Leu Asn Val Pro Arg Ser
```

```
            500                 505                 510

Gln Ile Pro Ala Val Thr His Val Asp Tyr Ser Ala Arg Ile Gln Thr
        515                 520                 525

Val His Lys Glu Thr Asn Pro Arg Tyr Tyr Glu Leu Ile Arg His Phe
    530                 535                 540

Glu Ala Arg Thr Gly Cys Ala Val Leu Val Asn Thr Ser Phe Asn Val
545                 550                 555                 560

Arg Gly Glu Pro Ile Val Cys Thr Pro Glu Asp Ala Tyr Arg Cys Phe
                565                 570                 575

Met Arg Thr Glu Met Asp Tyr Leu Val Met Glu Asn Phe Leu Leu Val
            580                 585                 590

Lys Ser Glu Gln Pro Arg Gly Asn Ser Asp Glu Ser Trp Gln Lys Glu
        595                 600                 605

Phe Glu Leu Asp
    610


<210> SEQ ID NO 26
<211> LENGTH: 444
<212> TYPE: DNA
<213> ORGANISM: Cylindrospermopsis raciborskii T3

<400> SEQUENCE: 26

atgagtgaat ttttcccaca aaaaagtggt aaattaaaga tggaacagat aaaagaactt      60

gacaaaaaag gattgcgtga gtttggactg attggcggtt ctatagtggc ggttttattc     120

ggctttttac tgccagttat acgccatcat tccttatcag ttatcccttg ggttgttgct     180

ggatttctct ggatttgggc aataatcgca cctacgactt taagttttat ttaccaaata     240

tggatgagga ttggacttgt tttaggatgg atacaaacac gaattatttt gggagtttta     300

ttttatataa tgatcacacc aataggattc ataagacggc tgttgaatca agatccaatg     360

acgcgaatct tcgagccaga gttgccaact tatcgccaat tgagtaagtc aagaactaca     420

caaagtatgg agaaaccatt ctaa                                            444


<210> SEQ ID NO 27
<211> LENGTH: 147
<212> TYPE: PRT
<213> ORGANISM: Cylindrospermopsis raciborskii T3

<400> SEQUENCE: 27

Met Ser Glu Phe Phe Pro Gln Lys Ser Gly Lys Leu Lys Met Glu Gln
1               5                   10                  15

Ile Lys Glu Leu Asp Lys Lys Gly Leu Arg Glu Phe Gly Leu Ile Gly
            20                  25                  30

Gly Ser Ile Val Ala Val Leu Phe Gly Phe Leu Leu Pro Val Ile Arg
        35                  40                  45

His His Ser Leu Ser Val Ile Pro Trp Val Val Ala Gly Phe Leu Trp
    50                  55                  60

Ile Trp Ala Ile Ile Ala Pro Thr Thr Leu Ser Phe Ile Tyr Gln Ile
65                  70                  75                  80

Trp Met Arg Ile Gly Leu Val Leu Gly Trp Ile Gln Thr Arg Ile Ile
                85                  90                  95

Leu Gly Val Leu Phe Tyr Ile Met Ile Thr Pro Ile Gly Phe Ile Arg
            100                 105                 110

Arg Leu Leu Asn Gln Asp Pro Met Thr Arg Ile Phe Glu Pro Glu Leu
        115                 120                 125
```

```
Pro Thr Tyr Arg Gln Leu Ser Lys Ser Arg Thr Thr Gln Ser Met Glu
    130                 135                 140

Lys Pro Phe
145


<210> SEQ ID NO 28
<211> LENGTH: 165
<212> TYPE: DNA
<213> ORGANISM: Cylindrospermopsis raciborskii T3

<400> SEQUENCE: 28

atgctaaaag acacttggga ttttattaaa gacattgccg gatttattaa agaacaaaaa      60

aactatttgt tgattcccct aattatcacc ctggtatcct tgggggcgct gattgtcttt     120

gctcaatctt ctgcgatcgc acctttcatt tacactcttt tttaa                     165


<210> SEQ ID NO 29
<211> LENGTH: 54
<212> TYPE: PRT
<213> ORGANISM: Cylindrospermopsis raciborskii T3

<400> SEQUENCE: 29

Met Leu Lys Asp Thr Trp Asp Phe Ile Lys Asp Ile Ala Gly Phe Ile
1               5                   10                  15

Lys Glu Gln Lys Asn Tyr Leu Leu Ile Pro Leu Ile Ile Thr Leu Val
            20                  25                  30

Ser Leu Gly Ala Leu Ile Val Phe Ala Gln Ser Ser Ala Ile Ala Pro
        35                  40                  45

Phe Ile Tyr Thr Leu Phe
    50


<210> SEQ ID NO 30
<211> LENGTH: 1299
<212> TYPE: DNA
<213> ORGANISM: Cylindrospermopsis raciborskii T3

<400> SEQUENCE: 30

atgagtaact tcaagggttc ggtaaagata gcattgatgg gaatattgat tttttgtggg      60

ctaatctttg gcgtagcatt tgttgaaatt gggttacgta ttgccgggat cgaacacata     120

gcattccata gcattgatga acacaggggg tgggtagggc gacctcatgt ttccgggtgg     180

tatagaaccg aaggtgaagc tcacatccaa atgaatagtg atggctttcg agatcgagaa     240

cacatcaagg tcaaaccaga aaataccttc aggatagcgc tgttgggaga ttcctttgta     300

gagtccatgc aagtaccgtt ggagcaaaat ttggcagcag ttatagaagg agaaatcagt     360

agttgtatag ctttagctgg acgaaaggcg gaagtgatta attttggagt gactggttat     420

ggaacagacc aagaactaat tactctacgg gagaaagttt gggactattc acctgatata     480

gtagtgctag atttttatac tggcaacgac attgttgata actcccgtgc gctgagtcag     540

aaattctatc ctaatgaact aggttcacta aagccgtttt ttatacttag agatggtaat     600

ctggtggttg atgcttcgtt tatcaatacg gataattatc gctcaaagct gacatggtgg     660

ggcaaaactt atatgaaaat aaaagaccac tcacggattt tacaggtttt aaacatggta     720

cgggatgctc ttaacaactc tagtagaggg ttttcttctc aagctataga ggaaccgtta     780

tttagtgatg gaaaacagga tacaaaattg agcgggtttt ttgatatcta caaaccacct     840

actgaccctg aatggcaaca ggcatggcaa gtcacagaga aactgattag ctcaatgcaa     900

cacgaggtga ctgcgaagaa agcagatttt ttagttgtta cttttggcgg tccctttcaa     960
```

```
cgagaacctt tagtgcgtca aaaagaaatg caagaattgg gtctgactga ttggttttac   1020

ccagagaagc gaattacacg tttgggtgag gatgaggggt tcagtgtact caatctcagc   1080

ccaaatttgc aggtttattc tgagcagaac aatgcttgcc tatatgggtt tgatgatact   1140

caaggctgtg tagggcattg gaatgcttta ggacatcagg tagcaggaaa aatgattgca   1200

tcgaagattt gtcaacagca gatgagagaa agtatattgc ctcataagca cgacccttca   1260

agccaaagct cacctattac ccaatcagtg atccaataa                          1299


<210> SEQ ID NO 31
<211> LENGTH: 432
<212> TYPE: PRT
<213> ORGANISM: Cylindrospermopsis raciborskii T3

<400> SEQUENCE: 31

Met Ser Asn Phe Lys Gly Ser Val Lys Ile Ala Leu Met Gly Ile Leu
1               5                   10                  15

Ile Phe Cys Gly Leu Ile Phe Gly Val Ala Phe Val Glu Ile Gly Leu
            20                  25                  30

Arg Ile Ala Gly Ile Glu His Ile Ala Phe His Ser Ile Asp Glu His
        35                  40                  45

Arg Gly Trp Val Gly Arg Pro His Val Ser Gly Trp Tyr Arg Thr Glu
    50                  55                  60

Gly Glu Ala His Ile Gln Met Asn Ser Asp Gly Phe Arg Asp Arg Glu
65                  70                  75                  80

His Ile Lys Val Lys Pro Glu Asn Thr Phe Arg Ile Ala Leu Leu Gly
                85                  90                  95

Asp Ser Phe Val Glu Ser Met Gln Val Pro Leu Glu Gln Asn Leu Ala
            100                 105                 110

Ala Val Ile Glu Gly Glu Ile Ser Ser Cys Ile Ala Leu Ala Gly Arg
        115                 120                 125

Lys Ala Glu Val Ile Asn Phe Gly Val Thr Gly Tyr Gly Thr Asp Gln
    130                 135                 140

Glu Leu Ile Thr Leu Arg Glu Lys Val Trp Asp Tyr Ser Pro Asp Ile
145                 150                 155                 160

Val Val Leu Asp Phe Tyr Thr Gly Asn Asp Ile Val Asp Asn Ser Arg
                165                 170                 175

Ala Leu Ser Gln Lys Phe Tyr Pro Asn Glu Leu Gly Ser Leu Lys Pro
            180                 185                 190

Phe Phe Ile Leu Arg Asp Gly Asn Leu Val Val Asp Ala Ser Phe Ile
        195                 200                 205

Asn Thr Asp Asn Tyr Arg Ser Lys Leu Thr Trp Trp Gly Lys Thr Tyr
    210                 215                 220

Met Lys Ile Lys Asp His Ser Arg Ile Leu Gln Val Leu Asn Met Val
225                 230                 235                 240

Arg Asp Ala Leu Asn Asn Ser Ser Arg Gly Phe Ser Ser Gln Ala Ile
                245                 250                 255

Glu Glu Pro Leu Phe Ser Asp Gly Lys Gln Asp Thr Lys Leu Ser Gly
            260                 265                 270

Phe Phe Asp Ile Tyr Lys Pro Pro Thr Asp Pro Glu Trp Gln Gln Ala
        275                 280                 285

Trp Gln Val Thr Glu Lys Leu Ile Ser Ser Met Gln His Glu Val Thr
    290                 295                 300

Ala Lys Lys Ala Asp Phe Leu Val Val Thr Phe Gly Gly Pro Phe Gln
```

-continued

```
305                 310                 315                 320

Arg Glu Pro Leu Val Arg Gln Lys Glu Met Gln Glu Leu Gly Leu Thr
                325                 330                 335

Asp Trp Phe Tyr Pro Glu Lys Arg Ile Thr Arg Leu Gly Glu Asp Glu
            340                 345                 350

Gly Phe Ser Val Leu Asn Leu Ser Pro Asn Leu Gln Val Tyr Ser Glu
        355                 360                 365

Gln Asn Asn Ala Cys Leu Tyr Gly Phe Asp Asp Thr Gln Gly Cys Val
    370                 375                 380

Gly His Trp Asn Ala Leu Gly His Gln Val Ala Gly Lys Met Ile Ala
385                 390                 395                 400

Ser Lys Ile Cys Gln Gln Gln Met Arg Glu Ser Ile Leu Pro His Lys
                405                 410                 415

His Asp Pro Ser Ser Gln Ser Ser Pro Ile Thr Gln Ser Val Ile Gln
            420                 425                 430


<210> SEQ ID NO 32
<211> LENGTH: 1449
<212> TYPE: DNA
<213> ORGANISM: Cylindrospermopsis raciborskii T3

<400> SEQUENCE: 32

atgacaaata ccgaaagagg attagcagaa ataacatcaa caggatataa gtcagagctt     60

agatcggagg cacgagttag cctccaactg gcaattccct tagtccttgt cgaaatatgc    120

ggaacgagta ttaatgtggt ggatgtagtc atgatgggct tacttggtac tcaagttttg    180

gctgctggtg ccttgggtgc gatcgctttt ttatctgtat cgaatacttg ttataatatg    240

cttttgtcgg gggtagcaaa ggcatctgag gcttttgggg caaacaaaat agatcaggtt    300

agtcgtattg cttctgggca aatatggctg gcactcacct tgtctttgcc tgcaatgctt    360

ttgctttggt atatggatac tatattggtg ctatttggtc aagttgaaag caacacatta    420

attgcaaaaa cgtatttaca ctcaattgtg tggggatttc cggcggcagt tggtattttg    480

atattaagag gcattgcctc tgctgtgaac gtcccccaat tggtaactgt gacgatgcta    540

gtagggctgg tcttgaatgc ccccggccaat tatgtattaa tgttcggtaa atttggtctt    600

cctgaacttg gtttagctgg aataggctgg gcaagtactt tggttttttg gattagtttt    660

ctagtggggg ttgtcttgct gattttctcc ccaaaagtta gagattataa acttttccgc    720

tacttgcatc agtttgatcg acagacggtt gtggaaattt ttcaaactgg atggcctatg    780

ggttttctac tgggagtgga atcagtagta ttgagcctca ccgcttggtt aacaggctat    840

ttgggaacag taacattagc agctcatgag atcgcgatcc aaacagcaga actggcgata    900

gtgataccac tcggaatcgg gaatgttgcc gtcacgagag taggtcagac tataggagaa    960

aaaaaccctt tgggtgctag aagggcagca ttgattggga ttatgattgg tggcatttat   1020

gccagtcttg tggcagtcat tttctggttg tttccatatc agattgcggg actttattta   1080

aaaataaacg atccagagag tatggaagca gttaagacag caactaattt tctcttcttg   1140

gcgggattat tccaattttt tcatagcgtt caaataattg ttgttggggt tttaataggg   1200

ttgcaggata cgtttatccc attgttaatg aatttggtag gctggggtct tggcttggca   1260

gtaagctatt acatgggaat cattttatgt tggggaggta tgggtatctg gttaggtctg   1320

gttttgagtc cactcctgtc cggacttatt ttaatggttc gtttttatca agagattgcc   1380

aataggattg ccaatagtga tgatgggcaa gagagtatat ctattgacaa cgttgaagaa   1440
```

-continued

```
ctctcctga                                                          1449


<210> SEQ ID NO 33
<211> LENGTH: 482
<212> TYPE: PRT
<213> ORGANISM: Cylindrospermopsis raciborskii T3

<400> SEQUENCE: 33

Met Thr Asn Thr Glu Arg Gly Leu Ala Glu Ile Thr Ser Thr Gly Tyr
1               5                   10                  15

Lys Ser Glu Leu Arg Ser Glu Ala Arg Val Ser Leu Gln Leu Ala Ile
            20                  25                  30

Pro Leu Val Leu Val Glu Ile Cys Gly Thr Ser Ile Asn Val Val Asp
        35                  40                  45

Val Val Met Met Gly Leu Leu Gly Thr Gln Val Leu Ala Ala Gly Ala
    50                  55                  60

Leu Gly Ala Ile Ala Phe Leu Ser Val Ser Asn Thr Cys Tyr Asn Met
65                  70                  75                  80

Leu Leu Ser Gly Val Ala Lys Ala Ser Glu Ala Phe Gly Ala Asn Lys
                85                  90                  95

Ile Asp Gln Val Ser Arg Ile Ala Ser Gly Gln Ile Trp Leu Ala Leu
            100                 105                 110

Thr Leu Ser Leu Pro Ala Met Leu Leu Leu Trp Tyr Met Asp Thr Ile
        115                 120                 125

Leu Val Leu Phe Gly Gln Val Glu Ser Asn Thr Leu Ile Ala Lys Thr
    130                 135                 140

Tyr Leu His Ser Ile Val Trp Gly Phe Pro Ala Ala Val Gly Ile Leu
145                 150                 155                 160

Ile Leu Arg Gly Ile Ala Ser Ala Val Asn Val Pro Gln Leu Val Thr
                165                 170                 175

Val Thr Met Leu Val Gly Leu Val Leu Asn Ala Pro Ala Asn Tyr Val
            180                 185                 190

Leu Met Phe Gly Lys Phe Gly Leu Pro Glu Leu Gly Leu Ala Gly Ile
        195                 200                 205

Gly Trp Ala Ser Thr Leu Val Phe Trp Ile Ser Phe Leu Val Gly Val
    210                 215                 220

Val Leu Leu Ile Phe Ser Pro Lys Val Arg Asp Tyr Lys Leu Phe Arg
225                 230                 235                 240

Tyr Leu His Gln Phe Asp Arg Gln Thr Val Val Glu Ile Phe Gln Thr
                245                 250                 255

Gly Trp Pro Met Gly Phe Leu Leu Gly Val Glu Ser Val Val Leu Ser
            260                 265                 270

Leu Thr Ala Trp Leu Thr Gly Tyr Leu Gly Thr Val Thr Leu Ala Ala
        275                 280                 285

His Glu Ile Ala Ile Gln Thr Ala Glu Leu Ala Ile Val Ile Pro Leu
    290                 295                 300

Gly Ile Gly Asn Val Ala Val Thr Arg Val Gly Gln Thr Ile Gly Glu
305                 310                 315                 320

Lys Asn Pro Leu Gly Ala Arg Arg Ala Ala Leu Ile Gly Ile Met Ile
                325                 330                 335

Gly Gly Ile Tyr Ala Ser Leu Val Ala Val Ile Phe Trp Leu Phe Pro
            340                 345                 350

Tyr Gln Ile Ala Gly Leu Tyr Leu Lys Ile Asn Asp Pro Glu Ser Met
        355                 360                 365
```

```
Glu Ala Val Lys Thr Ala Thr Asn Phe Leu Phe Leu Ala Gly Leu Phe
    370                 375                 380

Gln Phe Phe His Ser Val Gln Ile Ile Val Val Gly Val Leu Ile Gly
385                 390                 395                 400

Leu Gln Asp Thr Phe Ile Pro Leu Leu Met Asn Leu Val Gly Trp Gly
                405                 410                 415

Leu Gly Leu Ala Val Ser Tyr Tyr Met Gly Ile Ile Leu Cys Trp Gly
            420                 425                 430

Gly Met Gly Ile Trp Leu Gly Leu Val Leu Ser Pro Leu Leu Ser Gly
        435                 440                 445

Leu Ile Leu Met Val Arg Phe Tyr Gln Glu Ile Ala Asn Arg Ile Ala
    450                 455                 460

Asn Ser Asp Asp Gly Gln Glu Ser Ile Ser Ile Asp Asn Val Glu Glu
465                 470                 475                 480

Leu Ser


<210> SEQ ID NO 34
<211> LENGTH: 831
<212> TYPE: DNA
<213> ORGANISM: Cylindrospermopsis raciborskii T3

<400> SEQUENCE: 34

atgaaaacaa acaaacatat agctatgtgg gcttgtccta gaagtcgttc tactgtaatt      60

acccgtgctt ttgagaactt agatgggtgt gttgtttatg atgagcctct agaggctccg     120

aatgtcttga tgacaactta cacgatgagt aacagtcgta cgttagcaga agaagactta     180

aagcaattaa tactgcaaaa taatgtagaa acagacctca agaaagttat agaacaattg     240

actggagatt taccggacgg aaaattattc tcatttcaaa aaatgataac aggtgactat     300

agatctgaat ttggaataga ttgggcaaaa aagctaacta acttcttttt aataaggcat     360

ccccaagata ttattttttc tttcgatata gcggagagaa agacaggtat cacagaacca     420

ttcacacaac aaaatcttgg catgaaaaca ctttatgaag ttttccaaca aattgaagtt     480

attacagggc aaacaccttt agttattcac tcagatgata taattaaaaa ccctccttct     540

gctttgaaat ggctgtgtaa aaacttaggg cttgcatttg atgaaaagat gctgacatgg     600

aaagcaaatc tagaagactc caatttaaag tatacaaaat tatatgctaa ttctgcgtct     660

ggcagttcag aaccttggtt tgaaacttta agatcgacca aaacatttct cgcctatgaa     720

aagaaggaga aaaaattacc agctcggtta atacctctac tagatgaatc tattccttac     780

tatgaaaaac tcttacagca ttgtcatatt tttgaatggt cagaacactg a              831


<210> SEQ ID NO 35
<211> LENGTH: 276
<212> TYPE: PRT
<213> ORGANISM: Cylindrospermopsis raciborskii T3

<400> SEQUENCE: 35

Met Lys Thr Asn Lys His Ile Ala Met Trp Ala Cys Pro Arg Ser Arg
1               5                   10                  15

Ser Thr Val Ile Thr Arg Ala Phe Glu Asn Leu Asp Gly Cys Val Val
            20                  25                  30

Tyr Asp Glu Pro Leu Glu Ala Pro Asn Val Leu Met Thr Thr Tyr Thr
        35                  40                  45

Met Ser Asn Ser Arg Thr Leu Ala Glu Glu Asp Leu Lys Gln Leu Ile
    50                  55                  60
```

-continued

```
Leu Gln Asn Asn Val Glu Thr Asp Leu Lys Lys Val Ile Glu Gln Leu
65                  70                  75                  80

Thr Gly Asp Leu Pro Asp Gly Lys Leu Phe Ser Phe Gln Lys Met Ile
                85                  90                  95

Thr Gly Asp Tyr Arg Ser Glu Phe Gly Ile Asp Trp Ala Lys Lys Leu
            100                 105                 110

Thr Asn Phe Phe Leu Ile Arg His Pro Gln Asp Ile Ile Phe Ser Phe
        115                 120                 125

Asp Ile Ala Glu Arg Lys Thr Gly Ile Thr Glu Pro Phe Thr Gln Gln
    130                 135                 140

Asn Leu Gly Met Lys Thr Leu Tyr Glu Val Phe Gln Gln Ile Glu Val
145                 150                 155                 160

Ile Thr Gly Gln Thr Pro Leu Val Ile His Ser Asp Asp Ile Ile Lys
                165                 170                 175

Asn Pro Pro Ser Ala Leu Lys Trp Leu Cys Lys Asn Leu Gly Leu Ala
            180                 185                 190

Phe Asp Glu Lys Met Leu Thr Trp Lys Ala Asn Leu Glu Asp Ser Asn
        195                 200                 205

Leu Lys Tyr Thr Lys Leu Tyr Ala Asn Ser Ala Ser Gly Ser Ser Glu
    210                 215                 220

Pro Trp Phe Glu Thr Leu Arg Ser Thr Lys Thr Phe Leu Ala Tyr Glu
225                 230                 235                 240

Lys Lys Glu Lys Lys Leu Pro Ala Arg Leu Ile Pro Leu Leu Asp Glu
                245                 250                 255

Ser Ile Pro Tyr Tyr Glu Lys Leu Leu Gln His Cys His Ile Phe Glu
            260                 265                 270

Trp Ser Glu His
        275
```

<210> SEQ ID NO 36
<211> LENGTH: 774
<212> TYPE: DNA
<213> ORGANISM: Cylindrospermopsis raciborskii T3

<400> SEQUENCE: 36

```
ctaaaaattt ttttctactc ttttcaggat agaattccag tttctagagc cgttgtaacc      60

gtacatatct tgatagtacg tatcgatgag gtactcattt tcgtggagca ttaaccagct     120

ttttaactcc gctaatttct gctctccttt ttctattaat tcttgctcat ccaaatcatc     180

cctgtccaac tcctccctgt ccaactccca catagttttg ttggtatctt cgacaatcaa     240

gtagtctcca ctttttagac cgttttcgtg aaaatattca actactccca ccgcattagc     300

atgggcatct tctacgatca accagggatg agcaagccca gaaagcagtt ccgacgacat     360

tattgcaccc atattgttac aatccccctc taaaaaatga acgcgagagt cagtttttgc     420

tttctcgtcg agtagggaaa gatcgatatc gatacagtag acacaacctt ctatttggaa     480

cagttctaag tgatcggcta gccaaatcgc gctgccaccg cttaatgctc ctatttcgat     540

tattgttttc gggcgaagct catacaggag cattgaataa agagctattt cggtgcaccc     600

tttcaggaag ggtatccctt tccaagtgaa caaatcgcgg tttgccaaga gcgctctcca     660

agctggcact ggaatagcac atttatcttc tctttcagaa attttggcaa accgattagg     720

tttgaaaggt gcaactttat aggcggcttc ttgaacaaat ttttggaagc tcat           774
```

<210> SEQ ID NO 37
<211> LENGTH: 257

<212> TYPE: PRT
<213> ORGANISM: Cylindrospermopsis raciborskii T3

<400> SEQUENCE: 37

```
Met Ser Phe Gln Lys Phe Val Gln Glu Ala Ala Tyr Lys Val Ala Pro
1               5                   10                  15

Phe Lys Pro Asn Arg Phe Ala Lys Ile Ser Glu Arg Glu Asp Lys Cys
            20                  25                  30

Ala Ile Pro Val Pro Ala Trp Arg Ala Leu Leu Ala Asn Arg Asp Leu
        35                  40                  45

Phe Thr Trp Lys Gly Ile Pro Phe Leu Lys Gly Cys Thr Glu Ile Ala
    50                  55                  60

Leu Tyr Ser Met Leu Leu Tyr Glu Leu Arg Pro Lys Thr Ile Ile Glu
65                  70                  75                  80

Ile Gly Ala Leu Ser Gly Gly Ser Ala Ile Trp Leu Ala Asp His Leu
                85                  90                  95

Glu Leu Phe Gln Ile Glu Gly Cys Val Tyr Cys Ile Asp Ile Asp Leu
            100                 105                 110

Ser Leu Leu Asp Glu Lys Ala Lys Thr Asp Ser Arg Val His Phe Leu
        115                 120                 125

Glu Gly Asp Cys Asn Asn Met Gly Ala Ile Met Ser Ser Glu Leu Leu
    130                 135                 140

Ser Gly Leu Ala His Pro Trp Leu Ile Val Glu Asp Ala His Ala Asn
145                 150                 155                 160

Ala Val Gly Val Val Glu Tyr Phe His Glu Asn Gly Leu Lys Ser Gly
                165                 170                 175

Asp Tyr Leu Ile Val Glu Asp Thr Asn Lys Thr Met Trp Glu Leu Asp
            180                 185                 190

Arg Glu Glu Leu Asp Arg Asp Asp Leu Asp Glu Gln Glu Leu Ile Glu
        195                 200                 205

Lys Gly Glu Gln Lys Leu Ala Glu Leu Lys Ser Trp Leu Met Leu His
    210                 215                 220

Glu Asn Glu Tyr Leu Ile Asp Thr Tyr Tyr Gln Asp Met Tyr Gly Tyr
225                 230                 235                 240

Asn Gly Ser Arg Asn Trp Asn Ser Ile Leu Lys Arg Val Glu Lys Asn
                245                 250                 255

Phe
```

<210> SEQ ID NO 38
<211> LENGTH: 327
<212> TYPE: DNA
<213> ORGANISM: Cylindrospermopsis raciborskii T3

<400> SEQUENCE: 38

```
ttattcaaat agccgtagtt tatgatcggt atccaattcg ctattgtttt ttctgccata      60

tccccaacct aagatgcgac gatattcacc cataatgcca ctgtcaatta aatcatcctc     120

gttgactgca acattggtat gagattgcgg cgcaacatag agcgcatccg caggacaata     180

tgcttcacag atgaaacaag tttgacagtc ttcctgtcgg gcgatcgcag gcggttggtt     240

gggaactgca tcaaagacat tggtagggca tacttggacg caaacattac aattaataca     300

gagtttatgg ctgacaagct cgatcat                                         327
```

<210> SEQ ID NO 39
<211> LENGTH: 108
<212> TYPE: PRT

<213> ORGANISM: Cylindrospermopsis raciborskii T3

<400> SEQUENCE: 39

Met Ile Glu Leu Val Ser His Lys Leu Cys Ile Asn Cys Asn Val Cys
1 5 10 15

Val Gln Val Cys Pro Thr Asn Val Phe Asp Ala Val Pro Asn Gln Pro
20 25 30

Pro Ala Ile Ala Arg Gln Glu Asp Cys Gln Thr Cys Phe Ile Cys Glu
35 40 45

Ala Tyr Cys Pro Ala Asp Ala Leu Tyr Val Ala Pro Gln Ser His Thr
50 55 60

Asn Val Ala Val Asn Glu Asp Asp Leu Ile Asp Ser Gly Ile Met Gly
65 70 75 80

Glu Tyr Arg Arg Ile Leu Gly Trp Gly Tyr Gly Arg Lys Asn Asn Ser
85 90 95

Glu Leu Asp Thr Asp His Lys Leu Arg Leu Phe Glu
100 105

<210> SEQ ID NO 40
<211> LENGTH: 1653
<212> TYPE: DNA
<213> ORGANISM: Cylindrospermopsis raciborskii T3

<400> SEQUENCE: 40
ttaagtggtt aatactggtg gtgtagcgct cgcatccttc acccaatccc gtctcaccca 60
aagcctttct aagccgcccg tggcttggta ataaagctga tttggatcgg tttcaggata 120
gtctatgcga atatgttcgc tacgcgtttc cttgcgatgt aaagcgctaa aatatgccca 180
tcgtgctaca gacacaagag cagccgctcg acgagaaaat tccagatcgc gcactgtatc 240
ttgtttcggg ttcccttgta cttgctgcca cagcatttct aatttggcga gggaatccaa 300
aagtccctgc tcacagcgca agtaattctt ctctaatggg aacatctcgg cttgtacacc 360
gcggacaact gcctcgctat cgaatgtttc ggaaccaggg tactgggaac gtaatccggc 420
ttgacctgct ggacgcacaa cccgttcatg gacatgagcg cccaaactct tggcaaaggc 480
ggctgcacct tcccctgccc attgtcctgt agagattgcc caagcagcat taggaccatc 540
acccccagaa gctatcccag ctaaaaactc ccgcgatgct gcatctccgg cggcatacag 600
tccaggaact tttgtaccac aactatcatt cacaatccga attccacctg taccacggac 660
tgtaccttct aaaaccagtg ttacaggtac tcgttctgta taagggtcaa tgccagcttt 720
tttatagggt agaaaggcga tgaagtgaga cttttcaacc aatgcttgga tttcaggtgt 780
ggctcgatcc aaacgagcat aaacgggacc tttcaggagg gcattgggca ggaacgatgg 840
atcgcgacga ccattgatat agccaccaag atcgttacct gcctcatcgg tgtaactagc 900
ccagtaaaag ggagcagccc ttgtcactgt ggcattgaaa gcggtcgaga tggtatagtg 960
actggaagct tccatactgg agagttcgcc gccagcttcc accgccatca gcagtccatc 1020
gcctgtattg gtattgcaac ctaaagcttt acttaggaat gcacaaccgc cattcgctag 1080
aactactgca ccagcgcgaa cggtataggt gcgatgattt tgcctctgta cacctctagc 1140
tccagccacg gagccgtcct gggctaataa cagttctaga gccggacttt ggtcgaaaat 1200
ttgcacaccc acacgcaaca ggttcttgcg aagtacccgc atatattccg gaccataata 1260
actctggcgc acggattccc cattttcttt ggggaaacga tagccccaat cttccactaa 1320
gggcaaactc agccaagctt tttcaattac acgttcaatc caacgtaagt tagcgaggtt 1380

-continued atttcctttg ctgtaacatt cggatacatc tttctcccaa ttctctggag aaggtgccat 1440
gacgctattg ccactggcag cagctgcacc gctcgtacct agaaaacctt tatcaacaat 1500
gatgactttg acaccttggg ctccagccgc ccatgctgcc catgcggcgg caggaccacc 1560
accaattacc agcacgtcag cagttaattg tagttcagtg ccgctatagg ctgtaagcaa 1620
ttgcttttcc tccttgttta aagtcaagtt cat 1653

<210> SEQ ID NO 41
<211> LENGTH: 550
<212> TYPE: PRT
<213> ORGANISM: Cylindrospermopsis raciborskii T3

<400> SEQUENCE: 41

Met Asn Leu Thr Leu Asn Lys Glu Glu Lys Gln Leu Leu Thr Ala Tyr
1 5 10 15

Ser Gly Thr Glu Leu Gln Leu Thr Ala Asp Val Leu Val Ile Gly Gly
20 25 30

Gly Pro Ala Ala Ala Trp Ala Ala Trp Ala Ala Gly Ala Gln Gly Val
35 40 45

Lys Val Ile Ile Val Asp Lys Gly Phe Leu Gly Thr Ser Gly Ala Ala
50 55 60

Ala Ala Ser Gly Asn Ser Val Met Ala Pro Ser Pro Glu Asn Trp Glu
65 70 75 80

Lys Asp Val Ser Glu Cys Tyr Ser Lys Gly Asn Asn Leu Ala Asn Leu
85 90 95

Arg Trp Ile Glu Arg Val Ile Glu Lys Ala Trp Leu Ser Leu Pro Leu
100 105 110

Val Glu Asp Trp Gly Tyr Arg Phe Pro Lys Glu Asn Gly Glu Ser Val
115 120 125

Arg Gln Ser Tyr Tyr Gly Pro Glu Tyr Met Arg Val Leu Arg Lys Asn
130 135 140

Leu Leu Arg Val Gly Val Gln Ile Phe Asp Gln Ser Pro Ala Leu Glu
145 150 155 160

Leu Leu Leu Ala Gln Asp Gly Ser Val Ala Gly Ala Arg Gly Val Gln
165 170 175

Arg Gln Asn His Arg Thr Tyr Thr Val Arg Ala Gly Ala Val Val Leu
180 185 190

Ala Asn Gly Gly Cys Ala Phe Leu Ser Lys Ala Leu Gly Cys Asn Thr
195 200 205

Asn Thr Gly Asp Gly Leu Leu Met Ala Val Glu Ala Gly Gly Glu Leu
210 215 220

Ser Ser Met Glu Ala Ser Ser His Tyr Thr Ile Ser Thr Ala Phe Asn
225 230 235 240

Ala Thr Val Thr Arg Ala Ala Pro Phe Tyr Trp Ala Ser Tyr Thr Asp
245 250 255

Glu Ala Gly Asn Asp Leu Gly Gly Tyr Ile Asn Gly Arg Arg Asp Pro
260 265 270

Ser Phe Leu Pro Asn Ala Leu Leu Lys Gly Pro Val Tyr Ala Arg Leu
275 280 285

Asp Arg Ala Thr Pro Glu Ile Gln Ala Leu Val Glu Lys Ser His Phe
290 295 300

Ile Ala Phe Leu Pro Tyr Lys Lys Ala Gly Ile Asp Pro Tyr Thr Glu
305 310 315 320

Arg Val Pro Val Thr Leu Val Leu Glu Gly Thr Val Arg Gly Thr Gly

-continued

```
                325                 330                 335

Gly Ile Arg Ile Val Asn Asp Ser Cys Gly Thr Lys Val Pro Gly Leu
            340                 345                 350

Tyr Ala Ala Gly Asp Ala Ala Ser Arg Glu Phe Leu Ala Gly Ile Ala
        355                 360                 365

Ser Gly Gly Asp Gly Pro Asn Ala Ala Trp Ala Ile Ser Thr Gly Gln
    370                 375                 380

Trp Ala Gly Glu Gly Ala Ala Ala Phe Ala Lys Ser Leu Gly Ala His
385                 390                 395                 400

Val His Glu Arg Val Val Arg Pro Ala Gly Gln Ala Gly Leu Arg Ser
                405                 410                 415

Gln Tyr Pro Gly Ser Glu Thr Phe Asp Ser Glu Ala Val Val Arg Gly
            420                 425                 430

Val Gln Ala Glu Met Phe Pro Leu Glu Lys Asn Tyr Leu Arg Cys Glu
        435                 440                 445

Gln Gly Leu Leu Asp Ser Leu Ala Lys Leu Glu Met Leu Trp Gln Gln
    450                 455                 460

Val Gln Gly Asn Pro Lys Gln Asp Thr Val Arg Asp Leu Glu Phe Ser
465                 470                 475                 480

Arg Arg Ala Ala Ala Leu Val Ser Val Ala Arg Trp Ala Tyr Phe Ser
                485                 490                 495

Ala Leu His Arg Lys Glu Thr Arg Ser Glu His Ile Arg Ile Asp Tyr
            500                 505                 510

Pro Glu Thr Asp Pro Asn Gln Leu Tyr Tyr Gln Ala Thr Gly Gly Leu
        515                 520                 525

Glu Arg Leu Trp Val Arg Arg Asp Trp Val Lys Asp Ala Ser Ala Thr
    530                 535                 540

Pro Pro Val Leu Thr Thr
545                 550


<210> SEQ ID NO 42
<211> LENGTH: 750
<212> TYPE: DNA
<213> ORGANISM: Cylindrospermopsis raciborskii T3

<400> SEQUENCE: 42

ttaattatct tctgcagtcg gtcgaatcaa aatttcattt acatttacat gatcgggttg      60

tgtcactgca taaattatag ctcttgcaat atcctcactt tgtaaaggtg ttattgtact     120

aagttgttct ttactaagct gtttcgtgat cgggtcagaa attaagtcat taaatggcgt     180

atcgactaaa cctggctcaa tgatggtaac gcgaatgttg tctaaagata cctcctggcg     240

taatgcttct gaaagagcat tgacgcctga tttggcagca ctataaacga ccgcaccgga     300

ctgcgctatc ctgccatcga cagaagatat attgactata tgaccggatt tttgggcctt     360

cagaagaggc aaaactgcgt ggatagcata taaaactccc agaacattca catcgaatgc     420

tcgcctccag tctgcgggat ttccagtatc aattgcacca aacacaccaa ttcctgcatt     480

attcaccaaa atatctacat gtcctagctc aaccttggtc ttttggacta gatgatttac     540

ttgagattcg tctgtaatat ctgtaacaat aggcaatgct tgaccaccac tggcttcaat     600

ccgttttgct agtgcatgca aaagctcagc acgtcttgcg gcgatcgcaa cttttgcccc     660

ctccgcagct aaagcaaatg ctgtagcctc tccaatccca gaggaagctc cagtaataat     720

cgccactttt ccatccaatt tacctgccat                                      750
```

<210> SEQ ID NO 43
<211> LENGTH: 249
<212> TYPE: PRT
<213> ORGANISM: Cylindrospermopsis raciborskii T3

<400> SEQUENCE: 43

```
Met Ala Gly Lys Leu Asp Gly Lys Val Ala Ile Ile Thr Gly Ala Ser
1               5                   10                  15

Ser Gly Ile Gly Glu Ala Thr Ala Phe Ala Leu Ala Ala Glu Gly Ala
            20                  25                  30

Lys Val Ala Ile Ala Ala Arg Arg Ala Glu Leu Leu His Ala Leu Ala
        35                  40                  45

Lys Arg Ile Glu Ala Ser Gly Gly Gln Ala Leu Pro Ile Val Thr Asp
    50                  55                  60

Ile Thr Asp Glu Ser Gln Val Asn His Leu Val Gln Lys Thr Lys Val
65                  70                  75                  80

Glu Leu Gly His Val Asp Ile Leu Val Asn Asn Ala Gly Ile Gly Val
                85                  90                  95

Phe Gly Ala Ile Asp Thr Gly Asn Pro Ala Asp Trp Arg Arg Ala Phe
            100                 105                 110

Asp Val Asn Val Leu Gly Val Leu Tyr Ala Ile His Ala Val Leu Pro
        115                 120                 125

Leu Leu Lys Ala Gln Lys Ser Gly His Ile Val Asn Ile Ser Ser Val
    130                 135                 140

Asp Gly Arg Ile Ala Gln Ser Gly Ala Val Val Tyr Ser Ala Ala Lys
145                 150                 155                 160

Ser Gly Val Asn Ala Leu Ser Glu Ala Leu Arg Gln Glu Val Ser Leu
                165                 170                 175

Asp Asn Ile Arg Val Thr Ile Ile Glu Pro Gly Leu Val Asp Thr Pro
            180                 185                 190

Phe Asn Asp Leu Ile Ser Asp Pro Ile Thr Lys Gln Leu Ser Lys Glu
        195                 200                 205

Gln Leu Ser Thr Ile Thr Pro Leu Gln Ser Glu Asp Ile Ala Arg Ala
    210                 215                 220

Ile Ile Tyr Ala Val Thr Gln Pro Asp His Val Asn Val Asn Glu Ile
225                 230                 235                 240

Leu Ile Arg Pro Thr Ala Glu Asp Asn
                245
```

<210> SEQ ID NO 44
<211> LENGTH: 1005
<212> TYPE: DNA
<213> ORGANISM: Cylindrospermopsis raciborskii T3

<400> SEQUENCE: 44

```
ttaacaaacc ccataagtaa cacctagttg ctttagccat cgacgatagg caagtgtgca     60

tctatctgat ggtacgtgga tttcgtgtga aaacaattgt gtatttatct gctttggagt    120

taacagtggt aaacgtaccg gctgttgtgc atgtaagatc cgaatatctt gttctattgt    180

ttcgtcatat tcagttagca tctttgactc taacgtttca tacccgttcc acattatcaa    240

catacgcaat acactatttt cctcatcaat cggtgtgatc gtcattaaat ccacaatcct    300

catttcaggg gattctgaaa cgcagtattg acataaagga tgactaagcc tgaaccaatt    360

aacccaagag tcatcttcga tatggctgac aatccttgat gtctggaatt gatacttacc    420

catagtaagg ccatctttat ctaatttcac ctcaaattct tccacttttg tataattgcg    480
```

-continued

```
atcacctaac caaccgtcat ggataaaagg aaaatgagac acgtctaagg aattatccat    540

cacacgaaac gcactagctt taatcaagta agacttggta taagtcttgt gataattcgg    600

atcatcccat tcaggaaatg aaggtatatc attaacagga tcgcccaagc acacccacac    660

taagccatag cgctcctggg agtgatatgt cctggcttca gcacttgccg gtggtaccat    720

gccagggtga gctgggatct gtatgcattt accagcctca ttgtatctcc atccgtgata    780

cggacaaact aaagtattat tcgtaatttc tcccatagac agaggaacac ctcggtgggg    840

gcagtagtca agccatacct gtatgggtga attttgttca taactgcgcc ataataccaa    900

cttcactccc aacaaacgag atctggtgat acttccaggt ttacagtctt ctacattggc    960

gactacgtgc cagttattga ttaagattgg gtcggtagtt gtcat                   1005
```

<210> SEQ ID NO 45
<211> LENGTH: 334
<212> TYPE: PRT
<213> ORGANISM: Cylindrospermopsis raciborskii T3

<400> SEQUENCE: 45

```
Met Thr Thr Thr Asp Pro Ile Leu Ile Asn Asn Trp His Val Val Ala
1               5                   10                  15

Asn Val Glu Asp Cys Lys Pro Gly Ser Ile Thr Arg Ser Arg Leu Leu
            20                  25                  30

Gly Val Lys Leu Val Leu Trp Arg Ser Tyr Glu Gln Asn Ser Pro Ile
        35                  40                  45

Gln Val Trp Leu Asp Tyr Cys Pro His Arg Gly Val Pro Leu Ser Met
    50                  55                  60

Gly Glu Ile Thr Asn Asn Thr Leu Val Cys Pro Tyr His Gly Trp Arg
65                  70                  75                  80

Tyr Asn Glu Ala Gly Lys Cys Ile Gln Ile Pro Ala His Pro Gly Met
                85                  90                  95

Val Pro Pro Ala Ser Ala Glu Ala Arg Thr Tyr His Ser Gln Glu Arg
            100                 105                 110

Tyr Gly Leu Val Trp Val Cys Leu Gly Asp Pro Val Asn Asp Ile Pro
        115                 120                 125

Ser Phe Pro Glu Trp Asp Asp Pro Asn Tyr His Lys Thr Tyr Thr Lys
    130                 135                 140

Ser Tyr Leu Ile Lys Ala Ser Ala Phe Arg Val Met Asp Asn Ser Leu
145                 150                 155                 160

Asp Val Ser His Phe Pro Phe Ile His Asp Gly Trp Leu Gly Asp Arg
                165                 170                 175

Asn Tyr Thr Lys Val Glu Glu Phe Glu Val Lys Leu Asp Lys Asp Gly
            180                 185                 190

Leu Thr Met Gly Lys Tyr Gln Phe Gln Thr Ser Arg Ile Val Ser His
        195                 200                 205

Ile Glu Asp Asp Ser Trp Val Asn Trp Phe Arg Leu Ser His Pro Leu
    210                 215                 220

Cys Gln Tyr Cys Val Ser Glu Ser Pro Glu Met Arg Ile Val Asp Leu
225                 230                 235                 240

Met Thr Ile Thr Pro Ile Asp Glu Glu Asn Ser Val Leu Arg Met Leu
                245                 250                 255

Ile Met Trp Asn Gly Tyr Glu Thr Leu Glu Ser Lys Met Leu Thr Glu
            260                 265                 270

Tyr Asp Glu Thr Ile Glu Gln Asp Ile Arg Ile Leu His Ala Gln Gln
        275                 280                 285
```

```
Pro Val Arg Leu Pro Leu Leu Thr Pro Lys Gln Ile Asn Thr Gln Leu
    290                 295                 300

Phe Ser His Glu Ile His Val Pro Ser Asp Arg Cys Thr Leu Ala Tyr
305                 310                 315                 320

Arg Arg Trp Leu Lys Gln Leu Gly Val Thr Tyr Gly Val Cys
                325                 330


<210> SEQ ID NO 46
<211> LENGTH: 726
<212> TYPE: DNA
<213> ORGANISM: Cylindrospermopsis raciborskii T3

<400> SEQUENCE: 46

ctaaattatc cttttcaagg catccaccaa cagtggtttg atgttgtttt ttgtaaaaat      60

cagagttagc atcctgtaat cggtaattga agtgttggca gctgcggtat gccatacagt     120

tggtgtataa aacattgctg cccctcctgg aagtgaaaga catatttctg catttagtga     180

attggcagaa gatgaatcta atgagtgttc ccattggtgg ctacttggta taactcgcat     240

tgtacccata gtattatctg tatcctgtaa gtatatagtt atgaatacca tggcttgatt     300

ggctactgga accaacaacc gaagcgcgtc gtcatttaac tcgttttttg acatggatgc     360

aagtgcgttc aatacttcaa ctacatatcc atggtcttga tgccaagcaa tgtatcctgt     420

acctgcacga attatggcta gatcggtgat caataggaag atatcagacc caattagagc     480

ctgtactggt cccatcacag ttggaagctc taaaagcctc tgaattatct tttgatacct     540

aactggatct gggatagtat gctcagacca ccactcatag tcacccgcca atactccccc     600

acgtttttgt tcggtaataa gttctacttc atgccgtatt tcttcaatta acgcttttgg     660

tacagcttct tcaactgtga aataaccatc atttgtgtaa gcttgttttt gttccgctgt     720

gagcat                                                                726


<210> SEQ ID NO 47
<211> LENGTH: 241
<212> TYPE: PRT
<213> ORGANISM: Cylindrospermopsis raciborskii T3

<400> SEQUENCE: 47

Met Leu Thr Ala Glu Gln Lys Gln Ala Tyr Thr Asn Asp Gly Tyr Phe
1               5                   10                  15

Thr Val Glu Glu Ala Val Pro Lys Ala Leu Ile Glu Glu Ile Arg His
            20                  25                  30

Glu Val Glu Leu Ile Thr Glu Gln Lys Arg Gly Gly Val Leu Ala Gly
        35                  40                  45

Asp Tyr Glu Trp Trp Ser Glu His Thr Ile Pro Asp Pro Val Arg Tyr
    50                  55                  60

Gln Lys Ile Ile Gln Arg Leu Leu Glu Leu Pro Thr Val Met Gly Pro
65                  70                  75                  80

Val Gln Ala Leu Ile Gly Ser Asp Ile Phe Leu Leu Ile Thr Asp Leu
                85                  90                  95

Ala Ile Ile Arg Ala Gly Thr Gly Tyr Ile Ala Trp His Gln Asp His
            100                 105                 110

Gly Tyr Val Val Glu Val Leu Asn Ala Leu Ala Ser Met Ser Lys Asn
        115                 120                 125

Glu Leu Asn Asp Asp Ala Leu Arg Leu Leu Val Pro Val Ala Asn Gln
    130                 135                 140
```

```
Ala Met Val Phe Ile Thr Ile Tyr Leu Gln Asp Thr Asp Asn Thr Met
145                 150                 155                 160

Gly Thr Met Arg Val Ile Pro Ser Ser His Gln Trp Glu His Ser Leu
                165                 170                 175

Asp Ser Ser Ser Ala Asn Ser Leu Asn Ala Glu Ile Cys Leu Ser Leu
            180                 185                 190

Pro Gly Gly Ala Ala Met Phe Tyr Thr Pro Thr Val Trp His Thr Ala
        195                 200                 205

Ala Ala Asn Thr Ser Ile Thr Asp Tyr Arg Met Leu Thr Leu Ile Phe
    210                 215                 220

Thr Lys Asn Asn Ile Lys Pro Leu Leu Val Asp Ala Leu Lys Arg Ile
225                 230                 235                 240

Ile


<210> SEQ ID NO 48
<211> LENGTH: 576
<212> TYPE: DNA
<213> ORGANISM: Cylindrospermopsis raciborskii T3

<400> SEQUENCE: 48

tcaatggtta gtaggaatta tcctatagct gttctttctc tggatagaag aaaggttgtg      60

agaagctcgc tccgacttca tttcagccaa tttttctgca gaccaatact gaaaatatcc     120

caatcttaat aattcatcac tagcctcttg taactggctg aatgactgta ctgatgctaa     180

aacatactta gggtgagtta tgattacgtt attcacattc tccgcgtcat caccaacata     240

ttgtttgtct ggatgcgatc ctaaagctac caaatcgtat tctggtaata cataattcgc     300

cttggtaatg tacctttcca acctctgtgc atctaggttt tgagggtcgc agccaaaaat     360

caccatttca aagtcattat tccatgttct tatctgttcc attagaagct ctggcagttc     420

aggtccatga aaccaacgaa cactaacacg gttatttaac caagctgcct tcgcgtaagg     480

acagggtgga aaatttcctg ttagaggatt gggaatgctg acaacattga taatccaatc     540

ctctatttct tggcgaaatt gttcgatatt tatcat                               576


<210> SEQ ID NO 49
<211> LENGTH: 191
<212> TYPE: PRT
<213> ORGANISM: Cylindrospermopsis raciborskii T3

<400> SEQUENCE: 49

Met Ile Asn Ile Glu Gln Phe Arg Gln Glu Ile Glu Asp Trp Ile Ile
1               5                   10                  15

Asn Val Val Ser Ile Pro Asn Pro Leu Thr Gly Asn Phe Pro Pro Cys
            20                  25                  30

Pro Tyr Ala Lys Ala Ala Trp Leu Asn Asn Arg Val Ser Val Arg Trp
        35                  40                  45

Phe His Gly Pro Glu Leu Pro Glu Leu Leu Met Glu Gln Ile Arg Thr
    50                  55                  60

Trp Asn Asn Asp Phe Glu Met Val Ile Phe Gly Cys Asp Pro Gln Asn
65                  70                  75                  80

Leu Asp Ala Gln Arg Leu Glu Arg Tyr Ile Thr Lys Ala Asn Tyr Val
                85                  90                  95

Leu Pro Glu Tyr Asp Leu Val Ala Leu Gly Ser His Pro Asp Lys Gln
            100                 105                 110

Tyr Val Gly Asp Asp Ala Glu Asn Val Asn Asn Val Ile Ile Thr His
        115                 120                 125
```

```
Pro Lys Tyr Val Leu Ala Ser Val Gln Ser Phe Ser Gln Leu Gln Glu
    130                 135                 140

Ala Ser Asp Glu Leu Leu Arg Leu Gly Tyr Phe Gln Tyr Trp Ser Ala
145                 150                 155                 160

Glu Lys Leu Ala Glu Met Lys Ser Glu Arg Ala Ser His Asn Leu Ser
                165                 170                 175

Ser Ile Gln Arg Lys Asn Ser Tyr Arg Ile Ile Pro Thr Asn His
            180                 185                 190


<210> SEQ ID NO 50
<211> LENGTH: 777
<212> TYPE: DNA
<213> ORGANISM: Cylindrospermopsis raciborskii T3

<400> SEQUENCE: 50

ttaatctagg tcatagtata accatatatt aggctcgatg tatattccca tattgttggg     60

atagtcaatt ttgacaggta ctaagccttt gggaataata tagtcaccag tttctggaaa    120

acgcatccca actctatctt cccaaccgtc aatagtatca ttaattgttg tggatttaaa    180

acagatccct gcaattttag ccccatgttt gacattaact cgtaaccaag ggtcaaatat    240

aagaccattt ttatctcgcc aggtaatata ccgctctatg ggtataagtg ggtaaagata    300

ttttaggctt ggacgtgcag ccatgatcaa agaattaaga ccgtggtatt gagcaagttc    360

tttcatgtat ccaatcagat actgactcaa gtttttgcct tgatactctg gtaggattga    420

aatcgatact acacataacg cattaggcag gcggttctgt tctcggtctt caagccactt    480

ggctaaagcc cagtcacaac cttcgtccgg taactcatca aaacggcttt cataagttaa    540

agggatacag tttccttgcg ctatcataag ctgtgtggta gcttctacta acccaaactg    600

gaattctgga taaatttcaa atagagctaa ggaagctgga tctgcccaga catcatgtat    660

caaaaatttt gggtatgctt gatcaaagac actcatcgtc ctttccacaa aatcagaagt    720

ttcttttggg gttacaaagc tatactctaa attatgctgt acaatttgaa tggtcat       777


<210> SEQ ID NO 51
<211> LENGTH: 258
<212> TYPE: PRT
<213> ORGANISM: Cylindrospermopsis raciborskii T3

<400> SEQUENCE: 51

Met Thr Ile Gln Ile Val Gln His Asn Leu Glu Tyr Ser Phe Val Thr
1               5                   10                  15

Pro Lys Glu Thr Ser Asp Phe Val Glu Arg Thr Met Ser Val Phe Asp
            20                  25                  30

Gln Ala Tyr Pro Lys Phe Leu Ile His Asp Val Trp Ala Asp Pro Ala
        35                  40                  45

Ser Leu Ala Leu Phe Glu Ile Tyr Pro Glu Phe Gln Phe Gly Leu Val
    50                  55                  60

Glu Ala Thr Thr Gln Leu Met Ile Ala Gln Gly Asn Cys Ile Pro Leu
65                  70                  75                  80

Thr Tyr Glu Ser Arg Phe Asp Glu Leu Pro Asp Glu Gly Cys Asp Trp
                85                  90                  95

Ala Leu Ala Lys Trp Leu Glu Asp Arg Glu Gln Asn Arg Leu Pro Asn
            100                 105                 110

Ala Leu Cys Val Val Ser Ile Ser Ile Leu Pro Glu Tyr Gln Gly Lys
        115                 120                 125
```

```
Asn Leu Ser Gln Tyr Leu Ile Gly Tyr Met Lys Glu Leu Ala Gln Tyr
    130                 135                 140

His Gly Leu Asn Ser Leu Ile Met Ala Ala Arg Pro Ser Leu Lys Tyr
145                 150                 155                 160

Leu Tyr Pro Leu Ile Pro Ile Glu Arg Tyr Ile Thr Trp Arg Asp Lys
                165                 170                 175

Asn Gly Leu Ile Phe Asp Pro Trp Leu Arg Val Asn Val Lys His Gly
            180                 185                 190

Ala Lys Ile Ala Gly Ile Cys Phe Lys Ser Thr Thr Ile Asn Asp Thr
        195                 200                 205

Ile Asp Gly Trp Glu Asp Arg Val Gly Met Arg Phe Pro Glu Thr Gly
    210                 215                 220

Asp Tyr Ile Ile Pro Lys Gly Leu Val Pro Val Lys Ile Asp Tyr Pro
225                 230                 235                 240

Asn Asn Met Gly Ile Tyr Ile Glu Pro Asn Ile Trp Leu Tyr Tyr Asp
                245                 250                 255

Leu Asp


<210> SEQ ID NO 52
<211> LENGTH: 777
<212> TYPE: DNA
<213> ORGANISM: Cylindrospermopsis raciborskii T3

<400> SEQUENCE: 52

ctaatcctta aatttatact ggaagtcaaa tgagatctca ctatcgttat tatctggaag      60

tacttgcact gtcaattcat taccgacttt cccattccca ggcataatta ataagttagg     120

gtgaggtgga atgccgtcgt actgtcggac gcggcgaaaa atgctcgaat tctcgccacc     180

atgtttattc aagaggactt caactggtgt gatgacaaaa gtcattcctg acccaaggtg     240

gcgcgatcgc cgcttttgat ttgctggagt ggaaacacta acaaataagg cacaccctcc     300

tagagaataa gaccagttag cagactgcgg atcggcagac caatggcagg gacaagacac     360

cgcatcaagg ctatgtaacg cattcaaaaa atcaaatgct tgacctgcat attcctctac     420

tgtaagaact gttggttcag gtgggaaaaa gatgacaagt gtcagaagat ccgcattttc     480

gtgctgaagc aattcgtttt cattaacttc atcaatgtat ttgtagatac cctcaagcgt     540

atgctcaacc aagatcgggt cagttaaaga tgagactatc aggtatctaa tcattccctt     600

ctgttccccg atagttcccc agaagcaagg gaaggcagaa tcgctgattg tttcaacaaa     660

tgttgagtag ctagtgcgta cccaagcagg aaggcactcc tctagaagag aggattccat     720

ctggcttttg ttccagattg gtgtaactcc gtcaggacat aaattcttga ttaccat        777


<210> SEQ ID NO 53
<211> LENGTH: 258
<212> TYPE: PRT
<213> ORGANISM: Cylindrospermopsis raciborskii T3

<400> SEQUENCE: 53

Met Val Ile Lys Asn Leu Cys Pro Asp Gly Val Thr Pro Ile Trp Asn
1               5                   10                  15

Lys Ser Gln Met Glu Ser Ser Leu Leu Glu Glu Cys Leu Pro Ala Trp
            20                  25                  30

Val Arg Thr Ser Tyr Ser Thr Phe Val Glu Thr Ile Ser Asp Ser Ala
        35                  40                  45

Phe Pro Cys Phe Trp Gly Thr Ile Gly Glu Gln Lys Gly Met Ile Arg
    50                  55                  60
```

```
Tyr Leu Ile Val Ser Ser Leu Thr Asp Pro Ile Leu Val Glu His Thr
65                  70                  75                  80

Leu Glu Gly Ile Tyr Lys Tyr Ile Asp Glu Val Asn Glu Asn Glu Leu
                85                  90                  95

Leu Gln His Glu Asn Ala Asp Leu Leu Thr Leu Val Ile Phe Phe Pro
            100                 105                 110

Pro Glu Pro Thr Val Leu Thr Val Glu Glu Tyr Ala Gly Gln Ala Phe
        115                 120                 125

Asp Phe Leu Asn Ala Leu His Ser Leu Asp Ala Val Ser Cys Pro Cys
    130                 135                 140

His Trp Ser Ala Asp Pro Gln Ser Ala Asn Trp Ser Tyr Ser Leu Gly
145                 150                 155                 160

Gly Cys Ala Leu Phe Val Ser Val Ser Thr Pro Ala Asn Gln Lys Arg
                165                 170                 175

Arg Ser Arg His Leu Gly Ser Gly Met Thr Phe Val Ile Thr Pro Val
            180                 185                 190

Glu Val Leu Leu Asn Lys His Gly Gly Glu Asn Ser Ser Ile Phe Arg
        195                 200                 205

Arg Val Arg Gln Tyr Asp Gly Ile Pro Pro His Pro Asn Leu Leu Ile
    210                 215                 220

Met Pro Gly Asn Gly Lys Val Gly Asn Glu Leu Thr Val Gln Val Leu
225                 230                 235                 240

Pro Asp Asn Asn Asp Ser Glu Ile Ser Phe Asp Phe Gln Tyr Lys Phe
                245                 250                 255

Lys Asp


<210> SEQ ID NO 54
<211> LENGTH: 1227
<212> TYPE: DNA
<213> ORGANISM: Cylindrospermopsis raciborskii T3

<400> SEQUENCE: 54

ctatatctta ttttttggaa gtccctgaaa attattcaac aagatcgaga cgttgttgtt      60

gccagaattt gtgacagcca ggtcaagctt gctgtcgccg ttgaaatccg caattgctat     120

agattcagga ttagtaccga ctggaaagtt agtagctatg ccaaaagacc cattaccatt     180

tcctggtaag accgagacgt tattgctact ataatttgta acagccaggt caagtttact     240

gtcgccattc acatctctaa tcgctacaga gtagggatta gtaccggctg gaaagttagt     300

ggctgcgcca aaagacccat taccatttcc cagtaagacc gagacgttat tgctgctagt     360

atttgcaaca gccaggtcaa gcttgctgtc gccatttaca tccccagttg ctacaaatat     420

gggattagta ccgactggaa agttagtggc tgcgccaaaa gacccattac catttcccag     480

taagaccgag acgttattgc tgacccaatt tgtaatagca aggtcgagct tactgtcgct     540

attaaaatcc gcaatcgcta cggaaatcga ataagtatcg acagggaagc tgctggctgc     600

gccaaaagac ccattaccat ttcccagtaa aaccaagacc ttattgtcga accaatttgt     660

aaaagcaagg tcaagctcac tatcgttatt cacatctcca atggctacag aataagggtt     720

agtaccaact gaaaagttag tggctgcgcc aaaagaccca ttaccatttc ctagtaagac     780

cgagacgtta ttgctactaa aatttgcaac agccaggtca agcttgctgt cgccatttac     840

atccccagtc actacaaaga cgggattagt accgactgga aagttagtgg ctgcgccaaa     900

agacccatta ccatttccca gtaagaccga gacgttattg tcgaaccaat ttgtaacagc     960
```

caggtcgagc ttactatcgc tattgaaatc cccaactgct acagagtcag catcaagacc 1020
agttgggaag ttaatagcag tagcataact actcctgtgg gcaaatctca ctcctacgga 1080
caaattaacc ggaacactaa attgcccaga aagcttttca ttcttcagat aatagtcagt 1140
tatatttgct aatgcaacag gagttataca taaaaatgta ctaacagata atatccccgc 1200
tataattagt aaagtgagcc ttttcac 1227

<210> SEQ ID NO 55
<211> LENGTH: 408
<212> TYPE: PRT
<213> ORGANISM: Cylindrospermopsis raciborskii T3

<400> SEQUENCE: 55

```
Met Lys Arg Leu Thr Leu Leu Ile Ile Ala Gly Ile Leu Ser Val Ser
1               5                   10                  15

Thr Phe Leu Cys Ile Thr Pro Val Ala Leu Ala Asn Ile Thr Asp Tyr
            20                  25                  30

Tyr Leu Lys Asn Glu Lys Leu Ser Gly Gln Phe Ser Val Pro Val Asn
        35                  40                  45

Leu Ser Val Gly Val Arg Phe Ala His Arg Ser Ser Tyr Ala Thr Ala
    50                  55                  60

Ile Asn Phe Pro Thr Gly Leu Asp Ala Asp Ser Val Ala Val Gly Asp
65                  70                  75                  80

Phe Asn Ser Asp Ser Lys Leu Asp Leu Ala Val Thr Asn Trp Phe Asp
                85                  90                  95

Asn Asn Val Ser Val Leu Leu Gly Asn Gly Asn Gly Ser Phe Gly Ala
            100                 105                 110

Ala Thr Asn Phe Pro Val Gly Thr Asn Pro Val Phe Val Val Thr Gly
        115                 120                 125

Asp Val Asn Gly Asp Ser Lys Leu Asp Leu Ala Val Ala Asn Phe Ser
    130                 135                 140

Ser Asn Asn Val Ser Val Leu Leu Gly Asn Gly Asn Gly Ser Phe Gly
145                 150                 155                 160

Ala Ala Thr Asn Phe Ser Val Gly Thr Asn Pro Tyr Ser Val Ala Ile
                165                 170                 175

Gly Asp Val Asn Asn Asp Ser Glu Leu Asp Leu Ala Phe Thr Asn Trp
            180                 185                 190

Phe Asp Asn Lys Val Leu Val Leu Leu Gly Asn Gly Asn Gly Ser Phe
        195                 200                 205

Gly Ala Ala Ser Ser Phe Pro Val Asp Thr Tyr Ser Ile Ser Val Ala
    210                 215                 220

Ile Ala Asp Phe Asn Ser Asp Ser Lys Leu Asp Leu Ala Ile Thr Asn
225                 230                 235                 240

Trp Val Ser Asn Asn Val Ser Val Leu Leu Gly Asn Gly Asn Gly Ser
                245                 250                 255

Phe Gly Ala Ala Thr Asn Phe Pro Val Gly Thr Asn Pro Ile Phe Val
            260                 265                 270

Ala Thr Gly Asp Val Asn Gly Asp Ser Lys Leu Asp Leu Ala Val Ala
        275                 280                 285

Asn Thr Ser Ser Asn Asn Val Ser Val Leu Leu Gly Asn Gly Asn Gly
    290                 295                 300

Ser Phe Gly Ala Ala Thr Asn Phe Pro Ala Gly Thr Asn Pro Tyr Ser
305                 310                 315                 320

Val Ala Ile Arg Asp Val Asn Gly Asp Ser Lys Leu Asp Leu Ala Val
```

```
                325                 330                 335

Thr Asn Tyr Ser Ser Asn Asn Val Ser Val Leu Pro Gly Asn Gly Asn
            340                 345                 350

Gly Ser Phe Gly Ile Ala Thr Asn Phe Pro Val Gly Thr Asn Pro Glu
        355                 360                 365

Ser Ile Ala Ile Ala Asp Phe Asn Gly Asp Ser Lys Leu Asp Leu Ala
    370                 375                 380

Val Thr Asn Ser Gly Asn Asn Asn Val Ser Ile Leu Leu Asn Asn Phe
385                 390                 395                 400

Gln Gly Leu Pro Lys Asn Lys Ile
                405


<210> SEQ ID NO 56
<211> LENGTH: 603
<212> TYPE: DNA
<213> ORGANISM: Cylindrospermopsis raciborskii T3

<400> SEQUENCE: 56

ctattgtttg aaaattgtga atttgttttc cacgtatttg agtagttgtt ctaggctttc      60

ctcgacggtg agttcggatg tttccaccca taaatctggg ctattgggtg gttcataagg     120

ggcgctgatt cccgtaaatc catctatttc cccactgcgt gcttttagat aaagaccttt     180

cggatcacgc tgctcacaaa gttccagtgg agttgcaatg tatacttcat gaaatagatc     240

tccagctagt ctacgcacct gttctcggtc attcctgtag ggtgagatga aggcagtgat     300

cactaggcat cctgactccg caaagagttt ggcaacctca cccaaacgac ggatattttc     360

tgagcgatca ctagcagaaa atcctaaatc ggaacacagt ccatgacgaa cactatcacc     420

atctaaaaca aaggtagacc atcctttctc gaacaaagtc tgctctaatt ttaaagccaa     480

tgttgtttta ccagccccgg acagtccagt aaaccataga atcccgcttt tatgaccatt     540

ctttagataa cgatcatatg gagatataag atgttttgta tagtgaatat tagttgattt     600

cat                                                                   603


<210> SEQ ID NO 57
<211> LENGTH: 200
<212> TYPE: PRT
<213> ORGANISM: Cylindrospermopsis raciborskii T3

<400> SEQUENCE: 57

Met Lys Ser Thr Asn Ile His Tyr Thr Lys His Leu Ile Ser Pro Tyr
1               5                   10                  15

Asp Arg Tyr Leu Lys Asn Gly His Lys Ser Gly Ile Leu Trp Phe Thr
            20                  25                  30

Gly Leu Ser Gly Ala Gly Lys Thr Thr Leu Ala Leu Lys Leu Glu Gln
        35                  40                  45

Thr Leu Phe Glu Lys Gly Trp Ser Thr Phe Val Leu Asp Gly Asp Ser
    50                  55                  60

Val Arg His Gly Leu Cys Ser Asp Leu Gly Phe Ser Ala Ser Asp Arg
65                  70                  75                  80

Ser Glu Asn Ile Arg Arg Leu Gly Glu Val Ala Lys Leu Phe Ala Glu
                85                  90                  95

Ser Gly Cys Leu Val Ile Thr Ala Phe Ile Ser Pro Tyr Arg Asn Asp
            100                 105                 110

Arg Glu Gln Val Arg Arg Leu Ala Gly Asp Leu Phe His Glu Val Tyr
        115                 120                 125
```

-continued

Ile Ala Thr Pro Leu Glu Leu Cys Glu Gln Arg Asp Pro Lys Gly Leu
    130                 135                 140

Tyr Leu Lys Ala Arg Ser Gly Glu Ile Asp Gly Phe Thr Gly Ile Ser
145                 150                 155                 160

Ala Pro Tyr Glu Pro Pro Asn Ser Pro Asp Leu Trp Val Glu Thr Ser
                165                 170                 175

Glu Leu Thr Val Glu Glu Ser Leu Glu Gln Leu Leu Lys Tyr Val Glu
            180                 185                 190

Asn Lys Phe Thr Ile Phe Lys Gln
        195                 200

<210> SEQ ID NO 58
<211> LENGTH: 1350
<212> TYPE: DNA
<213> ORGANISM: Cylindrospermopsis raciborskii T3

<400> SEQUENCE: 58
ttaagaaaaa attatttcaa actcgctcgc caaacgctcc ataatcaaat taatttcaga 60
cgaaaaagga cagtaatatg gtagctctac caacaccctt cttgcggaaa ctgtcacctt 120
cgctgctatt ttgataatcg tttcccttaa cctaggaacc tgggctttag ccagttttgt 180
tccctgtgct gcttgccgaa ttcccaacat taaaatgtaa gctgcttgag ataaaaataa 240
ccgaaactga ttgacaataa atttctcaca gctgagtcta tctgatttta tccccagttt 300
taattcctta attctatgct ctgaagtagc tcctctttga acataaaatt tatcgtataa 360
atcctgagct tctgtttcca agctagtaat tataaatcta ggattgggtc ctttttctag 420
ccattctgct ttcataatta ctcgccgagg ttctgaccaa ctccgagctg cgtaatacac 480
atcatcaaat aaacgaactt tttctcctgt gcgacaatat tccagtctgg ctcggtcaag 540
aaggtaatta atttttcgtt ttaagacatc attattgctg aatccaaaaa catatccaac 600
cccgcttttt tcacaaacct caatgatttc tggtaacgag aaaccccgt ctcccctcag 660 aacaattcta atttcaggta aggctctttt gattcgcaaa aataaccatt ttagaatgcc 720
agctactcct ttaccagagt gagaatttcc cgcccttagt tgtagaacta atggataacc 780
actggaagct tcattaatca gaactggaaa gtagatatca tgcctatggt aaccattaaa 840
taagctcagt tgttgatgac catgagttag agcatcccac gcatctatgt ccaggacaat 900
ctcttttgat tcccgaggat aggattctag gaatttatca acaaataacc gacgaatttg 960
tttgatatct ttttgagtca cctgattttc taaacgactc atagttggtt gactagctaa 1020
taagttttct cctactgtgg gaacttgatt acaaactagc ttaaaaattg gatcttggcg 1080
caatttatta ctatcgttgc tatcttcata gccagcaatt atttgataaa ttcgttggct 1140
aattaattga gaaagagaat gtttgacttt agtttggtcc cgattatccg tcaaacaatc 1200
tgccatatct tgacaaattt ttaccttttc ttctacttgt cgtgccagaa taattccgcc 1260
atcactactt aaactcatat cagaaaaagt cagatctaaa gttttttat cgaagaaatt 1320 taaagataat cttgaggaag atttagtcat 1350

<210> SEQ ID NO 59
<211> LENGTH: 449
<212> TYPE: PRT
<213> ORGANISM: Cylindrospermopsis raciborskii T3

<400> SEQUENCE: 59

Met Thr Lys Ser Ser Ser Arg Leu Ser Leu Asn Phe Phe Asp Lys Lys
1               5                   10                  15

```
Thr Leu Asp Leu Thr Phe Ser Asp Met Ser Leu Ser Ser Asp Gly Gly
            20                  25                  30

Ile Ile Leu Ala Arg Gln Val Glu Glu Lys Val Lys Ile Cys Gln Asp
        35                  40                  45

Met Ala Asp Cys Leu Thr Asp Asn Arg Asp Gln Thr Lys Val Lys His
    50                  55                  60

Ser Leu Ser Gln Leu Ile Ser Gln Arg Ile Tyr Gln Ile Ile Ala Gly
65                  70                  75                  80

Tyr Glu Asp Ser Asn Asp Ser Asn Lys Leu Arg Gln Asp Pro Ile Phe
                85                  90                  95

Lys Leu Val Cys Asn Gln Val Pro Thr Val Gly Glu Asn Leu Leu Ala
            100                 105                 110

Ser Gln Pro Thr Met Ser Arg Leu Glu Asn Gln Val Thr Gln Lys Asp
        115                 120                 125

Ile Lys Gln Ile Arg Arg Leu Phe Val Asp Lys Phe Leu Glu Ser Tyr
    130                 135                 140

Pro Arg Glu Ser Lys Glu Ile Val Leu Asp Ile Asp Ala Trp Asp Ala
145                 150                 155                 160

Leu Thr His Gly His Gln Gln Leu Ser Leu Phe Asn Gly Tyr His Arg
                165                 170                 175

His Asp Ile Tyr Phe Pro Val Leu Ile Asn Glu Ala Ser Ser Gly Tyr
            180                 185                 190

Pro Leu Val Leu Gln Leu Arg Ala Gly Asn Ser His Ser Gly Lys Gly
        195                 200                 205

Val Ala Gly Ile Leu Lys Trp Leu Phe Leu Arg Ile Lys Arg Ala Leu
    210                 215                 220

Pro Glu Ile Arg Ile Val Leu Arg Gly Asp Gly Gly Phe Ser Leu Pro
225                 230                 235                 240

Glu Ile Ile Glu Val Cys Glu Lys Ser Gly Val Gly Tyr Val Phe Gly
                245                 250                 255

Phe Ser Asn Asn Asp Val Leu Lys Arg Lys Ile Asn Tyr Leu Leu Asp
            260                 265                 270

Arg Ala Arg Leu Glu Tyr Cys Arg Thr Gly Glu Lys Val Arg Leu Phe
        275                 280                 285

Asp Asp Val Tyr Tyr Ala Ala Arg Ser Trp Ser Glu Pro Arg Arg Val
    290                 295                 300

Ile Met Lys Ala Glu Trp Leu Glu Lys Gly Pro Asn Pro Arg Phe Ile
305                 310                 315                 320

Ile Thr Ser Leu Glu Thr Glu Ala Gln Asp Leu Tyr Asp Lys Phe Tyr
                325                 330                 335

Val Gln Arg Gly Ala Thr Ser Glu His Arg Ile Lys Glu Leu Lys Leu
            340                 345                 350

Gly Ile Lys Ser Asp Arg Leu Ser Cys Glu Lys Phe Ile Val Asn Gln
        355                 360                 365

Phe Arg Leu Phe Leu Ser Gln Ala Ala Tyr Ile Leu Met Leu Gly Ile
    370                 375                 380

Arg Gln Ala Ala Gln Gly Thr Lys Leu Ala Lys Ala Gln Val Pro Arg
385                 390                 395                 400

Leu Arg Glu Thr Ile Ile Lys Ile Ala Ala Lys Val Thr Val Ser Ala
                405                 410                 415

Arg Arg Val Leu Val Glu Leu Pro Tyr Tyr Cys Pro Phe Ser Ser Glu
            420                 425                 430
```

Ile Asn Leu Ile Met Glu Arg Leu Ala Ser Glu Phe Glu Ile Ile Phe
        435                 440                 445

Ser

<210> SEQ ID NO 60
<211> LENGTH: 666
<212> TYPE: DNA
<213> ORGANISM: Cylindrospermopsis raciborskii T3

<400> SEQUENCE: 60
ctatctttgc cctgtaacaa tgtatgctac cctttgacca atattagtag catgatctgc 60
cattctctct aaacactgaa ttgctaatgt taatagtaaa atgggctcca ctaccccggg 120
aacatctttc tgctgcgcca aattacgata taactttttg taagcatcat ctactgtatc 180
atctaataat ttaatccttc taccactaat ctcgtctaaa tccgctaaag ctactaggct 240
ggtagccaac atagattggg catgatcgga cataatggca acctccccca aagtaggatg 300
ggggggatag ggaaatattt tcattgctat ttctgccaaa tctttggcat agtccccaat 360
acgttccaag tctctaacta attgcatgaa tgagcttaaa caccgagatt cttggtctgt 420
gggagcttga ctgctcataa ttgtggcaca atcgacttct atttgtctgt agaagcgatc 480
aatttttttg tctaatctcc gtatttgctc agctgctgtt aaatcccgat tgaatagagc 540
ttggtgactc agacggaatg actgctctac taaagcaccc atacgcaaaa catctcgttc 600
cagtctttta atggcacgta taggttgagg tttttcaaaa attgtatatt tcacaacagc 660
tttcat 666

<210> SEQ ID NO 61
<211> LENGTH: 221
<212> TYPE: PRT
<213> ORGANISM: Cylindrospermopsis raciborskii T3

<400> SEQUENCE: 61

Met Lys Ala Val Val Lys Tyr Thr Ile Phe Glu Lys Pro Gln Pro Ile
1               5                   10                  15

Arg Ala Ile Lys Arg Leu Glu Arg Asp Val Leu Arg Met Gly Ala Leu
            20                  25                  30

Val Glu Gln Ser Phe Arg Leu Ser His Gln Ala Leu Phe Asn Arg Asp
        35                  40                  45

Leu Thr Ala Ala Glu Gln Ile Arg Arg Leu Asp Lys Lys Ile Asp Arg
    50                  55                  60

Phe Tyr Arg Gln Ile Glu Val Asp Cys Ala Thr Ile Met Ser Ser Gln
65                  70                  75                  80

Ala Pro Thr Asp Gln Glu Ser Arg Cys Leu Ser Ser Phe Met Gln Leu
                85                  90                  95

Val Arg Asp Leu Glu Arg Ile Gly Asp Tyr Ala Lys Asp Leu Ala Glu
            100                 105                 110

Ile Ala Met Lys Ile Phe Pro Tyr Pro Pro His Pro Thr Leu Gly Glu
        115                 120                 125

Val Ala Ile Met Ser Asp His Ala Gln Ser Met Leu Ala Thr Ser Leu
    130                 135                 140

Val Ala Leu Ala Asp Leu Asp Glu Ile Ser Gly Arg Arg Ile Lys Leu
145                 150                 155                 160

Leu Asp Asp Thr Val Asp Asp Ala Tyr Lys Lys Leu Tyr Arg Asn Leu
                165                 170                 175

Ala Gln Gln Lys Asp Val Pro Gly Val Val Glu Pro Ile Leu Leu Leu 180 185 190

Thr Leu Ala Ile Gln Cys Leu Glu Arg Met Ala Asp His Ala Thr Asn
195 200 205

Ile Gly Gln Arg Val Ala Tyr Ile Val Thr Gly Gln Arg
210 215 220

<210> SEQ ID NO 62
<211> LENGTH: 1353
<212> TYPE: DNA
<213> ORGANISM: Cylindrospermopsis raciborskii T3

<400> SEQUENCE: 62
tcagaaatat ccgccatcat gttgaaccac ctggggaaga tgaatttgta tccaagcacc 60
accggtatca ggatggttca tggccctgat tttgccacca tgagctataa ttatttggcg 120
gacaatggat aaccctaaac cactaccagt aatttctact gtttcattct cagagcggga 180
ctcgcggtgt ctagctttgt ccccccgata aaatctttga aagacatggg gtagatccat 240
gggagcaaat ccaaccccgg aatcaataat gttaatttct aaaatctgat ttgatacttg 300
gtttaatatt gtatctgctt ctggatcaac cccattaata gacttctccc cacaaactgg 360
attcatttca atgaaaatag taccgttcag gttgctgtat ttaatacagt tatctaacag 420
attaagaaac acttgataaa ttctggactt atcagcacat atatagacct tttccgggcc 480
ggagtaagaa atactaagat gctgattagc ggctaggggc tctaaattct cccagactga 540
aaaaattagg gagcggactt ctagcatttc caaattcagt tgtatggagg aggttatttc 600
catctgggtc aggtctaacc aattttggac taaattaatt agtctgtcaa cctcctgcat 660
caagcggatg acccaacggt ttagaggggg atctaagcga gtttgcaggg tttctgcgac 720
cagacgaatg gaagtcagag gtgttctcag ttcatgggcc aggtctgaaa aagagcggtc 780
acgttgctga tgaatgtcta caaattgttg gtgactttct agaaacacac ccacttgtcc 840
ccccggtagg ggaaaactgt tagctgctaa agacaatggc tttaatccta aaataccctg 900
accatgatct cgggaagggt gaaaaatcca ctcttgcatt tgcggttttt gccaatcccg 960
ggtttgctca attaactgat ccagctcata ggatctcact aattccagta gcaggcgcac 1020
ttgacccggt tgccatcttt gtaaatacag catttcccgc gcgcactgat tacaccatag 1080
tagttggttt tcttcatcta cttgtaaata tcccaaaggc gcagcatcca gcaactgttc 1140
ataagctttg agtgacaagc gtaagttttg ttgctcatct ctaacggtag atattttacg 1200
atgtaatcca gctaataggg gtaataatat cttttcagcg tgagggttta agggttgggt 1260
taactgctcc aaatgactgt taagttgaaa ttgttgccaa agccaaaaac caaaaccgac 1320
tgccaaaccc agaagaaatc ccaataagaa cat 1353

<210> SEQ ID NO 63
<211> LENGTH: 450
<212> TYPE: PRT
<213> ORGANISM: Cylindrospermopsis raciborskii T3

<400> SEQUENCE: 63

Met Phe Leu Leu Gly Phe Leu Leu Gly Leu Ala Val Gly Phe Gly Phe
1 5 10 15

Trp Leu Trp Gln Gln Phe Gln Leu Asn Ser His Leu Glu Gln Leu Thr
20 25 30

Gln Pro Leu Asn Pro His Ala Glu Lys Ile Leu Leu Pro Leu Leu Ala
35 40 45

-continued

```
Gly Leu His Arg Lys Ile Ser Thr Val Arg Asp Glu Gln Gln Asn Leu
    50                  55                  60

Arg Leu Ser Leu Lys Ala Tyr Glu Gln Leu Leu Asp Ala Ala Pro Leu
65                  70                  75                  80

Gly Tyr Leu Gln Val Asp Glu Glu Asn Gln Leu Leu Trp Cys Asn Gln
                85                  90                  95

Cys Ala Arg Glu Met Leu Tyr Leu Gln Arg Trp Gln Pro Gly Gln Val
            100                 105                 110

Arg Leu Leu Leu Glu Leu Val Arg Ser Tyr Glu Leu Asp Gln Leu Ile
        115                 120                 125

Glu Gln Thr Arg Asp Trp Gln Lys Pro Gln Met Gln Glu Trp Ile Phe
    130                 135                 140

His Pro Ser Arg Asp His Gly Gln Gly Ile Leu Gly Leu Lys Pro Leu
145                 150                 155                 160

Ser Leu Ala Ala Asn Ser Phe Pro Leu Pro Gly Gly Gln Val Gly Val
                165                 170                 175

Phe Leu Glu Ser His Gln Gln Phe Val Asp Ile His Gln Gln Arg Asp
            180                 185                 190

Arg Ser Phe Ser Asp Leu Ala His Glu Leu Arg Thr Pro Leu Thr Ser
        195                 200                 205

Ile Arg Leu Val Ala Glu Thr Leu Gln Thr Arg Leu Asp Pro Pro Leu
    210                 215                 220

Asn Arg Trp Val Ile Arg Leu Met Gln Glu Val Asp Arg Leu Ile Asn
225                 230                 235                 240

Leu Val Gln Asn Trp Leu Asp Leu Thr Gln Met Glu Ile Thr Ser Ser
                245                 250                 255

Ile Gln Leu Asn Leu Glu Met Leu Glu Val Arg Ser Leu Ile Phe Ser
            260                 265                 270

Val Trp Glu Asn Leu Glu Pro Leu Ala Ala Asn Gln His Leu Ser Ile
        275                 280                 285

Ser Tyr Ser Gly Pro Glu Lys Val Tyr Ile Cys Ala Asp Lys Ser Arg
    290                 295                 300

Ile Tyr Gln Val Phe Leu Asn Leu Leu Asp Asn Cys Ile Lys Tyr Ser
305                 310                 315                 320

Asn Leu Asn Gly Thr Ile Phe Ile Glu Met Asn Pro Val Cys Gly Glu
                325                 330                 335

Lys Ser Ile Asn Gly Val Asp Pro Glu Ala Asp Thr Ile Leu Asn Gln
            340                 345                 350

Val Ser Asn Gln Ile Leu Glu Ile Asn Ile Ile Asp Ser Gly Val Gly
        355                 360                 365

Phe Ala Pro Met Asp Leu Pro His Val Phe Gln Arg Phe Tyr Arg Gly
    370                 375                 380

Asp Lys Ala Arg His Arg Glu Ser Arg Ser Glu Asn Glu Thr Val Glu
385                 390                 395                 400

Ile Thr Gly Ser Gly Leu Gly Leu Ser Ile Val Arg Gln Ile Ile Ile
                405                 410                 415

Ala His Gly Gly Lys Ile Arg Ala Met Asn His Pro Asp Thr Gly Gly
            420                 425                 430

Ala Trp Ile Gln Ile His Leu Pro Gln Val Val Gln His Asp Gly Gly
        435                 440                 445

Tyr Phe
    450
```

<210> SEQ ID NO 64
<211> LENGTH: 819
<212> TYPE: DNA
<213> ORGANISM: Cylindrospermopsis raciborskii T3

<400> SEQUENCE: 64

```
tcaaccaaat ctatagccaa aacccctaac tgtgacaata tattctggat ggctagggtc      60

taactctaat ttttccctca gccatcgaat gtgaacatcc accgttttac tgtcaccaac     120

aaaatcagga ccccaaacct ggtctaataa ctgttcccgt gaccacaccc tgcgagcata     180

actcataaat agttctagta accggaattc tttcggtgac aagctcacct ccctccctct     240

cactaacacc cgacattcct gaggatttaa actgatatcc ttatatttta aagtgggtat     300

caagggcaaa ttagaaaacc gctgacgacg taacagggcg cgacacctag ccaccatttc     360

ccgtacgcta aaaggcttag ttaggtaatc atccgcccct acctctaaac ccagcacccg     420

gtcagtttca ctacctttcg cactcagaat taaaatcggt atggaattac cctggtgacg     480

taacaaacga caaatatcta atccgttgat ttgtggcaac atcaagtcta gcacaagcag     540

gtcgaaggat aactcaccag gttgggtctc taaattcctg attaattcca cagcacaacg     600

accatcctta gcagtcacaa cttcataacc ttcaccctct aaggctacta caagcatctc     660

tcggatcagt tcttcgtctt ccactattaa aacgcgacta actggttcaa tatccgattt     720

agtgaagtat ctagggtaat tcagtagtat acattgataa caaaaatttg taagaatgta     780

ctggtctggg tttcccacta gtatatgatc ctcactcat                            819
```

<210> SEQ ID NO 65
<211> LENGTH: 272
<212> TYPE: PRT
<213> ORGANISM: Cylindrospermopsis raciborskii T3

<400> SEQUENCE: 65

```
Met Ser Glu Asp His Ile Leu Val Gly Asn Pro Asp Gln Tyr Ile Leu
1               5                   10                  15

Thr Asn Phe Cys Tyr Gln Cys Ile Leu Leu Asn Tyr Pro Arg Tyr Phe
            20                  25                  30

Thr Lys Ser Asp Ile Glu Pro Val Ser Arg Val Leu Ile Val Glu Asp
        35                  40                  45

Glu Glu Leu Ile Arg Glu Met Leu Val Val Ala Leu Glu Gly Glu Gly
    50                  55                  60

Tyr Glu Val Val Thr Ala Lys Asp Gly Arg Cys Ala Val Glu Leu Ile
65                  70                  75                  80

Arg Asn Leu Glu Thr Gln Pro Gly Glu Leu Ser Phe Asp Leu Leu Val
                85                  90                  95

Leu Asp Leu Met Leu Pro Gln Ile Asn Gly Leu Asp Ile Cys Arg Leu
            100                 105                 110

Leu Arg His Gln Gly Asn Ser Ile Pro Ile Leu Ile Leu Ser Ala Lys
        115                 120                 125

Gly Ser Glu Thr Asp Arg Val Leu Gly Leu Glu Val Gly Ala Asp Asp
    130                 135                 140

Tyr Leu Thr Lys Pro Phe Ser Val Arg Glu Met Val Ala Arg Cys Arg
145                 150                 155                 160

Ala Leu Leu Arg Arg Gln Arg Phe Ser Asn Leu Pro Leu Ile Pro Thr
                165                 170                 175

Leu Lys Tyr Lys Asp Ile Ser Leu Asn Pro Gln Glu Cys Arg Val Leu
            180                 185                 190
```

```
Val Arg Gly Arg Glu Val Ser Leu Ser Pro Lys Glu Phe Arg Leu Leu
        195                 200                 205

Glu Leu Phe Met Ser Tyr Ala Arg Arg Val Trp Ser Arg Glu Gln Leu
    210                 215                 220

Leu Asp Gln Val Trp Gly Pro Asp Phe Val Gly Asp Ser Lys Thr Val
225                 230                 235                 240

Asp Val His Ile Arg Trp Leu Arg Glu Lys Leu Glu Leu Asp Pro Ser
                245                 250                 255

His Pro Glu Tyr Ile Val Thr Val Arg Gly Phe Gly Tyr Arg Phe Gly
            260                 265                 270


<210> SEQ ID NO 66
<211> LENGTH: 774
<212> TYPE: DNA
<213> ORGANISM: Cylindrospermopsis raciborskii T3

<400> SEQUENCE: 66

tcaggcaaaa cgagagaagt ctaaagtggg tggaatatcc tgaattcttc caggacctat      60

agcccgtagt gcttctggta aactaatatc cccagtatat agggctttac ccacaattac     120

tcctgtaacc ccctgatgtt ctaaagataa taaggttaat aggtcagtaa cagaacccac     180

acccccagag gcaatcacgg gtatggaaat agcagatacc aagtctctta atgctcgcaa     240

gtttggtccc tgaagcgtac catcacggtt tatatccgta taaataatag ctgccgcacc     300

caattcctgc atttgggttg ctagttgggg ggccaaaatt tgagaagttt ctaaccaacc     360

cctggtagca actagaccat tccgcgcatc aatcccaatt ataatttgct gggggaattg     420

ttcacacagt ccttgaacca gatctggttg ctctactgct acagttccca gaattgccca     480

ctgtacccca agattaaata actgtataac gctggagcta tcacgtattc ctccgccaac     540

ttcaataggt atggaaatag cattggtaat agcttctata gtagataaat taactatttt     600

accagttttt gctccatcta aatctactaa atgtagtctt gttgctcctt ggtctgccca     660

cattttagcg gtttccacag ggttatggct gtaaacctgg gattgtgcat agtcaccttt     720

gtagagtctt acacaacgcc cctctaatag atctattgct gggataactt ccat           774


<210> SEQ ID NO 67
<211> LENGTH: 257
<212> TYPE: PRT
<213> ORGANISM: Cylindrospermopsis raciborskii T3

<400> SEQUENCE: 67

Met Glu Val Ile Pro Ala Ile Asp Leu Leu Glu Gly Arg Cys Val Arg
1               5                   10                  15

Leu Tyr Lys Gly Asp Tyr Ala Gln Ser Gln Val Tyr Ser His Asn Pro
            20                  25                  30

Val Glu Thr Ala Lys Met Trp Ala Asp Gln Gly Ala Thr Arg Leu His
        35                  40                  45

Leu Val Asp Leu Asp Gly Ala Lys Thr Gly Lys Ile Val Asn Leu Ser
    50                  55                  60

Thr Ile Glu Ala Ile Thr Asn Ala Ile Ser Ile Pro Ile Glu Val Gly
65                  70                  75                  80

Gly Gly Ile Arg Asp Ser Ser Ser Val Ile Gln Leu Phe Asn Leu Gly
                85                  90                  95

Val Gln Trp Ala Ile Leu Gly Thr Val Ala Val Glu Gln Pro Asp Leu
            100                 105                 110

Val Gln Gly Leu Cys Glu Gln Phe Pro Gln Gln Ile Ile Ile Gly Ile
```

115 120 125

Asp Ala Arg Asn Gly Leu Val Ala Thr Arg Gly Trp Leu Glu Thr Ser
130 135 140

Gln Ile Leu Ala Pro Gln Leu Ala Thr Gln Met Gln Glu Leu Gly Ala
145 150 155 160

Ala Ala Ile Ile Tyr Thr Asp Ile Asn Arg Asp Gly Thr Leu Gln Gly
165 170 175

Pro Asn Leu Arg Ala Leu Arg Asp Leu Val Ser Ala Ile Ser Ile Pro
180 185 190

Val Ile Ala Ser Gly Gly Val Gly Ser Val Thr Asp Leu Leu Thr Leu
195 200 205

Leu Ser Leu Glu His Gln Gly Val Thr Gly Val Ile Val Gly Lys Ala
210 215 220

Leu Tyr Thr Gly Asp Ile Ser Leu Pro Glu Ala Leu Arg Ala Ile Gly
225 230 235 240

Pro Gly Arg Ile Gln Asp Ile Pro Pro Thr Leu Asp Phe Ser Arg Phe
245 250 255

Ala

<210> SEQ ID NO 68
<211> LENGTH: 396
<212> TYPE: DNA
<213> ORGANISM: Cylindrospermopsis raciborskii T3

<400> SEQUENCE: 68
atgagttggt ccacaatgaa ggacgtcttg attttaatag tcaaatccct ccaaatccat 60
tataatccca tgaatgctct ttcaattcct acctggatta tccatatttc tagtgtcatt 120
gaatgggtag ttgccatttc cctcatctgg aaatatggcg aactgaccca aaaccatagt 180
tggaggggat ttgccttagg tatgataccc gccttaatta gcgccctatc cgcttgtacc 240
tggcattatt tcgataatcc ccagtcccta gaatggttag tcaccctcca ggctactact 300
acgttaatag gtaattttac tctttgggca gcagcagtct gggtttggcg ttctactcga 360
ccgaatgagg ttctcagtat ctcaaataag gagtag 396

<210> SEQ ID NO 69
<211> LENGTH: 131
<212> TYPE: PRT
<213> ORGANISM: Cylindrospermopsis raciborskii T3

<400> SEQUENCE: 69

Met Ser Trp Ser Thr Met Lys Asp Val Leu Ile Leu Ile Val Lys Ser
1 5 10 15

Leu Gln Ile His Tyr Asn Pro Met Asn Ala Leu Ser Ile Pro Thr Trp
20 25 30

Ile Ile His Ile Ser Ser Val Ile Glu Trp Val Val Ala Ile Ser Leu
35 40 45

Ile Trp Lys Tyr Gly Glu Leu Thr Gln Asn His Ser Trp Arg Gly Phe
50 55 60

Ala Leu Gly Met Ile Pro Ala Leu Ile Ser Ala Leu Ser Ala Cys Thr
65 70 75 80

Trp His Tyr Phe Asp Asn Pro Gln Ser Leu Glu Trp Leu Val Thr Leu
85 90 95

Gln Ala Thr Thr Thr Leu Ile Gly Asn Phe Thr Leu Trp Ala Ala Ala
100 105 110

```
Val Trp Val Trp Arg Ser Thr Arg Pro Asn Glu Val Leu Ser Ile Ser
        115                 120                 125

Asn Lys Glu
    130


<210> SEQ ID NO 70
<211> LENGTH: 20
<212> TYPE: DNA
<213> ORGANISM: Artificial Sequence
<220> FEATURE:
<223> OTHER INFORMATION: Based on Cylindrospermopsis raciborskii T3
      sequence

<400> SEQUENCE: 70

ttaattgctt ggtctatctc                                                 20


<210> SEQ ID NO 71
<211> LENGTH: 20
<212> TYPE: DNA
<213> ORGANISM: Artificial Sequence
<220> FEATURE:
<223> OTHER INFORMATION: Based on Cylindrospermopsis raciborskii T3
      sequence

<400> SEQUENCE: 71

caataccgaa gaggagatag                                                 20


<210> SEQ ID NO 72
<211> LENGTH: 20
<212> TYPE: DNA
<213> ORGANISM: Artificial Sequence
<220> FEATURE:
<223> OTHER INFORMATION: Based on Cylindrospermopsis raciborskii T3
      sequence

<400> SEQUENCE: 72

taggcgtgtt agtgggagat                                                 20


<210> SEQ ID NO 73
<211> LENGTH: 20
<212> TYPE: DNA
<213> ORGANISM: Artificial Sequence
<220> FEATURE:
<223> OTHER INFORMATION: Based on Cylindrospermopsis raciborskii T3
      sequence

<400> SEQUENCE: 73

tgtgtaacca atttgtgagt                                                 20


<210> SEQ ID NO 74
<211> LENGTH: 20
<212> TYPE: DNA
<213> ORGANISM: Artificial Sequence
<220> FEATURE:
<223> OTHER INFORMATION: Based on Cylindrospermopsis raciborskii T3
      sequence

<400> SEQUENCE: 74

ttagccggat tacaggtgaa                                                 20


<210> SEQ ID NO 75
<211> LENGTH: 20
<212> TYPE: DNA
<213> ORGANISM: Artificial Sequence
<220> FEATURE:
<223> OTHER INFORMATION: Based on Cylindrospermopsis raciborskii T3
      sequence
```

<400> SEQUENCE: 75
ctggactcgg cttgttgctt 20

<210> SEQ ID NO 76
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 76
cagcgagtta cacccaccac 20

<210> SEQ ID NO 77
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 77
ctcgcactaa atattctacc 20

<210> SEQ ID NO 78
<211> LENGTH: 19
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 78
aaaacctcag cttccacaa 19

<210> SEQ ID NO 79
<211> LENGTH: 22
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 79
atgattttgg aggtccattg tt 22

<210> SEQ ID NO 80
<211> LENGTH: 42156
<212> TYPE: DNA
<213> ORGANISM: Cylindrospermopsis raciborskii AWT205

<400> SEQUENCE: 80
gtttttactg caaaagcata ttcatattat attctaatag ggttggtgga atattcaagg 60
ggaggttaga aaatgcgatc gctcttatga atgaggttgt ctatccgaat atcaaatatt 120
ggtggttgaa aaaagacctt atatgcggac acagattccc atgatgaaaa tatatcattg 180
tcaagtcaat tagtcaaccc cccaatagac atctccgaaa aagaatcaaa gtgtgataaa 240
atttgcagta cagcaggata taaaatagtt tttcctctat acttctgagt gtaggcttgc 300
gtccgccccc gggcgcacgt ttgcggtttg ctaaggagtt aaacacggtg cgttaatatg 360
tatcagcaac ctgagataac agctcgttga atgcttagcg gttaagtcca gtcattgctc 420

-continued

```
gtagcagtcg ctcttgattc aggatgcggt ctaagttcaa cattaatgtc accctacttg    480
tctgcttgat tattatccct tattttccaa caactctaat gaaagtacct ataacagcaa    540
acgaagatgc agctacatta cttcagcgtg ttggactgtc cctaaaggaa gcacaccaac    600
aacttgaggc aatgcaacgc cgagcgcacg aaccgatcgc aattgtgggg ctggggctgc    660
ggtttccggg agctgattca ccacagacat tctggaaact acttcagaat ggtgttgata    720
tggtcaccga aatccctagc gatcgctggg cagttgatga atactatgat ccccaacctg    780
ggtgtccagg caaaatgtat attcgtgaag ccgcttttgt tgatgcagtg gataaattcg    840
atgcctcgtt ttttgatatt tcgccacgtg aagcggccaa tatagatccc cagcatagaa    900
tgttgctgga ggtagcttgg gaggcactcg aaagggctgg cattgctccc agccaattga    960
tggatagcca aacgggggta tttgtcggga tgagcgaaaa tgactattat gctcacctag   1020
aaaatacagg ggatcatcat aatgtctatg cggcaacggg caatagcaat tactatgctc   1080
cggggcgttt atcctatcta ttggggcttc aaggacctaa catggtcgtt gatagtgcct   1140
gttcctcctc cttagtggct gtacatcttg cctgtaatag tttgcggatg ggagaatgtg   1200
atctggcact ggctggtggc gttcagctta tgttaatccc agaccctatg attgggactg   1260
cccagttaaa tgcctttgcg accgatggtc gtagtaaaac atttgacgct gccgccgatg   1320
gctatggacg cggcgaaggt tgtggcatga ttgtacttaa aagaataagt gacgcgatcg   1380
tggcagacga tccaatttta gccgtaatcc ggggtagtgc agtcaatcat ggcgggcgta   1440
gcagtggttt aactgcccct aataagctgt ctcaagaagc cttactgcgt caggcactac   1500
aaaacgccaa ggttcagccg gaagcagtca gttatatcga agcccatggc acagggacac   1560
aactgggcga cccgattgag gtgggagcat taacgaccgt ctttggatct tctcgttcag   1620
aacccttgtg gattggctct gtcaaaacta atatcggaca cctagaacca gccgctggta   1680
ttgcggggtt aataaaagtc attttatcat tacaagaaaa acagattcct cccagtctcc   1740
attttcaaaa ccctaatccc ttcattgatt gggaatcttc gccagttcaa gtgccgacac   1800
agtgtgtacc ctggactggg aaagagcgcg tcgctggagt tagctcgttt ggtatgagcg   1860
gtacaaactg tcatctagtt gtcgcagaag cacctgtccg ccaaaacgaa aaatctgaaa   1920
atgcaccgga gcgtccttgt cacattctga ccctttcagc caaaaccgaa gcggcactca   1980
acgcattggt agcccgttac atggcatttc tcagggaagc gcccgccata tccctagctg   2040
atctttgtta tagtgccaat gtcgggcgta atctttttgc ccatcgctta agttttatct   2100
ccgagaacat cgcgcagtta tcagaacaat tagaacactg cccacagcag gctacaatgc   2160
caacgcaaca taatgtgata ctagataatc aactcagccc tcaaatcgct tttctgttta   2220
ctggacaagg ttcgcagtac atcaacatgg ggcgtgagct ttacgaaact cagcccacct   2280
tccgtcggat tatggacgaa tgtgacgaca ttctgcatcc attgttgggt gaatcaattc   2340
tgaacatact ctacacttcc cctagcaaac ttaatcaaac cgtttatacc caacctgccc   2400
tttttgcttt tgaatatgcc ctagcaaaac tatggatatc atggggtatt gagcctgatg   2460
tcgtactggg tcacagcgtg ggtgaatatg tagccgcttg tctggcgggt gtctttagtt   2520
tagaagatgg gttaaaactc attgcatctc gtggatgttt gatgcaagcc ttaccgccgg   2580
ggaaaatgct tagtatcaga agcaatgaga tcggagtgaa agcgctcatc gcgccttata   2640
gtgcagaagt atcaattgca gcaatcaatg gacagcaaag cgtggtgatc tccggcaaag   2700
ctgaaattat agataattta gcagcagagt ttgcatcgga aggcatcaaa acacacctaa   2760
ttacagtctc ccacgctttc cactcgccaa tgatgacccc catgctgaaa gcattccgag   2820
```

-continued

```
acgttgccag caccatcagc tataggtcac ccagtttatc actgatttct aacggtacag   2880
ggcaattggc aacaaaggag gttgctacac ctgattattg ggtgcgtcat gtccattcta   2940
ccgtccgttt tgccgatggt attgccacat tggcagaaca gaatactgac atcctcctag   3000
aagtaggacc caaaccaata ttgttgggta tggcaaagca gatttatagt gaaaacggtt   3060
cagctagtca tccgctcatg ctacccagtt tgcgtgaaga tggcaacgat tggcagcaga   3120
tgctttctac ttgtggacaa cttgtagtta atggagtcaa gattgactgg gcgggttttg   3180
acaaggatta ttcacgacac aaaatattgt tgcccaccta tccgtttcag agagaacgat   3240
attggattga aagctccgtc aaaaagcccc aaaaacagga gctgcgccca atgttggata   3300
agatgatccg gctaccatca gagaacaaag tggtgtttga aaccgagttt ggcgtgcgac   3360
agatgcctca tatctccgat catcagatat acggtgaagt cattgtaccg ggggcagtat   3420
tagcttcctt aatcttcaat gcagcgcagg ttttataccc agactatcag catgaattaa   3480
ctgatattgc tttttatcag ccaattatct ttcatgacga cgatacggtg atcgtgcagg   3540
cgattttcag ccctgataag tcacaggaga atcaaagcca tcaaacattt ccacccatga   3600
gcttccagat tattagcttc atgccggatg gtcccttaga gaacaaaccg aaagtccatg   3660
tcacagggtg tctgagaatg ttgcgcgatg cccaaccgcc aacactctcc ccgaccgaaa   3720
tacgtcagcg ctgtccacat accgtaaatg gtcatgactg gtacaatagc ttagtcaaac   3780
aaaaatttga aatgggtcct tcctttaggt gggtacagca actttggcat ggggaaaatg   3840
aagcattgac ccgtcttcac ataccagatg tggtcggctc tgtatcagga catcaacttc   3900
acggcatatt gctcgatggt tcactttcaa ccaccgctgt catggagtac gagtacggag   3960
actccgcgac cagagttcct ttgtcatttg cttctctgca actgtacaaa cccgtcacgg   4020
gaacagagtg gtggtgctac gcgaggaaga ttggggaatt caaatatgac ttccagatta   4080
tgaatgaaat cggggaaacc ttggtgaaag caattggctt tgtacttcgt gaagcctctc   4140
ccgaaaaaatt cctcagaaca acatacgtac acaactggct tgtagacatt gaatggcaag   4200
ctcaatcaac ttccctagtc ccttctgatg gcactatctc tggcagttgt ttggttttat   4260
cagatcagca tggaacaggg gctgcattgg cacaaaggct agacaatgct ggagtgccag   4320
tgaccatgat ctatgctgat ctgatactgg acaattacga attaatattc cgtactttgc   4380
cagatttaca acaagtcgtc tatttatggg ggttggatca aaaagaggat tgtcacccca   4440
tgaagcaagc agaggataac tgtacatcgg tgctatatct tgtgcaagca ttactcaata   4500
cctactcaac cccgccatcc ctgcttattg tcacctgtga tgcacaagcg gtggttgaac   4560
aagatcgagt aaatggcttc gcccaatcgt ctttgttggg acttgccaaa gttatcatgc   4620
tagaacaccc agaattgtcc tgtgtttaca tggatgtgga agccggatat ttacagcaag   4680
atgtggcgaa cacgatattt acacagctaa aaagaggcca tctatcaaag gacggagaag   4740
agagtcagtt ggcttggcgc aatggacaag catacgtagc acgtcttagt caatataaac   4800
ccaaatccga acaactggtt gagatccgca gcgatcgcag ctatttgatc actggtggac   4860
ggggcggtgt cggcttacaa atcgcacggt ggttagtgga aaagggggct aaacatctcg   4920
ttttgttggg gcgcagtcag accagttccg aagtcagtct ggtgttggat gagctagaat   4980
cagccggggc gcaaatcatt gtggctcaag ctgatattag cgatgagaag gtattagcgc   5040
agattctgac caatctaacc gtacctctgt gtggtgtaat ccacgccgca ggagtgcttg   5100
atgatgcgag tctactccaa caaactccag ccaagctcaa aaaagttcta ttgccaaaag   5160
```

-continued cagagggggc ttggattctg cataatttga ccctggagca gcgactagac ttctttgttc 5220
tcttttcttc tgccagttct ctattaggtg cgccagggca ggccaactat tcagcagcca 5280
atgctttcct agatggttta gctgcctatc ggcgagggcg aggactcccc tgtttgtcta 5340
tctgctgggg ggcatgggat caagtcggta tggctgcacg acaagggcta ctggacaagt 5400
taccgcaaag aggtgaagag gccatcccgt tacagaaagg cttagacctc ttcggcgaat 5460
tactgaacga gccagccgct caaattggtg tgatcccaat tcaatggact cgcttcttgg 5520
atcatcaaaa aggtaatttg cctttttatg agaagttttc taagtctagc cggaaagcgc 5580
agagttacga ttcgatggca gtcagtcaca cagaagatat tcagaggaaa ctgaagcaag 5640
ctgctgtgca agatcgacca aaattattag aagtgcatct tcgctctcaa gtcgctcaac 5700
tgttaggaat aaacgtggca gagctaccaa atgaagaagg aattggtttt gttacattag 5760
gtcttgactc gctcacctct attgaactgc gtaacagttt acaacgcaca ttagattgtt 5820
cattacctgt cacctttgct tttgactacc caactataga aatagcggtt aagtacctaa 5880
cacaagttgt aattgcaccg atggaaagca cagcatcgca gcaaacagac tctttatcag 5940
caatgttcac agatacttcg tccatcggga gaattcttga caacgaaaca gatgtgttag 6000
acagcgaaat gcaaagtgat gaagatgaat ctttgtctac acttatacaa aaattatcaa 6060
cacatttgga ttaggagtga tcaataatta tacattgcgg acgtgagcat acaagtaaag 6120
gaaaaatgaa tgaacgcttt gtcagaaaat caggtaactt ctatagtcaa gaaggcattg 6180
aacaaaatag aggagttaca agccgaactt gaccgtttaa aatacgcgca acgggaacca 6240
atcgccatca ttggaatggg ctgtcgcttt cctggtgcag acacacctga agctttttgg 6300
aaattattgc acaatggggt tgatgctatc caagagattc caaaaagccg ttgggatatt 6360
gacgactatt atgatcccac accagcaaca cccggcaaaa tgtatacacg ttttggtggt 6420
tttctcgacc aaatagcagc cttcgaccct gagttctttc gcatttctac tcgtgaggca 6480
atcagcttag accctcaaca gagattgctt ctggaagtga gttgggaagc cttagaacgg 6540
gctgggctga caggcaataa actgactaca caaacaggtg tctttgttgg catcagtgaa 6600
agtgattatc gtgatttgat tatgcgtaat ggttctgacc tagatgtata ttctggttca 6660
ggtaactgcc atagtacagc cagcgggcgt ttatcttatt atttgggact tactggaccc 6720
aatttgtccc ttgataccgc ctgttcgtcc tctttggttt gtgtggcatt ggctgtcaag 6780
agcctacgtc aacaggagtg tgatttggca ttggcgggtg gtgtacagat acaagtgata 6840
ccagatggct ttatcaaagc ctgtcaatcc cgtatgttgt cgcctgatgg acggtgcaaa 6900
acatttgatt tccaggcaga tggttatgcc cgtgctgagg ggtgtgggat ggtagttctc 6960
aaacgcctat ccgatgcaat tgctgacaat gataatatcc tggccttgat tcgtggtgcc 7020
gcagtcaatc atgatggcta cacgagtgga ttaaccgttc ccagtggtcc ctcacaacgg 7080
gcggtgatcc aacaggcatt agcggatgct ggaatacacc cggatcaaat tagctatatt 7140
gaggcacatg gcacaggtac atccttaggc gatcctattg aaatgggtgc gattgggcaa 7200
gtctttggtc aacgctcaca gatgcttttc gtcggttcgg tcaagacgaa tattggtcat 7260
actgaggctg ctgctggtat tgctggtctc atcaaggttg tactctcaat gcagcacggt 7320
gaaatcccag caaacttaca cttcgaccag ccaagtcctt atattaactg ggatcaatta 7380
ccagtcagta tcccaacaga aacaatacct tggtctacta gcgatcgctt tgcaggagtc 7440
agtagctttg gctttagtgg cacaaactct catatcgtac tagaggcagc cccaaacata 7500
gagcaaccta ctgatgatat taatcaaacg ccgcatattt tgaccttagc tgcaaaaaca 7560

-continued

```
cccgcagccc tgcaagaact ggctcggcgt tatgcgactc agatagagac ctctcccgat   7620
gttcctctgg cggacatttg tttcacagca cacatagggc gtaaacattt taaacatagg   7680
tttgcggtag tcacggaatc taaagagcaa ctgcgtttgc aattggatgc atttgcacaa   7740
tcagggggtg tggggcgaga agtcaaatcg ctaccaaaga tagcctttct ttttacaggt   7800
caaggctcac agtatgtggg aatgggtcgt caactttacg aaaaccaacc taccttccga   7860
aaagcactcg cccattgtga tgacatcttg cgtgctggtg catatttcga ccgatcacta   7920
ctttcgattc tctacccaga gggaaaatca gaagccattc accaaaccgc ttatactcag   7980
cccgcgcttt ttgctcttga gtatgcgatc gctcagttgt ggcactcctg ggggtatcaaa   8040
ccagatatcg tgatggggca tagtgtaggt gaatacgtcg ccgcttgtgt ggcgggcata   8100
ttttctttag aggatgggct gaaactaatt gctactcgtg gtcgtctgat gcaatcccta   8160
cctcaagacg gaacgatggt ttcttctttg gcaagtgaag ctcgtatcca ggaagctatt   8220
acaccttacc gagatgatgt gtcaatcgca gcgataaatg ggacagaaag cgtggttatc   8280
tctggcaaac gcacctctgt gatggcaatt gctgaacaac tcgccaccgt tggcatcaag   8340
acacgccaac tgacggtttc ccatgccttc cattcaccac ttatgacacc catcttggat   8400
gagttccgcc aggtggcagc cagtatcacc tatcaccagc ccaagttgct acttgtctcc   8460
aacgtctccg ggaaagtggc cggccctgaa atcaccagac cagattactg ggtacgccat   8520
gtccgtgagg cagtgcgctt tgccgatgga gtgaggacgc tgaatgaaca aggtgtcaat   8580
atctttctgg aaatcggttc taccgctacc ctgttgggca tggcactgcg agtaaatgag   8640
gaagattcaa atgcctcaaa aggaacttcg tcttgctacc tgcccagttt acgggaaagc   8700
cagaaggatt gtcagcagat gttcactagt ctgggtgagt tgtacgtaca tggatatgat   8760
attgattggg gtgcatttaa tcggggatat caaggacgca aggtgatatt gccaacctat   8820
ccgtttcagc gacaacgtta ttggcttccc gaccctaagt tggcacaaag ttccgattta   8880
gataccttc aagctcagag cagcgcatca tcacaaaatc ctagcgctgt gtccacttta   8940
ctgatggaat atttgcaagc aggtgatgtc caatctttag ttgggctttt ggatgatgaa   9000
cggaaactct ctgctgctga acgaattgca ctacccagta ttttggagtt tttggtagag   9060
gaacaacagc gacaaataag ctcaaccaca actcctcaaa cagttttaca aaaaataagt   9120
caaacttccc atgaggacag atatgaaata ttgaagaacc tgatcaaatc tgaaatcgaa   9180
acgattatca aaagtgttcc ctccgatgaa caaatgtttt ctgacttagg aattgattcc   9240
ttgatggcga tcgaactgcg taataagctc cgttctgcta tagggttgga actgccagtg   9300
gcaatagtat ttgaccatcc cacgattaag cagttaacta acttcgtact ggacagaatt   9360
gtgccgcagg cagaccaaaa ggacgttccc accgaatcct tgtttgcttc taaacaggag   9420
atatcagttg aggagcagtc ttttgcaatt accaagctgg gcttatcccc tgcttcccac   9480
tccctgcatc ttcctccatg gacggttaga cctgcggtaa tggcagatgt aacaaaacta   9540
agccaacttg aaagagaggc ctatggctgg atcggagaag gagcgatcgc cccgccccat   9600
ctcattgccg atcgcatcaa tttactcaac agtggtgata tgccttggtt ctgggtaatg   9660
gagcgatcag gagagttggg cgcgtggcag gtgctacaac cgacatctgt tgatccatat   9720
acttatggaa gttgggatga agtaactgac caaggtaaac tgcaagcaac cttcgaccca   9780
agtggacgca atgtgtatat tgtcgcgggt gggtctagca acctccccac ggtagccagc   9840
cacctcatga cgcttcagac tttattgatg ctgcgggaaa ctggtcgtga cacaatcttt   9900
```

gtctgtctgg caatgccagg ttatgccaaa taccacagtc aaacaggaaa atcgccggaa 9960
gagtatattg cgctgactga cgaggatggt atcccaatgg acgagtttat tgcactttct 10020
gtctacgact ggcctgttac cccatcgttt cgtgttctgc gagacggtta tccacctgat 10080
cgagattctg gtggtcacgc agttagtacg gttttccagc tcaatgattt cgatggagcg 10140
atcgaagaaa catatcgtcg tattatccgc catgccgatg tccttggtct cgaaagaggc 10200
taaatttcag gcgttggtga atagaaccca cattccgcag ataaggtctt atgaataaaa 10260
aacaggtaga cacattgtta atacacgctc atctttttac catgcagggc aatggcctgg 10320
gatatattgc cgatggggca attgcggttc agggtagcca gatcgtagca gtggattcga 10380
cagaggcttt gctgagtcat tttgaaggaa ataaaacaat taatgcggta aattgtgcag 10440
tgttgcctgg actaattgat gctcatatac atacgacttg tgctattctg cgtggagtgg 10500
cacaggatgt aaccaattgg ctaatggacg cgacaattcc ttatgcactt cagatgacac 10560
ccgcagtaaa tatagccgga acgcgcttga gtgtactcga agggctgaaa gcaggaacaa 10620
ccacattcgg cgattctgag actccttacc cgctctgggg agagtttttc gatgaaattg 10680
gggtacgtgc tattctatcc cctgccttta acgcctttcc actagaatgg tcggcatgga 10740
aggagggaga cctctatccc ttcgatatga aggcaggacg acgtggtatg gaagaggctg 10800
tggattttgc ttgtgcatgg aatggagccg cagagggacg tatcaccact atgttgggac 10860
tacaggcggc ggatatgcta ccactggaga tcctacacgc agctaaagag attgcccaac 10920
gggaaggctt aatgctgcat attcatgtgg cccagggaga tcgagaaaca aaacaaattg 10980
tcaaacgata tggtaagcgt ccgatcgcat ttctagctga aattggctac ttggacgaac 11040
agttgctggc agttcacctc accgatgcca cagatgaaga agtgatacaa gtagccaaaa 11100
gtggtgctgg catggcactc tgttcgggcg ctattggcat cattgacggt cttgttccgc 11160
ccgctcatgt ttttcgacaa gcaggcggtt ccgttgcact cggttctgat caagcctgtg 11220
gcaacaactg ttgtaacatc ttcaatgaaa tgaagctgac cgccttattc aacaaaataa 11280
aatatcatga tccaaccatt atgccggctt gggaagtcct gcgtatggct accatcgaag 11340
gagcgcaggc gattggttta gatcacaaga ttggctctct tcaagtgggc aaagaagccg 11400
acctgatctt aatagacctc agttccccta acctctcgcc caccctgctc aaccctattc 11460
gtaaccttgt acctaacttg gtgtatgctg cttcaggaca tgaagttaaa agcgtcatgg 11520
tggcgggaaa acttttagtg gaagactacc aagtcctcac ggtagatgag tccgctattc 11580
tcgctgaagc gcaagtacaa gctcaacaac tctgccaacg tgtgaccgct gaccccattc 11640
acaaaaagat ggtgttaatg gaagcgatgg ctaagggtaa attatagata caggcttatc 11700
tgcaacaaca tttctgaatc aaacctggag ggcaaaccca atgaccatat atgaaaataa 11760
gttgagtagt tatcaaaaaa atcaagatgc cataatatct gcaaaagaac tcgaagaatg 11820
gcatttaatt ggacttctag accattcaat agatgcggta atagtaccga attattttct 11880
tgagcaagag tgtatgacaa tttcagagag aataaaaaag agtaaatatt ttagcgctta 11940
tcccggtcat ccatcagtaa gtagcttggg acaagagttg tatgaatgcg aaagtgagct 12000
tgaattagca aagtatcaag aagacgcacc cacattgatt aaagaaatgc ggaggctggt 12060
acatccgtac ataagtccaa ttgatagact tagggttgaa gttgatgata tttggagtta 12120
tggctgtaat ttagcaaaac ttggtgataa aaaactgttt gcgggtatcg ttagagagtt 12180
taaagaagat aaccctggcg caccacattg tgacgtaatg gcatggggtt ttctcgaata 12240
ttataaagat aaaccaaata tcataaatca aatcgcagca aatgtatatt taaaaacgtc 12300

-continued

```
tgcatcagga ggagaaatag tgctttggga tgaatggcca actcaaagcg aatatatagc  12360
atacaaaaca gatgatccag ctagtttcgg tcttgatagc aaaaagatcg cacaaccaaa  12420
acttgagatc caaccgaacc agggagattt aattctattc aattccatga gaattcatgc  12480
ggtgaaaaag atagaaactg gtgtacgtat gacatgggga tgtttgattg gatactctgg  12540
aactgataaa ccgcttgtta tttggactta atgtagcgtt tccatttgag tcaaggcacg  12600
agaagcttct aaagctggaa tagatacact atcattctca actacactct caaatgtcct  12660
aggtaactgt gccccaaaca tcagcattcc aatggcgttg aacaaaaaga aagccaacca  12720
caagatatgg ttactctcaa atttaacagc agctacatcc gcaggtaaaa atcctacacc  12780
aaacgcgatt aagttaacat tgcggagagt atgcccttga gccaaaccca agaagtaccc  12840
acatagtatg caacatactg aattgcatac taggacaagt accaaccagg gaataaaaat  12900
atcaatattc tcaataattt ctgcgtggtt ggttaacaac ccaaaaacat catcgggaaa  12960
tagccaacac gctccgccga aaaccagact cactagcaga gccattccca cagaaacttt  13020
tgccagaggt gctaactgtt ctgtggctcc tttcccttta aaatttcctg ccagagtttc  13080
tgtacagaat cccaatcctt caacaatgta gatgctcaaa gcccatatct gtaagagcaa  13140
ggcattttga gcgtagataa ttgtccccat ttgtgcccct tcgtagttaa acgttaagtt  13200
ggtaaacata caaactaaat tgctgacaaa gatgtttcca ttgagagtta aggtggagcg  13260
tatagctttt atgtcccaaa tttttccagc taattctttt acctcttgcc acgggatttc  13320
tttgcagaca aaaaacaatc ccaccaatag ggtgagatat tgacttgcag cagaagctac  13380
tcctgccccc atgctcgacc agtctaagtg gataataaac aagtagtcga gtgcgatatt  13440
ggcagcattg cccacaaccg acaacaacac aactaagcca tttttttccc gtcccagaaa  13500
ccagccaagc aggacaaagt tgagcaaaat ggcaggcgct ccccaactct gggtgttaaa  13560
atacgcttga gctgaagact tcacctctgg gccgacatct agtatagaaa accccaacac  13620
ccctaacggg tactgtaaca gtatgatcgc cacccccagc accagagcaa ttaaaccatt  13680
aagcagtccc gccaacagta cgccctctcg gtcatctcgt ccgactgctt gtgctgttaa  13740
cgcagtggta cccattcgta aaaacgataa aacaaagtag agaaagttaa gcaggtttcc  13800
agcaagggct actccagcta ggtagtggat ttccgagaga tgacctaaga acatgatact  13860
gactaaatta ctcagtggta ctataatatt cgataggacg ttggtaaaag ctagtcggaa  13920
gtagcggggt ataaagtcat actggcttgg aaatgtcagg ctcataagat taatttgaca  13980
gtagagttgt tggaaaataa gggataataa tcaagcagac aagtagggtg acattaatgt  14040
tgaacttaga ccgcatcctg aatcaagagc gactgctacg agaaatgact ggacttaacc  14100
gccaagcatt caacgagctg ttatctcagt ttgctgatac ctatgaacgc accgtgttca  14160
actccttagc aaaccgcaaa cgtgcgcccg ggggcggacg caagcctaca ctcagaagta  14220
tagaggaaaa actattttat atcctgctgt actgcaaatg ttatccgacg tttgacttgc  14280
tgagtgtgtt gttcaacttt gaccgctcct gtgctcatga ttgggtacat cgactactgt  14340
ctgtgctaga aaccacttta ggagaaaagc aagttttgcc agcacgcaaa ctcaggagca  14400
tggaggaatt caccaaaagg tttccagatg tgaaggaggt gattgtggat ggtacggagc  14460
gtccagtcca gcgtcctcaa aaccgagaac gccaaaaaga gtattactct ggcaagaaaa  14520
agcggcatac atgcaagcag attacagtca gcacaaggga gaaacgagtg attattcgga  14580
cggaaaccag agcaggtaaa gtgcatgaca aacggctact ccatgaatca gagatagtgc  14640
```

-continued

```
aatacattcc tgatgaagta gcaatagagg gagatttggg ttttcatggg ttggagaaag  14700
aatttgtcaa tgtccattta ccacacaaga aaccgaaagg tatcgaagca aggaggcatg  14760
gcggcgggat gggtcagttt ttataagaga gttttgacaa tataaataaa agacttttga  14820
caaccagact tggcattact tagtttcagt ctttcatctc aagtttacgt tattctgagg  14880
cgaacatgaa tcttataaca acaaaaaaac aggtagatac attagtgata cacgctcatc  14940
tttttaccat gcagggaaat ggtgtgggat atattgcaga tggggcactt gcggttgagg  15000
gtagccgtat tgtagcagtt gattcgacgg aggcgttgct gagtcatttt gagggcagaa  15060
aggttattga gtccgcgaat tgtgccgtct tgcctgggct gattaatgct cacgtagaca  15120
caagtttggt gctgatgcgt ggggcggcgc aagatgtaac taattggcta atggacgcga  15180
ccatgcctta ttttgctcac atgacacccg tggcgagtat ggctgcaaca cgcttaaggg  15240
tggtagaaga gttgaaagca ggcacaacaa cattctgtga caataaaatt attagccccc  15300
tgtggggcga atttttcgat gaaattggtg tacgggctag tttagctcct atgttcgatg  15360
cactcccact ggagatgcca ccgcttcaag acggggagct ttatcccttc gatatcaagg  15420
cgggacggcg ggcgatggca gaggctgtgg attttgcctg tgggtggaat ggggcagcag  15480
aggggcgtat cactaccatg ttaggaatgt attcgccaga tatgatgccg cttgagatgc  15540
tacgcgcagc caaagagatt gctcaacggg aaggcttaat gctgcatttt catgtagcgc  15600
agggagatcg ggaaacagag caaatcgtta aacgatatgg taagcgtccg atcgcatttc  15660
tagctgagat tggctacttg gacgaacagt tgctggcagt tcacctcacc gatgccaccg  15720
atgaagaggt gatacaagta gccaaaagtg gcgctggcat ggtactctgt tcgggaatga  15780
ttggcactat tgacggtatc gtgccgcccg ctcatgtgtt tcggcaagca ggcggacccg  15840
ttgcgctagg cagcagctac aataatattt tccatgagat gaagctgacc gccttattca  15900
acaaaataaa atatcacgat ccaaccatta tgccggcttg ggaagtcctg cgtatggcta  15960
ccatcgaagg agcgcgggcg attggtttag atcacaagat tggctctctt gaagttggca  16020
aagaagccga cctgatctta atagacctca gcacccctaa cctctcaccc actctgctta  16080
accccattcg taaccttgta cctaatttcg tgtacgctgc ttcaggacat gaagttaaaa  16140
gtgtcatggt ggcgggaaaa ctgttattgg aagactacca agtcctcaca gtagatgagt  16200
ctgctatcat tgctgaagca caattgcaag cccaacagat ttctcaatgc gtagcatctg  16260
accctatcca caaaaaaatg gtgctgatgg cggcgatggc aaggggccaa ttgtaggaat  16320
ggtcttgagt tatctagtaa gctaagttgc caactaacaa ttaaaaatac gaagcaggtg  16380
ataaggcaga attacagcag gttgtctttc ggatcgctcg ttggatcttt gtaccttccc  16440
tagtcatggc gatcgccctc atcgtcttcg cccaacccgt gatgagcctg ttcggtgcag  16500
agtttgctgt ggctcattgg tagccgatac catccctcca actgacttgt catgatagtc  16560
atggtgcgac tttcccttcg gtactgataa actgggattg aatccctttc agagtcatca  16620
tgatagattt gggaagtcta aatgtggtcg agaagaaagt gcttttccca tgttgagaat  16680
agtcacatta acatcagcat caaaacgcct aattctagat tttacctatg gtttcagcca  16740
aggtaaagga actgagtcta aattacacgc cgtcatgaga taatatgatt attaattttc  16800
tgtatagccc agttaattat acttgattgt aggctatttt tagcctcttc taatgaagaa  16860
tccagactaa tccttatgta cgggaatatg ttatgcaaga aaaacgaatc gcaatgtggt  16920
ctgtgccacg aagtttgggt acagtgctgc tacaagcctg gtcgagtcgg ccagataccg  16980
tagtctttga tgaacttctc tcctttccct atctctttat caaagggaaa gatatgggct  17040
```

-continued

```
ttacttggac agaccttgat tctagccaaa tgccccacgc agattggcga tccgtcatcg  17100
atctgttaaa ggctcccctg cctgaaggga aatcaatcat cgatctgtta aaggctcccc  17160
tgcctgaagg gaaatcaatt tgctatcaga agcatcaagc gtatcattta atcgaagaga  17220
ccatggggat tgagtggata ttgcccttca gcaactgctt tctgattcgc caacccaaag  17280
aaatgctctt atcttttcgt aagattgtgc cacattttac ctttgaagaa acaggctgga  17340
tcgaattaaa acggctgttt gactatgtac atcaaacgag cggagtaatc ccgcctgtca  17400
tagatgcaca cgacttgctg aacgatccgc ggagaatgct ctccaagctt tgtcaggttg  17460
taggggttga gtttaccgag acaatgctca gttggccccc catggaggtc gagttgaacg  17520
aaaaactagc cccttggtac agcaccgtag caagttctac gcattttcac tcgtatcaga  17580
ataaaaatga gtcgttgccg ctatatcttg tcgatatttg taaacgctgc gatgaaatat  17640
atcaggaatt atatcaattt cgactttatt agagagtatt ggtaatgaaa attttgaatt  17700
agtgaagaaa tagaagttga gaatatagac catctaggga tagagactta tgctggacgg  17760
attcaacaac atcaggacaa ttacccacgt cagagtgatt ttagctttgc tgtttacgga  17820
caattatgga tttatggcat ggaactatag gctgatttag ctctaagctt aattagtctt  17880
aaacctcata aacgcctctt tttcaagcgt ggctttcagg ctctatccct tatgaaacaa  17940
gctgtttgac cactttgtca cccggtaagg agaaaaacct taaacccaag cagaaaaaat  18000
tagcccgtaa aaaaaaggga agtaaatcaa ggaaatatag ggtaatatat ttttcacaag  18060
tttatcaatt gtaatctact tgattcagta aattaattaa ggtgttgaag agatgcaaac  18120
aagaattgta aatagctgga atgagtggga tgaactaaag gagatggttg tcgggattgc  18180
agatggtgct tattttgaac caactgagcc aggtaaccgc cctgctttac gcgataagaa  18240
cattgccaaa atgttctctt ttcccagggg tccgaaaaag caagaggtaa cagagaaagc  18300
taatgaggag ttgaatgggc tggtagcgct tctagaatca cagggcgtaa ctgtacgccg  18360
cccagagaaa cataactttg gcctgtctgt gaagacacca ttctttgagg tagagaatca  18420
atattgtgcg gtctgcccac gtgatgttat gatcaccttt gggaacgaaa ttctcgaagc  18480
aactatgtca cggcggtcac gcttctttga gtatttaccc tatcgcaaac tagtctatga  18540
atattggcat aaagatccag atatgatctg gaatgctgcg cctaaaccga ctatgcaaaa  18600
tgccatgtac cgcgaagatt tctgggagtg tccgatggaa gatcgatttg agagtatgca  18660
tgattttgag ttctgcgtca cccaggatga ggtgattttt gacgcagcag actgtagccg  18720
ctttggccgt gatattttg tgcaggagtc aatgacgact aatcgtgcag ggattcgctg  18780
gctcaaacgg catttagagc cgcgtcgctt ccgcgtgcat gatattcact tcccactaga  18840
tattttccca tcccacattg attgtacttt tgtccccctta gcacctgggg ttgtgttagt  18900
gaatccagat cgccccatca aagagggtga agagaaactc ttcatggata acggttggca  18960
attcatcgaa gcacccctcc ccacttccac cgacgatgag atgcctatgt tctgccagtc  19020
cagtaagtgg ttggcgatga atgtgttaag catttccccc aagaaggtca tctgtgaaga  19080
gcaagagcat ccgcttcatg agttgctaga taaacacggc tttgaggtct atccaattcc  19140
ctttcgcaat gtctttgagt ttggcggttc gctccattgt gccacctggg atatccatcg  19200
cacgggaacc tgtgaggatt acttccctaa actaaactat acgccggtaa ctgcatcaac  19260
caatggcgtt tctcgcttca tcatttagta ggttttatag ttatgcaaaa gagagaaagc  19320
ccacagatac tatttgatgg gaatggaaca caatctgagt ttccagatag ttgcattcac  19380
```

-continued

```
cacttgttcg aggatcaagc cgcaaagcga ccggatgcga tcgctctcat tgacggtgag  19440
caatccctta cctacgggga actaaatgta cgcgctaacc acctagccca gcatctcttg  19500
tccctaggct gtcaacccga tgacctcctc gccatctgca tcgagcgttc ggcagaactc  19560
tttattggtt tgttgggtat cctaaaagcc ggatgtgctt atgtgccttt ggatgtaggc  19620
tatcctggcg atcgcataga gtatatgttg cgggactcgg atgcgcgtat tttactaacc  19680
tcaacggatg tcgctaagaa acttgcctta accatacctg cattgcaaga gtgccaaacc  19740
gtctatttag atcaagagat atttgagtat gattttcatt ttttagcgat agctaaacta  19800
ttacataacc aatacttgag attattacat ttttattttt ataccttgat tcagcaatgc  19860
caggcaactt cggtttccca agggattcag acacaggttc tccccaataa tctcgcttac  19920
tgcatttaca cctctggctc taccggaaat cccaaaggga tcttgatgga acatcgctca  19980
ctggtgaata tgctttggtg gcatcagcaa acgcggcctt cggttcaggg tgttaggacg  20040
ctgcaatttt gtgcagtcag ctttgacttt tcctgccatg aaattttttc taccctctgt  20100
cttggcggga tattggtctt ggtgccagag gcagtgcgcc aaaatccctt tgcattggct  20160
gagttcatca gtcaacagaa aattgaaaaa ttgtttcttc ccgttatagc attactacag  20220
ttggccgaag ctgtaaatgg gaataaaagc acctccctcg cgctttgcga agttatcact  20280
accggggagc agatgcagat cacacctgct gtcgccaacc tctttcagaa aaccggggcg  20340
atgttgcata atcactacgg ggcaacagaa tttcaagatg ccaccactca taccctcaag  20400
ggcaatccag agggctggcc aacactggtg ccagtgggtc gtccactgca caatgttcaa  20460
gtgtatattc tggatgaggc acagcaacct gtacctcttg gtggagaggg tgaattctgt  20520
attggtggta ttggactggc tcgtggctat cacaatttgc ctgacctaac gaatgaaaaa  20580
tttattccca atccatttgg ggctaatgag aacgctaaaa aactctaccg cacaggggac  20640
ttggcacgct acctacccga cggcacgatt gagcatttag gacggataga ccaccaggtt  20700
aagatccgag gtttccgcgt ggaattgggg gaaattgagt ccgtgctggc aagtcaccaa  20760
gctgtgcgtg aatgtgccgt tgtggcacgg gagattgcag gtcatacaca gttggtaggg  20820
tatatcatag caaaggatac acttaatctc agtttcgaca aacttgaacc tatcctgcgt  20880
caatattcgg aagcggtgct gccagaatac atgataccca ctcggttcat caatatcagt  20940
aatatgccgt tgactcccag tggtaaactt gaccgcaggg cattacctga tcccaaaggc  21000
gatcgccctg cattgtctac cccacttgtc aagcctcgta cccagacaga gaaacgttta  21060
gcagagattt ggggcagtta tcttgctgta gatattgtgg gaacccacga caatttcttt  21120
gatctaggcg gtacgtcact gctattgact caagcgcaca aattcctgtg cgagaccttt  21180
aatattaatt tgtccgctgt ctcactcttt caatatccca caattcagac attggcacaa  21240
tatattgatt gccaaggaga cacaacctca agcgatacag catccaggca caagaaagta  21300
cgtaaaaagc agtccggtga cagcaacgat attgccatca tcagtgtggc aggtcgcttt  21360
ccgggtgctg aaacgattga gcagttctgg cataatctct gtaatggtgt tgaatccatc  21420
accctttttta gtgatgatga gctagagcag actttgcctg agttatttaa taatcccgct  21480
tatgtcaaag caggtgcggt gctagaaggc gttgaattat ttgatgctac cttttttggc  21540
tacagcccca aagaagctgc ggtgacagac cctcagcaac ggattttgct agagtgtgcc  21600
tgggaagcat ttgaacgggc tggctacaac cccgaaacct atccagaacc agttggtgtt  21660
tatgctggtt caagcctgag tacctatctg cttaacaata ttggctctgc tttaggcata  21720
attaccgagc aaccctttat tgaaacggat atggagcagt ttcaggctaa aattggcaat  21780
```

-continued

```
gaccggagct atcttgctac acgcatctct tacaagctga atctcaaggg tccaagcgtc  21840
aatgtgcaga ccgcctgctc aacctcgtta gttgcggttc acatggcctg tcagagtctc  21900
attagtggag agtgtcaaat ggctttagcc ggtggtattt ctgtggttgt accacagaag  21960
gggggctatc tctacgaaga aggcatggtt cgttcccagg atggtcattg tcgcgccttt  22020
gatgccgaag cccaagggac tatatttggc aatggcggcg gcttggtttt gcttaaacgg  22080
ttgcaggatg cactggacga taacgacaac attatggcag tcatcaaagc cacagccatc  22140
aacaacgacg gtgcgctcaa gatgggctac acagcaccga gcgtggatgg gcaagctgat  22200
gtaattagcg aggcgattgc tatcgctgac atagatgcaa gcaccattgg ctatgtagaa  22260
gctcatggca cagccaccca attgggtgat ccgattgaag tagcagggtt agcaagggca  22320
tttcagcgta gtacggacag cgtccttggt aaacaacaat gcgctattgg atcagttaaa  22380
actaatattg gccacttaga tgaggcggca ggcattgccg gactgataaa ggctgctcta  22440
gctctacaat atggacagat tccaccgagc ttgcactatg ccaatcctaa tccacggatt  22500
gattttgacg caaccccatt ttttgtcaac acagaactac gcgaatggtc aaggaatggt  22560
tatcctcggc gggcgggggt gagttctttt ggtgtgggtg gaactaacag ccatattgtg  22620
ctggaggagt cgcctgtaaa gcaacccaca ttgttctctt ctttgccaga acgcagtcat  22680
catctgctga cgctttctgc ccatacacaa gaggctttgc atgagttggt gcaacgctac  22740
atccaacata acgagacaca ccttgatatt aacttaggcg acctctgttt cacagccaat  22800
acgggacgca agcattttga gcatcgccta gcggttgtag ccgaatcaat ccctggctta  22860
caggcacaac tggaaactgc acagactgcg atttcagcac agaaaaaaaa tgccccgccg  22920
acgatcgcat tcctgtttac aggtcaaggc tcacaataca ttaacatggg gcgcaccctc  22980
tacgatactg aatcaacatt ccgtgcagcc cttgaccgat gtgaaaccat tctccaaaat  23040
ttagggatcg agtccattct ctccgttatt tttggttcat ctgagcatgg actctcatta  23100
gatgacacag cctataccca gcccgcactc tttgccatcg aatacgcgct ctatcaatta  23160
tggaagtcgt ggggcatcca gccctcagtg gtgataggtc atagtgtagg tgaatatgtg  23220
tccgcttgtg tggcgggagt ctttagctta gaggatgggt tgaaactgat tgcagaacga  23280
ggacgactga tacaggcact tcctcgtgat gggagcatgg tttccgtgat ggcaagcgag  23340
aagcgtattg cagatatcat tttaccttat gggggacagg tagggatcgc cgcgattaat  23400
ggcccacaaa gtgttgtaat ttctgggcaa cagcaagcga ttgatgctat ttgtgccatc  23460
ttggaaactg agggcatcaa aagcaagaag ctaaacgtct cccatgcctt ccactcgccg  23520
ctagtggaag caatgttaga ctctttcttg caggttgcac aagaggtcac ttactcgcaa  23580
cctcaaatca agcttatctc taatgtaacg ggaacattgg caagccatga atcttgtccc  23640
gatgaacttc cgatcaccac cgcagagtat tgggtacgtc atgtgcgaca gcccgtccgg  23700
tttgcggcgg gaatggagag ccttgagggt caaggggtaa acgtatttat agaaatcggt  23760
cctaaacctg ttcttttagg catgggacgc gactgcttgc ctgaacaaga gggactttgg  23820
ttgcctagtt tgcgcccaaa acaggatgat tggcaacagg tgttaagtag tttgcgtgat  23880
ctatacttag caggtgtaac cgtagattgg agcagtttcg atcaggggta tgctcgtcgc  23940
cgtgtgccac taccgactta tccttggcag cgagagcggc attgggtaga gccaattatt  24000
cgtcaacggc aatcagtatt acaagccaca aataccacca agctaactcg taacgccagc  24060
gtggcgcagc atcctctgct tggtcaacgg ctgcatttgt cgcggactca agagatttac  24120
```

-continued

```
tttcaaacct tcatccactc cgacttccca atatgggttg ctgatcataa agtatttgga  24180
aatgtcatca ttccgggtgt cgcctatttt gagatggcac tggcagcagg gaaggcactt  24240
aaaccagaca gtatattttg gctcgaagat gtatccatcg cccaagcact gattattccc  24300
gatgaagggc aaactgtgca aatagtatta agcccacagg aagagtcagc ttattttttt  24360
gaaatcctct ctttagaaaa agaaaactct tgggtgcttc atgcctctgg taagctagtc  24420
gcccaagagc aagtgctaga aaccgagcca attgacttga ttgcgttaca ggcacattgt  24480
tccgaagaag tgtcagtaga tgtgctatat caggaagaaa tggcgcgccg gctggatatg  24540
ggtccaatga tgcgtggggt gaagcagctt tggcgttatc cgctctcctt tgccaaaagt  24600
catgatgcga tcgcactcgc caaggtcagc ttgccagaaa tcttgcttca tgagtccaat  24660
gcctaccaat tccatcctgt aatcttggat gcggggctgc aaatgataac ggtctcttat  24720
cctgaagcaa accaaggcca gacttatgta cctgttggta tagagggtct acaagtctat  24780
ggtcgtccca gttcagaact ttggtgtcgc gcccaatatc ggcctccttt ggatacagat  24840
caaaggcagg gtattgattt gctgccaaag aaattgattg cagacttgca tctatttgat  24900
acccagggtc gtgtggttgc catcatgttt ggtgtgcaat ctgtccttgt gggacgggaa  24960
gcaatgttgc gatcgcaaga tacttggcga aattggcttt atcaagtcct gtggaaacct  25020
caagcctgtt ttggactttt accgaattac ctgccaaccc cagataagat tcggaaacgc  25080
ctggaaacaa agttagcgac attgatcatc gaagctaatt tggcgactta tgcgatcgcc  25140
tatacccaac tggaaaggtt aagtctagct tacgttgtgg cggctttccg acaaatgggc  25200
tggctgtttc aacccggtga gcgtttttcc accgcccaga aggtatcagc gttaggaatc  25260
gttgatcaac atcggcaact attcgctcgt ttgctcgaca ttctagccga agcagacata  25320
ctccgcagcg aaaacttgat gacgatatgg gaagtcattt catacccgga aacgattgat  25380
atacaggtac ttcttgacga cctcgaagcc aaagaagcag aagccgaagt cacactggtt  25440
tcccgttgca gtgcaaaatt ggccgaagta ttacaaggaa aatgtgaccc catacagttg  25500
ctctttcccg caggggacac aacaacgtta agcaaactct atcgtgaagc cccagttttg  25560
ggtgttacta atactctagt ccaagaagcg cttctttccg ccctggagca gttgccgccg  25620
gaacgtggtt ggcgaatttt agagattggt gctggaacag gtggaaccac agcctacttg  25680
ttaccgcatc tgcctgggga tcagacaaaa tatgtcttta ccgatattag tgcctttttt  25740
cttgccaaag cggaagagcg ttttaaagat tacccgtttg tacgttatca ggtattagat  25800
atcgaacaag caccacaggc gcaaggattt gaaccccaaa tatacgattt aatcgtagca  25860
gcggatgtct tgcatgctac tagtgacctg cgtcaaactc ttgtacatat ccggcaatta  25920
ttagcgccgg gcgggatgtt gatcctgatg gaagacagcg aacccgcacg ctgggctgat  25980
ttaacctttg gcttaacaga aggctggtgg aagtttacag accatgactt acgccccaac  26040
catccgctat tgtctcctga gcagtggcaa atcttgttgt cagaaatggg atttagtcaa  26100
acaaccgcct tatggccaaa aatagatagc cccccataaat tgccacggga ggcggtgatt  26160
gtggcgcgta atgaaccagc catcagaaaa ccccgaagat ggctgatctt ggctgacgag  26220
gagattggtg gactactagc caaacagcta cgtgaagaag gagaagattg tatactcctc  26280
ttgccagggg aaaagtacac agagagagat tcacaaacgt ttacaatcaa tcctggagat  26340
attgaagagt ggcaacagtt attgaaccga gtaccgaaca tacaagaaat tgtacattgt  26400
tggagtatgg tttccactga cttagatagatga gccactattt tcagttgcag cagtacgctg  26460
catttagttc aagcattagc aaactatcca aaaaaccctc gcttgtcact tgtcacccta  26520
```

```
ggcgcacaag ccgttaacga acatcatgtt caaaatgtag ttggagcagc cctctggggc  26580
atgggaaagg taattgcact cgaacaccca gagctacaag tagcacaaat ggatttagac  26640
ccgaatggga aggttaaggc gcaagtagaa gtgcttaggg atgaacttct cgccagaaaa  26700
gaccctgcat cagcaatgtc tgtgcctgat ctgcaaacac gacctcatga aaagcaaata  26760
gcctttcgtg agcaaacacg ttatgtggca agactttcgc ccttagaccg ccccaatcct  26820
ggagagaaag gcacacaaga ggctcttacc ttccgtgatg atggcagcta tctgattgct  26880
ggtggtttag gcggactggg gttagtggtg gctcgttttc tggttacaaa tggggctaaa  26940
taccttgtgc tagtcggacg acgtggtgcg agggaggaac agcaagctca attaagcgaa  27000
ctagagcaac tcggagcttc cgtgaaagtt ttacaagccg atattgctga tgcagaacaa  27060
ctagcccaag cactttcagc agtaacctac ccaccattac ggggtgttat tcatgcggca  27120
ggtacattga acgatgggat tctacagcag caaagttggc aagcctttaa agaagtgatg  27180
aatcccaagg tagcaggtgc gtggaaccta catatactga caaaaaatca gcctttagac  27240
ttctttgtcc tgttctcctc cgccacctct ttgttaggta acgctggaca agccaatcac  27300
gccgccgcaa atgctttcct tgatgggtta gcctcctatc gtcgtcactt aggactaccg  27360
agcctctcga ttaattgggg gacatggagc gaagtgggaa ttgcggctcg acttgaacta  27420
gataagttgt ccagcaaaca gggagaggga accattacgc taggacaggg cttacaaatt  27480
cttgagcagt tgctcaaaga cgagaatggg gtgtatcaag tgggtgtcat gcctatcaac  27540
tggacacaat tcttagcaag gcaattgact ccgcagccgt tcttcagcga tgccatgaag  27600
agtattgaca cctctgtagg taaactaacc ttgcaggagc gggactcttg cccccaaggt  27660
tacgggcata atattcgaga gcaattagag aacgctccgc ccaaagaggg tctgactctc  27720
ttgcaggctc atgttcggga gcaggtttcc caagttttgg ggatagacac gaagacatta  27780
ttggcagaac aagacgtggg tttctttacc ctggggatgg attcgctgac ctctgtcgag  27840
ttaagaaaca ggttacaagc cagtttgggc tgctctcttt cttccacttt ggcttttgac  27900
tatccaacac aacaggctct tgtgaattat cttgccaatg aattgctggg aacccctgag  27960
cagctacaag agcctgaatc tgatgaagaa gatcagatat cgtcaatgga tgacatcgtg  28020
cagttgctgt ccgcgaaact agagatggaa atttaagccc atggatgaaa aactaagaac  28080
atacgaacga ttaatcaagc aatcctatca caagatagag gctctggaag ctgaagttaa  28140
caggttgaag caaacccaat gtgaacctat cgccatcgtc ggcatgggct gtcgttttcc  28200
tggtgcgaat agtccagaag cgttttggca gttgttgtgt gatggggttg atgctattcg  28260
tgagatacca aaaaatcgat gggttgttga tgcctacata gatgaaaatt tggaccgcgc  28320
agacaagaca tcaatgcgat ttggcgggtt tgtcgagcaa cttgagaagt ttgatgccca  28380
attctttggc atatcaccgc gagaagcggt ttctcttgac cctcagcaac gtttgttatt  28440
agaagtaagt tgggaagcac tggaaaatgc agcggtgata ccaccttcgg caacgggcgt  28500
attcgtcggt attagtaacc ttgattatcg tgaaacgctc ttgaagcaag gagcaattgg  28560
tacttatttt gcttcgggta atgcccatag cacagccagt ggtcgcttgt cttactttct  28620
cggtctgaca ggcccctgtc tctcgataga tacagcttgt tcttcgtcgt tggtcgctgt  28680
acatcagtca ctgataagtc tgcgtcagcg agaatgtgac ttagcgttgg ttgggggagt  28740
ccatcggctg atagccccag aggaaagtgt ctcgttagca aaagcccata tgttatctcc  28800
cgatggtcgt tgcaaagtct ttgatgcgtc ggcaaacggg tatgtccgag ccgaaggatg  28860
```

-continued

```
tggcatgata gtcctcaaac gattatcgga cgcgcaagct gatggggata aaatcttggc  28920
gttgattcgc gggtcagcca taaatcaaga cggtcgcacg agtggcttga ccgttccaaa  28980
tggtccccaa caagccgacg tgattcgcca agccctcgcc aatagtggca taagaccaga  29040
acaagttaac tatgtagaag ctcatggcac agggacttcc ctaggagacc cgattgaggt  29100
cggcgcgttg ggaacgatct ttaatcaacg ctcccaacct ttaattattg gttcagttaa  29160
aacaaatatt gggcatctag aagcagcagc agggattgct ggactgatta aagtcgtcct  29220
tgccatgcag catggagaaa ttccacctaa tttacacttt caccagccca atcctcgcat  29280
taactgggat aaattgccaa tcaggatccc cacagaacga acagcttggc ctactggcga  29340
tcgcatcgca gggataagtt ctttcggctt tagtggcact aattctcatg tcgtgttaga  29400
ggaagcccca aaaatagagc cgtctacttt agagattcat tcaaagcagt atgtttttac  29460
cttatcagca gcgacacctc aagcactaca agaacttact cagcgttatg taacttatct  29520
cactgaacac ttacaagaga gtctggcgga tatttgcttt acagccaaca cagggcgcaa  29580
acactttaga catcgctttg cagtagtagc agagtctaaa acccagttgc gccaacaatt  29640
ggaaacgttt gcccaatcgg gagaggggca ggggaagagg acatctctct caaaaatagc  29700
ttttctcttt acaggtcaag gctcacagta tgtggggatg ggcaagaac tttatgagag  29760
ccaacccacc ttccggcaaa ccattgaccg atgtgatgag attcttcgtt cactgttggg  29820
caaatcaatc ctctcaatac tctatcccag ccaacaaatg ggattggaaa cgccatccca  29880
aattgatgaa accgcctata ctcaacccac tcttttttct cttgaatatg cactggcgca  29940
gttgtggcgc tcctggggta ttgagcctga tgtggtgatg ggcatagtg tgggagaata  30000
tgtggccgct tgtgtggcgg gtgtcttttc tttagaggat ggactcaaac taattgctga  30060
aagaggccgt ctgatgcaag aattgcctcc cgatggggcg atggtttcag ttatggccaa  30120
taaatcgcgc atagagcaag caattcaatc tgtcagccga gaggtttcta ttgcggccat  30180
caatggacct gagagtgtgg ttatctctgg taaaagggag atattacaac agattaccga  30240
acatctggtt gccgaaggca ttaagacacg ccaactgaag gtctctcatg cctttcactc  30300
accattgatg gagccaatat taggtcagtt ccgccgagtt gccaatacca tcacctatcg  30360
gccaccgcaa attaaccttg tctcaaatgt cacaggcgga caggtgtata aagaaatcgc  30420
tactcccgat tattgggtga gacatctgca agagactgtc cgttttgcgg atggggttaa  30480
ggtgttacat gaacagaatg tcaatttcat gctcgaaatt ggtcccaaac ccacactgct  30540
gggcatggtt gagttacaaa gttctgagaa tccattttct atgccaatga tgatgcccag  30600
tttgcgtcag aatcgtagcg actggcagca gatgttggag agcttgagtc aactctatgt  30660
tcatggtgtt gagattgact ggatcggttt taataaagac tatgtgcgac ataaagttgt  30720
cctgccgaca tacccatggc agaaggagcg ttactgggta gaattggatc aacagaagca  30780
cgccgctaaa aatctacatc ctctactgga caggtgcatg aagctgcctc gtcataacga  30840
aacaattttt gagaaagaat ttagtctaga gacattgccc tttcttgctg actatcgcat  30900
ttatggttca gttgtgtcgc caggtgcaag ttatctatca atgatactaa gtattgccga  30960
gtcgtatgca aatggtcatt tgaatggagg gaatagtgca aagcaaacca cttatttact  31020
aaaggatgtc acattcccag tacctcttgt gatctctgat gaggcaaatt acatggtgca  31080
agttgcttgt tctctctctt gtgctgcgcc acacaatcgt ggcgacgaga cgcagtttga  31140
attgttcagt tttgctgaga atgtacctga aagtagcagt ataaatgctg attttcagac  31200
acccattatt catgcaaaag ggcaatttaa gcttgaagat acagcacctc ctaaagtgga  31260
```

```
gctagaagaa ctacaagcgg gttgtcccca agaaattgat ctcaaccttt tctatcaaac  31320
attcacagac aaaggttttg tttttggatc tcgttttcgc tggttagaac aaatctgggt  31380
gggcgatgga gaagcattgg cgcgtctgcg acaaccggaa agtattgaat cgtttaaagg  31440
atatgtgatt catcccggtt tgttggatgc ctgtacacaa gtcccatttg caatttcgtc  31500
tgacgatgaa aataggcaat cagaaacgac aatgcccttt gcgctgaatg aattacgttg  31560
ttatcagcct gcaaacggac aaatgtggtg ggttcatgca acagaaaaag atagatatac  31620
atgggatgtt tctctgtttg atgagagcgg gcaagttatt gcggaattta taggtttaga  31680
agttcgtgct gctatgcccg aaggcttact aagggcagac ttttggcata actggctcta  31740
tacagtgaat tggcgatcgc aacctctaca aatcccagag gtgctggata ttaataagac  31800
aggtgcagaa acatggcttc tttttgcaca accagaggga ataggagcgg acttagccga  31860
atatttgcag agccaaggaa agcactgtgt ttttgtagtg cctgggagtg agtatacagt  31920
gaccgagcaa cacattggac gcactggaca tcttgatgtg acgaaactga caaaaattgt  31980
cacgatcaat cctgcttctc ctcatgacta taaatatttt ttagaaactc tgacggacat  32040
tagattacct tgtgaacata tactctattt atggaatcgt tatgatttaa caaatacttc  32100
taatcatcgg acagaattga ctgtaccaga tatagtctta aacttatgta ctagtcttac  32160
ttatttggta caagccctta gccacatggg tttttccccg aaattatggc taattacaca  32220
aaatagtcaa gcggttggta gtgacttagc gaatttagaa atcgaacaat ccccattatg  32280
ggcattgggt cgaagcatcc gcgccgaaca ccctgaattt gattgccgtt gtttagattt  32340
tgacacgctc tcaaatatcg caccactctt gttgaaagag atgcaagcta tagactatga  32400
atctcaaatt gcttaccgac aaggaacgcg ctatgttgca cgactaattc gtaatcaatc  32460
agaatgtcac gcaccgattc aaacaggaat ccgtcctgat ggcagctatt tgattacagg  32520
tggattaggc ggtctaggat tgcaggtagc actcgccctt gcggacgctg gagcaagaca  32580
cttgatcctc aatagtcgcc gtggtacggt ctccaaagaa gcccagttaa ttattgaccg  32640
actacgccaa gaggatgtta gggttgattt gattgcggca gatgtctctg atgcggcaga  32700
tagcgaacga ctcttagtag aaagtcagcg caagacctct cttcgaggga ttgtccatgt  32760
tgcgggagtc ttggatgatg gcatcctgct ccaacaaaat caagagcgtt ttgaaaaagt  32820
gatggcggct aaggtacgcg gagcttggca tctggaccaa cagagccaaa ccctcgattt  32880
agatttcttt gttgcgttct catctgttgc gtcgctcata gaagaaccag gacaagccaa  32940
ttacgccgca gcgaatgcgt tttggattc attaatgtat tatcgtcaca taaagggatc  33000
taatagcttg agtatcaact ggggggcttg ggcagaagtc ggcatggcag ccaatttatc  33060
atgggaacaa cggggaatcg cggcaatttc tccaaagcaa gggaggcata ttctcgtcca  33120
acttattcaa aaacttaatc agcatacaat cccccaagtt gctgtacaac cgaccaattg  33180
ggctgaatat ctatcccatg atggcgtgaa tatgccattc tatgaatatt ttacacacca  33240
cttgcgtaac gaaaaagaag ccaaattgcg gcaaacagca ggcagcacct cagaggaagt  33300
cagtctgcgg caacagcttc aaacactctc agagaaagac cgggatgccc ttttgatgga  33360
acatcttcaa aaaactgcga tcagagttct cggtttggca tctaatcaaa aaattgatcc  33420
ctatcaggga ttgatgaata tgggactaga ctctttgatg gcggttgaat ttcggaatca  33480
cttgatacgt agtttagaac gccctctgcc agccactctg ctctttaatt gcccaacact  33540
tgattcattg catgattacc tagtcgcaaa aatgtttgat gatgcccctc agaaggcaga  33600
```

-continued

```
gcaaatggca caaccaacaa cactgacagc acacagcata tcaatagaat ccaaaataga  33660
tgataacgaa agcgtggatg acattgcaca aatgctggca caagcactca atatcgcctt  33720
tgagtagcaa tgggcagccc ttaacctttc aaggtgacta atcaatagac ctcttgcaca  33780
attgtttctg tggtacaata agtggtttta ggttttatgt atatttgggt gttgttgcga  33840
tagctacgct cgccgaaggc atcacaaatt caaagatagg cgtgtgattc taacttttag  33900
cttaacgggt gacaaggcgg ctaaagagct tgtttcataa gggatagagc ctgaaagccc  33960
cgttgaaaaa agaggcgttt atgaggcttg agattgatta aattcagagc taaatcagcc  34020
cataattcca taccataaat ccatagttgt ccgtagagac caaagctaaa atcactttga  34080
cgtgggtact tgtcctgatg ttgttgaatc ccacattcag catgagtaaa tatactcaaa  34140
atatttttcc cagcaggtta agtgttctaa tcctaagtct gatatcttat ttttgataag  34200
ggacttaccg cgtaatagtt aaatttttgt atagcctaat tttacttggt ttaaggctct  34260
tttttgctct tttggtgaat tattcaggat aatcaaagat gagtcagccc aattatggca  34320
ttttgatgaa aaatgcgttg aacgaaataa atagcctacg atcgcaacta gctgcggtag  34380
aagcccaaaa aaatgagtct attgccattg ttggtatgag ttgccgtttt ccaggcggtg  34440
caactactcc agagcgtttt tgggtattac tgcgcgaggg tatatcagcc attacagaaa  34500
tccctgctga tcgctgggat gttgataaat attatgatgc tgaccccaca tcgtccggta  34560
aaatgcatac tcgttacggc ggttttctga atgaagttga tacatttgag ccatcattct  34620
ttaatattgc tgcccgtgaa gccgttagca tggatccaca gcaacgcttg ctacttgaag  34680
tcagttggga agctctggaa tccggtaata ttgttcctgc aactcttttt gatagttcca  34740
ctggtgtatt tatcggtatt ggtggtagca actacaaatc tttaatgatc gaaaacagga  34800
gtcggatcgg gaaaaccgat ttgtatgagt taagtggcac tgatgtgagt gttgctgccg  34860
gcaggatatc ctatgtcctg ggtttgatgg gtcccagttt tgtgattgat acagcttgtt  34920
catcttcttt ggtctcagtt catcaagcct gtcagagtct gcgtcagaga gaatgtgatc  34980
tagcactagc tggtggagtc ggtttactca ttgatccaga tgagatgatt ggtctttctc  35040
aagggggggat gctggcacct gatggtagtt gtaaaacatt tgatgccaat gcaaatggct  35100
atgtgcgagg cgaaggttgt gggatgattg ttctaaaacg tctctcggat gcaacagccg  35160
atggggataa tattcttgcc atcattcgtg ggtctatggt taatcatgat ggtcatagca  35220
gtggtttaac tgctccaaga ggccccgcac aagtctctgt cattaagcaa gccttagata  35280
gagcaggtat tgcaccggat gccgtaagtt atttagaagc ccatggtaca ggcacacccc  35340
ttggtgatcc tatcgagatg gattcattga acgaagtgtt tggtcggaga acagaaccac  35400
tttgggtcgg ctcagttaag acaaatattg gtcatttaga agccgcgtcc ggtattgcag  35460
ggctgattaa ggttgtcttg atgctaaaaa acaagcagat tcctcctcac ttgcatttca  35520
agacaccaaa tccatatatt gattggaaaa atctcccggt cgaaattccg accacccttc  35580
atgcttggga tgacaagaca ttgaaggaca gaaagcgaat tgcaggggtt agttctttta  35640
gtttcagtgg tactaacgcc cacattgtat tatctgaagc ccccatctagc gaactaatta  35700
gtaatcatgc ggcagtggaa agaccatggc acttgttaac ccttagtgct aagaatgagg  35760
aagcgttggc taacttggtt gggctttatc agtcatttat ttctactact gatgcaagtc  35820
ttgccgatat atgctacact gctaatacgg cacgaaccca tttttctcat cgccttgctc  35880
tatcggctac ttcacacatc caaatagagg ctcttttagc cgcttataag gaagggtcgg  35940
tgagtttgag catcaatcaa ggttgtgtcc tttccaacag tcgtgcgccg aaggtcgctt  36000
```

ttctctttac aggtcaaggt tcgcaatatg tgcaaatggc tggagaactt tatgagaccc 36060
agcctacttt ccgtaattgc ttagatcgct gtgccgaaat cttgcaatcc atcttttcat 36120
cgagaaacag cccttgggga aacccactgc tttcggtatt atatccaaac catgagtcaa 36180
aggaaattga ccagacggct tatacccaac ctgccctttt tgctgtagaa tatgccctag 36240
cacagatgtg gcggtcgtgg ggaatcgagc cagatatcgt aatgggtcat agcataggtg 36300
aatatgtggc agcttgtgtg gcggggatct tttctctgga ggatggtctc aaacttgctg 36360
ccgaaagagg ccgtttgatg caggcgctac cacaaaatgg cgagatggtt gctatatcgg 36420
cctcccttga ggaagttaag ccggctattc aatctgacca gcgagttgtg atagcggcgg 36480
taaatggacc acgaagtgtc gtcatttcgg gcgatcgcca agctgtgcaa gtcttcacca 36540
acaccctaga agatcaagga atccggtgca agagactgtc tgtttcacac gctttccact 36600
ctccattgat gaaaccaatg gagcaggagt tcgcacaggt ggccagggaa atcaactata 36660
gtcctccaaa aatagctctt gtcagtaatc taaccggcga cttgatttca cctgagtctt 36720
ccctggagga aggagtgatc gcttcccctg gttactgggt aaatcattta tgcaatcctg 36780
tcttgttcgc tgatggtatt gcaactatgc aagcgcagga tgtccaagtc ttccttgaag 36840
ttggaccaaa accgacctta tcaggactag tgcaacaata ttttgacgag gttgcccata 36900
gcgatcgccc tgtcaccatt cccaccttgc gccccaagca acccaactgg cagacactat 36960
tggagagttt gggacaactg tatgcgcttg gtgtccaggt aaattgggcg ggctttgata 37020
gagattacac cagacgcaaa gtaagcctac ccacctatgc ttggaagcgt caacgttatt 37080
ggctagagaa acagtccgct ccacgtttag aaacaacaca agttcgtccc gcaactgcca 37140
ttgtagagca tcttgaacaa ggcaatgtgc cgaaaatcgt ggacttgtta gcggcgacgg 37200
atgtactttc aggcgaagca cggaaattgc tacccagcat cattgaacta ttggttgcaa 37260
aacatcgtga ggaagcgaca cagaagccca tctgcgattg gctttatgaa gtggtttggc 37320
aaccccagtt gctgacccta tctaccttac ctgctgtgga aacagagggt agacaatggc 37380
tcatcttcgc cgatgctagt ggacacggtg aagcacttgc ggctcaatta cgtcagcaag 37440
gggatataat tacgcttgtc tatgctggtc taaaatatca ctcggctaat aataaacaaa 37500
ataccggggg ggacatccca tattttcaga ttgatccgat ccaaagggag gattatgaaa 37560
ggttgtttgc tgctttgcct ccactgtatg gtattgttca tctttggagt ttagatatac 37620
ttagcttgga caaagtatct aacctaattg aaaatgtaca attaggtagt ggcacgctat 37680
taaatttaat acagacagtc ttgcaacttg aaacgcccac ccctagcttg tggctcgtga 37740
caaagaacgc gcaagctgtg cgtaaaaacg atagcctagt cggagtgctt cagtcaccct 37800
tatggggtat gggtaaggtg atagccttag aacaccctga actcaactgt gtatcaatcg 37860
accttgatgg tgaagggctt ccagatgaac aagccaagtt tctggcggct gaactccgcg 37920
ccgcctccga gttcagacat accaccattc cccacgaaag tcaagttgct tggcgtaata 37980
ggactcgcta tgtgtcacgg ttcaaaggtt atcagaagca tcccgcgacc tcatcaaaaa 38040
tgcctattcg accagatgcc acttatttga tcacgggcgg ctttggtggt ttgggcttgc 38100
ttgtggctcg ttggatggtt gaacaggggg ctacccatct atttctgatg ggacgcagcc 38160
aacccaaacc agccgcccaa aaacaactgc aagagatagc cgcgctgggt gcaacagtga 38220
cggtggtgca agccgatgtt ggcatccgct cccaagtagc caatgtgttg gcacagattg 38280
ataaggcata tcctttggct ggtattattc atactgccgg tgtattagac gacggaatct 38340

```
tattgcagca aaattgggcg cgttttagca aggtgttcgc ccccaaacta gagggagctt  38400
ggcatctaca tacactgact gaagagatgc cgcttgattt ctttatttgt ttttcctcaa  38460
cagcaggatt gctgggcagt ggtggacaag ctaactatgc tgctgccaat gcctttttag  38520
atgcctttgc ccatcatcgg cgaatacaag gcttgccagc tctctcgatt aactgggacg  38580
cttggtctca agtgggaatg acggtacgtc tccaacaagc ttcttcacaa agcaccacag  38640
ttgggcaaga tattagcact ttggaaattt caccagaaca gggattgcaa atctttgcct  38700
atcttctgca acaaccatcc gcccaaatag cggccatttc taccgatggg cttcgcaaga  38760
tgtacgacac aagctcggcc ttttttgctt tacttgatct tgacaggtct tcctccacta  38820
cccaggagca atctacactt tctcatgaag ttggccttac cttactcgaa caattgcagc  38880
aagctcggcc aaaagagcga gagaaaatgt tactgcgcca tctacagacc caagttgctg  38940
cggtcttgcg tagtcccgaa ctgcccgcag ttcatcaacc cttcactgac ttggggatgg  39000
attcgttgat gtcacttgaa ttgatgcggc gtttggaaga aagtctgggg attcagatgc  39060
ctgcaacgct tgcattcgat tatcctatgg tagaccgttt ggctaagttt atactgactc  39120
aaatatgtat aaattctgag ccagatacct cagcagttct cacaccagat ggaaatgggg  39180
aggaaaaaga cagtaataag gacagaagta ccagcacttc cgttgactca aatattactt  39240
ccatggcaga agatttattc gcactcgaat ccttactaaa taaaataaaa agagatcaat  39300
aatagagctg ttgggaaata aaagcatatt tccggatgac agaacttccc ccatcccgat  39360
tgaatttatg ctgcatctaa atagaagttc catagccctg cactgaccaa catcaattga  39420
tcatcaaaat cggtcacacg attcctatat gtgggataaa atttgcagta cagcaggata  39480
taaaatagtt tttcctctat acttctgagt gtaggcttgc gtccgccccc gggcgcacgt  39540
ttgcggtttg ctaaggagtt gaacacggtg cgttcatagg tatcagcaaa ctgagataac  39600
agctcgttga atgcttggcg gttaagtcca gtcattgctc gtagcagtcg ctcttgattc  39660
aggatgcggt ctaagttcaa cattaatgtc accctacttg tctgcttgat tattatccct  39720
tattttccaa caactctatt atagcttatc ttattttgga gtttaactac atgaaaatcg  39780
ctgtaaagac tcctactgag tgaaagtgaa cttctttccc acgtattcga gtagctgttg  39840
taagctggcc tcgatggaaa gttccgaagt ttccaccagt aaatctggtg ttctcggtgg  39900
ttcgtaggga gcgctaattc ccgtaaaaga ctcaatttct ccacggcgtg cttttgcata  39960
gagacccttg ggtcacgtt  gttcacaaat ttccatcgga gttgcaatat atacttcatg  40020
aaacagatct ccggacagaa tacggatttg ctcccggtct ttcctgtaag gtgaaatgaa  40080
agcagtaatc actaaacaac ccgaatccgc aaaaagtttg gccacctcgc caatacgacg  40140
aatattttcc gcacgatcag cagcagaaaa tcccaagtca gcacataatc catgacggat  40200
attgtcacca tcaaggacaa aagtatacca acctttctgg aacaaaatcc gctctaattc  40260
tagagccaat gttgttttac ctgatcctga taatccagtg aaccatagaa ttccatttcg  40320
gtgaccattc tttaaacaac gatcaaatgg ggacacaaga tgttttgtat gttgaatatt  40380
gcttgatttc atatctatga taaatatgat aaaagtgatt ggccaaacag aactgctcac  40440
ccaataatat agttaaaggt tattttttca aaaactcctt ctaaattata gctcacaatt  40500
atgcctaaat actttaatac tgctggaccc tgtaaatccg aaatccacta tatgctctct  40560
cccacagctc gactaccgga tttgaaagca ctaattgacg gagaaaacta ctttataatt  40620
cacgcgccgc gacaagtcgg caaaactaca gctatgatag ccttagcacg agaattgact  40680
gatagtggaa aatataccgc agttattctt tccgttgaag tgggatcagt attctcccat  40740
```

```
aatccccagc aagcggagca ggttatttta gaagaatgga aacaggcaat caaattttat  40800

ttacccaaag aactacaacc atcctattgg ccagagcgtg aaacagactc aggaataggc  40860

aaaactttaa gtgagtggtc cgcacaatct ccaagacctc ttgtaatctt tttacatgaa  40920

atcgattccc taacagatga agctttaatc ctaattttaa gacaattacg ctcaggtttt  40980

ccccgtcgtc ctcggggatt tccccattcg gtggggttaa ttggtatgcg ggatgtgcgg  41040

gactataagg ttaaatctgg tggaagtgaa cgactgaata cgtcaagtcc tttcaatatc  41100

aaagcggaat ccttgacttt aagtaatttc actctgtcag aggtggaaga actttactta  41160

caacatacgc aagctacagg acaaattttt accccggaag caattaaaca agcattttat  41220

ttaaccgatg ggcaaccatg gttagtaaac gccctagctc gtcaagccac tcaggtgtta  41280

gtgaaagata ttactcaacc cattaccgct gaagtaatta accaagccaa agaagttctg  41340

attcagcgcc aggataccca tttggatagt ttggcagagc gcttacggga agatcgggtc  41400

aaagccatta ttcaacctat gttagctgga tcggacttac cagatacccc agaggatgat  41460

cgccgtttct tgctagattt aggcttggta aagcgcagtc ccttgggagg actaaccatt  41520

gccaatccca tttaccagga ggtgattcct cgtgttttgt cccagggtag tcaggatagt  41580

ctaccccaga ttcaacctac ttggttaaat actgataata ctttaaatcc tgacaaactc  41640

ttaaatgctt tcctagagtt ttggcgacaa catggggaac cattactcaa aagtgcgcct  41700

tatcatgaaa ttgctcccca tttagttttg atggcgtttt tacatcgggt agtgaatggt  41760

ggtggcactt tagaacggga atatgccgtt ggttctggaa gaatggatat ttgtttacgc  41820

tatggcaagg tagtgatggg catagagtta aaggtttggg ggggaaaatc ggatccgtta  41880

acgaagggtt tgacccaatt ggataaatat ctgggtgggt taggattaga tagaggttgg  41940

ttagtaattt ttgatcaccg tccgggatta ccacccatgg gtgagaggat tagtatggaa  42000

caggccatta gtccagaggg aagaaccatt acagtgattc gtagctagag cgttagatat  42060

cagatgattg aacctcaatt attgtgcaac gccacatttt ctttccaaag atgtatgtta  42120

aactctagta aactctaatt aggtcgagaa agagat                            42156
```

<210> SEQ ID NO 81
<211> LENGTH: 5631
<212> TYPE: DNA
<213> ORGANISM: Cylindrospermopsis raciborskii AWT205

<400> SEQUENCE: 81

```
atgcggtcta agttcaacat taatgtcacc ctacttgtct gcttgattat tatcccttat     60

tttccaacaa ctctaatgaa agtacctata acagcaaacg aagatgcagc tacattactt    120

cagcgtgttg gactgtccct aaaggaagca caccaacaac ttgaggcaat gcaacgccga    180

gcgcacgaac cgatcgcaat tgtggggctg gggctgcggt ttccgggagc tgattcacca    240

cagacattct ggaaactact tcagaatggt gttgatatgg tcaccgaaat ccctagcgat    300

cgctgggcag ttgatgaata ctatgatccc caacctgggt gtccaggcaa aatgtatatt    360

cgtgaagccg cttttgttga tgcagtggat aaattcgatg cctcgttttt tgatatttcg    420

ccacgtgaag cggccaatat agatccccag catagaatgt tgctggaggt agcttgggag    480

gcactcgaaa gggctggcat tgctcccagc caattgatgg atagccaaac gggggtattt    540

gtcgggatga gcgaaaatga ctattatgct cacctagaaa atacagggga tcatcataat    600

gtctatgcgg caacgggcaa tagcaattac tatgctccgg ggcgtttatc ctatctattg    660
```

-continued

```
gggcttcaag gacctaacat ggtcgttgat agtgcctgtt cctcctcctt agtggctgta    720
catcttgcct gtaatagttt gcggatggga gaatgtgatc tggcactggc tggtggcgtt    780
cagcttatgt taatcccaga ccctatgatt gggactgccc agttaaatgc ctttgcgacc    840
gatggtcgta gtaaaacatt tgacgctgcc gccgatggct atggacgcgg cgaaggttgt    900
ggcatgattg tacttaaaag aataagtgac gcgatcgtgg cagacgatcc aattttagcc    960
gtaatccggg gtagtgcagt caatcatggc gggcgtagca gtggtttaac tgcccctaat   1020
aagctgtctc aagaagcctt actgcgtcag gcactacaaa acgccaaggt tcagccggaa   1080
gcagtcagtt atatcgaagc ccatggcaca gggacacaac tgggcgaccc gattgaggtg   1140
ggagcattaa cgaccgtctt tggatcttct cgttcagaac ccttgtggat tggctctgtc   1200
aaaactaata tcggacacct agaaccagcc gctggtattg cggggttaat aaaagtcatt   1260
ttatcattac aagaaaaaca gattcctccc agtctccatt ttcaaaaccc taatcccttc   1320
attgattggg aatcttcgcc agttcaagtg ccgacacagt gtgtaccctg gactgggaaa   1380
gagcgcgtcg ctggagttag ctcgtttggt atgagcggta caaactgtca tctagttgtc   1440
gcagaagcac ctgtccgcca aaacgaaaaa tctgaaaatg caccggagcg tccttgtcac   1500
attctgaccc tttcagccaa aaccgaagcg gcactcaacg cattggtagc ccgttacatg   1560
gcatttctca gggaagcgcc cgccatatcc ctagctgatc tttgttatag tgccaatgtc   1620
gggcgtaatc tttttgccca tcgcttaagt tttatctccg agaacatcgc gcagttatca   1680
gaacaattag aacactgccc acagcaggct acaatgccaa cgcaacataa tgtgatacta   1740
gataatcaac tcagccctca aatcgctttt ctgtttactg gacaaggttc gcagtacatc   1800
aacatggggc gtgagcttta cgaaactcag cccaccttcc gtcggattat ggacgaatgt   1860
gacgacattc tgcatccatt gttgggtgaa tcaattctga acatactcta cacttcccct   1920
agcaaactta atcaaaccgt ttatacccaa cctgcccttt ttgcttttga atatgcccta   1980
gcaaaactat ggatatcatg ggtattgag cctgatgtcg tactgggtca cagcgtgggt   2040
gaatatgtag ccgcttgtct ggcgggtgtc tttagtttag aagatgggtt aaaactcatt   2100
gcatctcgtg gatgtttgat gcaagcctta ccgccgggga aaatgcttag tatcagaagc   2160
aatgagatcg gagtgaaagc gctcatcgcg ccttatagtg cagaagtatc aattgcagca   2220
atcaatggac agcaaagcgt ggtgatctcc ggcaaagctg aaattataga taatttagca   2280
gcagagtttg catcggaagg catcaaaaca cacctaatta cagtctccca cgctttccac   2340
tcgccaatga tgacccccat gctgaaagca ttccgagacg ttgccagcac catcagctat   2400
aggtcaccca gtttatcact gatttctaac ggtacagggc aattggcaac aaaggaggtt   2460
gctacacctg attattgggt gcgtcatgtc cattctaccg tccgttttgc cgatggtatt   2520
gccacattgg cagaacagaa tactgacatc ctcctagaag taggacccaa accaatattg   2580
ttgggtatgg caaagcagat ttatagtgaa aacggttcag ctagtcatcc gctcatgcta   2640
cccagtttgc gtgaagatgg caacgattgg cagcagatgc tttctacttg tggacaactt   2700
gtagttaatg gagtcaagat tgactgggcg ggttttgaca aggattattc acgacacaaa   2760
atattgttgc ccacctatcc gtttcagaga gaacgatatt ggattgaaag ctccgtcaaa   2820
aagccccaaa aacaggagct gcgcccaatg ttggataaga tgatccggct accatcagag   2880
aacaaagtgg tgtttgaaac cgagtttggc gtgcgacaga tgcctcatat ctccgatcat   2940
cagatatacg gtgaagtcat tgtaccgggg gcagtattag cttccttaat cttcaatgca   3000
gcgcaggttt tatacccaga ctatcagcat gaattaactg atattgcttt ttatcagcca   3060
```

```
attatctttc atgacgacga tacggtgatc gtgcaggcga ttttcagccc tgataagtca   3120
caggagaatc aaagccatca aacatttcca cccatgagct tccagattat tagcttcatg   3180
ccggatggtc ccttagagaa caaaccgaaa gtccatgtca cagggtgtct gagaatgttg   3240
cgcgatgccc aaccgccaac actctccccg accgaaatac gtcagcgctg tccacatacc   3300
gtaaatggtc atgactggta caatagctta gtcaaacaaa aatttgaaat gggtccttcc   3360
tttaggtggg tacagcaact ttggcatggg gaaaatgaag cattgacccg tcttcacata   3420
ccagatgtgg tcggctctgt atcaggacat caacttcacg gcatattgct cgatggttca   3480
ctttcaacca ccgctgtcat ggagtacgag tacggagact ccgcgaccag agttcctttg   3540
tcatttgctt ctctgcaact gtacaaaccc gtcacgggaa cagagtggtg gtgctacgcg   3600
aggaagattg gggaattcaa atatgacttc cagattatga atgaaatcgg ggaaaccttg   3660
gtgaaagcaa ttggctttgt acttcgtgaa gcctctcccg aaaaattcct cagaacaaca   3720
tacgtacaca actggcttgt agacattgaa tggcaagctc aatcaacttc cctagtccct   3780
tctgatggca ctatctctgg cagttgtttg gttttatcag atcagcatgg aacaggggct   3840
gcattggcac aaaggctaga caatgctgga gtgccagtga ccatgatcta tgctgatctg   3900
atactggaca attacgaatt aatattccgt actttgccag atttacaaca agtcgtctat   3960
ttatgggggt tggatcaaaa agaggattgt caccccatga agcaagcaga ggataactgt   4020
acatcggtgc tatatcttgt gcaagcatta ctcaatacct actcaacccc gccatccctg   4080
cttattgtca cctgtgatgc acaagcggtg gttgaacaag atcgagtaaa tggcttcgcc   4140
caatcgtctt tgttgggact tgccaaagtt atcatgctag aacacccaga attgtcctgt   4200
gtttacatgg atgtggaagc cggatattta cagcaagatg tggcgaacac gatatttaca   4260
cagctaaaaa gaggccatct atcaaaggac ggagaagaga gtcagttggc ttggcgcaat   4320
ggacaagcat acgtagcacg tcttagtcaa tataaaccca aatccgaaca actggttgag   4380
atccgcagcg atcgcagcta tttgatcact ggtggacggg gcggtgtcgg cttacaaatc   4440
gcacggtggt tagtggaaaa gggggctaaa catctcgttt tgttggggcg cagtcagacc   4500
agttccgaag tcagtctggt gttggatgag ctagaatcag ccggggcgca aatcattgtg   4560
gctcaagctg atattagcga tgagaaggta ttagcgcaga ttctgaccaa tctaaccgta   4620
cctctgtgtg gtgtaatcca cgccgcagga gtgcttgatg atgcgagtct actccaacaa   4680
actccagcca agctcaaaaa agttctattg ccaaaagcag agggggcttg gattctgcat   4740
aatttgaccc tggagcagcg actagacttc tttgttctct tttcttctgc cagttctcta   4800
ttaggtgcgc cagggcaggc caactattca gcagccaatg ctttcctaga tggtttagct   4860
gcctatcggc gagggcgagg actcccctgt ttgtctatct gctgggggc atgggatcaa   4920
gtcggtatgg ctgcacgaca agggctactg gacaagttac cgcaaagagg tgaagaggcc   4980
atcccgttac agaaaggctt agacctcttc ggcgaattac tgaacgagcc agccgctcaa   5040
attggtgtga tcccaattca atggactcgc ttcttggatc atcaaaaagg taatttgcct   5100
ttttatgaga agttttctaa gtctagccgg aaagcgcaga gttacgattc gatggcagtc   5160
agtcacacag aagatattca gaggaaactg aagcaagctg ctgtgcaaga tcgaccaaaa   5220
ttattagaag tgcatcttcg ctctcaagtc gctcaactgt taggaataaa cgtggcagag   5280
ctaccaaatg aagaaggaat tggttttgtt acattaggtc ttgactcgct cacctctatt   5340
gaactgcgta acagtttaca acgcacatta gattgttcat tacctgtcac ctttgctttt   5400
```

-continued gactacccaa ctatagaaat agcggttaag tacctaacac aagttgtaat tgcaccgatg 5460
gaaagcacag catcgcagca aacagactct ttatcagcaa tgttcacaga tacttcgtcc 5520
atcgggagaa ttcttgacaa cgaaacagat gtgttagaca gcgaaatgca aagtgatgaa 5580
gatgaatctt tgtctacact tatacaaaaa ttatcaacac atttggatta g 5631

<210> SEQ ID NO 82
<211> LENGTH: 1876
<212> TYPE: PRT
<213> ORGANISM: Cylindrospermopsis raciborskii AWT205

<400> SEQUENCE: 82

Met Arg Ser Lys Phe Asn Ile Asn Val Thr Leu Leu Val Cys Leu Ile
1 5 10 15

Ile Ile Pro Tyr Phe Pro Thr Thr Leu Met Lys Val Pro Ile Thr Ala
20 25 30

Asn Glu Asp Ala Ala Thr Leu Leu Gln Arg Val Gly Leu Ser Leu Lys
35 40 45

Glu Ala His Gln Gln Leu Glu Ala Met Gln Arg Arg Ala His Glu Pro
50 55 60

Ile Ala Ile Val Gly Leu Gly Leu Arg Phe Pro Gly Ala Asp Ser Pro
65 70 75 80

Gln Thr Phe Trp Lys Leu Leu Gln Asn Gly Val Asp Met Val Thr Glu
85 90 95

Ile Pro Ser Asp Arg Trp Ala Val Asp Glu Tyr Tyr Asp Pro Gln Pro
100 105 110

Gly Cys Pro Gly Lys Met Tyr Ile Arg Glu Ala Ala Phe Val Asp Ala
115 120 125

Val Asp Lys Phe Asp Ala Ser Phe Phe Asp Ile Ser Pro Arg Glu Ala
130 135 140

Ala Asn Ile Asp Pro Gln His Arg Met Leu Leu Glu Val Ala Trp Glu
145 150 155 160

Ala Leu Glu Arg Ala Gly Ile Ala Pro Ser Gln Leu Met Asp Ser Gln
165 170 175

Thr Gly Val Phe Val Gly Met Ser Glu Asn Asp Tyr Tyr Ala His Leu
180 185 190

Glu Asn Thr Gly Asp His His Asn Val Tyr Ala Ala Thr Gly Asn Ser
195 200 205

Asn Tyr Tyr Ala Pro Gly Arg Leu Ser Tyr Leu Leu Gly Leu Gln Gly
210 215 220

Pro Asn Met Val Val Asp Ser Ala Cys Ser Ser Ser Leu Val Ala Val
225 230 235 240

His Leu Ala Cys Asn Ser Leu Arg Met Gly Glu Cys Asp Leu Ala Leu
245 250 255

Ala Gly Gly Val Gln Leu Met Leu Ile Pro Asp Pro Met Ile Gly Thr
260 265 270

Ala Gln Leu Asn Ala Phe Ala Thr Asp Gly Arg Ser Lys Thr Phe Asp
275 280 285

Ala Ala Ala Asp Gly Tyr Gly Arg Gly Glu Gly Cys Gly Met Ile Val
290 295 300

Leu Lys Arg Ile Ser Asp Ala Ile Val Ala Asp Asp Pro Ile Leu Ala
305 310 315 320

Val Ile Arg Gly Ser Ala Val Asn His Gly Gly Arg Ser Ser Gly Leu
325 330 335

```
Thr Ala Pro Asn Lys Leu Ser Gln Glu Ala Leu Leu Arg Gln Ala Leu
            340                 345                 350

Gln Asn Ala Lys Val Gln Pro Glu Ala Val Ser Tyr Ile Glu Ala His
        355                 360                 365

Gly Thr Gly Thr Gln Leu Gly Asp Pro Ile Glu Val Gly Ala Leu Thr
    370                 375                 380

Thr Val Phe Gly Ser Ser Arg Ser Glu Pro Leu Trp Ile Gly Ser Val
385                 390                 395                 400

Lys Thr Asn Ile Gly His Leu Glu Pro Ala Ala Gly Ile Ala Gly Leu
                405                 410                 415

Ile Lys Val Ile Leu Ser Leu Gln Glu Lys Gln Ile Pro Pro Ser Leu
            420                 425                 430

His Phe Gln Asn Pro Asn Pro Phe Ile Asp Trp Glu Ser Ser Pro Val
        435                 440                 445

Gln Val Pro Thr Gln Cys Val Pro Trp Thr Gly Lys Glu Arg Val Ala
    450                 455                 460

Gly Val Ser Ser Phe Gly Met Ser Gly Thr Asn Cys His Leu Val Val
465                 470                 475                 480

Ala Glu Ala Pro Val Arg Gln Asn Glu Lys Ser Glu Asn Ala Pro Glu
                485                 490                 495

Arg Pro Cys His Ile Leu Thr Leu Ser Ala Lys Thr Glu Ala Ala Leu
            500                 505                 510

Asn Ala Leu Val Ala Arg Tyr Met Ala Phe Leu Arg Glu Ala Pro Ala
        515                 520                 525

Ile Ser Leu Ala Asp Leu Cys Tyr Ser Ala Asn Val Gly Arg Asn Leu
    530                 535                 540

Phe Ala His Arg Leu Ser Phe Ile Ser Glu Asn Ile Ala Gln Leu Ser
545                 550                 555                 560

Glu Gln Leu Glu His Cys Pro Gln Gln Ala Thr Met Pro Thr Gln His
                565                 570                 575

Asn Val Ile Leu Asp Asn Gln Leu Ser Pro Gln Ile Ala Phe Leu Phe
            580                 585                 590

Thr Gly Gln Gly Ser Gln Tyr Ile Asn Met Gly Arg Glu Leu Tyr Glu
        595                 600                 605

Thr Gln Pro Thr Phe Arg Arg Ile Met Asp Glu Cys Asp Asp Ile Leu
    610                 615                 620

His Pro Leu Leu Gly Glu Ser Ile Leu Asn Ile Leu Tyr Thr Ser Pro
625                 630                 635                 640

Ser Lys Leu Asn Gln Thr Val Tyr Thr Gln Pro Ala Leu Phe Ala Phe
                645                 650                 655

Glu Tyr Ala Leu Ala Lys Leu Trp Ile Ser Trp Gly Ile Glu Pro Asp
            660                 665                 670

Val Val Leu Gly His Ser Val Gly Glu Tyr Val Ala Ala Cys Leu Ala
        675                 680                 685

Gly Val Phe Ser Leu Glu Asp Gly Leu Lys Leu Ile Ala Ser Arg Gly
    690                 695                 700

Cys Leu Met Gln Ala Leu Pro Pro Gly Lys Met Leu Ser Ile Arg Ser
705                 710                 715                 720

Asn Glu Ile Gly Val Lys Ala Leu Ile Ala Pro Tyr Ser Ala Glu Val
                725                 730                 735

Ser Ile Ala Ala Ile Asn Gly Gln Gln Ser Val Val Ile Ser Gly Lys
            740                 745                 750

Ala Glu Ile Ile Asp Asn Leu Ala Ala Glu Phe Ala Ser Glu Gly Ile
```

-continued

```
        755                 760                 765

Lys Thr His Leu Ile Thr Val Ser His Ala Phe His Ser Pro Met Met
    770                 775                 780

Thr Pro Met Leu Lys Ala Phe Arg Asp Val Ala Ser Thr Ile Ser Tyr
785                 790                 795                 800

Arg Ser Pro Ser Leu Ser Leu Ile Ser Asn Gly Thr Gly Gln Leu Ala
                805                 810                 815

Thr Lys Glu Val Ala Thr Pro Asp Tyr Trp Val Arg His Val His Ser
            820                 825                 830

Thr Val Arg Phe Ala Asp Gly Ile Ala Thr Leu Ala Glu Gln Asn Thr
        835                 840                 845

Asp Ile Leu Leu Glu Val Gly Pro Lys Pro Ile Leu Leu Gly Met Ala
    850                 855                 860

Lys Gln Ile Tyr Ser Glu Asn Gly Ser Ala Ser His Pro Leu Met Leu
865                 870                 875                 880

Pro Ser Leu Arg Glu Asp Gly Asn Asp Trp Gln Gln Met Leu Ser Thr
                885                 890                 895

Cys Gly Gln Leu Val Val Asn Gly Val Lys Ile Asp Trp Ala Gly Phe
            900                 905                 910

Asp Lys Asp Tyr Ser Arg His Lys Ile Leu Leu Pro Thr Tyr Pro Phe
        915                 920                 925

Gln Arg Glu Arg Tyr Trp Ile Glu Ser Ser Val Lys Lys Pro Gln Lys
    930                 935                 940

Gln Glu Leu Arg Pro Met Leu Asp Lys Met Ile Arg Leu Pro Ser Glu
945                 950                 955                 960

Asn Lys Val Val Phe Glu Thr Glu Phe Gly Val Arg Gln Met Pro His
                965                 970                 975

Ile Ser Asp His Gln Ile Tyr Gly Glu Val Ile Val Pro Gly Ala Val
            980                 985                 990

Leu Ala Ser Leu Ile Phe Asn Ala  Ala Gln Val Leu Tyr  Pro Asp Tyr
        995                 1000                 1005

Gln His  Glu Leu Thr Asp Ile  Ala Phe Tyr Gln Pro  Ile Ile Phe
    1010                 1015                 1020

His Asp  Asp Asp Thr Val Ile  Val Gln Ala Ile Phe  Ser Pro Asp
    1025                 1030                 1035

Lys Ser  Gln Glu Asn Gln Ser  His Gln Thr Phe Pro  Pro Met Ser
    1040                 1045                 1050

Phe Gln  Ile Ile Ser Phe Met  Pro Asp Gly Pro Leu  Glu Asn Lys
    1055                 1060                 1065

Pro Lys  Val His Val Thr Gly  Cys Leu Arg Met Leu  Arg Asp Ala
    1070                 1075                 1080

Gln Pro  Pro Thr Leu Ser Pro  Thr Glu Ile Arg Gln  Arg Cys Pro
    1085                 1090                 1095

His Thr  Val Asn Gly His Asp  Trp Tyr Asn Ser Leu  Val Lys Gln
    1100                 1105                 1110

Lys Phe  Glu Met Gly Pro Ser  Phe Arg Trp Val Gln  Gln Leu Trp
    1115                 1120                 1125

His Gly  Glu Asn Glu Ala Leu  Thr Arg Leu His Ile  Pro Asp Val
    1130                 1135                 1140

Val Gly  Ser Val Ser Gly His  Gln Leu His Gly Ile  Leu Leu Asp
    1145                 1150                 1155

Gly Ser  Leu Ser Thr Thr Ala  Val Met Glu Tyr Glu  Tyr Gly Asp
    1160                 1165                 1170
```

-continued

Ser Ala Thr Arg Val Pro Leu Ser Phe Ala Ser Leu Gln Leu Tyr
1175 1180 1185

Lys Pro Val Thr Gly Thr Glu Trp Trp Cys Tyr Ala Arg Lys Ile
1190 1195 1200

Gly Glu Phe Lys Tyr Asp Phe Gln Ile Met Asn Glu Ile Gly Glu
1205 1210 1215

Thr Leu Val Lys Ala Ile Gly Phe Val Leu Arg Glu Ala Ser Pro
1220 1225 1230

Glu Lys Phe Leu Arg Thr Thr Tyr Val His Asn Trp Leu Val Asp
1235 1240 1245

Ile Glu Trp Gln Ala Gln Ser Thr Ser Leu Val Pro Ser Asp Gly
1250 1255 1260

Thr Ile Ser Gly Ser Cys Leu Val Leu Ser Asp Gln His Gly Thr
1265 1270 1275

Gly Ala Ala Leu Ala Gln Arg Leu Asp Asn Ala Gly Val Pro Val
1280 1285 1290

Thr Met Ile Tyr Ala Asp Leu Ile Leu Asp Asn Tyr Glu Leu Ile
1295 1300 1305

Phe Arg Thr Leu Pro Asp Leu Gln Gln Val Val Tyr Leu Trp Gly
1310 1315 1320

Leu Asp Gln Lys Glu Asp Cys His Pro Met Lys Gln Ala Glu Asp
1325 1330 1335

Asn Cys Thr Ser Val Leu Tyr Leu Val Gln Ala Leu Leu Asn Thr
1340 1345 1350

Tyr Ser Thr Pro Pro Ser Leu Leu Ile Val Thr Cys Asp Ala Gln
1355 1360 1365

Ala Val Val Glu Gln Asp Arg Val Asn Gly Phe Ala Gln Ser Ser
1370 1375 1380

Leu Leu Gly Leu Ala Lys Val Ile Met Leu Glu His Pro Glu Leu
1385 1390 1395

Ser Cys Val Tyr Met Asp Val Glu Ala Gly Tyr Leu Gln Gln Asp
1400 1405 1410

Val Ala Asn Thr Ile Phe Thr Gln Leu Lys Arg Gly His Leu Ser
1415 1420 1425

Lys Asp Gly Glu Glu Ser Gln Leu Ala Trp Arg Asn Gly Gln Ala
1430 1435 1440

Tyr Val Ala Arg Leu Ser Gln Tyr Lys Pro Lys Ser Glu Gln Leu
1445 1450 1455

Val Glu Ile Arg Ser Asp Arg Ser Tyr Leu Ile Thr Gly Gly Arg
1460 1465 1470

Gly Gly Val Gly Leu Gln Ile Ala Arg Trp Leu Val Glu Lys Gly
1475 1480 1485

Ala Lys His Leu Val Leu Leu Gly Arg Ser Gln Thr Ser Ser Glu
1490 1495 1500

Val Ser Leu Val Leu Asp Glu Leu Glu Ser Ala Gly Ala Gln Ile
1505 1510 1515

Ile Val Ala Gln Ala Asp Ile Ser Asp Glu Lys Val Leu Ala Gln
1520 1525 1530

Ile Leu Thr Asn Leu Thr Val Pro Leu Cys Gly Val Ile His Ala
1535 1540 1545

Ala Gly Val Leu Asp Asp Ala Ser Leu Leu Gln Gln Thr Pro Ala
1550 1555 1560

```
Lys Leu  Lys Lys Val Leu Leu  Pro Lys Ala Glu Gly  Ala Trp Ile
    1565                 1570                 1575

Leu His  Asn Leu Thr Leu Glu  Gln Arg Leu Asp Phe  Phe Val Leu
    1580                 1585                 1590

Phe Ser  Ser Ala Ser Ser Leu  Leu Gly Ala Pro Gly  Gln Ala Asn
    1595                 1600                 1605

Tyr Ser  Ala Ala Asn Ala Phe  Leu Asp Gly Leu Ala  Ala Tyr Arg
    1610                 1615                 1620

Arg Gly  Arg Gly Leu Pro Cys  Leu Ser Ile Cys Trp  Gly Ala Trp
    1625                 1630                 1635

Asp Gln  Val Gly Met Ala Ala  Arg Gln Gly Leu Leu  Asp Lys Leu
    1640                 1645                 1650

Pro Gln  Arg Gly Glu Glu Ala  Ile Pro Leu Gln Lys  Gly Leu Asp
    1655                 1660                 1665

Leu Phe  Gly Glu Leu Leu Asn  Glu Pro Ala Ala Gln  Ile Gly Val
    1670                 1675                 1680

Ile Pro  Ile Gln Trp Thr Arg  Phe Leu Asp His Gln  Lys Gly Asn
    1685                 1690                 1695

Leu Pro  Phe Tyr Glu Lys Phe  Ser Lys Ser Ser Arg  Lys Ala Gln
    1700                 1705                 1710

Ser Tyr  Asp Ser Met Ala Val  Ser His Thr Glu Asp  Ile Gln Arg
    1715                 1720                 1725

Lys Leu  Lys Gln Ala Ala Val  Gln Asp Arg Pro Lys  Leu Leu Glu
    1730                 1735                 1740

Val His  Leu Arg Ser Gln Val  Ala Gln Leu Leu Gly  Ile Asn Val
    1745                 1750                 1755

Ala Glu  Leu Pro Asn Glu Glu  Gly Ile Gly Phe Val  Thr Leu Gly
    1760                 1765                 1770

Leu Asp  Ser Leu Thr Ser Ile  Glu Leu Arg Asn Ser  Leu Gln Arg
    1775                 1780                 1785

Thr Leu  Asp Cys Ser Leu Pro  Val Thr Phe Ala Phe  Asp Tyr Pro
    1790                 1795                 1800

Thr Ile  Glu Ile Ala Val Lys  Tyr Leu Thr Gln Val  Val Ile Ala
    1805                 1810                 1815

Pro Met  Glu Ser Thr Ala Ser  Gln Gln Thr Asp Ser  Leu Ser Ala
    1820                 1825                 1830

Met Phe  Thr Asp Thr Ser Ser  Ile Gly Arg Ile Leu  Asp Asn Glu
    1835                 1840                 1845

Thr Asp  Val Leu Asp Ser Glu  Met Gln Ser Asp Glu  Asp Glu Ser
    1850                 1855                 1860

Leu Ser  Thr Leu Ile Gln Lys  Leu Ser Thr His Leu  Asp
    1865                 1870                 1875
```

<210> SEQ ID NO 83
<211> LENGTH: 4074
<212> TYPE: DNA
<213> ORGANISM: Cylindrospermopsis raciborskii AWT205

<400> SEQUENCE: 83

```
atgaacgctt tgtcagaaaa tcaggtaact tctatagtca agaaggcatt gaacaaaata      60

gaggagttac aagccgaact tgaccgttta aaatacgcgc aacgggaacc aatcgccatc     120

attggaatgg gctgtcgctt tcctggtgca gacacacctg aagctttttg gaaattattg     180

cacaatgggg ttgatgctat ccaagagatt ccaaaaagcc gttgggatat tgacgactat     240
```

-continued

```
tatgatccca caccagcaac acccggcaaa atgtatacac gttttggtgg ttttctcgac    300
caaatagcag ccttcgaccc tgagttcttt cgcatttcta ctcgtgaggc aatcagctta    360
gaccctcaac agagattgct tctggaagtg agttgggaag ccttagaacg ggctgggctg    420
acaggcaata aactgactac acaaacaggt gtctttgttg gcatcagtga aagtgattat    480
cgtgatttga ttatgcgtaa tggttctgac ctagatgtat attctggttc aggtaactgc    540
catagtacag ccagcgggcg tttatcttat tatttgggac ttactggacc caatttgtcc    600
cttgataccg cctgttcgtc ctctttggtt tgtgtggcat tggctgtcaa gagcctacgt    660
caacaggagt gtgatttggc attggcgggt ggtgtacaga tacaagtgat accagatggc    720
tttatcaaag cctgtcaatc ccgtatgttg tcgcctgatg gacggtgcaa aacatttgat    780
ttccaggcag atggttatgc ccgtgctgag gggtgtggga tggtagttct caaacgccta    840
tccgatgcaa ttgctgacaa tgataatatc ctggccttga ttcgtggtgc cgcagtcaat    900
catgatggct acacgagtgg attaaccgtt cccagtggtc cctcacaacg ggcggtgatc    960
caacaggcat tagcggatgc tggaatacac ccggatcaaa ttagctatat tgaggcacat   1020
ggcacaggta catccttagg cgatcctatt gaaatgggtg cgattgggca agtctttggt   1080
caacgctcac agatgctttt cgtcggttcg gtcaagacga atattggtca tactgaggct   1140
gctgctggta ttgctggtct catcaaggtt gtactctcaa tgcagcacgg tgaaatccca   1200
gcaaacttac acttcgacca gccaagtcct tatattaact gggatcaatt accagtcagt   1260
atcccaacag aaacaatacc ttggtctact agcgatcgct ttgcaggagt cagtagcttt   1320
ggctttagtg gcacaaactc tcatatcgta ctagaggcag ccccaaacat agagcaacct   1380
actgatgata ttaatcaaac gccgcatatt ttgaccttag ctgcaaaaac acccgcagcc   1440
ctgcaagaac tggctcggcg ttatgcgact cagatagaga cctctcccga tgttcctctg   1500
gcggacattt gtttcacagc acacataggg cgtaaacatt ttaaacatag gtttgcggta   1560
gtcacggaat ctaaagagca actgcgtttg caattggatg catttgcaca atcagggggt   1620
gtggggcgag aagtcaaatc gctaccaaag atagcctttc tttttacagg tcaaggctca   1680
cagtatgtgg gaatgggtcg tcaactttac gaaaaccaac ctaccttccg aaaagcactc   1740
gcccattgtg atgacatctt gcgtgctggt gcatatttcg accgatcact actttcgatt   1800
ctctacccag agggaaaatc agaagccatt caccaaaccg cttatactca gcccgcgctt   1860
tttgctcttg agtatgcgat cgctcagttg tggcactcct ggggtatcaa accagatatc   1920
gtgatggggc atagtgtagg tgaatacgtc gccgcttgtg tggcgggcat attttcttta   1980
gaggatgggc tgaaactaat tgctactcgt ggtcgtctga tgcaatccct acctcaagac   2040
ggaacgatgg tttcttcttt ggcaagtgaa gctcgtatcc aggaagctat tacaccttac   2100
cgagatgatg tgtcaatcgc agcgataaat gggacagaaa gcgtggttat ctctggcaaa   2160
cgcacctctg tgatggcaat tgctgaacaa ctcgccaccg ttggcatcaa gacacgccaa   2220
ctgacggttt cccatgcctt ccattcacca cttatgacac ccatcttgga tgagttccgc   2280
caggtggcag ccagtatcac ctatcaccag cccaagttgc tacttgtctc caacgtctcc   2340
gggaaagtgg ccggccctga aatcaccaga ccagattact gggtacgcca tgtccgtgag   2400
gcagtgcgct ttgccgatgg agtgaggacg ctgaatgaac aaggtgtcaa tatctttctg   2460
gaaatcggtt ctaccgctac cctgttgggc atggcactgc gagtaaatga ggaagattca   2520
aatgcctcaa aaggaacttc gtcttgctac ctgcccagtt tacgggaaag ccagaaggat   2580
tgtcagcaga tgttcactag tctgggtgag ttgtacgtac atggatatga tattgattgg   2640
```

```
ggtgcattta atcggggata tcaaggacgc aaggtgatat tgccaaccta tccgtttcag   2700

cgacaacgtt attggcttcc cgaccctaag ttggcacaaa gttccgattt agataccttt   2760

caagctcaga gcagcgcatc atcacaaaat cctagcgctg tgtccacttt actgatggaa   2820

tatttgcaag caggtgatgt ccaatcttta gttgggcttt tggatgatga acggaaactc   2880

tctgctgctg aacgaattgc actacccagt attttggagt ttttggtaga ggaacaacag   2940

cgacaaataa gctcaaccac aactcctcaa acagttttac aaaaaataag tcaaacttcc   3000

catgaggaca gatatgaaat attgaagaac ctgatcaaat ctgaaatcga aacgattatc   3060

aaaagtgttc cctccgatga acaaatgttt tctgacttag gaattgattc cttgatggcg   3120

atcgaactgc gtaataagct ccgttctgct atagggttgg aactgccagt ggcaatagta   3180

tttgaccatc ccacgattaa gcagttaact aacttcgtac tggacagaat tgtgccgcag   3240

gcagaccaaa aggacgttcc caccgaatcc ttgtttgctt ctaaacagga gatatcagtt   3300

gaggagcagt cttttgcaat taccaagctg ggcttatccc ctgcttccca ctccctgcat   3360

cttcctccat ggacggttag acctgcggta atggcagatg taacaaaact aagccaactt   3420

gaaagagagg cctatggctg gatcggagaa ggagcgatcg ccccgcccca tctcattgcc   3480

gatcgcatca atttactcaa cagtggtgat atgccttggt tctgggtaat ggagcgatca   3540

ggagagttgg gcgcgtggca ggtgctacaa ccgacatctg ttgatccata tacttatgga   3600

agttgggatg aagtaactga ccaaggtaaa ctgcaagcaa ccttcgaccc aagtggacgc   3660

aatgtgtata ttgtcgcggg tgggtctagc aacctcccca cggtagccag ccacctcatg   3720

acgcttcaga ctttattgat gctgcgggaa actggtcgtg acacaatctt tgtctgtctg   3780

gcaatgccag gttatgccaa ataccacagt caaacaggaa aatcgccgga agagtatatt   3840

gcgctgactg acgaggatgg tatcccaatg gacgagttta ttgcactttc tgtctacgac   3900

tggcctgtta ccccatcgtt tcgtgttctg cgagacggtt atccacctga tcgagattct   3960

ggtggtcacg cagttagtac ggttttccag ctcaatgatt tcgatggagc gatcgaagaa   4020

acatatcgtc gtattatccg ccatgccgat gtccttggtc tcgaaagagg ctaa          4074
```

```
<210> SEQ ID NO 84
<211> LENGTH: 1357
<212> TYPE: PRT
<213> ORGANISM: Cylindrospermopsis raciborskii AWT205

<400> SEQUENCE: 84

Met Asn Ala Leu Ser Glu Asn Gln Val Thr Ser Ile Val Lys Lys Ala
1               5                   10                  15

Leu Asn Lys Ile Glu Glu Leu Gln Ala Glu Leu Asp Arg Leu Lys Tyr
            20                  25                  30

Ala Gln Arg Glu Pro Ile Ala Ile Ile Gly Met Gly Cys Arg Phe Pro
        35                  40                  45

Gly Ala Asp Thr Pro Glu Ala Phe Trp Lys Leu Leu His Asn Gly Val
    50                  55                  60

Asp Ala Ile Gln Glu Ile Pro Lys Ser Arg Trp Asp Ile Asp Asp Tyr
65                  70                  75                  80

Tyr Asp Pro Thr Pro Ala Thr Pro Gly Lys Met Tyr Thr Arg Phe Gly
                85                  90                  95

Gly Phe Leu Asp Gln Ile Ala Ala Phe Asp Pro Glu Phe Phe Arg Ile
            100                 105                 110

Ser Thr Arg Glu Ala Ile Ser Leu Asp Pro Gln Gln Arg Leu Leu Leu
```

-continued

```
        115                 120                 125

Glu Val Ser Trp Glu Ala Leu Glu Arg Ala Gly Leu Thr Gly Asn Lys
    130                 135                 140

Leu Thr Thr Gln Thr Gly Val Phe Val Gly Ile Ser Glu Ser Asp Tyr
145                 150                 155                 160

Arg Asp Leu Ile Met Arg Asn Gly Ser Asp Leu Asp Val Tyr Ser Gly
                165                 170                 175

Ser Gly Asn Cys His Ser Thr Ala Ser Gly Arg Leu Ser Tyr Tyr Leu
            180                 185                 190

Gly Leu Thr Gly Pro Asn Leu Ser Leu Asp Thr Ala Cys Ser Ser Ser
        195                 200                 205

Leu Val Cys Val Ala Leu Ala Val Lys Ser Leu Arg Gln Gln Glu Cys
    210                 215                 220

Asp Leu Ala Leu Ala Gly Gly Val Gln Ile Gln Val Ile Pro Asp Gly
225                 230                 235                 240

Phe Ile Lys Ala Cys Gln Ser Arg Met Leu Ser Pro Asp Gly Arg Cys
                245                 250                 255

Lys Thr Phe Asp Phe Gln Ala Asp Gly Tyr Ala Arg Ala Glu Gly Cys
            260                 265                 270

Gly Met Val Val Leu Lys Arg Leu Ser Asp Ala Ile Ala Asp Asn Asp
        275                 280                 285

Asn Ile Leu Ala Leu Ile Arg Gly Ala Ala Val Asn His Asp Gly Tyr
    290                 295                 300

Thr Ser Gly Leu Thr Val Pro Ser Gly Pro Ser Gln Arg Ala Val Ile
305                 310                 315                 320

Gln Gln Ala Leu Ala Asp Ala Gly Ile His Pro Asp Gln Ile Ser Tyr
                325                 330                 335

Ile Glu Ala His Gly Thr Gly Thr Ser Leu Gly Asp Pro Ile Glu Met
            340                 345                 350

Gly Ala Ile Gly Gln Val Phe Gly Gln Arg Ser Gln Met Leu Phe Val
        355                 360                 365

Gly Ser Val Lys Thr Asn Ile Gly His Thr Glu Ala Ala Ala Gly Ile
    370                 375                 380

Ala Gly Leu Ile Lys Val Val Leu Ser Met Gln His Gly Glu Ile Pro
385                 390                 395                 400

Ala Asn Leu His Phe Asp Gln Pro Ser Pro Tyr Ile Asn Trp Asp Gln
                405                 410                 415

Leu Pro Val Ser Ile Pro Thr Glu Thr Ile Pro Trp Ser Thr Ser Asp
            420                 425                 430

Arg Phe Ala Gly Val Ser Ser Phe Gly Phe Ser Gly Thr Asn Ser His
        435                 440                 445

Ile Val Leu Glu Ala Ala Pro Asn Ile Glu Gln Pro Thr Asp Asp Ile
    450                 455                 460

Asn Gln Thr Pro His Ile Leu Thr Leu Ala Ala Lys Thr Pro Ala Ala
465                 470                 475                 480

Leu Gln Glu Leu Ala Arg Arg Tyr Ala Thr Gln Ile Glu Thr Ser Pro
                485                 490                 495

Asp Val Pro Leu Ala Asp Ile Cys Phe Thr Ala His Ile Gly Arg Lys
            500                 505                 510

His Phe Lys His Arg Phe Ala Val Val Thr Glu Ser Lys Glu Gln Leu
        515                 520                 525

Arg Leu Gln Leu Asp Ala Phe Ala Gln Ser Gly Gly Val Gly Arg Glu
    530                 535                 540
```

```
Val Lys Ser Leu Pro Lys Ile Ala Phe Leu Phe Thr Gly Gln Gly Ser
545                 550                 555                 560

Gln Tyr Val Gly Met Gly Arg Gln Leu Tyr Glu Asn Gln Pro Thr Phe
                565                 570                 575

Arg Lys Ala Leu Ala His Cys Asp Asp Ile Leu Arg Ala Gly Ala Tyr
            580                 585                 590

Phe Asp Arg Ser Leu Leu Ser Ile Leu Tyr Pro Glu Gly Lys Ser Glu
        595                 600                 605

Ala Ile His Gln Thr Ala Tyr Thr Gln Pro Ala Leu Phe Ala Leu Glu
    610                 615                 620

Tyr Ala Ile Ala Gln Leu Trp His Ser Trp Gly Ile Lys Pro Asp Ile
625                 630                 635                 640

Val Met Gly His Ser Val Gly Glu Tyr Val Ala Ala Cys Val Ala Gly
                645                 650                 655

Ile Phe Ser Leu Glu Asp Gly Leu Lys Leu Ile Ala Thr Arg Gly Arg
            660                 665                 670

Leu Met Gln Ser Leu Pro Gln Asp Gly Thr Met Val Ser Ser Leu Ala
        675                 680                 685

Ser Glu Ala Arg Ile Gln Glu Ala Ile Thr Pro Tyr Arg Asp Asp Val
    690                 695                 700

Ser Ile Ala Ala Ile Asn Gly Thr Glu Ser Val Val Ile Ser Gly Lys
705                 710                 715                 720

Arg Thr Ser Val Met Ala Ile Ala Glu Gln Leu Ala Thr Val Gly Ile
                725                 730                 735

Lys Thr Arg Gln Leu Thr Val Ser His Ala Phe His Ser Pro Leu Met
            740                 745                 750

Thr Pro Ile Leu Asp Glu Phe Arg Gln Val Ala Ala Ser Ile Thr Tyr
        755                 760                 765

His Gln Pro Lys Leu Leu Leu Val Ser Asn Val Ser Gly Lys Val Ala
    770                 775                 780

Gly Pro Glu Ile Thr Arg Pro Asp Tyr Trp Val Arg His Val Arg Glu
785                 790                 795                 800

Ala Val Arg Phe Ala Asp Gly Val Arg Thr Leu Asn Glu Gln Gly Val
                805                 810                 815

Asn Ile Phe Leu Glu Ile Gly Ser Thr Ala Thr Leu Leu Gly Met Ala
            820                 825                 830

Leu Arg Val Asn Glu Glu Asp Ser Asn Ala Ser Lys Gly Thr Ser Ser
        835                 840                 845

Cys Tyr Leu Pro Ser Leu Arg Glu Ser Gln Lys Asp Cys Gln Gln Met
    850                 855                 860

Phe Thr Ser Leu Gly Glu Leu Tyr Val His Gly Tyr Asp Ile Asp Trp
865                 870                 875                 880

Gly Ala Phe Asn Arg Gly Tyr Gln Gly Arg Lys Val Ile Leu Pro Thr
                885                 890                 895

Tyr Pro Phe Gln Arg Gln Arg Tyr Trp Leu Pro Asp Pro Lys Leu Ala
            900                 905                 910

Gln Ser Ser Asp Leu Asp Thr Phe Gln Ala Gln Ser Ser Ala Ser Ser
        915                 920                 925

Gln Asn Pro Ser Ala Val Ser Thr Leu Leu Met Glu Tyr Leu Gln Ala
    930                 935                 940

Gly Asp Val Gln Ser Leu Val Gly Leu Leu Asp Asp Glu Arg Lys Leu
945                 950                 955                 960
```

-continued

```
Ser Ala Ala Glu Arg Ile Ala Leu Pro Ser Ile Leu Glu Phe Leu Val
                965                 970                 975

Glu Glu Gln Gln Arg Gln Ile Ser Ser Thr Thr Thr Pro Gln Thr Val
            980                 985                 990

Leu Gln Lys Ile Ser Gln Thr Ser  His Glu Asp Arg Tyr  Glu Ile Leu
        995                 1000                 1005

Lys Asn  Leu Ile Lys Ser Glu  Ile Glu Thr Ile Ile  Lys Ser Val
    1010                 1015                 1020

Pro Ser  Asp Glu Gln Met Phe  Ser Asp Leu Gly Ile  Asp Ser Leu
    1025                 1030                 1035

Met Ala  Ile Glu Leu Arg Asn  Lys Leu Arg Ser Ala  Ile Gly Leu
    1040                 1045                 1050

Glu Leu  Pro Val Ala Ile Val  Phe Asp His Pro Thr  Ile Lys Gln
    1055                 1060                 1065

Leu Thr  Asn Phe Val Leu Asp  Arg Ile Val Pro Gln  Ala Asp Gln
    1070                 1075                 1080

Lys Asp  Val Pro Thr Glu Ser  Leu Phe Ala Ser Lys  Gln Glu Ile
    1085                 1090                 1095

Ser Val  Glu Glu Gln Ser Phe  Ala Ile Thr Lys Leu  Gly Leu Ser
    1100                 1105                 1110

Pro Ala  Ser His Ser Leu His  Leu Pro Pro Trp Thr  Val Arg Pro
    1115                 1120                 1125

Ala Val  Met Ala Asp Val Thr  Lys Leu Ser Gln Leu  Glu Arg Glu
    1130                 1135                 1140

Ala Tyr  Gly Trp Ile Gly Glu  Gly Ala Ile Ala Pro  Pro His Leu
    1145                 1150                 1155

Ile Ala  Asp Arg Ile Asn Leu  Leu Asn Ser Gly Asp  Met Pro Trp
    1160                 1165                 1170

Phe Trp  Val Met Glu Arg Ser  Gly Glu Leu Gly Ala  Trp Gln Val
    1175                 1180                 1185

Leu Gln  Pro Thr Ser Val Asp  Pro Tyr Thr Tyr Gly  Ser Trp Asp
    1190                 1195                 1200

Glu Val  Thr Asp Gln Gly Lys  Leu Gln Ala Thr Phe  Asp Pro Ser
    1205                 1210                 1215

Gly Arg  Asn Val Tyr Ile Val  Ala Gly Gly Ser Ser  Asn Leu Pro
    1220                 1225                 1230

Thr Val  Ala Ser His Leu Met  Thr Leu Gln Thr Leu  Leu Met Leu
    1235                 1240                 1245

Arg Glu  Thr Gly Arg Asp Thr  Ile Phe Val Cys Leu  Ala Met Pro
    1250                 1255                 1260

Gly Tyr  Ala Lys Tyr His Ser  Gln Thr Gly Lys Ser  Pro Glu Glu
    1265                 1270                 1275

Tyr Ile  Ala Leu Thr Asp Glu  Asp Gly Ile Pro Met  Asp Glu Phe
    1280                 1285                 1290

Ile Ala  Leu Ser Val Tyr Asp  Trp Pro Val Thr Pro  Ser Phe Arg
    1295                 1300                 1305

Val Leu  Arg Asp Gly Tyr Pro  Pro Asp Arg Asp Ser  Gly Gly His
    1310                 1315                 1320

Ala Val  Ser Thr Val Phe Gln  Leu Asn Asp Phe Asp  Gly Ala Ile
    1325                 1330                 1335

Glu Glu  Thr Tyr Arg Arg Ile  Ile Arg His Ala Asp  Val Leu Gly
    1340                 1345                 1350

Leu Glu  Arg Gly
```

1355

<210> SEQ ID NO 85
<211> LENGTH: 1437
<212> TYPE: DNA
<213> ORGANISM: Cylindrospermopsis raciborskii AWT205

<400> SEQUENCE: 85
atgaataaaa aacaggtaga cacattgtta atacacgctc atctttttac catgcagggc 60
aatggcctgg gatatattgc cgatggggca attgcggttc agggtagcca gatcgtagca 120
gtggattcga cagaggcttt gctgagtcat tttgaaggaa ataaaacaat taatgcggta 180
aattgtgcag tgttgcctgg actaattgat gctcatatac atacgacttg tgctattctg 240
cgtggagtgg cacaggatgt aaccaattgg ctaatggacg cgacaattcc ttatgcactt 300
cagatgacac ccgcagtaaa tatagccgga acgcgcttga gtgtactcga agggctgaaa 360
gcaggaacaa ccacattcgg cgattctgag actccttacc cgctctgggg agagtttttc 420
gatgaaattg ggtacgtgc tattctatcc cctgccttta acgcctttcc actagaatgg 480
tcggcatgga aggagggaga cctctatccc ttcgatatga aggcaggacg acgtggtatg 540
gaagaggctg tggattttgc ttgtgcatgg aatggagccg cagagggacg tatcaccact 600
atgttgggac tacaggcggc ggatatgcta ccactggaga tcctacacgc agctaaagag 660
attgcccaac gggaaggctt aatgctgcat attcatgtgg cccagggaga tcgagaaaca 720
aaacaaattg tcaaacgata tggtaagcgt ccgatcgcat ttctagctga aattggctac 780
ttggacgaac agttgctggc agttcacctc accgatgcca cagatgaaga agtgatacaa 840
gtagccaaaa gtggtgctgg catggcactc tgttcgggcg ctattggcat cattgacggt 900
cttgttccgc ccgctcatgt ttttcgacaa gcaggcggtt ccgttgcact cggttctgat 960
caagcctgtg gcaacaactg ttgtaacatc ttcaatgaaa tgaagctgac cgccttattc 1020
aacaaaataa aatatcatga tccaaccatt atgccggctt gggaagtcct gcgtatggct 1080
accatcgaag gagcgcaggc gattggttta gatcacaaga ttggctctct tcaagtgggc 1140
aaagaagccg acctgatctt aatagacctc agttccccta acctctcgcc caccctgctc 1200
aaccctattc gtaaccttgt acctaacttg gtgtatgctg cttcaggaca tgaagttaaa 1260
agcgtcatgg tggcgggaaa acttttagtg gaagactacc aagtcctcac ggtagatgag 1320
tccgctattc tcgctgaagc gcaagtacaa gctcaacaac tctgccaacg tgtgaccgct 1380
gaccccattc acaaaaagat ggtgttaatg gaagcgatgg ctaagggtaa attatag 1437

<210> SEQ ID NO 86
<211> LENGTH: 478
<212> TYPE: PRT
<213> ORGANISM: Cylindrospermopsis raciborskii AWT205

<400> SEQUENCE: 86

Met Asn Lys Lys Gln Val Asp Thr Leu Leu Ile His Ala His Leu Phe
1 5 10 15

Thr Met Gln Gly Asn Gly Leu Gly Tyr Ile Ala Asp Gly Ala Ile Ala
20 25 30

Val Gln Gly Ser Gln Ile Val Ala Val Asp Ser Thr Glu Ala Leu Leu
35 40 45

Ser His Phe Glu Gly Asn Lys Thr Ile Asn Ala Val Asn Cys Ala Val
50 55 60

Leu Pro Gly Leu Ile Asp Ala His Ile His Thr Thr Cys Ala Ile Leu

-continued

```
65                  70                  75                  80

Arg Gly Val Ala Gln Asp Val Thr Asn Trp Leu Met Asp Ala Thr Ile
                85                  90                  95

Pro Tyr Ala Leu Gln Met Thr Pro Ala Val Asn Ile Ala Gly Thr Arg
            100                 105                 110

Leu Ser Val Leu Glu Gly Leu Lys Ala Gly Thr Thr Thr Phe Gly Asp
        115                 120                 125

Ser Glu Thr Pro Tyr Pro Leu Trp Gly Glu Phe Phe Asp Glu Ile Gly
    130                 135                 140

Val Arg Ala Ile Leu Ser Pro Ala Phe Asn Ala Phe Pro Leu Glu Trp
145                 150                 155                 160

Ser Ala Trp Lys Glu Gly Asp Leu Tyr Pro Phe Asp Met Lys Ala Gly
                165                 170                 175

Arg Arg Gly Met Glu Glu Ala Val Asp Phe Ala Cys Ala Trp Asn Gly
            180                 185                 190

Ala Ala Glu Gly Arg Ile Thr Thr Met Leu Gly Leu Gln Ala Ala Asp
        195                 200                 205

Met Leu Pro Leu Glu Ile Leu His Ala Ala Lys Glu Ile Ala Gln Arg
    210                 215                 220

Glu Gly Leu Met Leu His Ile His Val Ala Gln Gly Asp Arg Glu Thr
225                 230                 235                 240

Lys Gln Ile Val Lys Arg Tyr Gly Lys Arg Pro Ile Ala Phe Leu Ala
                245                 250                 255

Glu Ile Gly Tyr Leu Asp Glu Gln Leu Leu Ala Val His Leu Thr Asp
            260                 265                 270

Ala Thr Asp Glu Glu Val Ile Gln Val Ala Lys Ser Gly Ala Gly Met
        275                 280                 285

Ala Leu Cys Ser Gly Ala Ile Gly Ile Ile Asp Gly Leu Val Pro Pro
    290                 295                 300

Ala His Val Phe Arg Gln Ala Gly Gly Ser Val Ala Leu Gly Ser Asp
305                 310                 315                 320

Gln Ala Cys Gly Asn Asn Cys Cys Asn Ile Phe Asn Glu Met Lys Leu
                325                 330                 335

Thr Ala Leu Phe Asn Lys Ile Lys Tyr His Asp Pro Thr Ile Met Pro
            340                 345                 350

Ala Trp Glu Val Leu Arg Met Ala Thr Ile Glu Gly Ala Gln Ala Ile
        355                 360                 365

Gly Leu Asp His Lys Ile Gly Ser Leu Gln Val Gly Lys Glu Ala Asp
    370                 375                 380

Leu Ile Leu Ile Asp Leu Ser Ser Pro Asn Leu Ser Pro Thr Leu Leu
385                 390                 395                 400

Asn Pro Ile Arg Asn Leu Val Pro Asn Leu Val Tyr Ala Ala Ser Gly
                405                 410                 415

His Glu Val Lys Ser Val Met Val Ala Gly Lys Leu Leu Val Glu Asp
            420                 425                 430

Tyr Gln Val Leu Thr Val Asp Glu Ser Ala Ile Leu Ala Glu Ala Gln
        435                 440                 445

Val Gln Ala Gln Gln Leu Cys Gln Arg Val Thr Ala Asp Pro Ile His
    450                 455                 460

Lys Lys Met Val Leu Met Glu Ala Met Ala Lys Gly Lys Leu
465                 470                 475

<210> SEQ ID NO 87
```

<211> LENGTH: 831
<212> TYPE: DNA
<213> ORGANISM: Cylindrospermopsis raciborskii AWT205

<400> SEQUENCE: 87

```
atgaccatat atgaaaataa gttgagtagt tatcaaaaaa atcaagatgc cataatatct      60

gcaaaagaac tcgaagaatg gcatttaatt ggacttctag accattcaat agatgcggta     120

atagtaccga attattttct tgagcaagag tgtatgacaa tttcagagag aataaaaaag     180

agtaaatatt ttagcgctta tcccggtcat ccatcagtaa gtagcttggg acaagagttg     240

tatgaatgcg aaagtgagct tgaattagca aagtatcaag aagacgcacc cacattgatt     300

aaagaaatgc ggaggctggt acatccgtac ataagtccaa ttgatagact tagggttgaa     360

gttgatgata tttggagtta tggctgtaat ttagcaaaac ttggtgataa aaaactgttt     420

gcgggtatcg ttagagagtt taaagaagat aaccctggcg caccacattg tgacgtaatg     480

gcatggggtt ttctcgaata ttataaagat aaaccaaata tcataaatca aatcgcagca     540

aatgtatatt taaaaacgtc tgcatcagga ggagaaatag tgctttggga tgaatggcca     600

actcaaagcg aatatatagc atacaaaaca gatgatccag ctagtttcgg tcttgatagc     660

aaaaagatcg cacaaccaaa acttgagatc caaccgaacc agggagattt aattctattc     720

aattccatga gaattcatgc ggtgaaaaag atagaaactg gtgtacgtat gacatgggga     780

tgtttgattg gatactctgg aactgataaa ccgcttgtta tttggactta a              831
```

<210> SEQ ID NO 88
<211> LENGTH: 276
<212> TYPE: PRT
<213> ORGANISM: Cylindrospermopsis raciborskii AWT205

<400> SEQUENCE: 88

```
Met Thr Ile Tyr Glu Asn Lys Leu Ser Ser Tyr Gln Lys Asn Gln Asp
1               5                   10                  15

Ala Ile Ile Ser Ala Lys Glu Leu Glu Glu Trp His Leu Ile Gly Leu
            20                  25                  30

Leu Asp His Ser Ile Asp Ala Val Ile Val Pro Asn Tyr Phe Leu Glu
        35                  40                  45

Gln Glu Cys Met Thr Ile Ser Glu Arg Ile Lys Lys Ser Lys Tyr Phe
    50                  55                  60

Ser Ala Tyr Pro Gly His Pro Ser Val Ser Ser Leu Gly Gln Glu Leu
65                  70                  75                  80

Tyr Glu Cys Glu Ser Glu Leu Glu Leu Ala Lys Tyr Gln Glu Asp Ala
                85                  90                  95

Pro Thr Leu Ile Lys Glu Met Arg Arg Leu Val His Pro Tyr Ile Ser
            100                 105                 110

Pro Ile Asp Arg Leu Arg Val Glu Val Asp Asp Ile Trp Ser Tyr Gly
        115                 120                 125

Cys Asn Leu Ala Lys Leu Gly Asp Lys Lys Leu Phe Ala Gly Ile Val
    130                 135                 140

Arg Glu Phe Lys Glu Asp Asn Pro Gly Ala Pro His Cys Asp Val Met
145                 150                 155                 160

Ala Trp Gly Phe Leu Glu Tyr Tyr Lys Asp Lys Pro Asn Ile Ile Asn
                165                 170                 175

Gln Ile Ala Ala Asn Val Tyr Leu Lys Thr Ser Ala Ser Gly Gly Glu
            180                 185                 190

Ile Val Leu Trp Asp Glu Trp Pro Thr Gln Ser Glu Tyr Ile Ala Tyr
```

-continued

```
        195                 200                 205

Lys Thr Asp Asp Pro Ala Ser Phe Gly Leu Asp Ser Lys Lys Ile Ala
    210                 215                 220

Gln Pro Lys Leu Glu Ile Gln Pro Asn Gln Gly Asp Leu Ile Leu Phe
225                 230                 235                 240

Asn Ser Met Arg Ile His Ala Val Lys Lys Ile Glu Thr Gly Val Arg
                245                 250                 255

Met Thr Trp Gly Cys Leu Ile Gly Tyr Ser Gly Thr Asp Lys Pro Leu
            260                 265                 270

Val Ile Trp Thr
        275
```

<210> SEQ ID NO 89
<211> LENGTH: 1398
<212> TYPE: DNA
<213> ORGANISM: Cylindrospermopsis raciborskii AWT205

<400> SEQUENCE: 89

```
ttaatgtagc gtttccattt gagtcaaggc acgagaagct tctaaagctg gaatagatac      60

actatcattc tcaactacac tctcaaatgt cctaggtaac tgtgccccaa acatcagcat     120

tccaatggcg ttgaacaaaa agaaagccaa ccacaagata tggttactct caaatttaac     180

agcagctaca tccgcaggta aaaatcctac accaaacgcg attaagttaa cattgcggag     240

agtatgccct tgagccaaac ccaagaagta cccacatagt atgcaacata ctgaattgca     300

tactaggaca agtaccaacc agggaataaa aatatcaata ttctcaataa tttctgcgtg     360

gttggttaac aacccaaaaa catcatcggg aaatagccaa cacgctccgc cgaaaaccag     420

actcactagc agagccattc ccacagaaac ttttgccaga ggtgctaact gttctgtggc     480

tcctttccct ttaaaatttc ctgccagagt ttctgtacag aatcccaatc cttcaacaat     540

gtagatgctc aaagcccata tctgtaagag caaggcattt tgagcgtaga taattgtccc     600

catttgtgcc ccttcgtagt taaacgttaa gttggtaaac atacaaacta aattgctgac     660

aaagatgttt ccattgagag ttaaggtgga gcgtatagct tttatgtccc aaatttttcc     720

agctaattct tttacctctt gccacgggat ttctttgcag acaaaaaaca atcccaccaa     780

tagggtgaga tattgacttg cagcagaagc tactcctgcc cccatgctcg accagtctaa     840

gtggataata aacaagtagt cgagtgcgat attggcagca ttgcccacaa ccgacaacaa     900

cacaactaag ccattttttt cccgtcccag aaaccagcca agcaggacaa agttgagcaa     960

aatggcaggc gctccccaac tctgggtgtt aaaatacgct tgagctgaag acttcacctc    1020

tgggccgaca tctagtatag aaaaccccaa cacccctaac gggtactgta acagtatgat    1080

cgccaccccc agcaccagag caattaaacc attaagcagt cccgccaaca gtacgccctc    1140

tcggtcatct cgtccgactg cttgtgctgt taacgcagtg gtacccattc gtaaaaacga    1200

taaaacaaag tagagaaagt taagcaggtt tccagcaagg gctactccag ctaggtagtg    1260

gatttccgag agatgaccta agaacatgat actgactaaa ttactcagtg gtactataat    1320

attcgatagg acgttggtaa aagctagtcg gaagtagcgg ggtataaagt catactggct    1380

tggaaatgtc aggctcat                                                  1398
```

<210> SEQ ID NO 90
<211> LENGTH: 465
<212> TYPE: PRT
<213> ORGANISM: Cylindrospermopsis raciborskii AWT205

<400> SEQUENCE: 90

Met Ser Leu Thr Phe Pro Ser Gln Tyr Asp Phe Ile Pro Arg Tyr Phe
1               5                   10                  15

Arg Leu Ala Phe Thr Asn Val Leu Ser Asn Ile Ile Val Pro Leu Ser
            20                  25                  30

Asn Leu Val Ser Ile Met Phe Leu Gly His Leu Ser Glu Ile His Tyr
        35                  40                  45

Leu Ala Gly Val Ala Leu Ala Gly Asn Leu Leu Asn Phe Leu Tyr Phe
    50                  55                  60

Val Leu Ser Phe Leu Arg Met Gly Thr Thr Ala Leu Thr Ala Gln Ala
65                  70                  75                  80

Val Gly Arg Asp Asp Arg Glu Gly Val Leu Leu Ala Gly Leu Leu Asn
                85                  90                  95

Gly Leu Ile Ala Leu Val Leu Gly Val Ala Ile Ile Leu Leu Gln Tyr
            100                 105                 110

Pro Leu Gly Val Leu Gly Phe Ser Ile Leu Asp Val Gly Pro Glu Val
        115                 120                 125

Lys Ser Ser Ala Gln Ala Tyr Phe Asn Thr Gln Ser Trp Gly Ala Pro
    130                 135                 140

Ala Ile Leu Leu Asn Phe Val Leu Leu Gly Trp Phe Leu Gly Arg Glu
145                 150                 155                 160

Lys Asn Gly Leu Val Val Leu Leu Ser Val Val Gly Asn Ala Ala Asn
                165                 170                 175

Ile Ala Leu Asp Tyr Leu Phe Ile Ile His Leu Asp Trp Ser Ser Met
            180                 185                 190

Gly Ala Gly Val Ala Ser Ala Ala Ser Gln Tyr Leu Thr Leu Leu Val
        195                 200                 205

Gly Leu Phe Phe Val Cys Lys Glu Ile Pro Trp Gln Glu Val Lys Glu
    210                 215                 220

Leu Ala Gly Lys Ile Trp Asp Ile Lys Ala Ile Arg Ser Thr Leu Thr
225                 230                 235                 240

Leu Asn Gly Asn Ile Phe Val Ser Asn Leu Val Cys Met Phe Thr Asn
                245                 250                 255

Leu Thr Phe Asn Tyr Glu Gly Ala Gln Met Gly Thr Ile Ile Tyr Ala
            260                 265                 270

Gln Asn Ala Leu Leu Leu Gln Ile Trp Ala Leu Ser Ile Tyr Ile Val
        275                 280                 285

Glu Gly Leu Gly Phe Cys Thr Glu Thr Leu Ala Gly Asn Phe Lys Gly
    290                 295                 300

Lys Gly Ala Thr Glu Gln Leu Ala Pro Leu Ala Lys Val Ser Val Gly
305                 310                 315                 320

Met Ala Leu Leu Val Ser Leu Val Phe Gly Gly Ala Cys Trp Leu Phe
                325                 330                 335

Pro Asp Asp Val Phe Gly Leu Leu Thr Asn His Ala Glu Ile Ile Glu
            340                 345                 350

Asn Ile Asp Ile Phe Ile Pro Trp Leu Val Leu Val Leu Val Cys Asn
        355                 360                 365

Ser Val Cys Cys Ile Leu Cys Gly Tyr Phe Leu Gly Leu Ala Gln Gly
    370                 375                 380

His Thr Leu Arg Asn Val Asn Leu Ile Ala Phe Gly Val Gly Phe Leu
385                 390                 395                 400

Pro Ala Asp Val Ala Ala Val Lys Phe Glu Ser Asn His Ile Leu Trp
                405                 410                 415

Leu Ala Phe Phe Leu Phe Asn Ala Ile Gly Met Leu Met Phe Gly Ala
            420                 425                 430

Gln Leu Pro Arg Thr Phe Glu Ser Val Val Glu Asn Asp Ser Val Ser
        435                 440                 445

Ile Pro Ala Leu Glu Ala Ser Arg Ala Leu Thr Gln Met Glu Thr Leu
    450                 455                 460

His
465

<210> SEQ ID NO 91
<211> LENGTH: 750
<212> TYPE: DNA
<213> ORGANISM: Cylindrospermopsis raciborskii AWT205

<400> SEQUENCE: 91
atgttgaact tagaccgcat cctgaatcaa gagcgactgc tacgagaaat gactggactt 60
aaccgccaag cattcaacga gctgttatct cagtttgctg atacctatga acgcaccgtg 120
ttcaactcct tagcaaaccg caaacgtgcg cccgggggcg gacgcaagcc tacactcaga 180
agtatagagg aaaaactatt ttatatcctg ctgtactgca aatgttatcc gacgtttgac 240
ttgctgagtg tgttgttcaa ctttgaccgc tcctgtgctc atgattgggt acatcgacta 300
ctgtctgtgc tagaaaccac tttaggagaa aagcaagttt tgccagcacg caaactcagg 360
agcatggagg aattcaccaa aaggtttcca gatgtgaagg aggtgattgt ggatggtacg 420
gagcgtccag tccagcgtcc tcaaaaccga gaacgccaaa aagagtatta ctctggcaag 480
aaaaagcggc atacatgcaa gcagattaca gtcagcacaa gggagaaacg agtgattatt 540
cggacggaaa ccagagcagg taaagtgcat gacaaacggc tactccatga atcagagata 600
gtgcaataca ttcctgatga agtagcaata gagggagatt tgggttttca tgggttggag 660
aaagaatttg tcaatgtcca tttaccacac aagaaaccga aaggtatcga agcaaggagg 720
catggcggcg ggatgggtca gtttttataa 750

<210> SEQ ID NO 92
<211> LENGTH: 249
<212> TYPE: PRT
<213> ORGANISM: Cylindrospermopsis raciborskii AWT205

<400> SEQUENCE: 92

Met Leu Asn Leu Asp Arg Ile Leu Asn Gln Glu Arg Leu Leu Arg Glu
1               5                   10                  15

Met Thr Gly Leu Asn Arg Gln Ala Phe Asn Glu Leu Leu Ser Gln Phe
            20                  25                  30

Ala Asp Thr Tyr Glu Arg Thr Val Phe Asn Ser Leu Ala Asn Arg Lys
        35                  40                  45

Arg Ala Pro Gly Gly Gly Arg Lys Pro Thr Leu Arg Ser Ile Glu Glu
    50                  55                  60

Lys Leu Phe Tyr Ile Leu Leu Tyr Cys Lys Cys Tyr Pro Thr Phe Asp
65                  70                  75                  80

Leu Leu Ser Val Leu Phe Asn Phe Asp Arg Ser Cys Ala His Asp Trp
                85                  90                  95

Val His Arg Leu Leu Ser Val Leu Glu Thr Thr Leu Gly Glu Lys Gln
            100                 105                 110

Val Leu Pro Ala Arg Lys Leu Arg Ser Met Glu Glu Phe Thr Lys Arg
        115                 120                 125

```
Phe Pro Asp Val Lys Glu Val Ile Val Asp Gly Thr Glu Arg Pro Val
    130                 135                 140

Gln Arg Pro Gln Asn Arg Glu Arg Gln Lys Glu Tyr Tyr Ser Gly Lys
145                 150                 155                 160

Lys Lys Arg His Thr Cys Lys Gln Ile Thr Val Ser Thr Arg Glu Lys
                165                 170                 175

Arg Val Ile Ile Arg Thr Glu Thr Arg Ala Gly Lys Val His Asp Lys
            180                 185                 190

Arg Leu Leu His Glu Ser Glu Ile Val Gln Tyr Ile Pro Asp Glu Val
        195                 200                 205

Ala Ile Glu Gly Asp Leu Gly Phe His Gly Leu Glu Lys Glu Phe Val
    210                 215                 220

Asn Val His Leu Pro His Lys Lys Pro Lys Gly Ile Glu Ala Arg Arg
225                 230                 235                 240

His Gly Gly Gly Met Gly Gln Phe Leu
                245


<210> SEQ ID NO 93
<211> LENGTH: 1431
<212> TYPE: DNA
<213> ORGANISM: Cylindrospermopsis raciborskii AWT205

<400> SEQUENCE: 93

atgaatctta taacaacaaa aaaacaggta gatacattag tgatacacgc tcatcttttt      60

accatgcagg gaaatggtgt gggatatatt gcagatgggg cacttgcggt tgagggtagc     120

cgtattgtag cagttgattc gacggaggcg ttgctgagtc attttgaggg cagaaaggtt     180

attgagtccg cgaattgtgc cgtcttgcct gggctgatta atgctcacgt agacacaagt     240

ttggtgctga tgcgtggggc ggcgcaagat gtaactaatt ggctaatgga cgcgaccatg     300

ccttattttg ctcacatgac acccgtggcg agtatggctg caacacgctt aagggtggta     360

gaagagttga aagcaggcac aacaacattc tgtgacaata aaattattag ccccctgtgg     420

ggcgaatttt tcgatgaaat tggtgtacgg gctagtttag ctcctatgtt cgatgcactc     480

ccactggaga tgccaccgct tcaagacggg gagctttatc ccttcgatat caaggcggga     540

cggcgggcga tggcagaggc tgtggatttt gcctgtgggt ggaatggggc agcagagggg     600

cgtatcacta ccatgttagg aatgtattcg ccagatatga tgccgcttga gatgctacgc     660

gcagccaaag agattgctca acgggaaggc ttaatgctgc attttcatgt agcgcaggga     720

gatcgggaaa cagagcaaat cgttaaacga tatggtaagc gtccgatcgc atttctagct     780

gagattggct acttggacga acagttgctg gcagttcacc tcaccgatgc caccgatgaa     840

gaggtgatac aagtagccaa aagtggcgct ggcatggtac tctgttcggg aatgattggc     900

actattgacg gtatcgtgcc gcccgctcat gtgtttcggc aagcaggcgg acccgttgcg     960

ctaggcagca gctacaataa tattttccat gagatgaagc tgaccgcctt attcaacaaa    1020

ataaaatatc acgatccaac cattatgccg gcttgggaag tcctgcgtat ggctaccatc    1080

gaaggagcgc gggcgattgg tttagatcac aagattggct ctcttgaagt tggcaaagaa    1140

gccgacctga tcttaataga cctcagcacc cctaacctct cacccactct gcttaacccc    1200

attcgtaacc ttgtacctaa tttcgtgtac gctgcttcag gacatgaagt taaaagtgtc    1260

atggtggcgg gaaaactgtt attggaagac taccaagtcc tcacagtaga tgagtctgct    1320

atcattgctg aagcacaatt gcaagcccaa cagatttctc aatgcgtagc atctgaccct    1380

atccacaaaa aaatggtgct gatggcggcg atggcaaggg gccaattgta g              1431
```

<210> SEQ ID NO 94
<211> LENGTH: 476
<212> TYPE: PRT
<213> ORGANISM: Cylindrospermopsis raciborskii AWT205

<400> SEQUENCE: 94

Met Asn Leu Ile Thr Thr Lys Lys Gln Val Asp Thr Leu Val Ile His
1 5 10 15

Ala His Leu Phe Thr Met Gln Gly Asn Gly Val Gly Tyr Ile Ala Asp
20 25 30

Gly Ala Leu Ala Val Glu Gly Ser Arg Ile Val Ala Val Asp Ser Thr
35 40 45

Glu Ala Leu Leu Ser His Phe Glu Gly Arg Lys Val Ile Glu Ser Ala
50 55 60

Asn Cys Ala Val Leu Pro Gly Leu Ile Asn Ala His Val Asp Thr Ser
65 70 75 80

Leu Val Leu Met Arg Gly Ala Ala Gln Asp Val Thr Asn Trp Leu Met
85 90 95

Asp Ala Thr Met Pro Tyr Phe Ala His Met Thr Pro Val Ala Ser Met
100 105 110

Ala Ala Thr Arg Leu Arg Val Val Glu Glu Leu Lys Ala Gly Thr Thr
115 120 125

Thr Phe Cys Asp Asn Lys Ile Ile Ser Pro Leu Trp Gly Glu Phe Phe
130 135 140

Asp Glu Ile Gly Val Arg Ala Ser Leu Ala Pro Met Phe Asp Ala Leu
145 150 155 160

Pro Leu Glu Met Pro Pro Leu Gln Asp Gly Glu Leu Tyr Pro Phe Asp
165 170 175

Ile Lys Ala Gly Arg Arg Ala Met Ala Glu Ala Val Asp Phe Ala Cys
180 185 190

Gly Trp Asn Gly Ala Ala Glu Gly Arg Ile Thr Thr Met Leu Gly Met
195 200 205

Tyr Ser Pro Asp Met Met Pro Leu Glu Met Leu Arg Ala Ala Lys Glu
210 215 220

Ile Ala Gln Arg Glu Gly Leu Met Leu His Phe His Val Ala Gln Gly
225 230 235 240

Asp Arg Glu Thr Glu Gln Ile Val Lys Arg Tyr Gly Lys Arg Pro Ile
245 250 255

Ala Phe Leu Ala Glu Ile Gly Tyr Leu Asp Glu Gln Leu Leu Ala Val
260 265 270

His Leu Thr Asp Ala Thr Asp Glu Glu Val Ile Gln Val Ala Lys Ser
275 280 285

Gly Ala Gly Met Val Leu Cys Ser Gly Met Ile Gly Thr Ile Asp Gly
290 295 300

Ile Val Pro Pro Ala His Val Phe Arg Gln Ala Gly Gly Pro Val Ala
305 310 315 320

Leu Gly Ser Ser Tyr Asn Asn Ile Phe His Glu Met Lys Leu Thr Ala
325 330 335

Leu Phe Asn Lys Ile Lys Tyr His Asp Pro Thr Ile Met Pro Ala Trp
340 345 350

Glu Val Leu Arg Met Ala Thr Ile Glu Gly Ala Arg Ala Ile Gly Leu
355 360 365

Asp His Lys Ile Gly Ser Leu Glu Val Gly Lys Glu Ala Asp Leu Ile

```
    370                 375                 380

Leu Ile Asp Leu Ser Thr Pro Asn Leu Ser Pro Thr Leu Leu Asn Pro
385                 390                 395                 400

Ile Arg Asn Leu Val Pro Asn Phe Val Tyr Ala Ala Ser Gly His Glu
                405                 410                 415

Val Lys Ser Val Met Val Ala Gly Lys Leu Leu Leu Glu Asp Tyr Gln
            420                 425                 430

Val Leu Thr Val Asp Glu Ser Ala Ile Ile Ala Glu Ala Gln Leu Gln
        435                 440                 445

Ala Gln Gln Ile Ser Gln Cys Val Ala Ser Asp Pro Ile His Lys Lys
    450                 455                 460

Met Val Leu Met Ala Ala Met Ala Arg Gly Gln Leu
465                 470                 475


<210> SEQ ID NO 95
<211> LENGTH: 780
<212> TYPE: DNA
<213> ORGANISM: Cylindrospermopsis raciborskii AWT205

<400> SEQUENCE: 95

atgcaagaaa aacgaatcgc aatgtggtct gtgccacgaa gtttgggtac agtgctgcta      60

caagcctggt cgagtcggcc agataccgta gtctttgatg aacttctctc ctttccctat     120

ctctttatca aagggaaaga tatgggcttt acttggacag accttgattc tagccaaatg     180

ccccacgcag attggcgatc cgtcatcgat ctgttaaagg ctcccctgcc tgaagggaaa     240

tcaatcatcg atctgttaaa ggctcccctg cctgaaggga aatcaatttg ctatcagaag     300

catcaagcgt atcatttaat cgaagagacc atggggattg agtggatatt gcccttcagc     360

aactgctttc tgattcgcca acccaaagaa atgctcttat cttttcgtaa gattgtgcca     420

cattttacct ttgaagaaac aggctggatc gaattaaaac ggctgtttga ctatgtacat     480

caaacgagcg gagtaatccc gcctgtcata gatgcacacg acttgctgaa cgatccgcgg     540

agaatgctct ccaagctttg tcaggttgta ggggttgagt ttaccgagac aatgctcagt     600

tggcccccca tggaggtcga gttgaacgaa aaactagccc cttggtacag caccgtagca     660

agttctacgc attttcactc gtatcagaat aaaaatgagt cgttgccgct atatcttgtc     720

gatatttgta aacgctgcga tgaaatatat caggaattat atcaatttcg actttattag     780


<210> SEQ ID NO 96
<211> LENGTH: 259
<212> TYPE: PRT
<213> ORGANISM: Cylindrospermopsis raciborskii AWT205

<400> SEQUENCE: 96

Met Gln Glu Lys Arg Ile Ala Met Trp Ser Val Pro Arg Ser Leu Gly
1               5                   10                  15

Thr Val Leu Leu Gln Ala Trp Ser Ser Arg Pro Asp Thr Val Val Phe
            20                  25                  30

Asp Glu Leu Leu Ser Phe Pro Tyr Leu Phe Ile Lys Gly Lys Asp Met
        35                  40                  45

Gly Phe Thr Trp Thr Asp Leu Asp Ser Ser Gln Met Pro His Ala Asp
    50                  55                  60

Trp Arg Ser Val Ile Asp Leu Leu Lys Ala Pro Leu Pro Glu Gly Lys
65                  70                  75                  80

Ser Ile Ile Asp Leu Leu Lys Ala Pro Leu Pro Glu Gly Lys Ser Ile
                85                  90                  95
```

-continued

```
Cys Tyr Gln Lys His Gln Ala Tyr His Leu Ile Glu Glu Thr Met Gly
            100                 105                 110

Ile Glu Trp Ile Leu Pro Phe Ser Asn Cys Phe Leu Ile Arg Gln Pro
        115                 120                 125

Lys Glu Met Leu Leu Ser Phe Arg Lys Ile Val Pro His Phe Thr Phe
    130                 135                 140

Glu Glu Thr Gly Trp Ile Glu Leu Lys Arg Leu Phe Asp Tyr Val His
145                 150                 155                 160

Gln Thr Ser Gly Val Ile Pro Pro Val Ile Asp Ala His Asp Leu Leu
                165                 170                 175

Asn Asp Pro Arg Arg Met Leu Ser Lys Leu Cys Gln Val Val Gly Val
            180                 185                 190

Glu Phe Thr Glu Thr Met Leu Ser Trp Pro Pro Met Glu Val Glu Leu
        195                 200                 205

Asn Glu Lys Leu Ala Pro Trp Tyr Ser Thr Val Ala Ser Ser Thr His
    210                 215                 220

Phe His Ser Tyr Gln Asn Lys Asn Glu Ser Leu Pro Leu Tyr Leu Val
225                 230                 235                 240

Asp Ile Cys Lys Arg Cys Asp Glu Ile Tyr Gln Glu Leu Tyr Gln Phe
                245                 250                 255

Arg Leu Tyr
```

<210> SEQ ID NO 97
<211> LENGTH: 1176
<212> TYPE: DNA
<213> ORGANISM: Cylindrospermopsis raciborskii AWT205

<400> SEQUENCE: 97

```
atgcaaacaa gaattgtaaa tagctggaat gagtgggatg aactaaagga gatggttgtc     60

gggattgcag atggtgctta ttttgaacca actgagccag gtaaccgccc tgctttacgc    120

gataagaaca ttgccaaaat gttctctttt cccaggggtc cgaaaaagca agaggtaaca    180

gagaaagcta atgaggagtt gaatgggctg gtagcgcttc tagaatcaca gggcgtaact    240

gtacgccgcc cagagaaaca taactttggc ctgtctgtga agacaccatt ctttgaggta    300

gagaatcaat attgtgcggt ctgcccacgt gatgttatga tcacctttgg gaacgaaatt    360

ctcgaagcaa ctatgtcacg gcggtcacgc ttctttgagt atttacccta tcgcaaacta    420

gtctatgaat attggcataa agatccagat atgatctgga atgctgcgcc taaaccgact    480

atgcaaaatg ccatgtaccg cgaagatttc tgggagtgtc cgatggaaga tcgatttgag    540

agtatgcatg attttgagtt ctgcgtcacc caggatgagg tgatttttga cgcagcagac    600

tgtagccgct ttggccgtga tatttttgtg caggagtcaa tgacgactaa tcgtgcaggg    660

attcgctggc tcaaacggca tttagagccg cgtcgcttcc gcgtgcatga tattcacttc    720

ccactagata ttttcccatc ccacattgat tgtacttttg tcccccttagc acctggggtt    780

gtgttagtga atccagatcg ccccatcaaa gagggtgaag agaaactctt catggataac    840

ggttggcaat tcatcgaagc acccctcccc acttccaccg acgatgagat gcctatgttc    900

tgccagtcca gtaagtggtt ggcgatgaat gtgttaagca tttcccccaa gaaggtcatc    960

tgtgaagagc aagagcatcc gcttcatgag ttgctagata aacacggctt tgaggtctat   1020

ccaattccct ttcgcaatgt ctttgagttt ggcggttcgc tccattgtgc cacctgggat   1080

atccatcgca cgggaacctg tgaggattac ttccctaaac taaactatac gccggtaact   1140
```

gcatcaacca atggcgtttc tcgcttcatc atttag 1176

<210> SEQ ID NO 98
<211> LENGTH: 391
<212> TYPE: PRT
<213> ORGANISM: Cylindrospermopsis raciborskii AWT205

<400> SEQUENCE: 98

```
Met Gln Thr Arg Ile Val Asn Ser Trp Asn Glu Trp Asp Glu Leu Lys
1               5                   10                  15

Glu Met Val Val Gly Ile Ala Asp Gly Ala Tyr Phe Glu Pro Thr Glu
            20                  25                  30

Pro Gly Asn Arg Pro Ala Leu Arg Asp Lys Asn Ile Ala Lys Met Phe
        35                  40                  45

Ser Phe Pro Arg Gly Pro Lys Lys Gln Glu Val Thr Glu Lys Ala Asn
    50                  55                  60

Glu Glu Leu Asn Gly Leu Val Ala Leu Leu Glu Ser Gln Gly Val Thr
65                  70                  75                  80

Val Arg Arg Pro Glu Lys His Asn Phe Gly Leu Ser Val Lys Thr Pro
                85                  90                  95

Phe Phe Glu Val Glu Asn Gln Tyr Cys Ala Val Cys Pro Arg Asp Val
            100                 105                 110

Met Ile Thr Phe Gly Asn Glu Ile Leu Glu Ala Thr Met Ser Arg Arg
        115                 120                 125

Ser Arg Phe Phe Glu Tyr Leu Pro Tyr Arg Lys Leu Val Tyr Glu Tyr
    130                 135                 140

Trp His Lys Asp Pro Asp Met Ile Trp Asn Ala Ala Pro Lys Pro Thr
145                 150                 155                 160

Met Gln Asn Ala Met Tyr Arg Glu Asp Phe Trp Glu Cys Pro Met Glu
                165                 170                 175

Asp Arg Phe Glu Ser Met His Asp Phe Glu Phe Cys Val Thr Gln Asp
            180                 185                 190

Glu Val Ile Phe Asp Ala Ala Asp Cys Ser Arg Phe Gly Arg Asp Ile
        195                 200                 205

Phe Val Gln Glu Ser Met Thr Thr Asn Arg Ala Gly Ile Arg Trp Leu
    210                 215                 220

Lys Arg His Leu Glu Pro Arg Arg Phe Arg Val His Asp Ile His Phe
225                 230                 235                 240

Pro Leu Asp Ile Phe Pro Ser His Ile Asp Cys Thr Phe Val Pro Leu
                245                 250                 255

Ala Pro Gly Val Val Leu Val Asn Pro Asp Arg Pro Ile Lys Glu Gly
            260                 265                 270

Glu Glu Lys Leu Phe Met Asp Asn Gly Trp Gln Phe Ile Glu Ala Pro
        275                 280                 285

Leu Pro Thr Ser Thr Asp Asp Glu Met Pro Met Phe Cys Gln Ser Ser
    290                 295                 300

Lys Trp Leu Ala Met Asn Val Leu Ser Ile Ser Pro Lys Lys Val Ile
305                 310                 315                 320

Cys Glu Glu Gln Glu His Pro Leu His Glu Leu Leu Asp Lys His Gly
                325                 330                 335

Phe Glu Val Tyr Pro Ile Pro Phe Arg Asn Val Phe Glu Phe Gly Gly
            340                 345                 350

Ser Leu His Cys Ala Thr Trp Asp Ile His Arg Thr Gly Thr Cys Glu
        355                 360                 365
```

```
Asp Tyr Phe Pro Lys Leu Asn Tyr Thr Pro Val Thr Ala Ser Thr Asn
    370                 375                 380

Gly Val Ser Arg Phe Ile Ile
385                 390


<210> SEQ ID NO 99
<211> LENGTH: 8754
<212> TYPE: DNA
<213> ORGANISM: Cylindrospermopsis raciborskii AWT205

<400> SEQUENCE: 99

atgcaaaaga gagaaagccc acagatacta tttgatggga atggaacaca atctgagttt     60

ccagatagtt gcattcacca cttgttcgag gatcaagccg caaagcgacc ggatgcgatc    120

gctctcattg acggtgagca atcccttacc tacggggaac taaatgtacg cgctaaccac    180

ctagcccagc atctcttgtc cctaggctgt caacccgatg acctcctcgc catctgcatc    240

gagcgttcgg cagaactctt tattggtttg ttgggtatcc taaaagccgg atgtgcttat    300

gtgcctttgg atgtaggcta tcctggcgat cgcatagagt atatgttgcg ggactcggat    360

gcgcgtattt tactaacctc aacggatgtc gctaagaaac ttgccttaac catacctgca    420

ttgcaagagt gccaaaccgt ctatttagat caagagatat ttgagtatga ttttcatttt    480

ttagcgatag ctaaactatt acataaccaa tacttgagat tattacattt ttatttttat    540

accttgattc agcaatgcca ggcaacttcg gtttcccaag ggattcagac acaggttctc    600

cccaataatc tcgcttactg catttacacc tctggctcta ccggaaatcc caaagggatc    660

ttgatggaac atcgctcact ggtgaatatg ctttggtggc atcagcaaac gcggccttcg    720

gttcagggtg ttaggacgct gcaattttgt gcagtcagct ttgacttttc ctgccatgaa    780

atttttttcta ccctctgtct tggcgggata ttggtcttgg tgccagaggc agtgcgccaa    840

aatccctttg cattggctga gttcatcagt caacagaaaa ttgaaaaatt gtttcttccc    900

gttatagcat tactacagtt ggccgaagct gtaaatggga ataaaagcac ctccctcgcg    960

ctttgcgaag ttatcactac cggggagcag atgcagatca cacctgctgt cgccaacctc   1020

tttcagaaaa ccggggcgat gttgcataat cactacgggg caacagaatt tcaagatgcc   1080

accactcata ccctcaaggg caatccagag ggctggccaa cactggtgcc agtgggtcgt   1140

ccactgcaca atgttcaagt gtatattctg gatgaggcac agcaacctgt acctcttggt   1200

ggagagggtg aattctgtat tggtggtatt ggactggctc gtggctatca caatttgcct   1260

gacctaacga atgaaaaatt tattcccaat ccatttgggg ctaatgagaa cgctaaaaaa   1320

ctctaccgca caggggactt ggcacgctac ctacccgacg gcacgattga gcatttagga   1380

cggatagacc accaggttaa gatccgaggt ttccgcgtgg aattgggggga aattgagtcc   1440

gtgctggcaa gtcaccaagc tgtgcgtgaa tgtgccgttg tggcacggga gattgcaggt   1500

catacacagt tggtagggta tatcatagca aaggatacac ttaatctcag tttcgacaaa   1560

cttgaaccta tcctgcgtca atattcggaa gcggtgctgc cagaatacat gatacccact   1620

cggttcatca atatcagtaa tatgccgttg actcccagtg gtaaacttga ccgcagggca   1680

ttacctgatc ccaaaggcga tcgccctgca ttgtctaccc cacttgtcaa gcctcgtacc   1740

cagacagaga aacgtttagc agagatttgg ggcagttatc ttgctgtaga tattgtggga   1800

acccacgaca atttctttga tctaggcggt acgtcactgc tattgactca agcgcacaaa   1860

ttcctgtgcg agacctttaa tattaatttg tccgctgtct cactctttca atatcccaca   1920

attcagacat tggcacaata tattgattgc caaggagaca caacctcaag cgatacagca   1980
```

-continued

```
tccaggcaca agaaagtacg taaaaagcag tccggtgaca gcaacgatat tgccatcatc   2040
agtgtggcag gtcgctttcc gggtgctgaa acgattgagc agttctggca taatctctgt   2100
aatggtgttg aatccatcac cctttttagt gatgatgagc tagagcagac tttgcctgag   2160
ttatttaata atcccgctta tgtcaaagca ggtgcggtgc tagaaggcgt tgaattattt   2220
gatgctacct tttttggcta cagccccaaa gaagctgcgg tgacagaccc tcagcaacgg   2280
attttgctag agtgtgcctg ggaagcattt gaacgggctg gctacaaccc cgaaacctat   2340
ccagaaccag ttggtgttta tgctggttca agcctgagta cctatctgct taacaatatt   2400
ggctctgctt taggcataat taccgagcaa ccctttattg aaacggatat ggagcagttt   2460
caggctaaaa ttggcaatga ccggagctat cttgctacac gcatctctta caagctgaat   2520
ctcaagggtc caagcgtcaa tgtgcagacc gcctgctcaa cctcgttagt tgcggttcac   2580
atggcctgtc agagtctcat tagtggagag tgtcaaatgg ctttagccgg tggtatttct   2640
gtggttgtac cacagaaggg ggctatctc tacgaagaag gcatggttcg ttcccaggat   2700
ggtcattgtc gcgcctttga tgccgaagcc caagggacta tatttggcaa tggcggcggc   2760
ttggttttgc ttaaacggtt gcaggatgca ctggacgata acgacaacat tatggcagtc   2820
atcaaagcca cagccatcaa caacgacggt gcgctcaaga tgggctacac agcaccgagc   2880
gtggatgggc aagctgatgt aattagcgag gcgattgcta tcgctgacat agatgcaagc   2940
accattggct atgtagaagc tcatggcaca gccacccaat tgggtgatcc gattgaagta   3000
gcagggttag caagggcatt tcagcgtagt acggacagcg tccttggtaa acaacaatgc   3060
gctattggat cagttaaaac taatattggc cacttagatg aggcggcagg cattgccgga   3120
ctgataaagg ctgctctagc tctacaatat ggacagattc caccgagctt gcactatgcc   3180
aatcctaatc cacggattga ttttgacgca accccatttt ttgtcaacac agaactacgc   3240
gaatggtcaa ggaatggtta tcctcggcgg gcgggggtga gttcttttgg tgtgggtgga   3300
actaacagcc atattgtgct ggaggagtcg cctgtaaagc aacccacatt gttctcttct   3360
ttgccagaac gcagtcatca tctgctgacg ctttctgccc atacacaaga ggctttgcat   3420
gagttggtgc aacgctacat ccaacataac gagacacacc ttgatattaa cttaggcgac   3480
ctctgtttca cagccaatac gggacgcaag cattttgagc atcgcctagc ggttgtagcc   3540
gaatcaatcc ctggcttaca ggcacaactg gaaactgcac agactgcgat ttcagcacag   3600
aaaaaaaatg ccccgccgac gatcgcattc ctgtttacag gtcaaggctc acaatacatt   3660
aacatggggc gcaccctcta cgatactgaa tcaacattcc gtgcagccct tgaccgatgt   3720
gaaaccattc tccaaaattt agggatcgag tccattctct ccgttatttt tggttcatct   3780
gagcatggac tctcattaga tgacacagcc tatacccagc ccgcactctt tgccatcgaa   3840
tacgcgctct atcaattatg gaagtcgtgg ggcatccagc cctcagtggt gataggtcat   3900
agtgtaggtg aatatgtgtc cgcttgtgtg gcgggagtct ttagcttaga ggatgggttg   3960
aaactgattg cagaacgagg acgactgata caggcacttc ctcgtgatgg gagcatggtt   4020
tccgtgatgg caagcgagaa gcgtattgca gatatcattt taccttatgg gggacaggta   4080
gggatcgccg cgattaatgg cccacaaagt gttgtaattt ctgggcaaca gcaagcgatt   4140
gatgctattt gtgccatctt ggaaactgag ggcatcaaaa gcaagaagct aaacgtctcc   4200
catgccttcc actcgccgct agtggaagca atgttagact ctttcttgca ggttgcacaa   4260
gaggtcactt actcgcaacc tcaaatcaag cttatctcta atgtaacggg aacattggca   4320
```

-continued

```
agccatgaat cttgtcccga tgaacttccg atcaccaccg cagagtattg ggtacgtcat   4380
gtgcgacagc ccgtccggtt tgcggcggga atggagagcc ttgagggtca aggggtaaac   4440
gtatttatag aaatcggtcc taaacctgtt cttttaggca tgggacgcga ctgcttgcct   4500
gaacaagagg gactttggtt gcctagtttg cgcccaaaac aggatgattg gcaacaggtg   4560
ttaagtagtt tgcgtgatct atacttagca ggtgtaaccg tagattggag cagtttcgat   4620
caggggtatg ctcgtcgccg tgtgccacta ccgacttatc cttggcagcg agagcggcat   4680
tgggtagagc caattattcg tcaacggcaa tcagtattac aagccacaaa taccaccaag   4740
ctaactcgta acgccagcgt ggcgcagcat cctctgcttg gtcaacggct gcatttgtcg   4800
cggactcaag agatttactt tcaaaccttc atccactccg acttcccaat atgggttgct   4860
gatcataaag tatttggaaa tgtcatcatt ccgggtgtcg cctattttga gatggcactg   4920
gcagcaggga aggcacttaa accagacagt atattttggc tcgaagatgt atccatcgcc   4980
caagcactga ttattcccga tgaagggcaa actgtgcaaa tagtattaag cccacaggaa   5040
gagtcagctt atttttttga aatcctctct ttagaaaaag aaaactcttg ggtgcttcat   5100
gcctctggta agctagtcgc ccaagagcaa gtgctagaaa ccgagccaat tgacttgatt   5160
gcgttacagg cacattgttc cgaagaagtg tcagtagatg tgctatatca ggaagaaatg   5220
gcgcgccggc tggatatggg tccaatgatg cgtggggtga agcagctttg gcgttatccg   5280
ctctcctttg ccaaaagtca tgatgcgatc gcactcgcca aggtcagctt gccagaaatc   5340
ttgcttcatg agtccaatgc ctaccaattc catcctgtaa tcttggatgc ggggctgcaa   5400
atgataacgg tctcttatcc tgaagcaaac caaggccaga cttatgtacc tgttggtata   5460
gagggtctac aagtctatgg tcgtcccagt tcagaacttt ggtgtcgcgc ccaatatcgg   5520
cctcctttgg atacagatca aaggcagggt attgatttgc tgccaaagaa attgattgca   5580
gacttgcatc tatttgatac ccagggtcgt gtggttgcca tcatgtttgg tgtgcaatct   5640
gtccttgtgg gacgggaagc aatgttgcga tcgcaagata cttggcgaaa ttggctttat   5700
caagtcctgt ggaaacctca agcctgtttt ggacttttac cgaattacct gccaacccca   5760
gataagattc ggaaacgcct ggaaacaaag ttagcgacat tgatcatcga agctaatttg   5820
gcgacttatg cgatcgccta tacccaactg gaaaggttaa gtctagctta cgttgtggcg   5880
gctttccgac aaatgggctg gctgtttcaa cccggtgagc gtttttccac cgcccagaag   5940
gtatcagcgt taggaatcgt tgatcaacat cggcaactat tcgctcgttt gctcgacatt   6000
ctagccgaag cagacatact ccgcagcgaa aacttgatga cgatatggga agtcatttca   6060
tacccggaaa cgattgatat acaggtactt cttgacgacc tcgaagccaa agaagcagaa   6120
gccgaagtca cactggtttc ccgttgcagt gcaaaattgg ccgaagtatt acaaggaaaa   6180
tgtgacccca tacagttgct ctttcccgca ggggacacaa caacgttaag caaactctat   6240
cgtgaagccc cagttttggg tgttactaat actctagtcc aagaagcgct tctttccgcc   6300
ctggagcagt tgccgccgga acgtggttgg cgaattttag agattggtgc tggaacaggt   6360
ggaaccacag cctacttgtt accgcatctg cctggggatc agacaaaata tgtctttacc   6420
gatattagtg cctttttttct tgccaaagcg gaagagcgtt ttaaagatta cccgtttgta   6480
cgttatcagg tattagatat cgaacaagca ccacaggcgc aaggatttga accccaaata   6540
tacgatttaa tcgtagcagc ggatgtcttg catgctacta gtgacctgcg tcaaactctt   6600
gtacatatcc ggcaattatt agcgccgggc gggatgttga tcctgatgga agacagcgaa   6660
cccgcacgct gggctgattt aacctttggc ttaacagaag gctggtggaa gtttacagac   6720
```

-continued catgacttac gccccaacca tccgctattg tctcctgagc agtggcaaat cttgttgtca 6780
gaaatgggat ttagtcaaac aaccgcctta tggccaaaaa tagatagccc ccataaattg 6840
ccacgggagg cggtgattgt ggcgcgtaat gaaccagcca tcagaaaacc ccgaagatgg 6900
ctgatcttgg ctgacgagga gattggtgga ctactagcca aacagctacg tgaagaagga 6960
gaagattgta tactcctctt gccaggggaa aagtacacag agagagattc acaaacgttt 7020
acaatcaatc ctggagatat tgaagagtgg caacagttat tgaaccgagt accgaacata 7080
caagaaattg tacattgttg gagtatggtt tccactgact tagatagagc cactattttc 7140
agttgcagca gtacgctgca tttagttcaa gcattagcaa actatccaaa aaaccctcgc 7200
ttgtcacttg tcaccctagg cgcacaagcc gttaacgaac atcatgttca aaatgtagtt 7260
ggagcagccc tctggggcat gggaaaggta attgcactcg aacacccaga gctacaagta 7320
gcacaaatgg atttagaccc gaatgggaag gttaaggcgc aagtagaagt gcttagggat 7380
gaacttctcg ccagaaaaga ccctgcatca gcaatgtctg tgcctgatct gcaaacacga 7440
cctcatgaaa agcaaatagc ctttcgtgag caaacacgtt atgtggcaag actttcgccc 7500
ttagaccgcc ccaatcctgg agagaaaggc acacaagagg ctcttacctt ccgtgatgat 7560
ggcagctatc tgattgctgg tggtttaggc ggactggggt tagtggtggc tcgttttctg 7620
gttacaaatg gggctaaata ccttgtgcta gtcggacgac gtggtgcgag ggaggaacag 7680
caagctcaat taagcgaact agagcaactc ggagcttccg tgaaagtttt acaagccgat 7740
attgctgatg cagaacaact agcccaagca ctttcagcag taacctaccc accattacgg 7800
ggtgttattc atgcggcagg tacattgaac gatgggattc tacagcagca aagttggcaa 7860
gcctttaaag aagtgatgaa tcccaaggta gcaggtgcgt ggaacctaca tatactgaca 7920
aaaaatcagc ctttagactt ctttgtcctg ttctcctccg ccacctcttt gttaggtaac 7980
gctggacaag ccaatcacgc cgccgcaaat gctttccttg atgggttagc ctcctatcgt 8040
cgtcacttag gactaccgag cctctcgatt aattggggga catggagcga agtgggaatt 8100
gcggctcgac ttgaactaga taagttgtcc agcaaacagg gagagggaac cattacgcta 8160
ggacagggct tacaaattct tgagcagttg ctcaaagacg agaatggggt gtatcaagtg 8220
ggtgtcatgc ctatcaactg gacacaattc ttagcaaggc aattgactcc gcagccgttc 8280
ttcagcgatg ccatgaagag tattgacacc tctgtaggta aactaacctt gcaggagcgg 8340
gactcttgcc cccaaggtta cgggcataat attcgagagc aattagagaa cgctccgccc 8400
aaagagggtc tgactctctt gcaggctcat gttcgggagc aggtttccca agtttggggg 8460
atagacacga agacattatt ggcagaacaa gacgtgggtt tctttaccct ggggatggat 8520
tcgctgacct ctgtcgagtt aagaaacagg ttacaagcca gtttgggctg ctctctttct 8580
tccactttgg cttttgacta tccaacacaa caggctcttg tgaattatct tgccaatgaa 8640
ttgctgggaa cccctgagca gctacaagag cctgaatctg atgaagaaga tcagatatcg 8700
tcaatggatg acatcgtgca gttgctgtcc gcgaaactag agatggaaat ttaa 8754

<210> SEQ ID NO 100
<211> LENGTH: 2917
<212> TYPE: PRT
<213> ORGANISM: Cylindrospermopsis raciborskii AWT205

<400> SEQUENCE: 100

Met Gln Lys Arg Glu Ser Pro Gln Ile Leu Phe Asp Gly Asn Gly Thr
1 5 10 15

-continued

```
Gln Ser Glu Phe Pro Asp Ser Cys Ile His His Leu Phe Glu Asp Gln
            20                  25                  30

Ala Ala Lys Arg Pro Asp Ala Ile Ala Leu Ile Asp Gly Glu Gln Ser
        35                  40                  45

Leu Thr Tyr Gly Glu Leu Asn Val Arg Ala Asn His Leu Ala Gln His
    50                  55                  60

Leu Leu Ser Leu Gly Cys Gln Pro Asp Asp Leu Leu Ala Ile Cys Ile
65                  70                  75                  80

Glu Arg Ser Ala Glu Leu Phe Ile Gly Leu Leu Gly Ile Leu Lys Ala
                85                  90                  95

Gly Cys Ala Tyr Val Pro Leu Asp Val Gly Tyr Pro Gly Asp Arg Ile
            100                 105                 110

Glu Tyr Met Leu Arg Asp Ser Asp Ala Arg Ile Leu Leu Thr Ser Thr
        115                 120                 125

Asp Val Ala Lys Lys Leu Ala Leu Thr Ile Pro Ala Leu Gln Glu Cys
    130                 135                 140

Gln Thr Val Tyr Leu Asp Gln Glu Ile Phe Glu Tyr Asp Phe His Phe
145                 150                 155                 160

Leu Ala Ile Ala Lys Leu Leu His Asn Gln Tyr Leu Arg Leu Leu His
                165                 170                 175

Phe Tyr Phe Tyr Thr Leu Ile Gln Gln Cys Gln Ala Thr Ser Val Ser
            180                 185                 190

Gln Gly Ile Gln Thr Gln Val Leu Pro Asn Asn Leu Ala Tyr Cys Ile
        195                 200                 205

Tyr Thr Ser Gly Ser Thr Gly Asn Pro Lys Gly Ile Leu Met Glu His
    210                 215                 220

Arg Ser Leu Val Asn Met Leu Trp Trp His Gln Gln Thr Arg Pro Ser
225                 230                 235                 240

Val Gln Gly Val Arg Thr Leu Gln Phe Cys Ala Val Ser Phe Asp Phe
                245                 250                 255

Ser Cys His Glu Ile Phe Ser Thr Leu Cys Leu Gly Gly Ile Leu Val
            260                 265                 270

Leu Val Pro Glu Ala Val Arg Gln Asn Pro Phe Ala Leu Ala Glu Phe
        275                 280                 285

Ile Ser Gln Gln Lys Ile Glu Lys Leu Phe Leu Pro Val Ile Ala Leu
    290                 295                 300

Leu Gln Leu Ala Glu Ala Val Asn Gly Asn Lys Ser Thr Ser Leu Ala
305                 310                 315                 320

Leu Cys Glu Val Ile Thr Thr Gly Glu Gln Met Gln Ile Thr Pro Ala
                325                 330                 335

Val Ala Asn Leu Phe Gln Lys Thr Gly Ala Met Leu His Asn His Tyr
            340                 345                 350

Gly Ala Thr Glu Phe Gln Asp Ala Thr Thr His Thr Leu Lys Gly Asn
        355                 360                 365

Pro Glu Gly Trp Pro Thr Leu Val Pro Val Gly Arg Pro Leu His Asn
    370                 375                 380

Val Gln Val Tyr Ile Leu Asp Glu Ala Gln Gln Pro Val Pro Leu Gly
385                 390                 395                 400

Gly Glu Gly Glu Phe Cys Ile Gly Gly Ile Gly Leu Ala Arg Gly Tyr
                405                 410                 415

His Asn Leu Pro Asp Leu Thr Asn Glu Lys Phe Ile Pro Asn Pro Phe
            420                 425                 430
```

-continued

```
Gly Ala Asn Glu Asn Ala Lys Lys Leu Tyr Arg Thr Gly Asp Leu Ala
        435                 440                 445

Arg Tyr Leu Pro Asp Gly Thr Ile Glu His Leu Gly Arg Ile Asp His
    450                 455                 460

Gln Val Lys Ile Arg Gly Phe Arg Val Glu Leu Gly Glu Ile Glu Ser
465                 470                 475                 480

Val Leu Ala Ser His Gln Ala Val Arg Glu Cys Ala Val Val Ala Arg
                485                 490                 495

Glu Ile Ala Gly His Thr Gln Leu Val Gly Tyr Ile Ile Ala Lys Asp
            500                 505                 510

Thr Leu Asn Leu Ser Phe Asp Lys Leu Glu Pro Ile Leu Arg Gln Tyr
        515                 520                 525

Ser Glu Ala Val Leu Pro Glu Tyr Met Ile Pro Thr Arg Phe Ile Asn
    530                 535                 540

Ile Ser Asn Met Pro Leu Thr Pro Ser Gly Lys Leu Asp Arg Arg Ala
545                 550                 555                 560

Leu Pro Asp Pro Lys Gly Asp Arg Pro Ala Leu Ser Thr Pro Leu Val
                565                 570                 575

Lys Pro Arg Thr Gln Thr Glu Lys Arg Leu Ala Glu Ile Trp Gly Ser
            580                 585                 590

Tyr Leu Ala Val Asp Ile Val Gly Thr His Asp Asn Phe Phe Asp Leu
        595                 600                 605

Gly Gly Thr Ser Leu Leu Leu Thr Gln Ala His Lys Phe Leu Cys Glu
    610                 615                 620

Thr Phe Asn Ile Asn Leu Ser Ala Val Ser Leu Phe Gln Tyr Pro Thr
625                 630                 635                 640

Ile Gln Thr Leu Ala Gln Tyr Ile Asp Cys Gln Gly Asp Thr Thr Ser
                645                 650                 655

Ser Asp Thr Ala Ser Arg His Lys Lys Val Arg Lys Lys Gln Ser Gly
            660                 665                 670

Asp Ser Asn Asp Ile Ala Ile Ile Ser Val Ala Gly Arg Phe Pro Gly
        675                 680                 685

Ala Glu Thr Ile Glu Gln Phe Trp His Asn Leu Cys Asn Gly Val Glu
    690                 695                 700

Ser Ile Thr Leu Phe Ser Asp Asp Glu Leu Glu Gln Thr Leu Pro Glu
705                 710                 715                 720

Leu Phe Asn Asn Pro Ala Tyr Val Lys Ala Gly Ala Val Leu Glu Gly
                725                 730                 735

Val Glu Leu Phe Asp Ala Thr Phe Phe Gly Tyr Ser Pro Lys Glu Ala
            740                 745                 750

Ala Val Thr Asp Pro Gln Gln Arg Ile Leu Leu Glu Cys Ala Trp Glu
        755                 760                 765

Ala Phe Glu Arg Ala Gly Tyr Asn Pro Glu Thr Tyr Pro Glu Pro Val
    770                 775                 780

Gly Val Tyr Ala Gly Ser Ser Leu Ser Thr Tyr Leu Leu Asn Asn Ile
785                 790                 795                 800

Gly Ser Ala Leu Gly Ile Ile Thr Glu Gln Pro Phe Ile Glu Thr Asp
                805                 810                 815

Met Glu Gln Phe Gln Ala Lys Ile Gly Asn Asp Arg Ser Tyr Leu Ala
            820                 825                 830

Thr Arg Ile Ser Tyr Lys Leu Asn Leu Lys Gly Pro Ser Val Asn Val
        835                 840                 845

Gln Thr Ala Cys Ser Thr Ser Leu Val Ala Val His Met Ala Cys Gln
```

-continued

```
    850                 855                 860

Ser Leu Ile Ser Gly Glu Cys Gln Met Ala Leu Ala Gly Gly Ile Ser
865                 870                 875                 880

Val Val Val Pro Gln Lys Gly Gly Tyr Leu Tyr Glu Glu Gly Met Val
                885                 890                 895

Arg Ser Gln Asp Gly His Cys Arg Ala Phe Asp Ala Glu Ala Gln Gly
            900                 905                 910

Thr Ile Phe Gly Asn Gly Gly Gly Leu Val Leu Leu Lys Arg Leu Gln
        915                 920                 925

Asp Ala Leu Asp Asp Asn Asp Asn Ile Met Ala Val Ile Lys Ala Thr
    930                 935                 940

Ala Ile Asn Asn Asp Gly Ala Leu Lys Met Gly Tyr Thr Ala Pro Ser
945                 950                 955                 960

Val Asp Gly Gln Ala Asp Val Ile Ser Glu Ala Ile Ala Ile Ala Asp
                965                 970                 975

Ile Asp Ala Ser Thr Ile Gly Tyr Val Glu Ala His Gly Thr Ala Thr
            980                 985                 990

Gln Leu Gly Asp Pro Ile Glu Val  Ala Gly Leu Ala Arg  Ala Phe Gln
        995                 1000                1005

Arg Ser  Thr Asp Ser Val Leu  Gly Lys Gln Gln Cys  Ala Ile Gly
    1010                 1015                 1020

Ser Val  Lys Thr Asn Ile Gly  His Leu Asp Glu Ala  Ala Gly Ile
    1025                 1030                 1035

Ala Gly  Leu Ile Lys Ala Ala  Leu Ala Leu Gln Tyr  Gly Gln Ile
    1040                 1045                 1050

Pro Pro  Ser Leu His Tyr Ala  Asn Pro Asn Pro Arg  Ile Asp Phe
    1055                 1060                 1065

Asp Ala  Thr Pro Phe Phe Val  Asn Thr Glu Leu Arg  Glu Trp Ser
    1070                 1075                 1080

Arg Asn  Gly Tyr Pro Arg Arg  Ala Gly Val Ser Ser  Phe Gly Val
    1085                 1090                 1095

Gly Gly  Thr Asn Ser His Ile  Val Leu Glu Glu Ser  Pro Val Lys
    1100                 1105                 1110

Gln Pro  Thr Leu Phe Ser Ser  Leu Pro Glu Arg Ser  His His Leu
    1115                 1120                 1125

Leu Thr  Leu Ser Ala His Thr  Gln Glu Ala Leu His  Glu Leu Val
    1130                 1135                 1140

Gln Arg  Tyr Ile Gln His Asn  Glu Thr His Leu Asp  Ile Asn Leu
    1145                 1150                 1155

Gly Asp  Leu Cys Phe Thr Ala  Asn Thr Gly Arg Lys  His Phe Glu
    1160                 1165                 1170

His Arg  Leu Ala Val Val Ala  Glu Ser Ile Pro Gly  Leu Gln Ala
    1175                 1180                 1185

Gln Leu  Glu Thr Ala Gln Thr  Ala Ile Ser Ala Gln  Lys Lys Asn
    1190                 1195                 1200

Ala Pro  Pro Thr Ile Ala Phe  Leu Phe Thr Gly Gln  Gly Ser Gln
    1205                 1210                 1215

Tyr Ile  Asn Met Gly Arg Thr  Leu Tyr Asp Thr Glu  Ser Thr Phe
    1220                 1225                 1230

Arg Ala  Ala Leu Asp Arg Cys  Glu Thr Ile Leu Gln  Asn Leu Gly
    1235                 1240                 1245

Ile Glu  Ser Ile Leu Ser Val  Ile Phe Gly Ser Ser  Glu His Gly
    1250                 1255                 1260
```

```
Leu Ser  Leu Asp Asp Thr Ala  Tyr Thr Gln Pro Ala  Leu Phe Ala
    1265                 1270                 1275

Ile Glu  Tyr Ala Leu Tyr Gln  Leu Trp Lys Ser Trp  Gly Ile Gln
    1280                 1285                 1290

Pro Ser  Val Val Ile Gly His  Ser Val Gly Glu Tyr  Val Ser Ala
    1295                 1300                 1305

Cys Val  Ala Gly Val Phe Ser  Leu Glu Asp Gly Leu  Lys Leu Ile
    1310                 1315                 1320

Ala Glu  Arg Gly Arg Leu Ile  Gln Ala Leu Pro Arg  Asp Gly Ser
    1325                 1330                 1335

Met Val  Ser Val Met Ala Ser  Glu Lys Arg Ile Ala  Asp Ile Ile
    1340                 1345                 1350

Leu Pro  Tyr Gly Gly Gln Val  Gly Ile Ala Ala Ile  Asn Gly Pro
    1355                 1360                 1365

Gln Ser  Val Val Ile Ser Gly  Gln Gln Gln Ala Ile  Asp Ala Ile
    1370                 1375                 1380

Cys Ala  Ile Leu Glu Thr Glu  Gly Ile Lys Ser Lys  Lys Leu Asn
    1385                 1390                 1395

Val Ser  His Ala Phe His Ser  Pro Leu Val Glu Ala  Met Leu Asp
    1400                 1405                 1410

Ser Phe  Leu Gln Val Ala Gln  Glu Val Thr Tyr Ser  Gln Pro Gln
    1415                 1420                 1425

Ile Lys  Leu Ile Ser Asn Val  Thr Gly Thr Leu Ala  Ser His Glu
    1430                 1435                 1440

Ser Cys  Pro Asp Glu Leu Pro  Ile Thr Thr Ala Glu  Tyr Trp Val
    1445                 1450                 1455

Arg His  Val Arg Gln Pro Val  Arg Phe Ala Ala Gly  Met Glu Ser
    1460                 1465                 1470

Leu Glu  Gly Gln Gly Val Asn  Val Phe Ile Glu Ile  Gly Pro Lys
    1475                 1480                 1485

Pro Val  Leu Leu Gly Met Gly  Arg Asp Cys Leu Pro  Glu Gln Glu
    1490                 1495                 1500

Gly Leu  Trp Leu Pro Ser Leu  Arg Pro Lys Gln Asp  Asp Trp Gln
    1505                 1510                 1515

Gln Val  Leu Ser Ser Leu Arg  Asp Leu Tyr Leu Ala  Gly Val Thr
    1520                 1525                 1530

Val Asp  Trp Ser Ser Phe Asp  Gln Gly Tyr Ala Arg  Arg Arg Val
    1535                 1540                 1545

Pro Leu  Pro Thr Tyr Pro Trp  Gln Arg Glu Arg His  Trp Val Glu
    1550                 1555                 1560

Pro Ile  Ile Arg Gln Arg Gln  Ser Val Leu Gln Ala  Thr Asn Thr
    1565                 1570                 1575

Thr Lys  Leu Thr Arg Asn Ala  Ser Val Ala Gln His  Pro Leu Leu
    1580                 1585                 1590

Gly Gln  Arg Leu His Leu Ser  Arg Thr Gln Glu Ile  Tyr Phe Gln
    1595                 1600                 1605

Thr Phe  Ile His Ser Asp Phe  Pro Ile Trp Val Ala  Asp His Lys
    1610                 1615                 1620

Val Phe  Gly Asn Val Ile Ile  Pro Gly Val Ala Tyr  Phe Glu Met
    1625                 1630                 1635

Ala Leu  Ala Ala Gly Lys Ala  Leu Lys Pro Asp Ser  Ile Phe Trp
    1640                 1645                 1650
```

Leu Glu Asp Val Ser Ile Ala Gln Ala Leu Ile Ile Pro Asp Glu
1655 1660 1665

Gly Gln Thr Val Gln Ile Val Leu Ser Pro Gln Glu Glu Ser Ala
1670 1675 1680

Tyr Phe Phe Glu Ile Leu Ser Leu Glu Lys Glu Asn Ser Trp Val
1685 1690 1695

Leu His Ala Ser Gly Lys Leu Val Ala Gln Glu Gln Val Leu Glu
1700 1705 1710

Thr Glu Pro Ile Asp Leu Ile Ala Leu Gln Ala His Cys Ser Glu
1715 1720 1725

Glu Val Ser Val Asp Val Leu Tyr Gln Glu Glu Met Ala Arg Arg
1730 1735 1740

Leu Asp Met Gly Pro Met Met Arg Gly Val Lys Gln Leu Trp Arg
1745 1750 1755

Tyr Pro Leu Ser Phe Ala Lys Ser His Asp Ala Ile Ala Leu Ala
1760 1765 1770

Lys Val Ser Leu Pro Glu Ile Leu Leu His Glu Ser Asn Ala Tyr
1775 1780 1785

Gln Phe His Pro Val Ile Leu Asp Ala Gly Leu Gln Met Ile Thr
1790 1795 1800

Val Ser Tyr Pro Glu Ala Asn Gln Gly Gln Thr Tyr Val Pro Val
1805 1810 1815

Gly Ile Glu Gly Leu Gln Val Tyr Gly Arg Pro Ser Ser Glu Leu
1820 1825 1830

Trp Cys Arg Ala Gln Tyr Arg Pro Pro Leu Asp Thr Asp Gln Arg
1835 1840 1845

Gln Gly Ile Asp Leu Leu Pro Lys Lys Leu Ile Ala Asp Leu His
1850 1855 1860

Leu Phe Asp Thr Gln Gly Arg Val Val Ala Ile Met Phe Gly Val
1865 1870 1875

Gln Ser Val Leu Val Gly Arg Glu Ala Met Leu Arg Ser Gln Asp
1880 1885 1890

Thr Trp Arg Asn Trp Leu Tyr Gln Val Leu Trp Lys Pro Gln Ala
1895 1900 1905

Cys Phe Gly Leu Leu Pro Asn Tyr Leu Pro Thr Pro Asp Lys Ile
1910 1915 1920

Arg Lys Arg Leu Glu Thr Lys Leu Ala Thr Leu Ile Ile Glu Ala
1925 1930 1935

Asn Leu Ala Thr Tyr Ala Ile Ala Tyr Thr Gln Leu Glu Arg Leu
1940 1945 1950

Ser Leu Ala Tyr Val Val Ala Ala Phe Arg Gln Met Gly Trp Leu
1955 1960 1965

Phe Gln Pro Gly Glu Arg Phe Ser Thr Ala Gln Lys Val Ser Ala
1970 1975 1980

Leu Gly Ile Val Asp Gln His Arg Gln Leu Phe Ala Arg Leu Leu
1985 1990 1995

Asp Ile Leu Ala Glu Ala Asp Ile Leu Arg Ser Glu Asn Leu Met
2000 2005 2010

Thr Ile Trp Glu Val Ile Ser Tyr Pro Glu Thr Ile Asp Ile Gln
2015 2020 2025

Val Leu Leu Asp Asp Leu Glu Ala Lys Glu Ala Glu Ala Glu Val
2030 2035 2040

Thr Leu Val Ser Arg Cys Ser Ala Lys Leu Ala Glu Val Leu Gln

```
    2045                2050                2055

Gly Lys  Cys Asp Pro Ile Gln  Leu Leu Phe Pro Ala  Gly Asp Thr
    2060                2065                2070

Thr Thr  Leu Ser Lys Leu Tyr  Arg Glu Ala Pro Val  Leu Gly Val
    2075                2080                2085

Thr Asn  Thr Leu Val Gln Glu  Ala Leu Leu Ser Ala  Leu Glu Gln
    2090                2095                2100

Leu Pro  Pro Glu Arg Gly Trp  Arg Ile Leu Glu Ile  Gly Ala Gly
    2105                2110                2115

Thr Gly  Gly Thr Thr Ala Tyr  Leu Leu Pro His Leu  Pro Gly Asp
    2120                2125                2130

Gln Thr  Lys Tyr Val Phe Thr  Asp Ile Ser Ala Phe  Phe Leu Ala
    2135                2140                2145

Lys Ala  Glu Glu Arg Phe Lys  Asp Tyr Pro Phe Val  Arg Tyr Gln
    2150                2155                2160

Val Leu  Asp Ile Glu Gln Ala  Pro Gln Ala Gln Gly  Phe Glu Pro
    2165                2170                2175

Gln Ile  Tyr Asp Leu Ile Val  Ala Ala Asp Val Leu  His Ala Thr
    2180                2185                2190

Ser Asp  Leu Arg Gln Thr Leu  Val His Ile Arg Gln  Leu Leu Ala
    2195                2200                2205

Pro Gly  Gly Met Leu Ile Leu  Met Glu Asp Ser Glu  Pro Ala Arg
    2210                2215                2220

Trp Ala  Asp Leu Thr Phe Gly  Leu Thr Glu Gly Trp  Trp Lys Phe
    2225                2230                2235

Thr Asp  His Asp Leu Arg Pro  Asn His Pro Leu Leu  Ser Pro Glu
    2240                2245                2250

Gln Trp  Gln Ile Leu Leu Ser  Glu Met Gly Phe Ser  Gln Thr Thr
    2255                2260                2265

Ala Leu  Trp Pro Lys Ile Asp  Ser Pro His Lys Leu  Pro Arg Glu
    2270                2275                2280

Ala Val  Ile Val Ala Arg Asn  Glu Pro Ala Ile Arg  Lys Pro Arg
    2285                2290                2295

Arg Trp  Leu Ile Leu Ala Asp  Glu Glu Ile Gly Gly  Leu Leu Ala
    2300                2305                2310

Lys Gln  Leu Arg Glu Glu Gly  Glu Asp Cys Ile Leu  Leu Leu Pro
    2315                2320                2325

Gly Glu  Lys Tyr Thr Glu Arg  Asp Ser Gln Thr Phe  Thr Ile Asn
    2330                2335                2340

Pro Gly  Asp Ile Glu Glu Trp  Gln Gln Leu Leu Asn  Arg Val Pro
    2345                2350                2355

Asn Ile  Gln Glu Ile Val His  Cys Trp Ser Met Val  Ser Thr Asp
    2360                2365                2370

Leu Asp  Arg Ala Thr Ile Phe  Ser Cys Ser Ser Thr  Leu His Leu
    2375                2380                2385

Val Gln  Ala Leu Ala Asn Tyr  Pro Lys Asn Pro Arg  Leu Ser Leu
    2390                2395                2400

Val Thr  Leu Gly Ala Gln Ala  Val Asn Glu His His  Val Gln Asn
    2405                2410                2415

Val Val  Gly Ala Ala Leu Trp  Gly Met Gly Lys Val  Ile Ala Leu
    2420                2425                2430

Glu His  Pro Glu Leu Gln Val  Ala Gln Met Asp Leu  Asp Pro Asn
    2435                2440                2445
```

-continued

```
Gly Lys  Val Lys Ala Gln Val  Glu Val Leu Arg Asp  Glu Leu Leu
    2450                 2455                 2460

Ala Arg  Lys Asp Pro Ala Ser  Ala Met Ser Val Pro  Asp Leu Gln
    2465                 2470                 2475

Thr Arg  Pro His Glu Lys Gln  Ile Ala Phe Arg Glu  Gln Thr Arg
    2480                 2485                 2490

Tyr Val  Ala Arg Leu Ser Pro  Leu Asp Arg Pro Asn  Pro Gly Glu
    2495                 2500                 2505

Lys Gly  Thr Gln Glu Ala Leu  Thr Phe Arg Asp Asp  Gly Ser Tyr
    2510                 2515                 2520

Leu Ile  Ala Gly Gly Leu Gly  Gly Leu Gly Leu Val  Val Ala Arg
    2525                 2530                 2535

Phe Leu  Val Thr Asn Gly Ala  Lys Tyr Leu Val Leu  Val Gly Arg
    2540                 2545                 2550

Arg Gly  Ala Arg Glu Glu Gln  Gln Ala Gln Leu Ser  Glu Leu Glu
    2555                 2560                 2565

Gln Leu  Gly Ala Ser Val Lys  Val Leu Gln Ala Asp  Ile Ala Asp
    2570                 2575                 2580

Ala Glu  Gln Leu Ala Gln Ala  Leu Ser Ala Val Thr  Tyr Pro Pro
    2585                 2590                 2595

Leu Arg  Gly Val Ile His Ala  Ala Gly Thr Leu Asn  Asp Gly Ile
    2600                 2605                 2610

Leu Gln  Gln Gln Ser Trp Gln  Ala Phe Lys Glu Val  Met Asn Pro
    2615                 2620                 2625

Lys Val  Ala Gly Ala Trp Asn  Leu His Ile Leu Thr  Lys Asn Gln
    2630                 2635                 2640

Pro Leu  Asp Phe Phe Val Leu  Phe Ser Ser Ala Thr  Ser Leu Leu
    2645                 2650                 2655

Gly Asn  Ala Gly Gln Ala Asn  His Ala Ala Ala Asn  Ala Phe Leu
    2660                 2665                 2670

Asp Gly  Leu Ala Ser Tyr Arg  Arg His Leu Gly Leu  Pro Ser Leu
    2675                 2680                 2685

Ser Ile  Asn Trp Gly Thr Trp  Ser Glu Val Gly Ile  Ala Ala Arg
    2690                 2695                 2700

Leu Glu  Leu Asp Lys Leu Ser  Ser Lys Gln Gly Glu  Gly Thr Ile
    2705                 2710                 2715

Thr Leu  Gly Gln Gly Leu Gln  Ile Leu Glu Gln Leu  Leu Lys Asp
    2720                 2725                 2730

Glu Asn  Gly Val Tyr Gln Val  Gly Val Met Pro Ile  Asn Trp Thr
    2735                 2740                 2745

Gln Phe  Leu Ala Arg Gln Leu  Thr Pro Gln Pro Phe  Phe Ser Asp
    2750                 2755                 2760

Ala Met  Lys Ser Ile Asp Thr  Ser Val Gly Lys Leu  Thr Leu Gln
    2765                 2770                 2775

Glu Arg  Asp Ser Cys Pro Gln  Gly Tyr Gly His Asn  Ile Arg Glu
    2780                 2785                 2790

Gln Leu  Glu Asn Ala Pro Pro  Lys Glu Gly Leu Thr  Leu Leu Gln
    2795                 2800                 2805

Ala His  Val Arg Glu Gln Val  Ser Gln Val Leu Gly  Ile Asp Thr
    2810                 2815                 2820

Lys Thr  Leu Leu Ala Glu Gln  Asp Val Gly Phe Phe  Thr Leu Gly
    2825                 2830                 2835
```

```
Met Asp  Ser Leu Thr Ser Val  Glu Leu Arg Asn Arg  Leu Gln Ala
    2840                2845                2850

Ser Leu  Gly Cys Ser Leu Ser  Ser Thr Leu Ala Phe  Asp Tyr Pro
    2855                2860                2865

Thr Gln  Gln Ala Leu Val Asn  Tyr Leu Ala Asn Glu  Leu Leu Gly
    2870                2875                2880

Thr Pro  Glu Gln Leu Gln Glu  Pro Glu Ser Asp Glu  Glu Asp Gln
    2885                2890                2895

Ile Ser  Ser Met Asp Asp Ile  Val Gln Leu Leu Ser  Ala Lys Leu
    2900                2905                2910

Glu Met  Glu Ile
    2915


<210> SEQ ID NO 101
<211> LENGTH: 5667
<212> TYPE: DNA
<213> ORGANISM: Cylindrospermopsis raciborskii AWT205

<400> SEQUENCE: 101

atggatgaaa aactaagaac atacgaacga ttaatcaagc aatcctatca caagatagag     60

gctctggaag ctgaagttaa caggttgaag caaacccaat gtgaacctat cgccatcgtc    120

ggcatgggct gtcgttttcc tggtgcgaat agtccagaag cgttttggca gttgttgtgt    180

gatggggttg atgctattcg tgagatacca aaaaatcgat gggttgttga tgcctacata    240

gatgaaaatt tggaccgcgc agacaagaca tcaatgcgat ttggcgggtt tgtcgagcaa    300

cttgagaagt ttgatgccca attctttggc atatcaccgc gagaagcggt ttctcttgac    360

cctcagcaac gtttgttatt agaagtaagt tgggaagcac tggaaaatgc agcggtgata    420

ccaccttcgg caacgggcgt attcgtcggt attagtaacc ttgattatcg tgaaacgctc    480

ttgaagcaag gagcaattgg tacttatttt gcttcgggta atgcccatag cacagccagt    540

ggtcgcttgt cttactttct cggtctgaca ggcccctgtc tctcgataga tacagcttgt    600

tcttcgtcgt tggtcgctgt acatcagtca ctgataagtc tgcgtcagcg agaatgtgac    660

ttagcgttgg ttgggggagt ccatcggctg atagccccag aggaaagtgt ctcgttagca    720

aaagcccata tgttatctcc cgatggtcgt tgcaaagtct ttgatgcgtc ggcaaacggg    780

tatgtccgag ccgaaggatg tggcatgata gtcctcaaac gattatcgga cgcgcaagct    840

gatggggata aaatcttggc gttgattcgc gggtcagcca taaatcaaga cggtcgcacg    900

agtggcttga ccgttccaaa tggtccccaa caagccgacg tgattcgcca agccctcgcc    960

aatagtggca taagaccaga acaagttaac tatgtagaag ctcatggcac agggacttcc   1020

ctaggagacc cgattgaggt cggcgcgttg ggaacgatct ttaatcaacg ctcccaacct   1080

ttaattattg gttcagttaa aacaaatatt gggcatctag aagcagcagc agggattgct   1140

ggactgatta aagtcgtcct tgccatgcag catggagaaa ttccacctaa tttacacttt   1200

caccagccca atcctcgcat taactgggat aaattgccaa tcaggatccc cacagaacga   1260

acagcttggc ctactggcga tcgcatcgca gggataagtt ctttcggctt tagtggcact   1320

aattctcatg tcgtgttaga ggaagcccca aaaatagagc cgtctacttt agagattcat   1380

tcaaagcagt atgtttttac cttatcagca gcgacacctc aagcactaca agaacttact   1440

cagcgttatg taacttatct cactgaacac ttacaagaga gtctggcgga tatttgcttt   1500

acagccaaca cagggcgcaa acactttaga catcgctttg cagtagtagc agagtctaaa   1560

acccagttgc gccaacaatt ggaaacgttt gcccaatcgg gagaggggca ggggaagagg   1620
```

-continued acatctctct caaaaatagc ttttctcttt acaggtcaag gctcacagta tgtggggatg 1680
gggcaagaac tttatgagag ccaacccacc ttccggcaaa ccattgaccg atgtgatgag 1740
attcttcgtt cactgttggg caaatcaatc ctctcaatac tctatcccag ccaacaaatg 1800
ggattggaaa cgccatccca aattgatgaa accgcctata ctcaacccac tctttttct 1860 cttgaatatg cactggcgca gttgtggcgc tcctggggta ttgagcctga tgtggtgatg 1920
gggcatagtg tgggagaata tgtggccgct tgtgtggcgg gtgtcttttc tttagaggat 1980
ggactcaaac taattgctga aagaggccgt ctgatgcaag aattgcctcc cgatggggcg 2040
atggtttcag ttatggccaa taaatcgcgc atagagcaag caattcaatc tgtcagccga 2100
gaggtttcta ttgcggccat caatggacct gagagtgtgg ttatctctgg taaaagggag 2160
atattacaac agattaccga acatctggtt gccgaaggca ttaagacacg ccaactgaag 2220
gtctctcatg cctttcactc accattgatg gagccaatat taggtcagtt ccgccgagtt 2280
gccaatacca tcacctatcg gccaccgcaa attaaccttg tctcaaatgt cacaggcgga 2340
caggtgtata aagaaatcgc tactcccgat tattgggtga gacatctgca agagactgtc 2400
cgttttgcgg atggggttaa ggtgttacat gaacagaatg tcaatttcat gctcgaaatt 2460
ggtcccaaac ccacactgct gggcatggtt gagttacaaa gttctgagaa tccattttct 2520
atgccaatga tgatgcccag tttgcgtcag aatcgtagcg actggcagca gatgttggag 2580
agcttgagtc aactctatgt tcatggtgtt gagattgact ggatcggttt taataaagac 2640
tatgtgcgac ataaagttgt cctgccgaca tacccatggc agaaggagcg ttactgggta 2700
gaattggatc aacagaagca cgccgctaaa aatctacatc ctctactgga caggtgcatg 2760
aagctgcctc gtcataacga aacaattttt gagaaagaat ttagtctaga gacattgccc 2820
tttcttgctg actatcgcat ttatggttca gttgtgtcgc caggtgcaag ttatctatca 2880
atgatactaa gtattgccga gtcgtatgca aatggtcatt tgaatggagg gaatagtgca 2940
aagcaaacca cttatttact aaaggatgtc acattcccag tacctcttgt gatctctgat 3000
gaggcaaatt acatggtgca agttgcttgt tctctctctt gtgctgcgcc acacaatcgt 3060
ggcgacgaga cgcagtttga attgttcagt tttgctgaga atgtacctga aagtagcagt 3120
ataaatgctg attttcagac acccattatt catgcaaaag ggcaatttaa gcttgaagat 3180
acagcacctc ctaaagtgga gctagaagaa ctacaagcgg gttgtcccca agaaattgat 3240
ctcaaccttt tctatcaaac attcacagac aaaggttttg tttttggatc tcgttttcgc 3300
tggttagaac aaatctgggt gggcgatgga gaagcattgg cgcgtctgcg acaaccggaa 3360
agtattgaat cgtttaaagg atatgtgatt catcccggtt tgttggatgc ctgtacacaa 3420
gtcccatttg caatttcgtc tgacgatgaa aataggcaat cagaaacgac aatgcccttt 3480
gcgctgaatg aattacgttg ttatcagcct gcaaacggac aaatgtggtg ggttcatgca 3540
acagaaaaag atagatatac atgggatgtt tctctgtttg atgagagcgg gcaagttatt 3600
gcggaattta taggtttaga agttcgtgct gctatgcccg aaggcttact aagggcagac 3660
ttttggcata actggctcta tacagtgaat tggcgatcgc aacctctaca aatcccagag 3720
gtgctggata ttaataagac aggtgcagaa acatggcttc tttttgcaca accagaggga 3780
ataggagcgg acttagccga atatttgcag agccaaggaa agcactgtgt ttttgtagtg 3840
cctgggagtg agtatacagt gaccgagcaa cacattggac gcactggaca tcttgatgtg 3900
acgaaactga caaaaattgt cacgatcaat cctgcttctc ctcatgacta taaatatttt 3960

```
ttagaaactc tgacggacat tagattacct tgtgaacata tactctattt atggaatcgt   4020
tatgatttaa caaatacttc taatcatcgg acagaattga ctgtaccaga tatagtctta   4080
aacttatgta ctagtcttac ttatttggta caagccctta gccacatggg tttttccccg   4140
aaattatggc taattacaca aaatagtcaa gcggttggta gtgacttagc gaatttagaa   4200
atcgaacaat ccccattatg ggcattgggt cgaagcatcc gcgccgaaca ccctgaattt   4260
gattgccgtt gtttagattt tgacacgctc tcaaatatcg caccactctt gttgaaagag   4320
atgcaagcta tagactatga atctcaaatt gcttaccgac aaggaacgcg ctatgttgca   4380
cgactaattc gtaatcaatc agaatgtcac gcaccgattc aaacaggaat ccgtcctgat   4440
ggcagctatt tgattacagg tggattaggc ggtctaggat tgcaggtagc actcgccctt   4500
gcggacgctg gagcaagaca cttgatcctc aatagtcgcc gtggtacggt ctccaaagaa   4560
gcccagttaa ttattgaccg actacgccaa gaggatgtta gggttgattt gattgcggca   4620
gatgtctctg atgcggcaga tagcgaacga ctcttagtag aaagtcagcg caagacctct   4680
cttcgaggga ttgtccatgt tgcgggagtc ttggatgatg gcatcctgct ccaacaaaat   4740
caagagcgtt ttgaaaaagt gatggcggct aaggtacgcg gagcttggca tctggaccaa   4800
cagagccaaa ccctcgattt agatttcttt gttgcgttct catctgttgc gtcgctcata   4860
gaagaaccag gacaagccaa ttacgccgca gcgaatgcgt tttggattc attaatgtat    4920
tatcgtcaca taaagggatc taatagcttg agtatcaact ggggggcttg ggcagaagtc   4980
ggcatggcag ccaatttatc atgggaacaa cggggaatcg cggcaatttc tccaaagcaa   5040
gggaggcata ttctcgtcca acttattcaa aaacttaatc agcatacaat cccccaagtt   5100
gctgtacaac cgaccaattg ggctgaatat ctatcccatg atggcgtgaa tatgccattc   5160
tatgaatatt ttacacacca cttgcgtaac gaaaaagaag ccaaattgcg gcaaacagca   5220
ggcagcacct cagaggaagt cagtctgcgg caacagcttc aaacactctc agagaaagac   5280
cgggatgccc ttttgatgga acatcttcaa aaaactgcga tcagagttct cggtttggca   5340
tctaatcaaa aaattgatcc ctatcaggga ttgatgaata tgggactaga ctctttgatg   5400
gcggttgaat ttcggaatca cttgatacgt agtttagaac gccctctgcc agccactctg   5460
ctctttaatt gcccaacact tgattcattg catgattacc tagtcgcaaa aatgtttgat   5520
gatgcccctc agaaggcaga gcaaatggca caaccaacaa cactgacagc acacagcata   5580
tcaatagaat ccaaaataga tgataacgaa agcgtggatg acattgcaca aatgctggca   5640
caagcactca atatcgcctt tgagtag                                       5667
```

```
<210> SEQ ID NO 102
<211> LENGTH: 1888
<212> TYPE: PRT
<213> ORGANISM: Cylindrospermopsis raciborskii AWT205

<400> SEQUENCE: 102

Met Asp Glu Lys Leu Arg Thr Tyr Glu Arg Leu Ile Lys Gln Ser Tyr
1               5                   10                  15

His Lys Ile Glu Ala Leu Glu Ala Glu Val Asn Arg Leu Lys Gln Thr
            20                  25                  30

Gln Cys Glu Pro Ile Ala Ile Val Gly Met Gly Cys Arg Phe Pro Gly
        35                  40                  45

Ala Asn Ser Pro Glu Ala Phe Trp Gln Leu Leu Cys Asp Gly Val Asp
    50                  55                  60

Ala Ile Arg Glu Ile Pro Lys Asn Arg Trp Val Val Asp Ala Tyr Ile
```

-continued

```
65                  70                  75                  80

Asp Glu Asn Leu Asp Arg Ala Asp Lys Thr Ser Met Arg Phe Gly Gly
                85                  90                  95

Phe Val Glu Gln Leu Glu Lys Phe Asp Ala Gln Phe Phe Gly Ile Ser
            100                 105                 110

Pro Arg Glu Ala Val Ser Leu Asp Pro Gln Gln Arg Leu Leu Leu Glu
        115                 120                 125

Val Ser Trp Glu Ala Leu Glu Asn Ala Ala Val Ile Pro Pro Ser Ala
    130                 135                 140

Thr Gly Val Phe Val Gly Ile Ser Asn Leu Asp Tyr Arg Glu Thr Leu
145                 150                 155                 160

Leu Lys Gln Gly Ala Ile Gly Thr Tyr Phe Ala Ser Gly Asn Ala His
                165                 170                 175

Ser Thr Ala Ser Gly Arg Leu Ser Tyr Phe Leu Gly Leu Thr Gly Pro
            180                 185                 190

Cys Leu Ser Ile Asp Thr Ala Cys Ser Ser Ser Leu Val Ala Val His
        195                 200                 205

Gln Ser Leu Ile Ser Leu Arg Gln Arg Glu Cys Asp Leu Ala Leu Val
    210                 215                 220

Gly Gly Val His Arg Leu Ile Ala Pro Glu Glu Ser Val Ser Leu Ala
225                 230                 235                 240

Lys Ala His Met Leu Ser Pro Asp Gly Arg Cys Lys Val Phe Asp Ala
                245                 250                 255

Ser Ala Asn Gly Tyr Val Arg Ala Glu Gly Cys Gly Met Ile Val Leu
            260                 265                 270

Lys Arg Leu Ser Asp Ala Gln Ala Asp Gly Asp Lys Ile Leu Ala Leu
        275                 280                 285

Ile Arg Gly Ser Ala Ile Asn Gln Asp Gly Arg Thr Ser Gly Leu Thr
    290                 295                 300

Val Pro Asn Gly Pro Gln Gln Ala Asp Val Ile Arg Gln Ala Leu Ala
305                 310                 315                 320

Asn Ser Gly Ile Arg Pro Glu Gln Val Asn Tyr Val Glu Ala His Gly
                325                 330                 335

Thr Gly Thr Ser Leu Gly Asp Pro Ile Glu Val Gly Ala Leu Gly Thr
            340                 345                 350

Ile Phe Asn Gln Arg Ser Gln Pro Leu Ile Ile Gly Ser Val Lys Thr
        355                 360                 365

Asn Ile Gly His Leu Glu Ala Ala Ala Gly Ile Ala Gly Leu Ile Lys
    370                 375                 380

Val Val Leu Ala Met Gln His Gly Glu Ile Pro Pro Asn Leu His Phe
385                 390                 395                 400

His Gln Pro Asn Pro Arg Ile Asn Trp Asp Lys Leu Pro Ile Arg Ile
                405                 410                 415

Pro Thr Glu Arg Thr Ala Trp Pro Thr Gly Asp Arg Ile Ala Gly Ile
            420                 425                 430

Ser Ser Phe Gly Phe Ser Gly Thr Asn Ser His Val Val Leu Glu Glu
        435                 440                 445

Ala Pro Lys Ile Glu Pro Ser Thr Leu Glu Ile His Ser Lys Gln Tyr
    450                 455                 460

Val Phe Thr Leu Ser Ala Ala Thr Pro Gln Ala Leu Gln Glu Leu Thr
465                 470                 475                 480

Gln Arg Tyr Val Thr Tyr Leu Thr Glu His Leu Gln Glu Ser Leu Ala
                485                 490                 495
```

```
Asp Ile Cys Phe Thr Ala Asn Thr Gly Arg Lys His Phe Arg His Arg
            500                 505                 510

Phe Ala Val Val Ala Glu Ser Lys Thr Gln Leu Arg Gln Gln Leu Glu
        515                 520                 525

Thr Phe Ala Gln Ser Gly Glu Gly Gln Gly Lys Arg Thr Ser Leu Ser
    530                 535                 540

Lys Ile Ala Phe Leu Phe Thr Gly Gln Gly Ser Gln Tyr Val Gly Met
545                 550                 555                 560

Gly Gln Glu Leu Tyr Glu Ser Gln Pro Thr Phe Arg Gln Thr Ile Asp
                565                 570                 575

Arg Cys Asp Glu Ile Leu Arg Ser Leu Leu Gly Lys Ser Ile Leu Ser
            580                 585                 590

Ile Leu Tyr Pro Ser Gln Gln Met Gly Leu Glu Thr Pro Ser Gln Ile
        595                 600                 605

Asp Glu Thr Ala Tyr Thr Gln Pro Thr Leu Phe Ser Leu Glu Tyr Ala
    610                 615                 620

Leu Ala Gln Leu Trp Arg Ser Trp Gly Ile Glu Pro Asp Val Val Met
625                 630                 635                 640

Gly His Ser Val Gly Glu Tyr Val Ala Ala Cys Val Ala Gly Val Phe
                645                 650                 655

Ser Leu Glu Asp Gly Leu Lys Leu Ile Ala Glu Arg Gly Arg Leu Met
            660                 665                 670

Gln Glu Leu Pro Pro Asp Gly Ala Met Val Ser Val Met Ala Asn Lys
        675                 680                 685

Ser Arg Ile Glu Gln Ala Ile Gln Ser Val Ser Arg Glu Val Ser Ile
    690                 695                 700

Ala Ala Ile Asn Gly Pro Glu Ser Val Val Ile Ser Gly Lys Arg Glu
705                 710                 715                 720

Ile Leu Gln Gln Ile Thr Glu His Leu Val Ala Glu Gly Ile Lys Thr
                725                 730                 735

Arg Gln Leu Lys Val Ser His Ala Phe His Ser Pro Leu Met Glu Pro
            740                 745                 750

Ile Leu Gly Gln Phe Arg Arg Val Ala Asn Thr Ile Thr Tyr Arg Pro
        755                 760                 765

Pro Gln Ile Asn Leu Val Ser Asn Val Thr Gly Gly Gln Val Tyr Lys
    770                 775                 780

Glu Ile Ala Thr Pro Asp Tyr Trp Val Arg His Leu Gln Glu Thr Val
785                 790                 795                 800

Arg Phe Ala Asp Gly Val Lys Val Leu His Glu Gln Asn Val Asn Phe
                805                 810                 815

Met Leu Glu Ile Gly Pro Lys Pro Thr Leu Leu Gly Met Val Glu Leu
            820                 825                 830

Gln Ser Ser Glu Asn Pro Phe Ser Met Pro Met Met Met Pro Ser Leu
        835                 840                 845

Arg Gln Asn Arg Ser Asp Trp Gln Gln Met Leu Glu Ser Leu Ser Gln
    850                 855                 860

Leu Tyr Val His Gly Val Glu Ile Asp Trp Ile Gly Phe Asn Lys Asp
865                 870                 875                 880

Tyr Val Arg His Lys Val Val Leu Pro Thr Tyr Pro Trp Gln Lys Glu
                885                 890                 895

Arg Tyr Trp Val Glu Leu Asp Gln Gln Lys His Ala Ala Lys Asn Leu
            900                 905                 910
```

-continued

```
His Pro Leu Leu Asp Arg Cys Met Lys Leu Pro Arg His Asn Glu Thr
        915                 920                 925

Ile Phe Glu Lys Glu Phe Ser Leu Glu Thr Leu Pro Phe Leu Ala Asp
    930                 935                 940

Tyr Arg Ile Tyr Gly Ser Val Val Ser Pro Gly Ala Ser Tyr Leu Ser
945                 950                 955                 960

Met Ile Leu Ser Ile Ala Glu Ser Tyr Ala Asn Gly His Leu Asn Gly
                965                 970                 975

Gly Asn Ser Ala Lys Gln Thr Thr Tyr Leu Leu Lys Asp Val Thr Phe
            980                 985                 990

Pro Val Pro Leu Val Ile Ser Asp  Glu Ala Asn Tyr Met  Val Gln Val
        995                 1000                1005

Ala Cys  Ser Leu Ser Cys Ala  Ala Pro His Asn Arg  Gly Asp Glu
    1010                1015                1020

Thr Gln  Phe Glu Leu Phe Ser  Phe Ala Glu Asn Val  Pro Glu Ser
    1025                1030                1035

Ser Ser  Ile Asn Ala Asp Phe  Gln Thr Pro Ile Ile  His Ala Lys
    1040                1045                1050

Gly Gln  Phe Lys Leu Glu Asp  Thr Ala Pro Pro Lys  Val Glu Leu
    1055                1060                1065

Glu Glu  Leu Gln Ala Gly Cys  Pro Gln Glu Ile Asp  Leu Asn Leu
    1070                1075                1080

Phe Tyr  Gln Thr Phe Thr Asp  Lys Gly Phe Val Phe  Gly Ser Arg
    1085                1090                1095

Phe Arg  Trp Leu Glu Gln Ile  Trp Val Gly Asp Gly  Glu Ala Leu
    1100                1105                1110

Ala Arg  Leu Arg Gln Pro Glu  Ser Ile Glu Ser Phe  Lys Gly Tyr
    1115                1120                1125

Val Ile  His Pro Gly Leu Leu  Asp Ala Cys Thr Gln  Val Pro Phe
    1130                1135                1140

Ala Ile  Ser Ser Asp Asp Glu  Asn Arg Gln Ser Glu  Thr Thr Met
    1145                1150                1155

Pro Phe  Ala Leu Asn Glu Leu  Arg Cys Tyr Gln Pro  Ala Asn Gly
    1160                1165                1170

Gln Met  Trp Trp Val His Ala  Thr Glu Lys Asp Arg  Tyr Thr Trp
    1175                1180                1185

Asp Val  Ser Leu Phe Asp Glu  Ser Gly Gln Val Ile  Ala Glu Phe
    1190                1195                1200

Ile Gly  Leu Glu Val Arg Ala  Ala Met Pro Glu Gly  Leu Leu Arg
    1205                1210                1215

Ala Asp  Phe Trp His Asn Trp  Leu Tyr Thr Val Asn  Trp Arg Ser
    1220                1225                1230

Gln Pro  Leu Gln Ile Pro Glu  Val Leu Asp Ile Asn  Lys Thr Gly
    1235                1240                1245

Ala Glu  Thr Trp Leu Leu Phe  Ala Gln Pro Glu Gly  Ile Gly Ala
    1250                1255                1260

Asp Leu  Ala Glu Tyr Leu Gln  Ser Gln Gly Lys His  Cys Val Phe
    1265                1270                1275

Val Val  Pro Gly Ser Glu Tyr  Thr Val Thr Glu Gln  His Ile Gly
    1280                1285                1290

Arg Thr  Gly His Leu Asp Val  Thr Lys Leu Thr Lys  Ile Val Thr
    1295                1300                1305

Ile Asn  Pro Ala Ser Pro His  Asp Tyr Lys Tyr Phe  Leu Glu Thr
```

```
    1310                1315                1320

Leu Thr  Asp Ile Arg Leu Pro  Cys Glu His Ile Leu  Tyr Leu Trp
    1325                1330                1335

Asn Arg  Tyr Asp Leu Thr Asn  Thr Ser Asn His Arg  Thr Glu Leu
    1340                1345                1350

Thr Val  Pro Asp Ile Val Leu  Asn Leu Cys Thr Ser  Leu Thr Tyr
    1355                1360                1365

Leu Val  Gln Ala Leu Ser His  Met Gly Phe Ser Pro  Lys Leu Trp
    1370                1375                1380

Leu Ile  Thr Gln Asn Ser Gln  Ala Val Gly Ser Asp  Leu Ala Asn
    1385                1390                1395

Leu Glu  Ile Glu Gln Ser Pro  Leu Trp Ala Leu Gly  Arg Ser Ile
    1400                1405                1410

Arg Ala  Glu His Pro Glu Phe  Asp Cys Arg Cys Leu  Asp Phe Asp
    1415                1420                1425

Thr Leu  Ser Asn Ile Ala Pro  Leu Leu Leu Lys Glu  Met Gln Ala
    1430                1435                1440

Ile Asp  Tyr Glu Ser Gln Ile  Ala Tyr Arg Gln Gly  Thr Arg Tyr
    1445                1450                1455

Val Ala  Arg Leu Ile Arg Asn  Gln Ser Glu Cys His  Ala Pro Ile
    1460                1465                1470

Gln Thr  Gly Ile Arg Pro Asp  Gly Ser Tyr Leu Ile  Thr Gly Gly
    1475                1480                1485

Leu Gly  Gly Leu Gly Leu Gln  Val Ala Leu Ala Leu  Ala Asp Ala
    1490                1495                1500

Gly Ala  Arg His Leu Ile Leu  Asn Ser Arg Arg Gly  Thr Val Ser
    1505                1510                1515

Lys Glu  Ala Gln Leu Ile Ile  Asp Arg Leu Arg Gln  Glu Asp Val
    1520                1525                1530

Arg Val  Asp Leu Ile Ala Ala  Asp Val Ser Asp Ala  Ala Asp Ser
    1535                1540                1545

Glu Arg  Leu Leu Val Glu Ser  Gln Arg Lys Thr Ser  Leu Arg Gly
    1550                1555                1560

Ile Val  His Val Ala Gly Val  Leu Asp Asp Gly Ile  Leu Leu Gln
    1565                1570                1575

Gln Asn  Gln Glu Arg Phe Glu  Lys Val Met Ala Ala  Lys Val Arg
    1580                1585                1590

Gly Ala  Trp His Leu Asp Gln  Gln Ser Gln Thr Leu  Asp Leu Asp
    1595                1600                1605

Phe Phe  Val Ala Phe Ser Ser  Val Ala Ser Leu Ile  Glu Glu Pro
    1610                1615                1620

Gly Gln  Ala Asn Tyr Ala Ala  Ala Asn Ala Phe Leu  Asp Ser Leu
    1625                1630                1635

Met Tyr  Tyr Arg His Ile Lys  Gly Ser Asn Ser Leu  Ser Ile Asn
    1640                1645                1650

Trp Gly  Ala Trp Ala Glu Val  Gly Met Ala Ala Asn  Leu Ser Trp
    1655                1660                1665

Glu Gln  Arg Gly Ile Ala Ala  Ile Ser Pro Lys Gln  Gly Arg His
    1670                1675                1680

Ile Leu  Val Gln Leu Ile Gln  Lys Leu Asn Gln His  Thr Ile Pro
    1685                1690                1695

Gln Val  Ala Val Gln Pro Thr  Asn Trp Ala Glu Tyr  Leu Ser His
    1700                1705                1710
```

```
Asp Gly  Val Asn Met Pro Phe  Tyr Glu Tyr Phe Thr  His His Leu
    1715                 1720                 1725

Arg Asn  Glu Lys Glu Ala Lys  Leu Arg Gln Thr Ala  Gly Ser Thr
    1730                 1735                 1740

Ser Glu  Glu Val Ser Leu Arg  Gln Gln Leu Gln Thr  Leu Ser Glu
    1745                 1750                 1755

Lys Asp  Arg Asp Ala Leu Leu  Met Glu His Leu Gln  Lys Thr Ala
    1760                 1765                 1770

Ile Arg  Val Leu Gly Leu Ala  Ser Asn Gln Lys Ile  Asp Pro Tyr
    1775                 1780                 1785

Gln Gly  Leu Met Asn Met Gly  Leu Asp Ser Leu Met  Ala Val Glu
    1790                 1795                 1800

Phe Arg  Asn His Leu Ile Arg  Ser Leu Glu Arg Pro  Leu Pro Ala
    1805                 1810                 1815

Thr Leu  Leu Phe Asn Cys Pro  Thr Leu Asp Ser Leu  His Asp Tyr
    1820                 1825                 1830

Leu Val  Ala Lys Met Phe Asp  Asp Ala Pro Gln Lys  Ala Glu Gln
    1835                 1840                 1845

Met Ala  Gln Pro Thr Thr Leu  Thr Ala His Ser Ile  Ser Ile Glu
    1850                 1855                 1860

Ser Lys  Ile Asp Asp Asn Glu  Ser Val Asp Asp Ile  Ala Gln Met
    1865                 1870                 1875

Leu Ala  Gln Ala Leu Asn Ile  Ala Phe Glu
    1880                 1885
```

<210> SEQ ID NO 103
<211> LENGTH: 5004
<212> TYPE: DNA
<213> ORGANISM: Cylindrospermopsis raciborskii AWT205

<400> SEQUENCE: 103

```
atgagtcagc ccaattatgg cattttgatg aaaaatgcgt tgaacgaaat aaatagccta     60

cgatcgcaac tagctgcggt agaagcccaa aaaaatgagt ctattgccat tgttggtatg    120

agttgccgtt ttccaggcgg tgcaactact ccagagcgtt tttgggtatt actgcgcgag    180

ggtatatcag ccattacaga aatccctgct gatcgctggg atgttgataa atattatgat    240

gctgacccca catcgtccgg taaaatgcat actcgttacg gcggttttct gaatgaagtt    300

gatacatttg agccatcatt ctttaatatt gctgcccgtg aagccgttag catggatcca    360

cagcaacgct tgctacttga agtcagttgg gaagctctgg aatccggtaa tattgttcct    420

gcaactcttt ttgatagttc cactggtgta tttatcggta ttggtggtag caactacaaa    480

tctttaatga tcgaaaacag gagtcggatc gggaaaaccg atttgtatga gttaagtggc    540

actgatgtga gtgttgctgc cggcaggata tcctatgtcc tgggtttgat gggtcccagt    600

tttgtgattg atacagcttg ttcatcttct ttggtctcag ttcatcaagc ctgtcagagt    660

ctgcgtcaga gagaatgtga tctagcacta gctggtggag tcggtttact cattgatcca    720

gatgagatga ttggtctttc tcaagggggg atgctggcac ctgatggtag ttgtaaaaca    780

tttgatgcca atgcaaatgg ctatgtgcga ggcgaaggtt gtgggatgat tgttctaaaa    840

cgtctctcgg atgcaacagc cgatggggat aatattcttg ccatcattcg tgggtctatg    900

gttaatcatg atggtcatag cagtggttta actgctccaa gaggccccgc acaagtctct    960

gtcattaagc aagccttaga tagagcaggt attgcaccgg atgccgtaag ttatttagaa   1020
```

-continued

```
gcccatggta caggcacacc ccttggtgat cctatcgaga tggattcatt gaacgaagtg   1080
tttggtcgga gaacagaacc actttgggtc ggctcagtta agacaaatat tggtcattta   1140
gaagccgcgt ccggtattgc agggctgatt aaggttgtct tgatgctaaa aaacaagcag   1200
attcctcctc acttgcattt caagacacca aatccatata ttgattggaa aaatctcccg   1260
gtcgaaattc cgaccaccct tcatgcttgg gatgacaaga cattgaagga cagaaagcga   1320
attgcagggg ttagttcttt tagtttcagt ggtactaacg cccacattgt attatctgaa   1380
gccccatcta gcgaactaat tagtaatcat gcggcagtgg aaagaccatg gcacttgtta   1440
acccttagtg ctaagaatga ggaagcgttg gctaacttgg ttgggcttta tcagtcattt   1500
atttctacta ctgatgcaag tcttgccgat atatgctaca ctgctaatac ggcacgaacc   1560
catttttctc atcgccttgc tctatcggct acttcacaca tccaaataga ggctctttta   1620
gccgcttata aggaagggtc ggtgagtttg agcatcaatc aaggttgtgt cctttccaac   1680
agtcgtgcgc cgaaggtcgc ttttctcttt acaggtcaag gttcgcaata tgtgcaaatg   1740
gctggagaac tttatgagac ccagcctact ttccgtaatt gcttagatcg ctgtgccgaa   1800
atcttgcaat ccatcttttc atcgagaaac agcccttggg gaaacccact gctttcggta   1860
ttatatccaa accatgagtc aaaggaaatt gaccagacgg cttataccca acctgccctt   1920
tttgctgtag aatatgccct agcacagatg tggcggtcgt ggggaatcga gccagatatc   1980
gtaatgggtc atagcatagg tgaatatgtg gcagcttgtg tggcggggat cttttctctg   2040
gaggatggtc tcaaacttgc tgccgaaaga ggccgtttga tgcaggcgct accacaaaat   2100
ggcgagatgg ttgctatatc ggcctccctt gaggaagtta agccggctat tcaatctgac   2160
cagcgagttg tgatagcggc ggtaaatgga ccacgaagtg tcgtcatttc gggcgatcgc   2220
caagctgtgc aagtcttcac caacacccta gaagatcaag gaatccggtg caagagactg   2280
tctgtttcac acgctttcca ctctccattg atgaaaccaa tggagcagga gttcgcacag   2340
gtggccaggg aaatcaacta tagtcctcca aaaatagctc ttgtcagtaa tctaaccggc   2400
gacttgattt cacctgagtc ttccctggag gaaggagtga tcgcttcccc tggttactgg   2460
gtaaatcatt tatgcaatcc tgtcttgttc gctgatggta ttgcaactat gcaagcgcag   2520
gatgtccaag tcttccttga agttggacca aaaccgacct tatcaggact agtgcaacaa   2580
tattttgacg aggttgccca tagcgatcgc cctgtcacca ttcccacctt gcgccccaag   2640
caacccaact ggcagacact attggagagt ttgggacaac tgtatgcgct tggtgtccag   2700
gtaaattggg cgggctttga tagagattac accagacgca aagtaagcct acccacctat   2760
gcttggaagc gtcaacgtta ttggctagag aaacagtccg ctccacgttt agaaacaaca   2820
caagttcgtc ccgcaactgc cattgtagag catcttgaac aaggcaatgt gccgaaaatc   2880
gtggacttgt tagcggcgac ggatgtactt tcaggcgaag cacggaaatt gctacccagc   2940
atcattgaac tattggttgc aaaacatcgt gaggaagcga cacagaagcc catctgcgat   3000
tggctttatg aagtggtttg gcaaccccag ttgctgaccc tatctacctt acctgctgtg   3060
gaaacagagg gtagacaatg gctcatcttc gccgatgcta gtggacacgg tgaagcactt   3120
gcggctcaat tacgtcagca aggggatata attacgcttg tctatgctgg tctaaaatat   3180
cactcggcta ataataaaca aaataccggg ggggacatcc catattttca gattgatccg   3240
atccaaaggg aggattatga aaggttgttt gctgctttgc ctccactgta tggtattgtt   3300
catctttgga gtttagatat acttagcttg gacaaagtat ctaacctaat tgaaaatgta   3360
caattaggta gtggcacgct attaaattta atacagacag tcttgcaact tgaaacgccc   3420
```

```
acccctagct tgtggctcgt gacaaagaac gcgcaagctg tgcgtaaaaa cgatagccta   3480
gtcggagtgc ttcagtcacc cttatggggt atgggtaagg tgatagcctt agaacaccct   3540
gaactcaact gtgtatcaat cgaccttgat ggtgaagggc ttccagatga acaagccaag   3600
tttctggcgg ctgaactccg cgccgcctcc gagttcagac ataccaccat tccccacgaa   3660
agtcaagttg cttggcgtaa taggactcgc tatgtgtcac ggttcaaagg ttatcagaag   3720
catcccgcga cctcatcaaa aatgcctatt cgaccagatg ccacttattt gatcacgggc   3780
ggctttggtg gtttgggctt gcttgtggct cgttggatgg ttgaacaggg ggctacccat   3840
ctatttctga tgggacgcag ccaacccaaa ccagccgccc aaaaacaact gcaagagata   3900
gccgcgctgg gtgcaacagt gacggtggtg caagccgatg ttggcatccg ctcccaagta   3960
gccaatgtgt tggcacagat tgataaggca tatcctttgg ctggtattat tcatactgcc   4020
ggtgtattag acgacggaat cttattgcag caaaattggg cgcgttttag caaggtgttc   4080
gcccccaaac tagagggagc ttggcatcta catacactga ctgaagagat gccgcttgat   4140
ttctttattt gtttttcctc aacagcagga ttgctgggca gtggtggaca agctaactat   4200
gctgctgcca atgccttttt agatgccttt gcccatcatc ggcgaataca aggcttgcca   4260
gctctctcga ttaactggga cgcttggtct caagtgggaa tgacggtacg tctccaacaa   4320
gcttcttcac aaagcaccac agttgggcaa gatattagca ctttggaaat ttcaccagaa   4380
cagggattgc aaatctttgc ctatcttctg caacaaccat ccgcccaaat agcggccatt   4440
tctaccgatg ggcttcgcaa gatgtacgac acaagctcgg ccttttttgc tttacttgat   4500
cttgacaggt cttcctccac tacccaggag caatctacac tttctcatga agttggcctt   4560
accttactcg aacaattgca gcaagctcgg ccaaaagagc gagagaaaat gttactgcgc   4620
catctacaga cccaagttgc tgcggtcttg cgtagtcccg aactgcccgc agttcatcaa   4680
cccttcactg acttggggat ggattcgttg atgtcacttg aattgatgcg gcgtttggaa   4740
gaaagtctgg ggattcagat gcctgcaacg cttgcattcg attatcctat ggtagaccgt   4800
ttggctaagt ttatactgac tcaaatatgt ataaattctg agccagatac ctcagcagtt   4860
ctcacaccag atggaaatgg ggaggaaaaa gacagtaata aggacagaag taccagcact   4920
tccgttgact caaatattac ttccatggca gaagatttat tcgcactcga atccttacta   4980
aataaaataa aaagagatca ataa                                          5004
```

<210> SEQ ID NO 104
<211> LENGTH: 1667
<212> TYPE: PRT
<213> ORGANISM: Cylindrospermopsis raciborskii AWT205

<400> SEQUENCE: 104

```
Met Ser Gln Pro Asn Tyr Gly Ile Leu Met Lys Asn Ala Leu Asn Glu
1               5                   10                  15

Ile Asn Ser Leu Arg Ser Gln Leu Ala Ala Val Glu Ala Gln Lys Asn
            20                  25                  30

Glu Ser Ile Ala Ile Val Gly Met Ser Cys Arg Phe Pro Gly Gly Ala
        35                  40                  45

Thr Thr Pro Glu Arg Phe Trp Val Leu Leu Arg Glu Gly Ile Ser Ala
    50                  55                  60

Ile Thr Glu Ile Pro Ala Asp Arg Trp Asp Val Asp Lys Tyr Tyr Asp
65                  70                  75                  80

Ala Asp Pro Thr Ser Ser Gly Lys Met His Thr Arg Tyr Gly Gly Phe
```

-continued

```
                85                  90                  95

Leu Asn Glu Val Asp Thr Phe Glu Pro Ser Phe Phe Asn Ile Ala Ala
            100                 105                 110

Arg Glu Ala Val Ser Met Asp Pro Gln Gln Arg Leu Leu Leu Glu Val
        115                 120                 125

Ser Trp Glu Ala Leu Glu Ser Gly Asn Ile Val Pro Ala Thr Leu Phe
    130                 135                 140

Asp Ser Ser Thr Gly Val Phe Ile Gly Ile Gly Gly Ser Asn Tyr Lys
145                 150                 155                 160

Ser Leu Met Ile Glu Asn Arg Ser Arg Ile Gly Lys Thr Asp Leu Tyr
                165                 170                 175

Glu Leu Ser Gly Thr Asp Val Ser Val Ala Ala Gly Arg Ile Ser Tyr
            180                 185                 190

Val Leu Gly Leu Met Gly Pro Ser Phe Val Ile Asp Thr Ala Cys Ser
        195                 200                 205

Ser Ser Leu Val Ser Val His Gln Ala Cys Gln Ser Leu Arg Gln Arg
    210                 215                 220

Glu Cys Asp Leu Ala Leu Ala Gly Gly Val Gly Leu Leu Ile Asp Pro
225                 230                 235                 240

Asp Glu Met Ile Gly Leu Ser Gln Gly Gly Met Leu Ala Pro Asp Gly
                245                 250                 255

Ser Cys Lys Thr Phe Asp Ala Asn Ala Asn Gly Tyr Val Arg Gly Glu
            260                 265                 270

Gly Cys Gly Met Ile Val Leu Lys Arg Leu Ser Asp Ala Thr Ala Asp
        275                 280                 285

Gly Asp Asn Ile Leu Ala Ile Ile Arg Gly Ser Met Val Asn His Asp
    290                 295                 300

Gly His Ser Ser Gly Leu Thr Ala Pro Arg Gly Pro Ala Gln Val Ser
305                 310                 315                 320

Val Ile Lys Gln Ala Leu Asp Arg Ala Gly Ile Ala Pro Asp Ala Val
                325                 330                 335

Ser Tyr Leu Glu Ala His Gly Thr Gly Thr Pro Leu Gly Asp Pro Ile
            340                 345                 350

Glu Met Asp Ser Leu Asn Glu Val Phe Gly Arg Arg Thr Glu Pro Leu
        355                 360                 365

Trp Val Gly Ser Val Lys Thr Asn Ile Gly His Leu Glu Ala Ala Ser
    370                 375                 380

Gly Ile Ala Gly Leu Ile Lys Val Val Leu Met Leu Lys Asn Lys Gln
385                 390                 395                 400

Ile Pro Pro His Leu His Phe Lys Thr Pro Asn Pro Tyr Ile Asp Trp
                405                 410                 415

Lys Asn Leu Pro Val Glu Ile Pro Thr Thr Leu His Ala Trp Asp Asp
            420                 425                 430

Lys Thr Leu Lys Asp Arg Lys Arg Ile Ala Gly Val Ser Ser Phe Ser
        435                 440                 445

Phe Ser Gly Thr Asn Ala His Ile Val Leu Ser Glu Ala Pro Ser Ser
    450                 455                 460

Glu Leu Ile Ser Asn His Ala Ala Val Glu Arg Pro Trp His Leu Leu
465                 470                 475                 480

Thr Leu Ser Ala Lys Asn Glu Glu Ala Leu Ala Asn Leu Val Gly Leu
                485                 490                 495

Tyr Gln Ser Phe Ile Ser Thr Thr Asp Ala Ser Leu Ala Asp Ile Cys
            500                 505                 510
```

-continued

```
Tyr Thr Ala Asn Thr Ala Arg Thr His Phe Ser His Arg Leu Ala Leu
        515                 520                 525

Ser Ala Thr Ser His Ile Gln Ile Glu Ala Leu Leu Ala Ala Tyr Lys
    530                 535                 540

Glu Gly Ser Val Ser Leu Ser Ile Asn Gln Gly Cys Val Leu Ser Asn
545                 550                 555                 560

Ser Arg Ala Pro Lys Val Ala Phe Leu Phe Thr Gly Gln Gly Ser Gln
                565                 570                 575

Tyr Val Gln Met Ala Gly Glu Leu Tyr Glu Thr Gln Pro Thr Phe Arg
            580                 585                 590

Asn Cys Leu Asp Arg Cys Ala Glu Ile Leu Gln Ser Ile Phe Ser Ser
        595                 600                 605

Arg Asn Ser Pro Trp Gly Asn Pro Leu Leu Ser Val Leu Tyr Pro Asn
    610                 615                 620

His Glu Ser Lys Glu Ile Asp Gln Thr Ala Tyr Thr Gln Pro Ala Leu
625                 630                 635                 640

Phe Ala Val Glu Tyr Ala Leu Ala Gln Met Trp Arg Ser Trp Gly Ile
                645                 650                 655

Glu Pro Asp Ile Val Met Gly His Ser Ile Gly Glu Tyr Val Ala Ala
            660                 665                 670

Cys Val Ala Gly Ile Phe Ser Leu Glu Asp Gly Leu Lys Leu Ala Ala
        675                 680                 685

Glu Arg Gly Arg Leu Met Gln Ala Leu Pro Gln Asn Gly Glu Met Val
    690                 695                 700

Ala Ile Ser Ala Ser Leu Glu Glu Val Lys Pro Ala Ile Gln Ser Asp
705                 710                 715                 720

Gln Arg Val Val Ile Ala Ala Val Asn Gly Pro Arg Ser Val Val Ile
                725                 730                 735

Ser Gly Asp Arg Gln Ala Val Gln Val Phe Thr Asn Thr Leu Glu Asp
            740                 745                 750

Gln Gly Ile Arg Cys Lys Arg Leu Ser Val Ser His Ala Phe His Ser
        755                 760                 765

Pro Leu Met Lys Pro Met Glu Gln Glu Phe Ala Gln Val Ala Arg Glu
    770                 775                 780

Ile Asn Tyr Ser Pro Pro Lys Ile Ala Leu Val Ser Asn Leu Thr Gly
785                 790                 795                 800

Asp Leu Ile Ser Pro Glu Ser Ser Leu Glu Glu Gly Val Ile Ala Ser
                805                 810                 815

Pro Gly Tyr Trp Val Asn His Leu Cys Asn Pro Val Leu Phe Ala Asp
            820                 825                 830

Gly Ile Ala Thr Met Gln Ala Gln Asp Val Gln Val Phe Leu Glu Val
        835                 840                 845

Gly Pro Lys Pro Thr Leu Ser Gly Leu Val Gln Gln Tyr Phe Asp Glu
    850                 855                 860

Val Ala His Ser Asp Arg Pro Val Thr Ile Pro Thr Leu Arg Pro Lys
865                 870                 875                 880

Gln Pro Asn Trp Gln Thr Leu Leu Glu Ser Leu Gly Gln Leu Tyr Ala
                885                 890                 895

Leu Gly Val Gln Val Asn Trp Ala Gly Phe Asp Arg Asp Tyr Thr Arg
            900                 905                 910

Arg Lys Val Ser Leu Pro Thr Tyr Ala Trp Lys Arg Gln Arg Tyr Trp
        915                 920                 925
```

-continued

```
Leu Glu Lys Gln Ser Ala Pro Arg Leu Glu Thr Thr Gln Val Arg Pro
    930                 935                 940

Ala Thr Ala Ile Val Glu His Leu Glu Gln Gly Asn Val Pro Lys Ile
945                 950                 955                 960

Val Asp Leu Leu Ala Ala Thr Asp Val Leu Ser Gly Glu Ala Arg Lys
                965                 970                 975

Leu Leu Pro Ser Ile Ile Glu Leu Leu Val Ala Lys His Arg Glu Glu
            980                 985                 990

Ala Thr Gln Lys Pro Ile Cys Asp  Trp Leu Tyr Glu Val  Val Trp Gln
        995                 1000                1005

Pro Gln  Leu Leu Thr Leu Ser  Thr Leu Pro Ala Val  Glu Thr Glu
    1010                1015                1020

Gly Arg  Gln Trp Leu Ile Phe  Ala Asp Ala Ser Gly  His Gly Glu
    1025                1030                1035

Ala Leu  Ala Ala Gln Leu Arg  Gln Gln Gly Asp Ile  Ile Thr Leu
    1040                1045                1050

Val Tyr  Ala Gly Leu Lys Tyr  His Ser Ala Asn Asn  Lys Gln Asn
    1055                1060                1065

Thr Gly  Gly Asp Ile Pro Tyr  Phe Gln Ile Asp Pro  Ile Gln Arg
    1070                1075                1080

Glu Asp  Tyr Glu Arg Leu Phe  Ala Ala Leu Pro Pro  Leu Tyr Gly
    1085                1090                1095

Ile Val  His Leu Trp Ser Leu  Asp Ile Leu Ser Leu  Asp Lys Val
    1100                1105                1110

Ser Asn  Leu Ile Glu Asn Val  Gln Leu Gly Ser Gly  Thr Leu Leu
    1115                1120                1125

Asn Leu  Ile Gln Thr Val Leu  Gln Leu Glu Thr Pro  Thr Pro Ser
    1130                1135                1140

Leu Trp  Leu Val Thr Lys Asn  Ala Gln Ala Val Arg  Lys Asn Asp
    1145                1150                1155

Ser Leu  Val Gly Val Leu Gln  Ser Pro Leu Trp Gly  Met Gly Lys
    1160                1165                1170

Val Ile  Ala Leu Glu His Pro  Glu Leu Asn Cys Val  Ser Ile Asp
    1175                1180                1185

Leu Asp  Gly Glu Gly Leu Pro  Asp Glu Gln Ala Lys  Phe Leu Ala
    1190                1195                1200

Ala Glu  Leu Arg Ala Ala Ser  Glu Phe Arg His Thr  Thr Ile Pro
    1205                1210                1215

His Glu  Ser Gln Val Ala Trp  Arg Asn Arg Thr Arg  Tyr Val Ser
    1220                1225                1230

Arg Phe  Lys Gly Tyr Gln Lys  His Pro Ala Thr Ser  Ser Lys Met
    1235                1240                1245

Pro Ile  Arg Pro Asp Ala Thr  Tyr Leu Ile Thr Gly  Gly Phe Gly
    1250                1255                1260

Gly Leu  Gly Leu Leu Val Ala  Arg Trp Met Val Glu  Gln Gly Ala
    1265                1270                1275

Thr His  Leu Phe Leu Met Gly  Arg Ser Gln Pro Lys  Pro Ala Ala
    1280                1285                1290

Gln Lys  Gln Leu Gln Glu Ile  Ala Ala Leu Gly Ala  Thr Val Thr
    1295                1300                1305

Val Val  Gln Ala Asp Val Gly  Ile Arg Ser Gln Val  Ala Asn Val
    1310                1315                1320

Leu Ala  Gln Ile Asp Lys Ala  Tyr Pro Leu Ala Gly  Ile Ile His
```

```
    1325                1330                1335

Thr Ala  Gly Val Leu Asp Asp  Gly Ile Leu Leu Gln  Gln Asn Trp
    1340                1345                1350

Ala Arg  Phe Ser Lys Val Phe  Ala Pro Lys Leu Glu  Gly Ala Trp
    1355                1360                1365

His Leu  His Thr Leu Thr Glu  Glu Met Pro Leu Asp  Phe Phe Ile
    1370                1375                1380

Cys Phe  Ser Ser Thr Ala Gly  Leu Leu Gly Ser Gly  Gly Gln Ala
    1385                1390                1395

Asn Tyr  Ala Ala Ala Asn Ala  Phe Leu Asp Ala Phe  Ala His His
    1400                1405                1410

Arg Arg  Ile Gln Gly Leu Pro  Ala Leu Ser Ile Asn  Trp Asp Ala
    1415                1420                1425

Trp Ser  Gln Val Gly Met Thr  Val Arg Leu Gln Gln  Ala Ser Ser
    1430                1435                1440

Gln Ser  Thr Thr Val Gly Gln  Asp Ile Ser Thr Leu  Glu Ile Ser
    1445                1450                1455

Pro Glu  Gln Gly Leu Gln Ile  Phe Ala Tyr Leu Leu  Gln Gln Pro
    1460                1465                1470

Ser Ala  Gln Ile Ala Ala Ile  Ser Thr Asp Gly Leu  Arg Lys Met
    1475                1480                1485

Tyr Asp  Thr Ser Ser Ala Phe  Phe Ala Leu Leu Asp  Leu Asp Arg
    1490                1495                1500

Ser Ser  Ser Thr Thr Gln Glu  Gln Ser Thr Leu Ser  His Glu Val
    1505                1510                1515

Gly Leu  Thr Leu Leu Glu Gln  Leu Gln Gln Ala Arg  Pro Lys Glu
    1520                1525                1530

Arg Glu  Lys Met Leu Leu Arg  His Leu Gln Thr Gln  Val Ala Ala
    1535                1540                1545

Val Leu  Arg Ser Pro Glu Leu  Pro Ala Val His Gln  Pro Phe Thr
    1550                1555                1560

Asp Leu  Gly Met Asp Ser Leu  Met Ser Leu Glu Leu  Met Arg Arg
    1565                1570                1575

Leu Glu  Glu Ser Leu Gly Ile  Gln Met Pro Ala Thr  Leu Ala Phe
    1580                1585                1590

Asp Tyr  Pro Met Val Asp Arg  Leu Ala Lys Phe Ile  Leu Thr Gln
    1595                1600                1605

Ile Cys  Ile Asn Ser Glu Pro  Asp Thr Ser Ala Val  Leu Thr Pro
    1610                1615                1620

Asp Gly  Asn Gly Glu Glu Lys  Asp Ser Asn Lys Asp  Arg Ser Thr
    1625                1630                1635

Ser Thr  Ser Val Asp Ser Asn  Ile Thr Ser Met Ala  Glu Asp Leu
    1640                1645                1650

Phe Ala  Leu Glu Ser Leu Leu  Asn Lys Ile Lys Arg  Asp Gln
    1655                1660                1665
```

<210> SEQ ID NO 105
<211> LENGTH: 318
<212> TYPE: DNA
<213> ORGANISM: Cylindrospermopsis raciborskii AWT205

<400> SEQUENCE: 105

```
ttatgctgca tctaaataga agttccatag ccctgcactg accaacatca attgatcatc     60

aaaatcggtc acacgattcc tatatgtggg ataaaatttg cagtacagca ggatataaaa    120
```

```
tagtttttcc tctatacttc tgagtgtagg cttgcgtccg cccccgggcg cacgtttgcg    180

gtttgctaag gagttgaaca cggtgcgttc ataggtatca gcaaactgag ataacagctc    240

gttgaatgct tggcggttaa gtccagtcat tgctcgtagc agtcgctctt gattcaggat    300

gcggtctaag ttcaacat                                                  318
```

<210> SEQ ID NO 106
<211> LENGTH: 105
<212> TYPE: PRT
<213> ORGANISM: Cylindrospermopsis raciborskii AWT205

<400> SEQUENCE: 106

```
Met Leu Asn Leu Asp Arg Ile Leu Asn Gln Glu Arg Leu Leu Arg Ala
1               5                   10                  15

Met Thr Gly Leu Asn Arg Gln Ala Phe Asn Glu Leu Leu Ser Gln Phe
            20                  25                  30

Ala Asp Thr Tyr Glu Arg Thr Val Phe Asn Ser Leu Ala Asn Arg Lys
        35                  40                  45

Arg Ala Pro Gly Gly Gly Arg Lys Pro Thr Leu Arg Ser Ile Glu Glu
    50                  55                  60

Lys Leu Phe Tyr Ile Leu Leu Tyr Cys Lys Phe Tyr Pro Thr Tyr Arg
65                  70                  75                  80

Asn Arg Val Thr Asp Phe Asp Asp Gln Leu Met Leu Val Ser Ala Gly
                85                  90                  95

Leu Trp Asn Phe Tyr Leu Asp Ala Ala
            100                 105
```

<210> SEQ ID NO 107
<211> LENGTH: 600
<212> TYPE: DNA
<213> ORGANISM: Cylindrospermopsis raciborskii AWT205

<400> SEQUENCE: 107

```
ctactgagtg aaagtgaact tctttcccac gtattcgagt agctgttgta agctggcctc     60

gatggaaagt tccgaagttt ccaccagtaa atctggtgtt ctcggtggtt cgtagggagc    120

gctaattccc gtaaaagact caatttctcc acggcgtgct tttgcataga gacccttggg    180

gtcacgttgt tcacaaattt ccatcggagt tgcaatatat acttcatgaa acagatctcc    240

ggacagaata cggatttgct cccggtcttt cctgtaaggt gaaatgaaag cagtaatcac    300

taaacaaccc gaatccgcaa aaagtttggc cacctcgcca atacgacgaa tattttccgc    360

acgatcagca gcagaaaatc ccaagtcagc acataatcca tgacggatat tgtcaccatc    420

aaggacaaaa gtataccaac ctttctggaa caaaatccgc tctaattcta gagccaatgt    480

tgttttacct gatcctgata atccagtgaa ccatagaatt ccatttcggt gaccattctt    540

taaacaacga tcaaatgggg acacaagatg ttttgtatgt tgaatattgc ttgatttcat    600
```

<210> SEQ ID NO 108
<211> LENGTH: 199
<212> TYPE: PRT
<213> ORGANISM: Cylindrospermopsis raciborskii AWT205

<400> SEQUENCE: 108

```
Met Lys Ser Ser Asn Ile Gln His Thr Lys His Leu Val Ser Pro Phe
1               5                   10                  15

Asp Arg Cys Leu Lys Asn Gly His Arg Asn Gly Ile Leu Trp Phe Thr
            20                  25                  30
```

-continued

```
Gly Leu Ser Gly Ser Gly Lys Thr Thr Leu Ala Leu Glu Leu Glu Arg
        35                  40                  45

Ile Leu Phe Gln Lys Gly Trp Tyr Thr Phe Val Leu Asp Gly Asp Asn
    50                  55                  60

Ile Arg His Gly Leu Cys Ala Asp Leu Gly Phe Ser Ala Ala Asp Arg
65                  70                  75                  80

Ala Glu Asn Ile Arg Arg Ile Gly Glu Val Ala Lys Leu Phe Ala Asp
                85                  90                  95

Ser Gly Cys Leu Val Ile Thr Ala Phe Ile Ser Pro Tyr Arg Lys Asp
            100                 105                 110

Arg Glu Gln Ile Arg Ile Leu Ser Gly Asp Leu Phe His Glu Val Tyr
        115                 120                 125

Ile Ala Thr Pro Met Glu Ile Cys Glu Gln Arg Asp Pro Lys Gly Leu
    130                 135                 140

Tyr Ala Lys Ala Arg Arg Gly Glu Ile Glu Ser Phe Thr Gly Ile Ser
145                 150                 155                 160

Ala Pro Tyr Glu Pro Pro Arg Thr Pro Asp Leu Leu Val Glu Thr Ser
                165                 170                 175

Glu Leu Ser Ile Glu Ala Ser Leu Gln Gln Leu Leu Glu Tyr Val Gly
            180                 185                 190

Lys Lys Phe Thr Phe Thr Gln
        195
```

<210> SEQ ID NO 109
<211> LENGTH: 1548
<212> TYPE: DNA
<213> ORGANISM: Cylindrospermopsis raciborskii AWT205

<400> SEQUENCE: 109

```
atgcctaaat actttaatac tgctggaccc tgtaaatccg aaatccacta tatgctctct      60

cccacagctc gactaccgga tttgaaagca ctaattgacg gagaaaacta ctttataatt     120

cacgcgccgc gacaagtcgg caaaactaca gctatgatag ccttagcacg agaattgact     180

gatagtggaa aatataccgc agttattctt tccgttgaag tgggatcagt attctcccat     240

aatccccagc aagcggagca ggttatttta gaagaatgga aacaggcaat caaattttat     300

ttacccaaag aactacaacc atcctattgg ccagagcgtg aaacagactc aggaataggc     360

aaaactttaa gtgagtggtc cgcacaatct ccaagacctc ttgtaatctt tttacatgaa     420

atcgattccc taacagatga agctttaatc ctaattttaa gacaattacg ctcaggtttt     480

ccccgtcgtc ctcggggatt tccccattcg gtggggttaa ttggtatgcg ggatgtgcgg     540

gactataagg ttaaatctgg tggaagtgaa cgactgaata cgtcaagtcc tttcaatatc     600

aaagcggaat ccttgacttt aagtaatttc actctgtcag aggtggaaga actttactta     660

caacatacgc aagctacagg acaaattttt accccggaag caattaaaca agcattttat     720

ttaaccgatg ggcaaccatg gttagtaaac gccctagctc gtcaagccac tcaggtgtta     780

gtgaaagata ttactcaacc cattaccgct gaagtaatta accaagccaa agaagttctg     840

attcagcgcc aggataccca tttggatagt ttggcagagc gcttacggga agatcgggtc     900

aaagccatta ttcaacctat gttagctgga tcggacttac cagatacccc agaggatgat     960

cgccgtttct tgctagattt aggcttggta aagcgcagtc ccttgggagg actaaccatt    1020

gccaatccca tttaccagga ggtgattcct cgtgttttgt cccagggtag tcaggatagt    1080

ctaccccaga ttcaacctac ttggttaaat actgataata ctttaaatcc tgacaaactc    1140
```

```
ttaaatgctt tcctagagtt ttggcgacaa catggggaac cattactcaa aagtgcgcct   1200

tatcatgaaa ttgctcccca tttagttttg atggcgtttt tacatcgggt agtgaatggt   1260

ggtggcactt tagaacggga atatgccgtt ggttctggaa gaatggatat ttgtttacgc   1320

tatggcaagg tagtgatggg catagagtta aaggtttggg ggggaaaatc ggatccgtta   1380

acgaagggtt tgacccaatt ggataaatat ctgggtgggt taggattaga tagaggttgg   1440

ttagtaattt ttgatcaccg tccgggatta ccacccatgg gtgagaggat tagtatggaa   1500

caggccatta gtccagaggg aagaaccatt acagtgattc gtagctag                1548


<210> SEQ ID NO 110
<211> LENGTH: 515
<212> TYPE: PRT
<213> ORGANISM: Cylindrospermopsis raciborskii AWT205

<400> SEQUENCE: 110

Met Pro Lys Tyr Phe Asn Thr Ala Gly Pro Cys Lys Ser Glu Ile His
1               5                   10                  15

Tyr Met Leu Ser Pro Thr Ala Arg Leu Pro Asp Leu Lys Ala Leu Ile
            20                  25                  30

Asp Gly Glu Asn Tyr Phe Ile Ile His Ala Pro Arg Gln Val Gly Lys
        35                  40                  45

Thr Thr Ala Met Ile Ala Leu Ala Arg Glu Leu Thr Asp Ser Gly Lys
    50                  55                  60

Tyr Thr Ala Val Ile Leu Ser Val Glu Val Gly Ser Val Phe Ser His
65                  70                  75                  80

Asn Pro Gln Gln Ala Glu Gln Val Ile Leu Glu Glu Trp Lys Gln Ala
                85                  90                  95

Ile Lys Phe Tyr Leu Pro Lys Glu Leu Gln Pro Ser Tyr Trp Pro Glu
            100                 105                 110

Arg Glu Thr Asp Ser Gly Ile Gly Lys Thr Leu Ser Glu Trp Ser Ala
        115                 120                 125

Gln Ser Pro Arg Pro Leu Val Ile Phe Leu His Glu Ile Asp Ser Leu
    130                 135                 140

Thr Asp Glu Ala Leu Ile Leu Ile Leu Arg Gln Leu Arg Ser Gly Phe
145                 150                 155                 160

Pro Arg Arg Pro Arg Gly Phe Pro His Ser Val Gly Leu Ile Gly Met
                165                 170                 175

Arg Asp Val Arg Asp Tyr Lys Val Lys Ser Gly Gly Ser Glu Arg Leu
            180                 185                 190

Asn Thr Ser Ser Pro Phe Asn Ile Lys Ala Glu Ser Leu Thr Leu Ser
        195                 200                 205

Asn Phe Thr Leu Ser Glu Val Glu Glu Leu Tyr Leu Gln His Thr Gln
    210                 215                 220

Ala Thr Gly Gln Ile Phe Thr Pro Glu Ala Ile Lys Gln Ala Phe Tyr
225                 230                 235                 240

Leu Thr Asp Gly Gln Pro Trp Leu Val Asn Ala Leu Ala Arg Gln Ala
                245                 250                 255

Thr Gln Val Leu Val Lys Asp Ile Thr Gln Pro Ile Thr Ala Glu Val
            260                 265                 270

Ile Asn Gln Ala Lys Glu Val Leu Ile Gln Arg Gln Asp Thr His Leu
        275                 280                 285

Asp Ser Leu Ala Glu Arg Leu Arg Glu Asp Arg Val Lys Ala Ile Ile
    290                 295                 300
```

```
Gln Pro Met Leu Ala Gly Ser Asp Leu Pro Asp Thr Pro Glu Asp Asp
305                 310                 315                 320

Arg Arg Phe Leu Leu Asp Leu Gly Leu Val Lys Arg Ser Pro Leu Gly
                325                 330                 335

Gly Leu Thr Ile Ala Asn Pro Ile Tyr Gln Glu Val Ile Pro Arg Val
            340                 345                 350

Leu Ser Gln Gly Ser Gln Asp Ser Leu Pro Gln Ile Gln Pro Thr Trp
        355                 360                 365

Leu Asn Thr Asp Asn Thr Leu Asn Pro Asp Lys Leu Leu Asn Ala Phe
    370                 375                 380

Leu Glu Phe Trp Arg Gln His Gly Glu Pro Leu Leu Lys Ser Ala Pro
385                 390                 395                 400

Tyr His Glu Ile Ala Pro His Leu Val Leu Met Ala Phe Leu His Arg
                405                 410                 415

Val Val Asn Gly Gly Gly Thr Leu Glu Arg Glu Tyr Ala Val Gly Ser
            420                 425                 430

Gly Arg Met Asp Ile Cys Leu Arg Tyr Gly Lys Val Val Met Gly Ile
        435                 440                 445

Glu Leu Lys Val Trp Gly Gly Lys Ser Asp Pro Leu Thr Lys Gly Leu
    450                 455                 460

Thr Gln Leu Asp Lys Tyr Leu Gly Gly Leu Gly Leu Asp Arg Gly Trp
465                 470                 475                 480

Leu Val Ile Phe Asp His Arg Pro Gly Leu Pro Pro Met Gly Glu Arg
                485                 490                 495

Ile Ser Met Glu Gln Ala Ile Ser Pro Glu Gly Arg Thr Ile Thr Val
            500                 505                 510

Ile Arg Ser
        515
```

<210> SEQ ID NO 111
<211> LENGTH: 20
<212> TYPE: DNA
<213> ORGANISM: Artificial Sequence
<220> FEATURE:
<223> OTHER INFORMATION: Based on Cylindrospermopsis raciborskii AWT205 sequence

<400> SEQUENCE: 111
acttctctcc tttccctatc 20

<210> SEQ ID NO 112
<211> LENGTH: 22
<212> TYPE: DNA
<213> ORGANISM: Artificial Sequence
<220> FEATURE:
<223> OTHER INFORMATION: Based on Cylindrospermopsis raciborskii AWT205 sequence

<400> SEQUENCE: 112
gagtgaaaat gcgtagaact tg 22

<210> SEQ ID NO 113
<211> LENGTH: 22
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 113
cccaatatct ccctgtaaaa ct 22

<210> SEQ ID NO 114
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 114
tggcaattgt ctctccgtat 20

<210> SEQ ID NO 115
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 115
ctcgccgatg aaagtcctct 20

<210> SEQ ID NO 116
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 116
gcgtgtcgag aaaaaggtgt 20

<210> SEQ ID NO 117
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 117
ctcgacacgc aagaataacg 20

<210> SEQ ID NO 118
<211> LENGTH: 21
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 118
atgcttctgc tttggcatgg c 21

<210> SEQ ID NO 119
<211> LENGTH: 21
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 119

-continued taactcgacg aactttgacc c 21

<210> SEQ ID NO 120
<211> LENGTH: 19
<212> TYPE: DNA
<213> ORGANISM: Artificial Sequence
<220> FEATURE:
<223> OTHER INFORMATION: Based on Cylindrospermopsis raciborskii T3

<400> SEQUENCE: 120
gccgccaatc ctcgcgatg 19

<210> SEQ ID NO 121
<211> LENGTH: 22
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 121
gaacgtctaa tgttgcacag tg 22

<210> SEQ ID NO 122
<211> LENGTH: 23
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 122
ctggtacgta gtcgcaaagg tgg 23

<210> SEQ ID NO 123
<211> LENGTH: 26
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 123
ctgacggtac atgtatttcc tgtgac 26

<210> SEQ ID NO 124
<211> LENGTH: 30
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 124
cgtctcatat gcagatctta ggaatttcag 30

<210> SEQ ID NO 125
<211> LENGTH: 25
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 125
gcttactacc acgatagtgc tgccg 25

<210> SEQ ID NO 126
<211> LENGTH: 22
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 126
tctatgttta gcaggtggtg tc 22

<210> SEQ ID NO 127
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 127
ttctgcaaga cgagccataa 20

<210> SEQ ID NO 128
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 128
ggttcgccgc ggacattaaa 20

<210> SEQ ID NO 129
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 129
atgctaatgc ggtgggagta 20

<210> SEQ ID NO 130
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 130
aaagcagttc cgacgacatt 20

<210> SEQ ID NO 131
<211> LENGTH: 23
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 131
cctatttcga ttattgtttt cgg 23

<210> SEQ ID NO 132
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 132
gataccgatc ataaactacg 20

<210> SEQ ID NO 133
<211> LENGTH: 21
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 133
gcaaattttg caggagtaat g 21

<210> SEQ ID NO 134
<211> LENGTH: 21
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 134
gcaaattttg caggagtaat g 21

<210> SEQ ID NO 135
<211> LENGTH: 23
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 135
ttttgggtaa actttatagc cat 23

<210> SEQ ID NO 136
<211> LENGTH: 22
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 136
tgggtctgga cagttgtaga ta 22

<210> SEQ ID NO 137
<211> LENGTH: 23
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 137
aaggggaaaa caaaattatc aat 23

<210> SEQ ID NO 138

<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 138
ggcgatcgcc tgctaaaaat 20

<210> SEQ ID NO 139
<211> LENGTH: 23
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 139
cctcattttc atttctagac gtt 23

<210> SEQ ID NO 140
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 140
ccacttcaac taaaacagca 20

<210> SEQ ID NO 141
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 141
aaaaattttg gaggggtagc 20

<210> SEQ ID NO 142
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 142
atccaagatg cgacaacact 20

<210> SEQ ID NO 143
<211> LENGTH: 21
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 143
ggtccttgcg cagatagagt g 21

<210> SEQ ID NO 144
<211> LENGTH: 21

<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 144
cactctatct gcgcaaggac c 21

<210> SEQ ID NO 145
<211> LENGTH: 21
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 145
tgactgcatt cgctgtataa a 21

<210> SEQ ID NO 146
<211> LENGTH: 22
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 146
ttcataagac ggctgttgaa tc 22

<210> SEQ ID NO 147
<211> LENGTH: 30
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 147
ctcgagttaa aaaagagtgt aaatgaaagg 30

<210> SEQ ID NO 148
<211> LENGTH: 23
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 148
ttctataact gctgccaaat ttt 23

<210> SEQ ID NO 149
<211> LENGTH: 23
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 149
aattttggag tgactggtta tgg 23

<210> SEQ ID NO 150
<211> LENGTH: 23
<212> TYPE: DNA

<213> ORGANISM: Artificial Sequence
<220> FEATURE:
<223> OTHER INFORMATION: Based on Cylindrospermopsis raciborskii T3
sequence

<400> SEQUENCE: 150
ccataaccag tcactccaaa att 23

<210> SEQ ID NO 151
<211> LENGTH: 21
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 151
ttttagttgt tacttttggc g 21

<210> SEQ ID NO 152
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 152
acagcagatg agagaaagta 20

<210> SEQ ID NO 153
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 153
gggttgtctt gctgattttc 20

<210> SEQ ID NO 154
<211> LENGTH: 22
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 154
cattaaaata agtccggaca gg 22

<210> SEQ ID NO 155
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 155
ttaaacagaa tgaggagcaa 20

<210> SEQ ID NO 156
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 156
aaacaacaca cccatctaag 20

<210> SEQ ID NO 157
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 157
ttaataaggc atccccaaga 20

<210> SEQ ID NO 158
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 158
gaaatggctg tgtaaaaact 20

<210> SEQ ID NO 159
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 159
tctgccatat ccccaaccta 20

<210> SEQ ID NO 160
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 160
gatcgcccga caggaagact 20

<210> SEQ ID NO 161
<211> LENGTH: 20
<212> TYPE: DNA
<213> ORGANISM: Artificial Sequence
<220> FEATURE:
<223> OTHER INFORMATION: Based on Cylindrospermopsis raciborskii T3
sequence

<400> SEQUENCE: 161
tccggcttga cctgctggac 20

<210> SEQ ID NO 162
<211> LENGTH: 20
<212> TYPE: DNA
<213> ORGANISM: Artificial Sequence
<220> FEATURE:

<223> OTHER INFORMATION: Based on Cylindrospermopsis raciborskii T3
      sequence

<400> SEQUENCE: 162
tgcgatgatt ttgcctctgt 20

<210> SEQ ID NO 163
<211> LENGTH: 20
<212> TYPE: DNA
<213> ORGANISM: Artificial Sequence
<220> FEATURE:
<223> OTHER INFORMATION: Based on Cylindrospermopsis raciborskii T3
      sequence

<400> SEQUENCE: 163
aaaatttgca cacccacacg 20

<210> SEQ ID NO 164
<211> LENGTH: 27
<212> TYPE: DNA
<213> ORGANISM: Artificial Sequence
<220> FEATURE:
<223> OTHER INFORMATION: Based on Cylindrospermopsis raciborskii T3
      sequence

<400> SEQUENCE: 164
ttggattgaa cgtgtaattg aaaaagc 27

<210> SEQ ID NO 165
<211> LENGTH: 27
<212> TYPE: DNA
<213> ORGANISM: Artificial Sequence
<220> FEATURE:
<223> OTHER INFORMATION: Based on Cylindrospermopsis raciborskii T3
      sequence

<400> SEQUENCE: 165
gctttttcaa ttacacgttc aatccaa 27

<210> SEQ ID NO 166
<211> LENGTH: 19
<212> TYPE: DNA
<213> ORGANISM: Artificial Sequence
<220> FEATURE:
<223> OTHER INFORMATION: Based on Cylindrospermopsis raciborskii T3
      sequence

<400> SEQUENCE: 166
aaatggcgta tcgactaac 19

<210> SEQ ID NO 167
<211> LENGTH: 21
<212> TYPE: DNA
<213> ORGANISM: Artificial Sequence
<220> FEATURE:
<223> OTHER INFORMATION: Based on Cylindrospermopsis raciborskii T3
      sequence

<400> SEQUENCE: 167
atataggagc gcataaagtg c 21

<210> SEQ ID NO 168
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 168
cttggtataa gtcttgtgat 20

<210> SEQ ID NO 169
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 169
aacactcatt agattcatct 20

<210> SEQ ID NO 170
<211> LENGTH: 21
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 170
tccactaaat cctttgaatt g 21

<210> SEQ ID NO 171
<211> LENGTH: 21
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 171
tgtttgtctg gatgcgatcc t 21

<210> SEQ ID NO 172
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 172
gcagttcagg tccatgaaac 20

<210> SEQ ID NO 173
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 173
agcccagtca caaccttcgt 20

<210> SEQ ID NO 174
<211> LENGTH: 21
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 174
tctggaagta cttgcactgt c 21

<210> SEQ ID NO 175
<211> LENGTH: 22
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 175
tgtaactccg tcaggacata aa 22

<210> SEQ ID NO 176
<211> LENGTH: 23
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 176
tgcaaatttt agtagcaata acg 23

<210> SEQ ID NO 177
<211> LENGTH: 27
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 177
ctttactaat tatagcgggg atattat 27

<210> SEQ ID NO 178
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 178
cagtggggaa atagatggat 20

<210> SEQ ID NO 179
<211> LENGTH: 20
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 179
tggtcataaa agcgggattc 20

<210> SEQ ID NO 180
<211> LENGTH: 18
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 180
ggatcttggc gcaattta 18

<210> SEQ ID NO 181
<211> LENGTH: 23
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 181
gttagagact tggaacgtat tgg 23

<210> SEQ ID NO 182
<211> LENGTH: 19
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 182
ccaaacccag aagaaatcc 19

<210> SEQ ID NO 183
<211> LENGTH: 22
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 183
aatctatagc caaaacccct aa 22

<210> SEQ ID NO 184
<211> LENGTH: 19
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 184
actgtgtgaa caattcccc 19

<210> SEQ ID NO 185
<211> LENGTH: 29
<212> TYPE: DNA
<213> ORGANISM: Artificial Sequence
<220> FEATURE:
<223> OTHER INFORMATION: Based on Cylindrospermopsis raciborskii T3 sequence

<400> SEQUENCE: 185
gcaacaagac tacatttagt agatttaga 29

<210> SEQ ID NO 186
<211> LENGTH: 27
<212> TYPE: DNA

-continued

```
<213> ORGANISM: Artificial Sequence
<220> FEATURE:
<223> OTHER INFORMATION: Based on Cylindrospermopsis raciborskii T3
      sequence

<400> SEQUENCE: 186

gctttttcaa ttacacgttc aatccaa                                    27
```